United States Patent
Lubell et al.

(10) Patent No.: US 11,879,021 B2
(45) Date of Patent: Jan. 23, 2024

(54) CYCLIC PEPTIDES AND USES THEREOF

(71) Applicant: UNIVERSITÉ DE MONTRÉAL, Montreal (CA)

(72) Inventors: William D. Lubell, Outremont (CA); Huy Ong, Ville Mont-Royal (CA); Jinqiang Zhang, Chongqing (CN); Dilan Mukandila Mulumba, Laval (CA); Sylvie Marleau, Rosemère (CA); Ragnhild Gaard Ohm, Copenhagen (DK); Ahsanullah, Montreal (CA); Samy Omri, Montreal (CA); Ramesh Chingle, Frederick, MD (US)

(73) Assignee: UNIVERSITÉ DE MONTRÉAL

( * ) Notice: Subject to any disclaimer, the term of this patent is extended or adjusted under 35 U.S.C. 154(b) by 394 days.

(21) Appl. No.: 16/311,996

(22) PCT Filed: Jun. 28, 2017

(86) PCT No.: PCT/CA2017/000163
§ 371 (c)(1),
(2) Date: Dec. 20, 2018

(87) PCT Pub. No.: WO2018/000079
PCT Pub. Date: Jan. 4, 2018

(65) Prior Publication Data
US 2019/0202863 A1    Jul. 4, 2019

Related U.S. Application Data

(60) Provisional application No. 62/383,016, filed on Sep. 2, 2016, provisional application No. 62/355,496, filed on Jun. 28, 2016.

(51) Int. Cl.
| | |
|---|---|
| *C07K 7/64* | (2006.01) |
| *C07K 7/06* | (2006.01) |
| *C07K 7/00* | (2006.01) |
| *C07K 7/02* | (2006.01) |
| *A61K 38/00* | (2006.01) |

(52) U.S. Cl.
CPC .............. *C07K 7/64* (2013.01); *C07K 7/00* (2013.01); *C07K 7/02* (2013.01); *C07K 7/06* (2013.01); *A61K 38/00* (2013.01)

(58) Field of Classification Search
None
See application file for complete search history.

(56) References Cited

U.S. PATENT DOCUMENTS 8,993,515 B2    3/2015    Lubell et al.

FOREIGN PATENT DOCUMENTS

| | | |
|---|---|---|
| CA | 2399548 A1 | 2/2004 |
| WO | 2004017986 A1 | 3/2004 |
| WO | 2008154738 A1 | 12/2008 |
| WO | 20160299324 A1 | 3/2016 |

OTHER PUBLICATIONS

Chen et al. (Prognostic and immunological role of CD36: A pan cancer analysis J Cancer 2021; 12(16)).*
The Merck Manual (https://www.merckmanuals.com/professional/neurologic-disorders/intracranial-and-spinal-tumors/gliomas accessed Aug. 8, 2022).*
NIH, (http://www.nhlbi.nih.gov/health/health-topics/topics/stroke/treatment> accessed Aug. 8, 2022).*
André, F., et al., "Aza-peptides. III. Experimental structural analysis of aza-alanine and aza-asparagine-containing peptides", J. Pept. Res. 1997, 50, 372-381.
André F., et al. ,"Aza-peptides. II. X-Ray structures of aza-alanine and aza-asparagine-containing peptides", J. Pept. Res. 1997, 49, 556-562.
Assem N., et al. "Acetone-Linked Peptides: A Convergent Approach for Peptide Macrocyclization and Labeling", Chem. Int. Ed. 2015, 54, 8665 8668.
Blackwell, H. E., et al., "Highly Efficient Synthesis of Covalently Cross-Linked Peptide Helices by Ring-Closing Metathesis", Chem. Int. Ed. 1998, 37, 3281-3284.
Beck, J. G., et al., "Intestinal Permeability of Cyclic Peptides: Common Key Backbone Motifs Identified", J. Am. Chem. Soc. 2012, 134, 12125-12133.
Bessi, V. L., et al., "EP 80317, a selective CD36 ligand, shows cardioprotective effects against post-ischaemic myocardial damage in mice", Cardiovasc. Res. 2012, 96, 99-108.
Bird, G. H., "Hydrocarbon double-stapling remedies the proteolytic instability of a lengthy peptide therapeutic", Proc. Natl. Acad. Sci. U.S.A. 2010, 107, 14093-14098.
Bouck, N., et al., "Signals leading to apoptosis-dependent inhibition of neovascularization by thrombospondin-1", Nat. Med. 2000, 6, 41-48.
Biron E., et al., "Optimized selective N-methylation of peptides on solid support", Pept. Sci. 2006, 12, 213-219.

(Continued)

*Primary Examiner* — Julie Ha
*Assistant Examiner* — Tara L Martinez
(74) *Attorney, Agent, or Firm* — LAVERY, DE BILLY, LLP; Alain Dumont

(57) ABSTRACT

Novel cyclic peptide GHRP-6 analogs of formula (I): (I) or pharmaceutically acceptable esters or salts thereof, are described. These cyclic peptide GHRP-6 analogs may be used for modulating CD36 activity, for example for the treatment of CD36-related diseases, disorders or conditions in a subject, such as atherosclerosis and age-related macular degeneration.

(I)

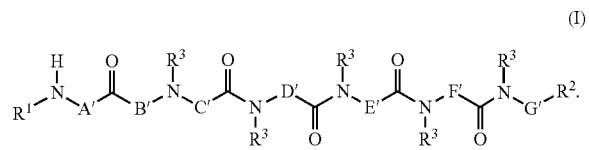

15 Claims, 19 Drawing Sheets

(56) References Cited

OTHER PUBLICATIONS

Craik, D.J., et al., "The Future of Peptide-based Drugs", Chem. Biol. Drug Des. 2013,81, 136-147.
De Araujo, et al.,"Comparative a-Helicity of Cyclic Pentapeptides in Water", Angew. Chem. Int. Ed. 2014, 53, 6965-6969.
Driggers, E. M., et al., "The exploration of macrocycles for drug discovery—an underexploited structural class", Nat. Rev. Drug Discov. 2008, 7, 608-624.
Endemann, G. et al., "CD36 Is a Receptor for Oxidized Low Density Lipoprotein", J. Bio. Chem. 1993, 268, 11811-11816.
Fairlie, D. P., et al."Macrocyclic Peptidomimetics—Forcing Peptides into Bioactive Conformations", Curr. med. chem. 1995, 2, 654-686.
Febbraio, M., et al., "CD36: Implications in Cardioascular Disease", Int. J. Biochem. Cell Biol. 2007, 39, 2012-2030.
Felix, A. M., et al., "Synthesis, biological activity and conformational analysis of cyclic GRF analogs", Int. J. Pept. Protein Res. 1988, 32, 441-454.
Frankiewicz, L. et al., "Stabilisation of a short a-helical VIP fragment by side chain to side chain cyclisation: a comparison of common cyclisation motifs by circular dichroism", J. Pept. Sci. 2013, 19, 423-432.
Gottschling, D., et al., "Combinatorial and Rational Strategies to Develop Nonpeptidic a487-Integrin Antagonists from Cyclic Peptides", Angew. Chem. Int. Ed. 2002, 41, 3007-3011.
Grieco, P., et al., "Design and Microwave-Assisted Synthesis of Novel Macrocyclic Peptides Actives at Melanocortin Receptors: Discovery of Potent and Selective hMC5R Receptor Antagonists", J. Med. Chem. 2008, 51, 2701-2707.
Havlir, D. V., et al., "Atazanavir: New option for Treatment of HIV Infection", Clin. Infect. Dis. 2004, 38, 1599-604.
Henchey, L. K., et al., "Contemporary Strategies for the Stabilization of Peptides in the a-Helical Conformation", Curr. Opin. Chem. Biol. 2008, 12, 692-697.
Hilinski, G.J., et al., "Stitched a-Helical Peptides via Bis Ring-Closing Metatheis", J. Am. Chem. Soc.2014, 136, 12314-12322.
Isidro-Llobet, A., et al., "Diversity oriented synthesis of macrocyclic peptidomimetics", Proc. Natl. Acad. Sci. U.S.A. 2011, 108, 6793-6798.
Jang, S., et al., "Cell-Penetrating, Dimeric a-Helical Peptides: Nanomolar Inhibitors of HIV-1 Transcription", Angew. Chem. Int. Ed. 2014, 53, 10086-10089.
Kessler, H., "Conformation and Biological Activity of Cyclic Peptides", Angew. Chem. Int. Ed. 1982, 21, 512-523.
Lawson, K. V., et al., Proc. Natl. Acad. Sci. U.S.A. 2013, 110, E3753-E3760.
McGeary, R. P., et al., "Macrocyclic peptidomimetics: potential for drug development", Curr. Opin. Drug Discov. Devel. 1998,1, 208-17.
Marsault, E., et al., "Macrocycles Are Great Cycles: Applications, Opportunities and Challenges of Synthetic Macrocycles in Drug Discovery", J. Med. Chem. 2011, 54, 1961-2004.
Pauletti, G. M., et al., "Improvement of oral peptide bioavailability: Peptidomimetics and prodrug strategies", Adv. Drug Deliv. Rev. 1997, 27, 236-256.
Pawlikowski, M., et al., "Somatostatin analogs—from new molecules to new applications", Curr. Opin. Pharmacology 2004, 4, 608-613.
Proulx, C., et al., "Azapeptides and their therapeutic potential", Future med. chem. 2011, 3, 1139-1164.
Proulx, C., et al., "Azapeptides Analogues of the Growth Hormone Releasing Peptide 6 as Cluster of Differentiation 36 Receptor with Reduced Affinity for the Growth Secretagogue Receptor 1a", J. Med. Chem. 2012, vol. 55, 6502-6511.
Punna, S., et al., "Head-to-Tail Peptide Cyclodimerization by Copper-Catalyzed Azide-Alkyne Cycloaddition", Angew. Chem. Int. Ed. 2005, 44, 2215-2220.
Randolph, J. T., et al., "Synthesis, antiviral activity, and conformational studies of a P3 aza-peptide analog of a potent macrocyclic tripeptide HCV protease inhibitor", Bioorg. Med. Chem. Lett. 2008, 18, 2745-2750.
Rezai, T., et al., "Conformational Flexibility, Internal Hydrogen Bonding, and Passive Membrane Permeability: Succesful in Silico Prediction of the Relative Permeabilities of Cyclic Peptides", J. Am. Chem. Soc. 2006, 128, 14073-14080.
Rostovtsev, V, V., et al., A Stepwise Huisgen Cycloaddition Process: Copper(I)-Catalyzed Regioselective "Litigation" of Azides and Terminal Alkynes, Angew. Chem. Int. Ed. 2002, 41, 2596-2599.
Sabatino, D., et al., "Exploring Side-Chain Diversity by Submonomer Solid-Phase Aza-Peptide Synthesis", Org. Lett. 2009, 11, 3650-3653.
Schafmeister, C. E., et al., "An All-Hydrocarbon Cross-Linking System for Enhancing the Helicity and Metabolic Stability of Peptides", J. Am. Chem. Soc. 2000, 122, 5891-5892.
Spiegel, J., et al., "Cyclic Aza-peptide Integrin Ligand Synthesis and Biological Activity", J. Org. Chem.2012, 77, 5271-6278.
Sugimoto, H., et al., "Activin-like kinase 3 is important for kidney regeneration and reversal of fibrosis", Nat. Med. 2012, 18, 396-404.
Tal-Gan, Y., et al., "Metabolic Stability of Peptidomimetics: N-Methy and Aza Heptapeptide Analogs of a PKB/Akt Inhibitor", Chem. Biol. Drug Des. 2011, 78, 887-892.
Tyndall, J. D. A., et al., "Proteases Universally Recognize Beta Strands in Their Active Sites", Chem. Rev. 2005, 105, 973-999.
Tornøe, C. W., et al., "Peptidotriazoles on Solid Phase: [1,2,3]-Triazoles by Regiospecific Copper(I)-Catalyzed 1,3-Dipolar Cycloadditions of Terminal Alkynes to Azides", J. Org. Chem. 2002, 67, 3057-3064.
Venkatraman, S., et al., "Potent aza-peptide derived inhibitors of HCV NS3 protease", Bioorg. Med. Chem. Lett. 2009, 19, 4760-4763.
Verhelst, S. H. L., et al.,"Novel Aza Peptide Inhibitors and Active-Site Probes of Papain-Family Cysteine Proteases", ChemBioChem 2006, 7, 943-950.
Walensky, L. D., et al., "Activation of Apoptosis in Vivo by a Hydrocarbon-Stapled BH3 Helix", Science 2004, 305, 1466-1470.
Weber, D., et al., "Design of Selective Peptidomimetic Agonists for the Human Orphan Receptor BRS-3", J. med. chem. 2003, 46, 1918-1930.
White, C.J., et al., "Contemporary strategies for peptide macrocyclization", Nat. Chem. 2011, 3, 509-524.
Zhang, J., et al., "Cu(I)- and Ru(II)-Mediated "Click" Cyclization of Tripeptides Toward Vancomycin-Inspired Mimics", Org. Lett. 2011, 13, 3438-3441.
Zhang J., et al., "Synthesis of 1,5-triazole bridged vancomycin CDE-ring bicyclic mimics using RuAAC macrocyclization†", Chem. Commun. 2013, 49, 4498-4500.
Zhang, J., et al., "Multicomponent Diversity-Oriented Synthesis of Aza-Lysine-Peptide Mimics", Org. Lett. 2014, vol. 16, 298-301.
International Search Report and Written Opinion in respect of PCT Application No. PCT/CA2017/000163.

* cited by examiner

MPE-189

MPE-191

MPE-193

MPE-192

*, P < 0,05; **, P < 0,01 vs. RFSL-1

CYCLIC PEPTIDES AND USES THEREOF

CROSS REFERENCE TO RELATED APPLICATIONS

The present application claims the benefits of U.S. Provisional Application Ser. No. 62/355,496 filed Jun. 28, 2016, and of U.S. Provisional Application Ser. No. 62/823,016 filed Sep. 2, 2016, which are incorporated herein by reference in their entirety.

TECHNICAL FIELD

The present invention relates generally to the modulation of CD36, and more specifically to inhibitors of CD36 and their uses.

BACKGROUND ART

CD36, also known as FAT, SCARB3, GP88, glycoprotein IV (gpIV) and glycoprotein IIIb (gpIIIb), is an integral membrane protein found on the surface of many cell types, notably macrophage foam cells, in vertebrate animals. CD36 is a member of the class B scavenger receptor family of cell surface proteins. CD36 has been shown to bind many ligands including collagen, thrombospondin, erythrocytes parasitized with *Plasmodium falciparum*, oxidized low density lipoproteins, native lipoproteins, oxidized phospholipids, beta-amyloid and long-chain fatty acids. The Toll-like receptor-2 (TLR2) is co-expressed with CD36, which serves as a co-receptor on TLR2-bearing cells, such as macrophages and microvascular endothelial cells. Furthermore, CD36 has been shown to modulate the inflammatory response mediated by TLR2. Ligands that interact with CD36 may thus have potential to regulate TLR2 signaling pathways by an allosteric mechanism. TLR2 antagonism with an anti-Toll-like receptor-2 antibody was found to reduce the risk of ischemia reperfusion injury, as well as subsequent inflammation following renal transplantation[10]. In the light of the success with an antibody, antagonists of TLR2-mediated signalling are attractive therapeutic targets.

Dysregulated or unregulated CD36 activity has been associated with several pathological conditions including atherosclerosis, inflammation (e.g., TLR2-related inflammation), abnormal angiogenesis, age-related macular degeneration (dry and/or wet forms), abnormal lipid metabolism, nonalcoholic fatty liver disease (NAFLD), nonalcoholic steatohepatitis (NASH), abnormal removal of apoptotic cells, ischemia such as cerebral ischemia and myocardial ischemia, ischemia-reperfusion injury, ureteral obstruction, fibrinogenesis in chronic kidney diseases, stroke, Alzheimer's disease, diabetes, diabetic nephropathy and obesity[1-14].

There is thus a need for the development of novel modulators of CD36 that may be useful for the treatment of pathological conditions associated with dysregulated or unregulated CD36 activity.

The present description refers to a number of documents, the content of which is herein incorporated by reference in their entirety.

SUMMARY OF THE INVENTION

The present invention provides the following items 1 to 176:
1. A cyclic peptide of formula (I):

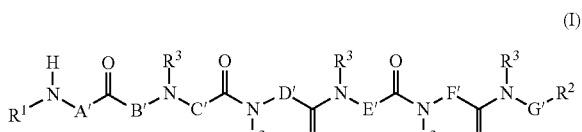

wherein:
R$^1$ represents a hydrogen atom or an amino-terminal modifying group;
R$^2$ represents —CO$_2$H, —C(=O)—NH$_2$ or a carboxy-terminal modifying group;
R$^3$ represents a hydrogen atom, alkyl, alkenyl, alkynyl, alkenynyl, or aryl;
A' represents —C(R$^{10}$)(R$^{16}$)—, —N(R$^{10}$)—, or —X—;
B' represents a covalent bond or —N(R$^3$)—X—C(=O)—;
C' represents —C(R$^{11}$)(R$^{16}$)—, —N(R$^3$)—, or —X—;
D' represents —C(R$^{12}$)(R$^{16}$)—, —N(R$^{12}$)—, or —X—;
E' represents —C(R$^{13}$)(R$^{16}$)—, —N(R$^{13}$)—, —X—, or —Y—;
F' represents —C(R$^{14}$)(R$^{16}$)— or —N(R$^{14}$)—; and
G' represents —C(R$^{15}$)(R$^{16}$)—, —N(R$^{15}$)—, or —Y—;
in which:
R$^{10}$ represents a hydrogen atom, alkyl, aryl, arylalkyl, heteroaryl, or heteroarylalkyl;
R$^{11}$ represents a hydrogen atom, alkyl, aryl, arylalkyl, heteroaryl, or heteroarylalkyl;
R$^{12}$ represents a hydrogen atom, alkyl optionally interrupted by —N(R$^3$)— and/or —O—, aryl, arylalkyl, heteroaryl, or heteroarylalkyl;
R$^{13}$ represents a hydrogen atom, alkyl, aryl, arylalkyl, heteroaryl, or heteroarylalkyl;
R$^{14}$ represents a hydrogen atom, alkyl, aryl, arylalkyl, heteroaryl, or heteroarylalkyl;
R$^{15}$ represents -alkyl-N(R$^4$)$_2$, each R$^4$ independently representing a hydrogen atom, alkyl, alkenyl, alkynyl, alkenynyl, aryl, or C(=NH)—NH$_2$; and
R$^{16}$ represents independently a hydrogen atom, alkyl, aryl, arylalkyl, heteroaryl, or heteroarylalkyl;
the aryl, arylalkyl, heteroaryl, and heteroarylalkyl in R$^{10}$, R$^{11}$, R$^{12}$, R$^{13}$, R$^{14}$, and R$^{16}$ being optionally substituted with one or more: hydroxy, halogen atom, alkyl, alkylamino, haloalkyl, alkoxy, cyano, amino, alkylamino, nitro, —N(haloalkyl)$_2$, aryl, arylalkyl, arylalkyloxy, or —C(=O)aryl, with the proviso that the cyclic peptide comprises exactly one —X— and exactly one —Y—, and
with the proviso that no more than two of R$^{11}$, R$^{13}$, and R$^{14}$ are a hydrogen atom, wherein —X— and —Y— together form a bridge of formula (II) or (II'):

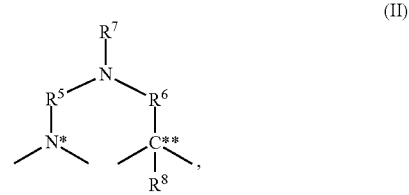

-continued

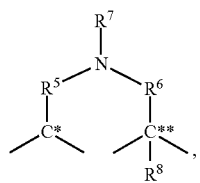
(II')

in which:
* identifies the first atom of —X—,
** identifies the first atom of —Y—,
$R^5$ represents alkylene, alkenylene, alkynylene, or alkenynylene, the alkylene, alkenylene, alkynylene, or alkenynylene being optionally interrupted by —N($R^9$)— and/or —C(=O)—, and the alkylene, alkenylene, alkynylene, or alkenynylene being optionally substituted with one or more alkyl or hydroxyl,
$R^6$ represents alkylene, alkenylene, alkynylene, alkenynylene, or arylalkylene,
$R^7$ represents a hydrogen atom, alkyl, alkenyl, cycloalkylalkyl, or arylalkyl,
$R^8$ represents a hydrogen atom or alkyl, and
$R^9$ represents a hydrogen atom, alkyl, or aryl,
or a pharmaceutically acceptable salt or ester thereof.

2. The cyclic peptide or pharmaceutically acceptable salt or ester thereof of item 1, wherein the amino-terminal modifying group is:
a straight chained or branched alkyl group of one to eight carbons,
an acyl group $R^A$—CO—, wherein $R^A$ is a hydrophobic moiety, or
an aroyl group (Ar—CO—), wherein Ar is an aryl group; preferably the amino-terminal modifying group is said acyl group.

3. The cyclic peptide or pharmaceutically acceptable salt or ester thereof of item 2, wherein the acyl group is a linear or branched, saturated or unsaturated $C_1$-$C_{16}$ or $C_3$-$C_{16}$ acyl group; preferably a linear or branched, saturated $C_1$-$C_6$ acyl group or a linear or branched unsaturated $C_3$-$C_6$ acyl group, more preferably a saturated $C_1$-$C_6$ acyl group, and most preferably an acetyl group.

4. The cyclic peptide or pharmaceutically acceptable salt or ester thereof of any one of items 1 to 3, wherein $R^1$ represents a hydrogen atom.

5. The cyclic peptide or pharmaceutically acceptable salt or ester thereof of any one of items 1 to 4, wherein the carboxy-terminal modifying group is:
—C(=O)—NHOH,
—C(=O)—NR$^{20}$R$^{21}$, wherein $R^{20}$ and $R^{21}$ independently represent a hydrogen atom, alkyl, preferably of one to ten carbons, aryl or arylalkyl,
a nitrile group, or
a hydroxyalkyl, preferably $CH_2OH$.

6. The cyclic peptide or pharmaceutically acceptable salt or ester thereof of item 5, wherein —NR$^{20}$R$^{21}$ is an aliphatic amine, preferably methyl amine, iso-butylamine, iso-valerylamine or cyclohexylamine.

7. The cyclic peptide or pharmaceutically acceptable salt or ester thereof of item 5 or 6, wherein —NR$^{20}$R$^{21}$ is an aromatic amine or arylalkyl amine, preferably aniline, napthylamine, benzylamine, cinnamylamine, or phenylethylamine.

8. The cyclic peptide or pharmaceutically acceptable salt or ester thereof of any one of items 1 to 7, wherein $R^2$ represents —$CO_2H$.

9. The cyclic peptide or pharmaceutically acceptable salt or ester thereof of any one of items 1 to 7, wherein $R^2$ represents a carboxy-terminal modifying group.

10. The cyclic peptide or pharmaceutically acceptable salt or ester thereof of any one of items 1 to 7, wherein $R^2$ represents —C(=O)—$NH_2$.

11. The cyclic peptide or pharmaceutically acceptable salt or ester thereof of any one of items 1 to 10, wherein $R^3$ represents a hydrogen atom.

12. The cyclic peptide or pharmaceutically acceptable salt or ester thereof of any one of items 1 to 11, wherein the alkylene, alkenylene, alkynylene or alkenynylene in $R^5$ is $C_3$-$C_6$, preferably $C_3$-$C_5$, and more preferably $C_4$.

13. The cyclic peptide or pharmaceutically acceptable salt or ester thereof of any one of items 1 to 12, wherein $R^5$ represents alkylene, alkenylene or alkynylene, preferably alkylene or alkynylene, more preferably alkynylene.

14. The cyclic peptide or pharmaceutically acceptable salt or ester thereof of any one of items 1 to 13, wherein the alkylene, alkenylene, alkynylene, or alkenynylene in $R^5$ is interrupted by —N($R^9$)— and/or —C(=O)—.

15. The cyclic peptide or pharmaceutically acceptable salt or ester thereof of any one of items 1 to 13, wherein the alkylene, alkenylene, alkynylene, or alkenynylene in $R^5$ is uninterrupted.

16. The cyclic peptide or pharmaceutically acceptable salt or ester thereof of any one of items 1 to 15, wherein the alkylene, alkenylene, alkynylene, or alkenynylene in $R^5$ is substituted with one or more alkyl or hydroxyl.

17. The cyclic peptide or pharmaceutically acceptable salt or ester thereof of any one of items 1 to 15, wherein the alkylene, alkenylene, alkynylene, or alkenynylene in $R^5$ is unsubstituted.

18. The cyclic peptide or pharmaceutically acceptable salt or ester thereof of any one of items 1 to 17, wherein $R^5$ represents $C_4$ alkynylene or $C_4$ alkynylene, preferably n-but-2-ynylene or n-butylene, more preferably n-but-2-ynylene.

19. The cyclic peptide or pharmaceutically acceptable salt or ester thereof of any one of items 1 to 18, wherein $R^6$ represents $C_3$-$C_6$ alkylene, $C_3$-$C_6$ alkenylene, $C_3$-$C_6$ alkynylene, $C_3$-$C_6$ alkenynylene, or aryl-$C_3$-$C_6$ alkylene, preferably $C_3$-$C_5$ alkylene, $C_3$-$C_5$ alkenylene, $C_3$-$C_5$ alkynylene, $C_3$-$C_5$ alkenynylene, or aryl-$C_3$-$C_5$alkylene, and more preferably $C_3$-$C_4$ alkylene, $C_3$-$C_4$ alkenylene, $C_3$-$C_4$ alkynylene, $C_3$-$C_6$ alkenynylene, or aryl-$C_3$-$C_4$ alkylene.

20. The cyclic peptide or pharmaceutically acceptable salt or ester thereof of any one of items 1 to 19, wherein $R^6$ represents alkylene, preferably $C_3$-$C_6$ alkylene or $C_3$—C alkylene, more preferably $C_3$-$C_4$ alkylene, and most preferably n-propylene or n-butylene.

21. The cyclic peptide or pharmaceutically acceptable salt or ester thereof of any one of items 1 to 20, wherein the arylalkyl in $R^7$ is arylmethyl, preferably benzyl.

22. The cyclic peptide or pharmaceutically acceptable salt or ester thereof of any one of items 1 to 21, wherein the alkyl in $R^7$ is $C_2$-$C_6$ alkyl, preferably $C_2$-$C_4$ alkyl, more preferably $C_3$ alkyl, most preferably n-propyl and i-propyl.

23. The cyclic peptide or pharmaceutically acceptable salt or ester thereof of any one of items 1 to 22, wherein the alkenyl in $R^7$ is $C_2$-$C_6$ alkenyl, preferably $C_2$-$C_4$ alkenyl, more preferably $C_3$ alkenyl, most preferably n-prop-2-enyl.

24. The cyclic peptide or pharmaceutically acceptable salt or ester thereof of any one of items 1 to 23, wherein the cycloalkyl in the cycloalkylalkyl in $R^7$ is $C_{3-6}$ cycloalkyl, preferably $C_{3-5}$ cycloalkyl, and more preferably $C_3$ cycloalkyl.

25. The cyclic peptide or pharmaceutically acceptable salt or ester thereof of any one of items 1 to 24, wherein the alkyl in the cycloalkylalkyl in $R^7$ is $C_1$-$C_6$ alkyl, preferably $C_1$-$C_3$ alkyl, and more preferably methyl.

26. The cyclic peptide or pharmaceutically acceptable salt or ester thereof of any one of items 1 to 25, wherein the cycloalkylalkyl in $R^7$ is cyclopropylmethyl.

27. The cyclic peptide or pharmaceutically acceptable salt or ester thereof of any one of items 1 to 26, wherein $R^7$ represents alkyl, alkenyl, cycloalkylalkyl, or arylalkyl, preferably alkenyl.

28. The cyclic peptide or pharmaceutically acceptable salt or ester thereof of any one of items 1 to 27, wherein $R^8$ represents alkyl.

29. The cyclic peptide or pharmaceutically acceptable salt or ester thereof of any one of items 1 to 27, wherein $R^8$ represents a hydrogen atom.

30. The cyclic peptide or pharmaceutically acceptable salt or ester thereof of any one of items 1 to 29, wherein the bridge of formula (II) is the (S)-enantiomer of the bridge of formula (II).

31. The cyclic peptide or pharmaceutically acceptable salt or ester thereof of any one of items 1 to 29, wherein the bridge of formula (II) is the (R)-enantiomer of the bridge of formula (II).

32. The cyclic peptide or pharmaceutically acceptable salt or ester thereof of of of any one of items 1 to 29, wherein the bridge of formula (II) is a mixture of enantiomers of the bridge of formula (II).

33. The cyclic peptide or pharmaceutically acceptable salt or ester thereof of any one of items 1 to 32, wherein the bridge of formula (II) is a bridge of formula (III):

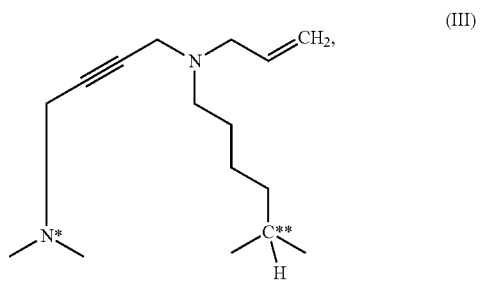

wherein * identifies the first atom of —X— and ** identifies the first atom of —Y—.

34. The cyclic peptide or pharmaceutically acceptable salt or ester thereof of any one of items 1 to 33, wherein the bridge of formula (II) is a bridge of formula (IV):

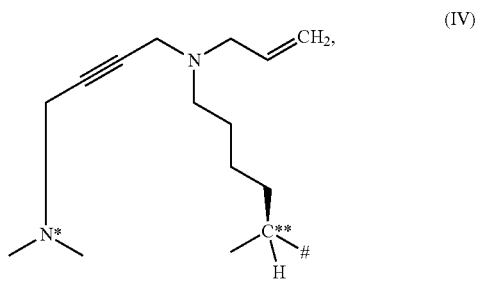

wherein * identifies the first atom of —X—, ** identifies the first atom of —Y—, and a pound sign (#) identifies the bond of the —Y— group that is attached to the neighbouring carbonyl group.

35. The cyclic peptide or pharmaceutically acceptable salt or ester thereof of any one of items 1 to 34, wherein the bridge of formula (II') is the cis-diastereomer of the bridge of formula (II').

36. The cyclic peptide or pharmaceutically acceptable salt or ester thereof of any one of items 1 to 34, wherein the bridge of formula (II') is the trans-diastereomer of the bridge of formula (II') 37. The cyclic peptide or pharmaceutically acceptable salt or ester thereof of any one of items 1 to 36, wherein the bridge of formula (II') is a mixture of diastereomers of the bridge of formula (II').

38. The cyclic peptide or pharmaceutically acceptable salt or ester thereof of any one of items 1 to 37, the bridge of formula (II') is a bridge of formula (V):

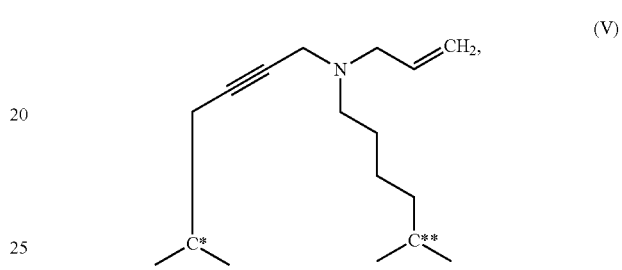

wherein * identifies the first atom of —X— and ** identifies the first atom of —Y—.

39. The cyclic peptide or pharmaceutically acceptable salt or ester thereof of any one of items 1 to 38, the bridge of formula (II') is a bridge of formula (VI):

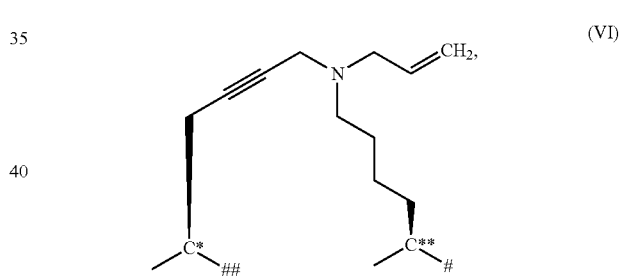

wherein:
* identifies the first atom of —X—,
** identifies the first atom of —Y—,
a pound sign (#) identifies the bond of the —Y— group that is attached to the neighbouring carbonyl (C=O) group, and
two pound signs (##) identifies the bond of the —X— group that is attached to the neighbouring carbonyl (C=O) group.

40. The cyclic peptide or pharmaceutically acceptable salt or ester thereof of any one of items 1 to 39, wherein said —X— and said —Y— form the bridge of formula (II).

41. The cyclic peptide or pharmaceutically acceptable salt or ester thereof of any one of items 1 to 39, wherein said —X— and said —Y— form the bridge of formula (II').

42. The cyclic peptide or pharmaceutically acceptable salt or ester thereof of any one of items 1 to 41, wherein the carbon atom bearing $R^{10}$ and $R^{16}$ is in the D- or L-configuration or any mixture thereof.

43. The cyclic peptide or pharmaceutically acceptable salt or ester thereof of any one of items 1 to 41, wherein the carbon atom bearing $R^{10}$ and $R^{16}$ is in the L configuration.

44. The cyclic peptide or pharmaceutically acceptable salt or ester thereof of any one of items 1 to 41, wherein the carbon atom bearing $R^{10}$ and $R^{16}$ is in the D configuration.

45. The cyclic peptide or pharmaceutically acceptable salt or ester thereof of any one of items 1 to 44, wherein the carbon atom bearing $R^{11}$ and $R^{16}$ is in the D- or L-configuration or any mixture thereof.

46. The cyclic peptide or pharmaceutically acceptable salt or ester thereof of any one of items 1 to 44, wherein the carbon atom bearing $R^{11}$ and $R^{16}$ is in the L configuration.

47. The cyclic peptide or pharmaceutically acceptable salt or ester thereof of any one of items 1 to 44, wherein the carbon atom bearing $R^{11}$ and $R^{16}$ is in the D configuration.

48. The cyclic peptide or pharmaceutically acceptable salt or ester thereof of any one of items 1 to 47, wherein the carbon atom bearing $R^{12}$ and $R^{16}$ is in the D- or L-configuration or any mixture thereof.

49. The cyclic peptide or pharmaceutically acceptable salt or ester thereof of any one of items 1 to 47, wherein the carbon atom bearing $R^{12}$ and $R^{18}$ is in the L configuration.

50. The cyclic peptide or pharmaceutically acceptable salt or ester thereof of any one of items 1 to 47, wherein the carbon atom bearing $R^{12}$ and $R^{16}$ is in the D configuration.

51. The cyclic peptide or pharmaceutically acceptable salt or ester thereof of any one of items 1 to 50, wherein the carbon atom bearing $R^{13}$ and $R^{16}$ is in the D- or L-configuration or any mixture thereof.

52. The cyclic peptide or pharmaceutically acceptable salt or ester thereof of any one of items 1 to 50, wherein the carbon atom bearing $R^{13}$ and $R^{16}$ is in the L configuration.

53. The cyclic peptide or pharmaceutically acceptable salt or ester thereof of any one of items 1 to 50, wherein the carbon atom bearing $R^{13}$ and $R^{16}$ is in the D configuration.

54. The cyclic peptide or pharmaceutically acceptable salt or ester thereof of any one of items 1 to 53, wherein the carbon atom bearing $R^{14}$ and $R^{16}$ is in the D- or L-configuration or any mixture thereof.

55. The cyclic peptide or pharmaceutically acceptable salt or ester thereof of any one of items 1 to 53, wherein the carbon atom bearing $R^{14}$ and $R^{16}$ is in the L-configuration.

56. The cyclic peptide or pharmaceutically acceptable salt or ester thereof of any one of items 1 to 53, wherein the carbon atom bearing $R^{14}$ and $R^{16}$ is in the D-configuration.

57. The cyclic peptide or pharmaceutically acceptable salt or ester thereof of any one of items 1 to 56, wherein the carbon atom bearing $R^{15}$ and $R^{16}$ is in the D- or L-configuration or any mixture thereof.

58. The cyclic peptide or pharmaceutically acceptable salt or ester thereof of any one of items 1 to 56, wherein the carbon atom bearing $R^{15}$ and $R^{16}$ is in the L-configuration.

59. The cyclic peptide or pharmaceutically acceptable salt or ester thereof of any one of items 1 to 56, wherein the carbon atom bearing $R^{15}$ and $R^{16}$ is in the D-configuration.

60. The cyclic peptide or pharmaceutically acceptable salt or ester thereof of any one of items 1 to 59, wherein the alkyl, haloalkyl, and/or alkoxy optionally substituting the aryl, arylalkyl, heteroaryl, and/or heteroarylalkyl in $R^{10}$, $R^{11}$, $R^{12}$, $R^{13}$, $R^{14}$ and/or $R^{16}$ is $C_{1-6}$, preferably $C_{1-4}$, more preferably $C_{1-2}$, preferably $C_1$ alkyl, haloalkyl, or alkoxy.

61. The cyclic peptide or pharmaceutically acceptable salt or ester thereof of any one of items 1 to 60, wherein the haloalkyl optionally substituting the aryl, arylalkyl, heteroaryl, and/or heteroarylalkyl in $R^{10}$, $R^{11}$, $R^{12}$, $R^{13}$, $R^{14}$ and/or $R^{16}$ is perhaloalkyl, preferably perfluoroalkyl, more preferably —$CF_3$.

62. The cyclic peptide or pharmaceutically acceptable salt or ester thereof of any one of items 1 to 61, wherein the —N(haloalkyl)$_2$ optionally substituting the aryl, arylalkyl, heteroaryl, and/or heteroarylalkyl in $R^{10}$, $R^{11}$, $R^{12}$, $R^{13}$, $R^{14}$ and/or $R^{16}$ is —N(2-chloroethyl)$_2$.

63. The cyclic peptide or pharmaceutically acceptable salt or ester thereof of any one of items 1 to 62, wherein the aryl optionally substituting the aryl, arylalkyl, heteroaryl, and/or heteroarylalkyl in $R^{10}$, $R^{11}$, $R^{12}$, $R^{13}$, $R^{14}$ and/or $R^{16}$ is phenyl.

64. The cyclic peptide or pharmaceutically acceptable salt or ester thereof of any one of items 1 to 63, wherein the arylalkyloxy optionally substituting the aryl, arylalkyl, heteroaryl, and/or heteroarylalkyl in $R^{10}$, $R^{11}$, $R^{12}$, $R^{13}$, $R^{14}$ and/or $R^{16}$ is benzyloxy.

65. The cyclic peptide or pharmaceutically acceptable salt or ester thereof of any one of items 1 to 64, wherein the —C(=O)aryl optionally substituting the aryl, arylalkyl, heteroaryl, and/or heteroarylalkyl in $R^{10}$, $R^{11}$, $R^{12}$, $R^{13}$, $R^{14}$ and/or $R^{16}$ is benzoyl.

66. The cyclic peptide or pharmaceutically acceptable salt or ester thereof of any one of items 1 to 65, wherein the alkyl in the arylalkyl and/or heteroarylalkyl in $R^{10}$, $R^{11}$, $R^{12}$, $R^{13}$, $R^{14}$ and/or $R^{16}$ is optionally substituted with alkyl, hydroxy, or aryl.

67. The cyclic peptide or pharmaceutically acceptable salt or ester thereof of any one of items 1 to 66, wherein the aryl, arylalkyl, heteroaryl, and/or heteroarylalkyl in $R^{10}$, $R^{11}$, $R^{12}$, $R^{13}$, $R^{14}$ and/or $R^{16}$ is optionally substituted by 2 or 3 substituents, which are the same or different, preferably the same, and which are preferably halogen atoms, hydroxy, or alkoxy.

68. The cyclic peptide or pharmaceutically acceptable salt or ester thereof of any one of items 1 to 67, wherein the alkyl in the arylalkyl and/or heteroarylalkyl in $R^{10}$, $R^{11}$, $R^{12}$, $R^{13}$, $R^{14}$ and/or $R^{16}$ is $C_{1-6}$ alkyl, preferably $C_{1-3}$ alkyl, more preferably $C_{1-2}$ alkyl, and most preferably methyl 69. The cyclic peptide or pharmaceutically acceptable salt or ester thereof of any one of items 1 to 68, wherein the aryl in the aryl and/or arylalkyl in $R^{10}$, $R^{11}$, $R^{12}$, $R^{13}$, $R^{14}$ and/or $R^{16}$ is phenyl or naphthyl, preferably phenyl.

70. The cyclic peptide or pharmaceutically acceptable salt or ester thereof of any one of items 1 to 69, wherein the aryl in the aryl and/or arylalkyl in $R^{10}$, $R^{11}$, $R^{12}$, $R^{13}$, $R^{14}$ and/or $R^{16}$ is unsubstituted or substituted, preferably unsubstituted or substituted with one hydroxy group, preferably at position 4 on the phenyl.

71. The cyclic peptide or pharmaceutically acceptable salt or ester thereof of any one of items 1 to 70, wherein the arylalkyl in $R^{10}$, $R^{11}$, $R^{12}$, $R^{13}$, $R^{14}$ and/or $R^{16}$ is:
    unsubstituted benzyl (thus forming the side chain of a phenylalanine residue),
    benzyl substituted with hydroxy, preferably at the para (4) position on the phenyl ring (thus forming the side chain of a tyrosine residue), or
    —$CH_2$—$CH_2$-phenyl (thus forming the side chain of a homophenylalanine residue).

72. The cyclic peptide or pharmaceutically acceptable salt or ester thereof of any one of items 1 to 71, wherein the heteroaryl in the heteroaryl and/or heteroarylalkyl in $R^{10}$, $R^{11}$, $R^{12}$, $R^{13}$, $R^{14}$ and/or $R^{16}$ is triazolyl, imidazolyl or indolyl, preferably imidazolyl or indolyl, preferably 1H-imidazol-4-yl or 1H-indol-3-yl-.

73. The cyclic peptide or pharmaceutically acceptable salt or ester thereof of any one of items 1 to 72, wherein the heteroaryl and/or heteroarylalkyl in $R^{10}$, $R^{11}$, $R^{12}$, $R^{13}$, $R^{14}$ and/or $R^{16}$ is unsubstituted.

74. The cyclic peptide or pharmaceutically acceptable salt or ester thereof of any one of items 1 to 73, wherein the heteroarylalkyl in $R^{10}$, $R^{11}$, $R^{12}$, $R^{13}$, $R^{14}$ and/or $R^{16}$ is:
  1H-indol-3-yl-methyl (thus forming the side chain of a tryptophan residue), or
  1H-imidazol-4-yl-methyl (thus forming the side chain of a histidine residue).
75. The cyclic peptide or pharmaceutically acceptable salt or ester thereof of any one of items 1 to 74, wherein the alkyl in $R^{16}$ is $C_{1-6}$ alkyl, preferably $C_{1-3}$ alkyl, more preferably $C_{1-2}$ alkyl, and most preferably methyl.
76. The cyclic peptide or pharmaceutically acceptable salt or ester thereof of any one of items 1 to 75, wherein $R^{16}$ represents a hydrogen atom or alkyl, preferably a hydrogen atom.
77. The cyclic peptide or pharmaceutically acceptable salt or ester thereof of any one of items 1 to 76, wherein A' represents —$C(R^{10})(R^{16})$— or —$N(R^{10})$—.
78. The cyclic peptide or pharmaceutically acceptable salt or ester thereof of any one of items 1 to 76, wherein A' represents —$C(R^{10})(R^{16})$—.
79. The cyclic peptide or pharmaceutically acceptable salt or ester thereof of any one of items 1 to 76, wherein A' represents —$N(R^{10})$—.
80. The cyclic peptide or pharmaceutically acceptable salt or ester thereof of any one of items 1 to 76, wherein A' represents —X—.
81. The cyclic peptide or pharmaceutically acceptable salt or ester thereof of any one of items 1 to 80, wherein the alkyl in $R^{10}$ is $C_{1-6}$ alkyl, preferably $C_{1-4}$ alkyl, more preferably $C_{1-4}$ alkyl, yet more preferably methyl, propyl, or butyl, even more preferably methyl (thus forming the side chain of an alanine residue, preferably a L-alanine residue), isopropyl (thus forming the side chain of a valine residue, preferably a L-valine residue), sec-butyl (thus forming the side chain of a leucine residue, preferably a L-leucine residue) and isobutyl (thus forming the side chain of an isoleucine residue, preferably a L-isoleucine residue), more preferably methyl or isopropyl and most preferably methyl.
82. The cyclic peptide or pharmaceutically acceptable salt or ester thereof of any one of items 1 to 81, wherein the heteroaryl in the heteroarylalkyl in $R^{10}$ is imidazolyl, preferably 1H-imidazol-4-yl.
83. The cyclic peptide or pharmaceutically acceptable salt or ester thereof of any one of items 1 to 84, wherein the alkyl in the arylalkyl and/or heteroarylalkyl in $R^{10}$ is $C_{1-6}$ alkyl, preferably $C_{1-3}$ alkyl, more preferably $C_{1-2}$ alkyl, and most preferably methyl.
84. The cyclic peptide or pharmaceutically acceptable salt or ester thereof of any one of items 1 to 83, wherein the heteroarylalkyl in $R^{10}$ is 1H-imidazol-4-yl-methyl (thus forming the side chain of a histidine residue, preferably a L-histidine residue).
85. The cyclic peptide or pharmaceutically acceptable salt or ester thereof of any one of items 1 to 84, wherein $R^{10}$ is a hydrogen atom, alkyl, arylalkyl or heteroarylalkyl, more preferably a hydrogen atom, alkyl, or heteroarylalkyl, most preferably alkyl.
86. The cyclic peptide or pharmaceutically acceptable salt or ester thereof of any one of items 1 to 85, wherein $R^{10}$ forms the side chain of a glycine residue, an alanine residue (preferably a L-alanine residue), a valine residue (preferably a L-valine residue), or a histidine residue (preferably a L-histidine residue);
87. The cyclic peptide or pharmaceutically acceptable salt or ester thereof of any one of items 1 to 86, wherein $R^{10}$ forms an alanine residue (preferably a L-alanine residue).
88. The cyclic peptide or pharmaceutically acceptable salt or ester thereof of any one of items 1 to 87, wherein B' represents a covalent bond.
89. The cyclic peptide or pharmaceutically acceptable salt or ester thereof of any one of items 1 to 87, wherein B' represents —$N(R^3)$—X—$C(=O)$—.
90. The cyclic peptide or pharmaceutically acceptable salt or ester thereof of any one of items 1 to 89, wherein C' represents —$C(R^{11})(R^{16})$— or —X—.
91. The cyclic peptide or pharmaceutically acceptable salt or ester thereof of any one of items 1 to 89, wherein C' represents —$C(R^{11})(R^{16})$—.
92. The cyclic peptide or pharmaceutically acceptable salt or ester thereof of any one of items 1 to 89, wherein C' represents —$N(R^{11})$—.
93. The cyclic peptide or pharmaceutically acceptable salt or ester thereof of any one of items 1 to 89, wherein C' represents —X—.
94. The cyclic peptide or pharmaceutically acceptable salt or ester thereof of any one of items 1 to 93, wherein the aryl, arylalkyl, heteroaryl, and/or heteroarylalkyl in $R^{11}$ is substituted, preferably with hydroxy.
95. The cyclic peptide or pharmaceutically acceptable salt or ester thereof of any one of items 1 to 93, wherein the aryl, arylalkyl, heteroaryl, and/or heteroarylalkyl group in $R^{11}$ is unsubstituted.
96. The cyclic peptide or pharmaceutically acceptable salt or ester thereof of any one of items 1 to 95, wherein aryl group in the arylalkyl in $R^{11}$ is substituted, more preferably substituted with one hydroxy group, preferably at position 4.
97. The cyclic peptide or pharmaceutically acceptable salt or ester thereof of any one of items 1 to 96, wherein the aryl forming the aryl and/or the arylalkyl in $R^{11}$ is substituted or unsubstituted phenyl or naphthyl, preferably phenyl unsubstituted or substituted with hydroxy, preferably at position 4.
98. The cyclic peptide or pharmaceutically acceptable salt or ester thereof of any one of items 1 to 97, wherein the heteroaryl forming the heteroaryl and/or heteroarylalkyl in $R^{11}$ is substituted or unsubstituted triazolyl, imidazolyl or indolyl, preferably imidazolyl or indolyl, more preferably 1H-imidazol-4-yl or 1H-indol-3-yl-, more preferably unsubstituted.
99. The cyclic peptide or pharmaceutically acceptable salt or ester thereof of any one of items 1 to 98, wherein the alkyl in the arylalkyl and/or heteroarylalkyl in $R^{11}$ is $C_{1-6}$ alkyl, preferably $C_{1-3}$ alkyl, more preferably $C_{1-2}$ alkyl, and most preferably methyl.
100. The cyclic peptide or pharmaceutically acceptable salt or ester thereof of any one of items 1 to 99, wherein the heteroarylalkyl in $R^{11}$ is 1H-indol-3-yl-methyl (thus forming the side chain of a tryptophan residue, preferably a D-tryptophan residue) or 1H-imidazol-4-yl-methyl (thus forming the side chain of a histidine residue, preferably a D-histidine residue), preferably 1H-imidazol-4-yl-methyl.
101. The cyclic peptide or pharmaceutically acceptable salt or ester thereof of any one of items 1 to 100, wherein the arylalkyl in $R^{11}$ is:
  unsubstituted benzyl (thus forming the side chain of a phenylalanine residue, preferably a D-phenylalanine residue),
  benzyl substituted with hydroxy, preferably at the para position on the phenyl ring (thus forming the side chain of a tyrosine residue, preferably a D-tyrosine residue), or
  —$CH_2$—$CH_2$-phenyl (thus forming the side chain of a homophenylalanine residue, preferably a D-homophenylalanine residue).

102. The cyclic peptide or pharmaceutically acceptable salt or ester thereof of any one of items 1 to 101, wherein $R^{11}$ represents aryl, arylalkyl, heteroaryl, or heteroarylalkyl, preferably arylalkyl or heteroarylalkyl, and more preferably heteroarylalkyl.

103. The cyclic peptide or pharmaceutically acceptable salt or ester thereof of any one of items 1 to 102, wherein $R^1$ forms the side chain of a tryptophan residue (preferably a D-tryptophan residue).

104. The cyclic peptide or pharmaceutically acceptable salt or ester thereof of any one of items 1 to 103, wherein D' represents —$C(R^{12})(R^{16})$— or —X—.

105. The cyclic peptide or pharmaceutically acceptable salt or ester thereof of any one of items 1 to 103, wherein D' represents —$C(R^{12})(R^{16})$—.

106. The cyclic peptide or pharmaceutically acceptable salt or ester thereof of any one of items 1 to 103, wherein D' represents —$N(R^{12})$—.

107. The cyclic peptide or pharmaceutically acceptable salt or ester thereof of any one of items 1 to 103, wherein D' represents —X—.

108. The cyclic peptide or pharmaceutically acceptable salt or ester thereof of any one of items 1 to 107, wherein $R^{12}$ is alkyl optionally interrupted by —$N(R^3)$— and/or —O—, the alkyl in $R^{12}$ preferably being is uninterrupted.

109. The cyclic peptide or pharmaceutically acceptable salt or ester thereof of any one of items 1 to 108, wherein the alkyl in $R^{12}$ is $C_{1-6}$ alkyl, preferably $C_{1-4}$ alkyl, more preferably $C_{1-3}$ alkyl, and yet more preferably methyl (thus forming the side chain of an alanine residue, preferably a L-alanine residue).

110. The cyclic peptide or pharmaceutically acceptable salt or ester thereof of any one of items 1 to 109, wherein E' represents —$C(R^{13})(R^{16})$—.

111. The cyclic peptide or pharmaceutically acceptable salt or ester thereof of any one of items 1 to 109, wherein E' represents —$N(R^{13})$—.

112. The cyclic peptide or pharmaceutically acceptable salt or ester thereof of any one of items 1 to 109, wherein E' represents —X—.

113. The cyclic peptide or pharmaceutically acceptable salt or ester thereof of any one of items 1 to 109, wherein E' represents —Y—.

114. The cyclic peptide or pharmaceutically acceptable salt or ester thereof of any one of items 1 to 113, wherein the aryl, arylalkyl, heteroaryl, and/or heteroarylalkyl in $R^{13}$ is substituted, preferably with hydroxy or alkoxy, preferably alkoxy, more preferably methoxy, preferably at the para position.

115. The cyclic peptide or pharmaceutically acceptable salt or ester thereof of any one of items 1 to 113, wherein the aryl, arylalkyl, heteroaryl, and/or heteroarylalkyl group in $R^{13}$ is unsubstituted.

116. The cyclic peptide or pharmaceutically acceptable salt or ester thereof of any one of items 1 to 115, wherein the aryl forming the aryl and/or the arylalkyl in $R^{13}$ is substituted or unsubstituted phenyl or naphthyl, preferably phenyl unsubstituted or substituted with hydroxy or alkoxy, preferably alkoxy, more preferably methoxy, preferably at the para position.

117. The cyclic peptide or pharmaceutically acceptable salt or ester thereof of any one of items 1 to 116, wherein the heteroaryl forming the heteroaryl and/or heteroarylalkyl in $R^{13}$ is substituted or unsubstituted triazolyl, imidazolyl or indolyl, preferably imidazolyl or indolyl, more preferably 1H-imidazol-4-yl or 1H-indol-3-yl-, most preferably unsubstituted.

118. The cyclic peptide or pharmaceutically acceptable salt or ester thereof of any one of items 1 to 117, wherein the alkyl in the arylalkyl and/or heteroarylalkyl in $R^{13}$ is $C_{1-6}$ alkyl, preferably $C_{1-3}$ alkyl, more preferably $C_{1-2}$ alkyl, and most preferably methyl.

119. The cyclic peptide or pharmaceutically acceptable salt or ester thereof of any one of items 1 to 118, wherein the heteroarylalkyl in $R^{13}$ is 1H-indol-3-yl-methyl (thus forming the side chain of a tryptophan residue, preferably a L-tryptophan residue), or 1H-imidazol-4-yl-methyl (thus forming the side chain of a histidine residue, preferably a L-histidine residue), preferably 1H-indol-3-yl-methyl.

120. The cyclic peptide or pharmaceutically acceptable salt or ester thereof of any one of items 1 to 119, wherein the arylalkyl in $R^{13}$ is:
  unsubstituted benzyl (thus forming the side chain of a phenylalanine residue, preferably a L-phenylalanine residue),
  benzyl substituted with hydroxy, preferably at the para position on the phenyl ring (thus forming the side chain of a tyrosine residue, preferably a L-tyrosine residue), or
  benzyl substituted with alkoxy, preferably methoxy, preferably at the para position on the phenyl ring (thus forming the side chain of a O-methyltyrosine residue, preferably a L-O-methyltyrosine residue), or
  —$CH_2$—$CH_2$-phenyl (thus forming the side chain of a homophenylalanine residue, preferably a L-homophenylalanine residue),
preferably, the arylalkyl is benzyl substituted with methoxy at the para position.

121. The cyclic peptide or pharmaceutically acceptable salt or ester thereof of any one of items 1 to 120, wherein $R^{13}$ forms a tryptophan residue (preferably a L-tryptophan residue), or an O-methyltyrosine residue (preferably a L-O-methyltyrosine residue), more preferably $R^{13}$ forms a tryptophan residue (preferably a L-tryptophan residue).

122. The cyclic peptide or pharmaceutically acceptable salt or ester thereof of any one of items 1 to 121, wherein $R^{13}$ represents aryl, arylalkyl, heteroaryl, or heteroarylalkyl, preferably heteroarylalkyl or arylalkyl, and more preferably heteroarylalkyl.

123. The cyclic peptide or pharmaceutically acceptable salt or ester thereof of any one of items 1 to 122, wherein F' represents —$C(R^{14})$—.

124. The cyclic peptide or pharmaceutically acceptable salt or ester thereof of any one of items 1 to 122, wherein F' represents —$N(R^{14})$—.

125. The cyclic peptide or pharmaceutically acceptable salt or ester thereof of any one of items 1 to 124, wherein the aryl, arylalkyl, heteroaryl, and/or heteroarylalkyl in $R^{14}$ is substituted, preferably with hydroxy, preferably at the para position on the phenyl ring.

126. The cyclic peptide or pharmaceutically acceptable salt or ester thereof of any one of items 1 to 124, wherein the aryl, arylalkyl, heteroaryl, and/or heteroarylalkyl group in $R^{14}$ is unsubstituted.

127. The cyclic peptide or pharmaceutically acceptable salt or ester thereof of any one of items 1 to 126, wherein the aryl forming the aryl and/or the arylalkyl in $R^{14}$ is substituted or unsubstituted phenyl or naphthyl, preferably phenyl unsubstituted or substituted with hydroxy, preferably at the para position on the phenyl ring.

128. The cyclic peptide or pharmaceutically acceptable salt or ester thereof of any one of items 1 to 127, wherein the heteroaryl forming the heteroaryl and/or heteroarylalkyl in $R^{14}$ is substituted or unsubstituted triazolyl, imidazolyl or indolyl, preferably imidazolyl or indolyl, more preferably 1H-imidazol-4-yl or 1H-indol-3-yl-, more preferably unsubstituted.

129. The cyclic peptide or pharmaceutically acceptable salt or ester thereof of any one of items 1 to 128, wherein the alkyl in the arylalkyl and/or heteroarylalkyl in $R^{14}$ is $C_{1-6}$ alkyl, preferably $C_{1-3}$ alkyl, more preferably $C_{1-2}$ alkyl, and most preferably methyl.

130. The cyclic peptide or pharmaceutically acceptable salt or ester thereof of any one of items 1 to 129, wherein the heteroarylalkyl in $R^{14}$ is 1H-indol-3-yl-methyl (thus forming a tryptophan residue, preferably a D-tryptophan residue), or 1H-imidazol-4-yl-methyl (thus forming a histidine residue, preferably a D-histidine residue).

131. The cyclic peptide or pharmaceutically acceptable salt or ester thereof of any one of items 1 to 130, wherein the arylalkyl in $R^{14}$ is:
   unsubstituted benzyl, thus forming a phenylalanine residue, preferably a D-phenylalanine residue,
   benzyl substituted with hydroxy, preferably at the para position on the phenyl ring, thus forming a tyrosine residue, preferably a D-tyrosine residue, or
   benzyl substituted with alkoxy, preferably methoxy, preferably at the para position, thus forming a O-methyl-tyrosine residue, preferably a D-O-methyltyrosine residue, or
   —$CH_2$—$CH_2$-phenyl, thus forming a homophenylalanine residue, preferably a D-homophenylalanine residue, preferably the arylalkyl is unsubstituted benzyl.

132. The cyclic peptide or pharmaceutically acceptable salt or ester thereof of any one of items 1 to 131, wherein $R^{14}$ represents aryl, arylalkyl, heteroaryl, or heteroarylalkyl, preferably arylalkyl.

133. The cyclic peptide or pharmaceutically acceptable salt or ester thereof of any one of items 1 to 132, wherein $R^{14}$ forms a phenylalanine residue (preferably a D-phenylalanine residue).

134. The cyclic peptide or pharmaceutically acceptable salt or ester thereof of any one of items 1 to 133, wherein G' represents —$C(R^{15})(R^{16})$— or —Y—.

135. The cyclic peptide or pharmaceutically acceptable salt or ester thereof of any one of items 1 to 133, wherein G' represents —$C(R^{15})$—.

136. The cyclic peptide or pharmaceutically acceptable salt or ester thereof of any one of items 1 to 133, wherein G' represents —$N(R^{15})$—.

137. The cyclic peptide or pharmaceutically acceptable salt or ester thereof of any one of items 1 to 133, wherein G' represents —Y—.

138. The cyclic peptide or pharmaceutically acceptable salt or ester thereof of any one of items 1 to 137, wherein the alkyl in -alkyl-$N(R^4)_2$ in $R^{15}$ is $C_{1-6}$ alkyl, preferably $C_{3-5}$ alkyl, more preferably $C_4$ alkyl, preferably n-butyl.

139. The cyclic peptide or pharmaceutically acceptable salt or ester thereof of any one of items 1 to 138, wherein one or both, preferably both, $R^4$ represents a hydrogen atom.

140. The cyclic peptide or pharmaceutically acceptable salt or ester thereof of any one of items 1 to 139, wherein $R^{15}$ represents aminobutyl (thus forming a lysine residue, preferably a L-lysine residue).

141. The cyclic peptide or pharmaceutically acceptable salt or ester thereof of any one of items 1 to 140, wherein A' represents —$C(R^{10})$— or —$N(R^{10})$—.

142. The cyclic peptide or pharmaceutically acceptable salt or ester thereof of any one of items 1 to 140, wherein A' represents —X—.

143. The cyclic peptide or pharmaceutically acceptable salt or ester thereof of any one of items 1 to 141, wherein B' represents —$N(R^3)$—X—$C(=O)$—.

144. The cyclic peptide or pharmaceutically acceptable salt or ester thereof of any one of items 1 to 141, wherein C' represents —X—.

145. The cyclic peptide or pharmaceutically acceptable salt or ester thereof of any one of items 1 to 141, wherein D' represents —X—.

146. The cyclic peptide or pharmaceutically acceptable salt or ester thereof of any one of items 1 to 141, wherein E' represents —X—.

147. The cyclic peptide or pharmaceutically acceptable salt or ester thereof of any one of items 1 to 145, wherein E' represents —Y—.

148. The cyclic peptide or pharmaceutically acceptable salt or ester thereof of any one of items 1 to 146, wherein G' represents —Y—.

149. The cyclic peptide or pharmaceutically acceptable salt or ester thereof of any one of items 1 to 148, with the proviso that when E' represents —Y—, A' represents —X— or B' represents —$N(R^3)$—X—$C(=O)$—.

150. The cyclic peptide or pharmaceutically acceptable salt or ester thereof of any one of items 1 to 149, with the proviso that when A' represents —X—, G' represents —$C(R^{15})$— or —$N(R^{15})$—.

151. The cyclic peptide or pharmaceutically acceptable salt or ester thereof of any one of items 1 to 150, being:

MPE-048

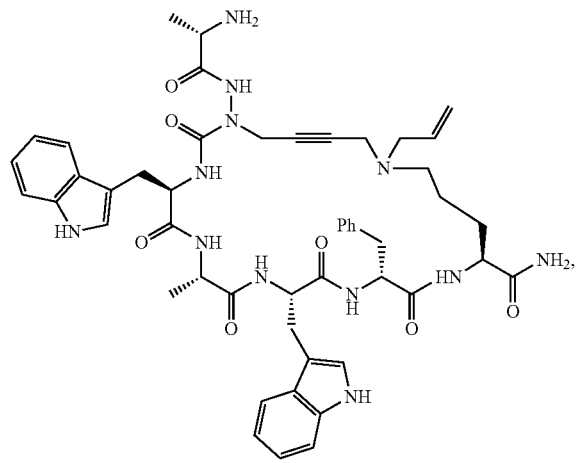

MPE-074

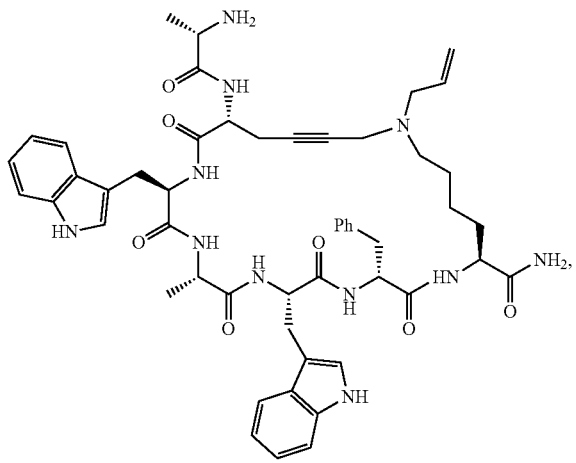

-continued
MPE-075
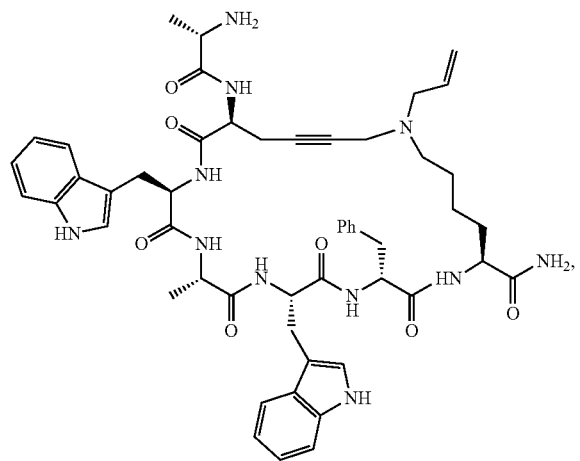
MPE-110
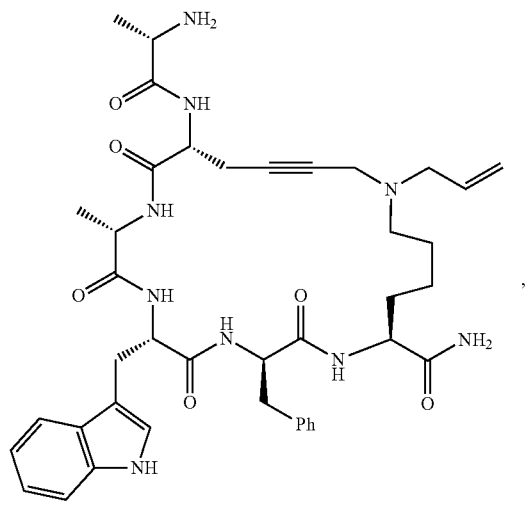
MPE-111
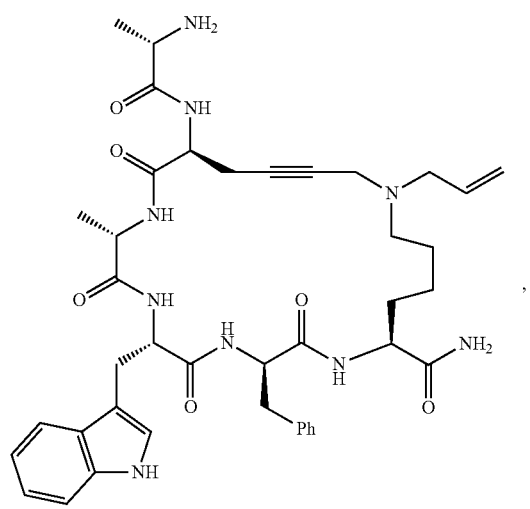
MPE-189
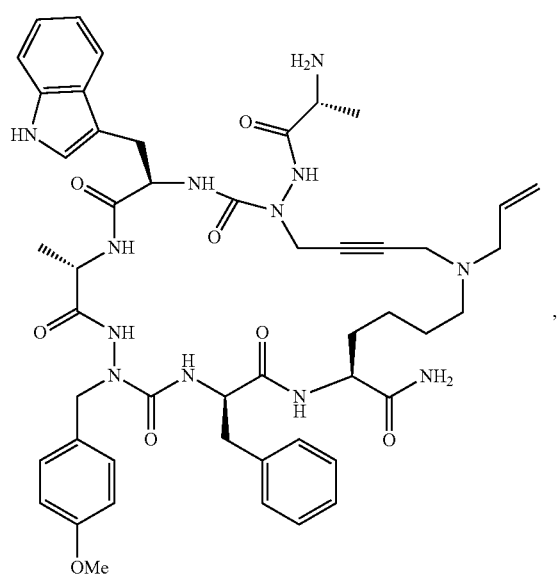
MPE-191
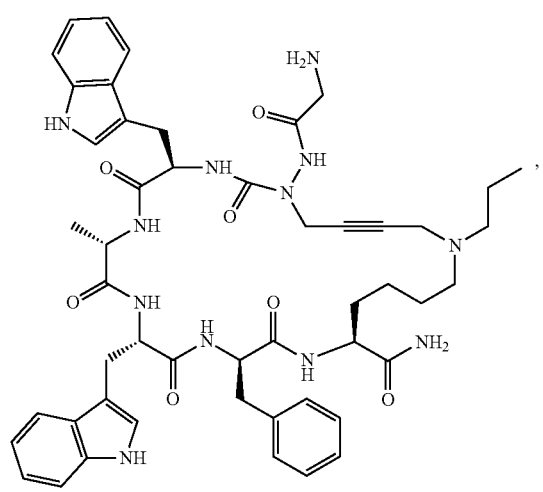
MPE-192
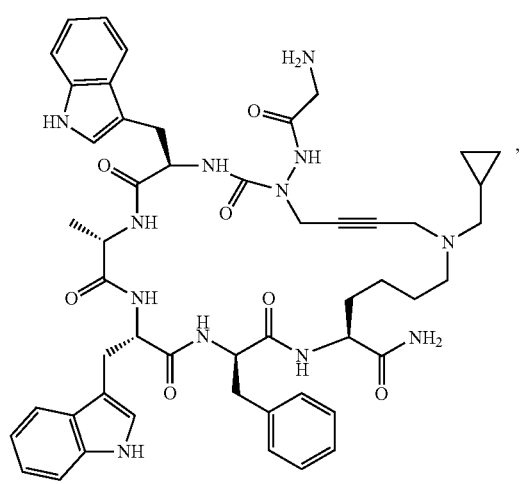

-continued
MPE-193
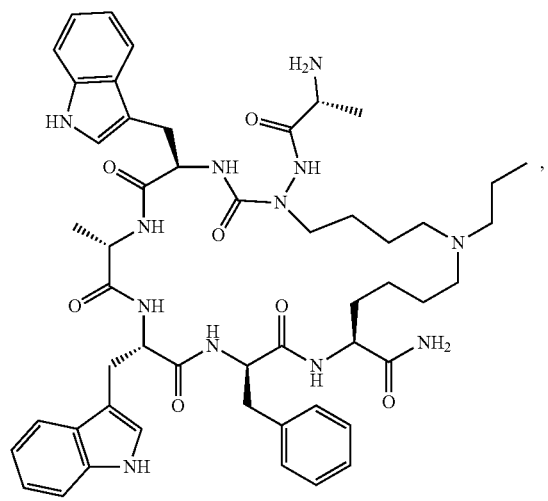
MPE-201
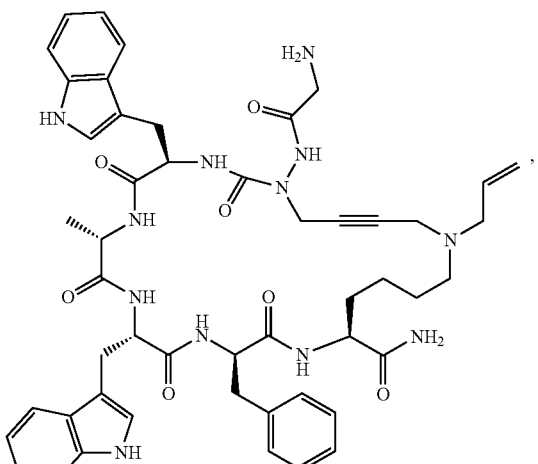
MPE-202
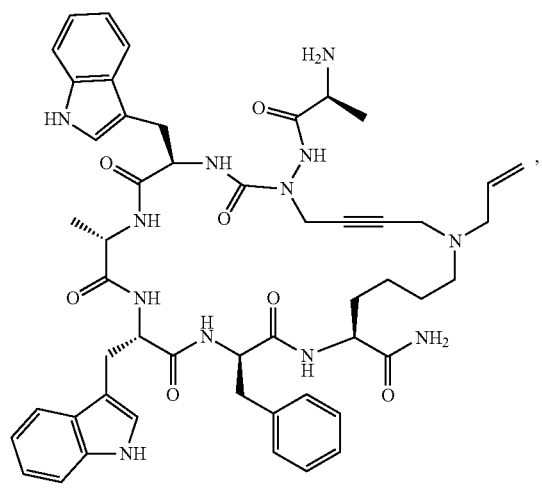
MPE-203
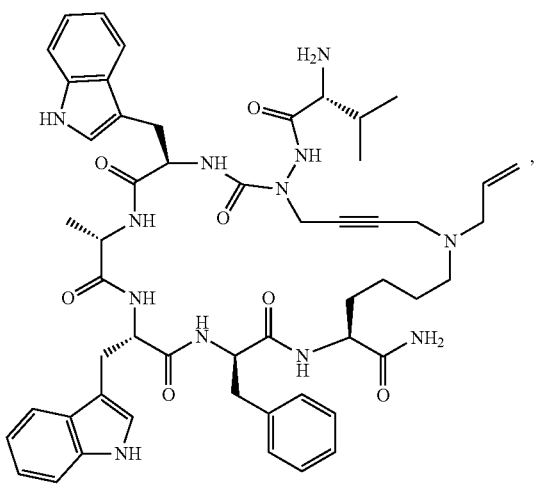
MPE-206 (8)
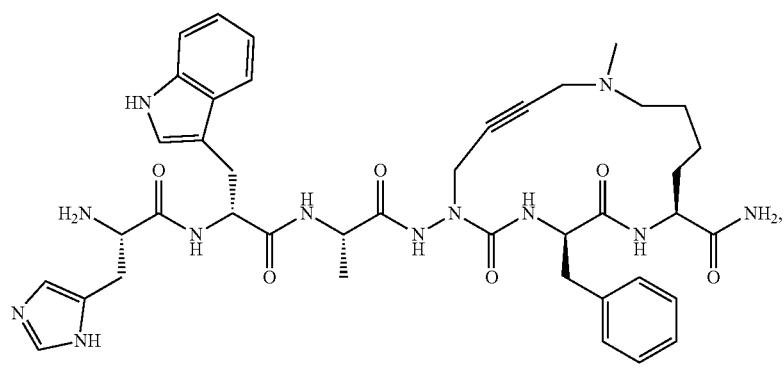

-continued
MPE-210 (9)
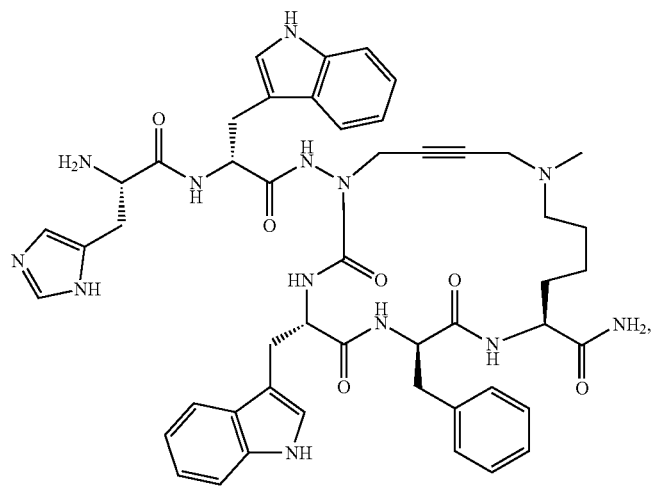
MPE -265 (17)
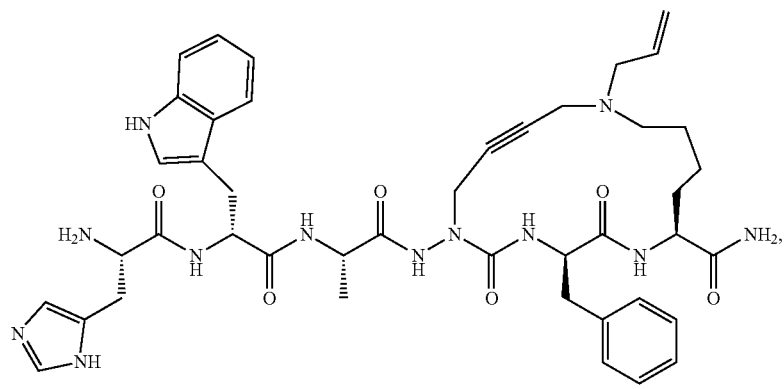
MPE-266
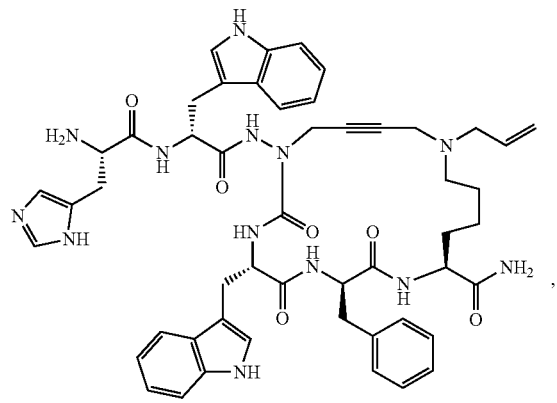
MPE-267
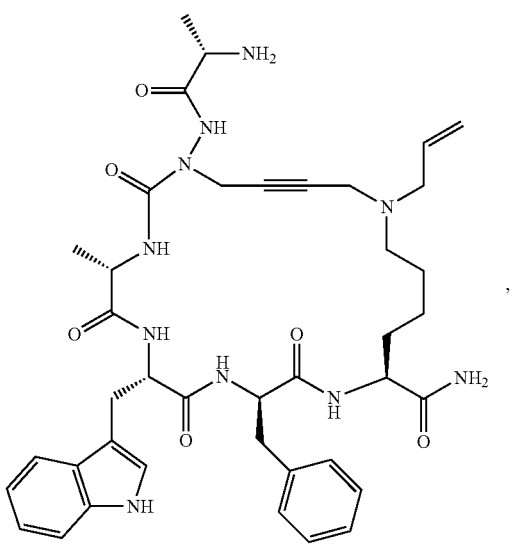

-continued
MPE-290 (30)
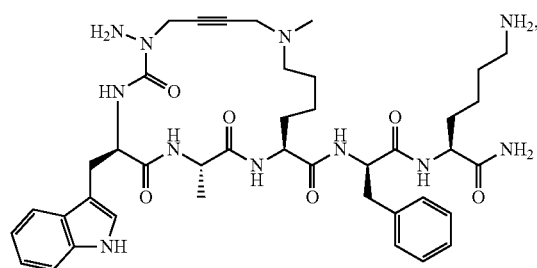
MPE-291 (31)
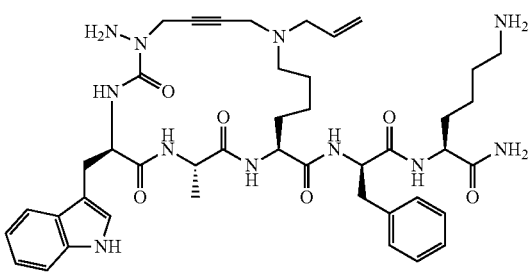
MPE-293 (32)
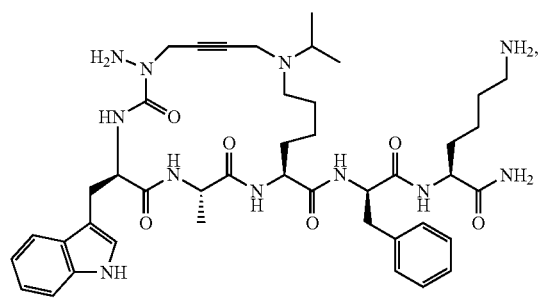
MPE-298
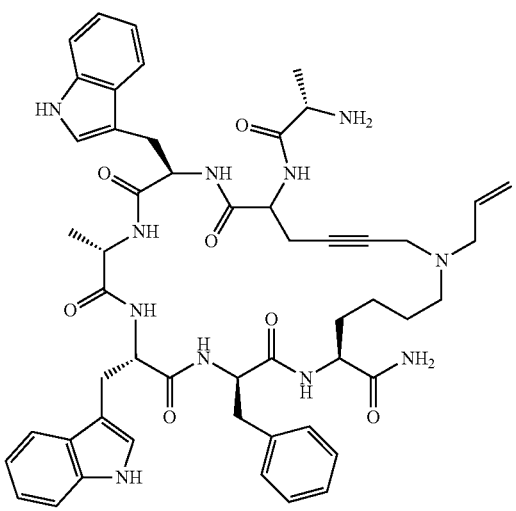
MPE-300
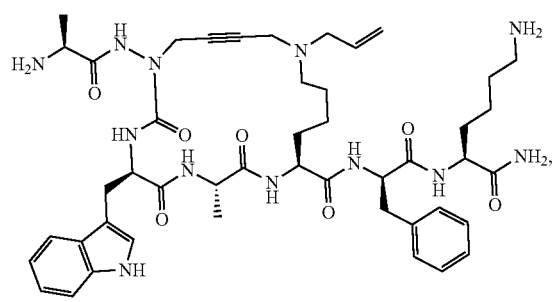
MPE-308
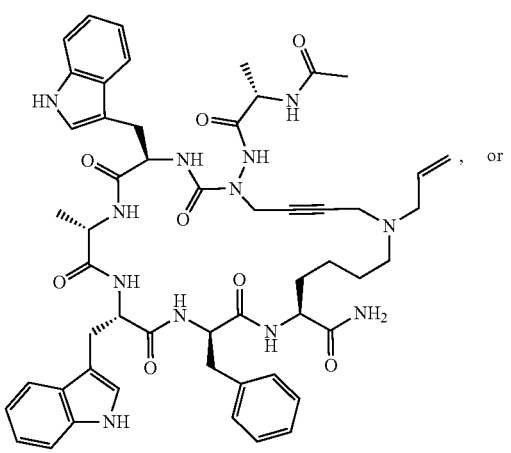
, or

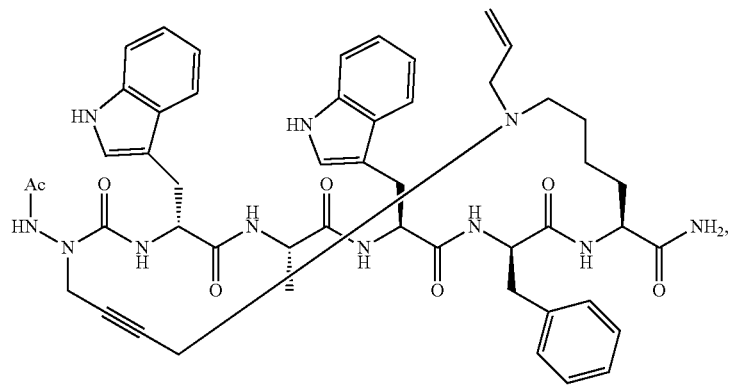

MPE-310

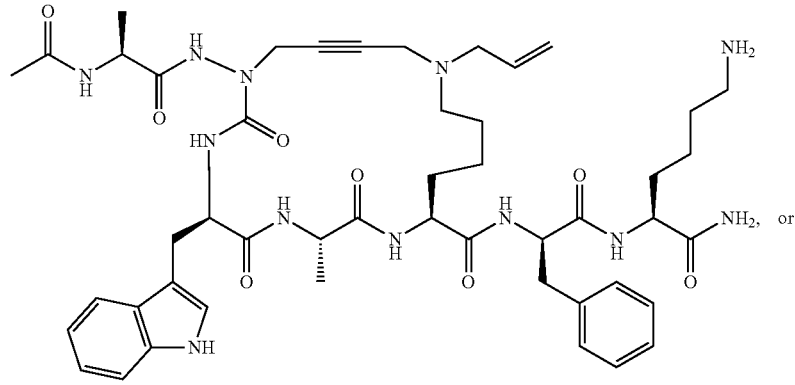

MPE-312 (34)

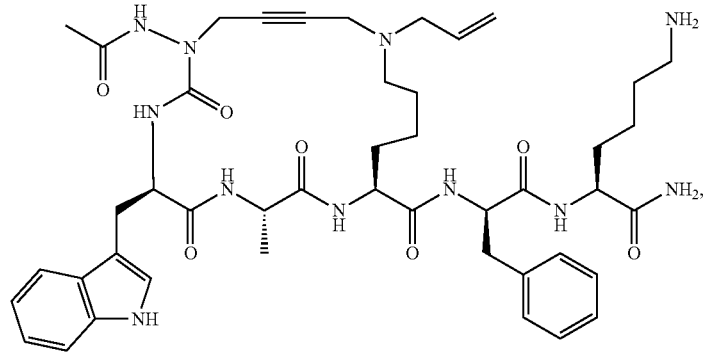

MPE-314 (35)

or a pharmaceutically acceptable salt thereof.

152. The cyclic peptide or pharmaceutically acceptable salt or ester thereof of item 151, being MPE-075, MPE-111, MPE-189, MPE-191, MPE-192, MPE-266, MPE-267, MPE-298, MPE-300, MPE-308, or MPE-310 or a pharmaceutically acceptable salt thereof.

153. The cyclic peptide or pharmaceutically acceptable salt or ester thereof of item 152, being MPE-267, MPE-298, MPE-075, or MPE-192 or a pharmaceutically acceptable salt thereof.

154. The cyclic peptide or pharmaceutically acceptable salt or ester thereof of item 153, being MPE-267 or a pharmaceutically acceptable salt thereof.

155. The cyclic peptide or pharmaceutically acceptable salt or ester thereof of item 153, being MPE-075 or a pharmaceutically acceptable salt thereof.

156. The cyclic peptide or pharmaceutically acceptable salt or ester thereof of item 53, being MPE-298 or a pharmaceutically acceptable salt thereof.

157. The cyclic peptide or pharmaceutically acceptable salt or ester thereof of item 153, being MPE-192 or a pharmaceutically acceptable salt thereof.

158. A pharmaceutical composition comprising the cyclic peptide, pharmaceutically acceptable salt or ester of any one of items 1 to 157, and one or more pharmaceutically acceptable excipients.

159. A method of treating a CD36-related disease, disorder or condition, the method comprising administering to a subject in need thereof an effective amount of the cyclic peptide, pharmaceutically acceptable salt or ester thereof of any one of items 1 to 157, or of the pharmaceutical composition of item 158.

160. The method of item 159, wherein said disease, disorder or condition is a TLR2-mediated inflammatory disease, disorder or condition.

161. The method of item 159 or 160, wherein said disease, disorder or condition is atherosclerosis, abnormal angiogenesis, age-related macular degeneration, abnormal lipid metabolism, nonalcoholic fatty liver disease (NAFLD), nonalcoholic steatohepatitis (NASH), abnormal removal of apoptotic cells, ischemia, ischemia-reperfusion injury, ureteral obstruction, fibrinogenesis in chronic kidney diseases, stroke, Alzheimer's disease, diabetes, diabetic nephropathy or obesity.

162. The method of item 161, wherein said disease, disorder or condition is atherosclerosis.

163. The method of item 161, wherein said disease, disorder or condition is age-related macular degeneration.

164. The method of any one of items 159 to 163, wherein the subject is a human subject.

165. Use of the cyclic peptide, pharmaceutically acceptable ester or salt thereof of any one of items 1 to 157, or of the pharmaceutical composition of item 158, for treating a CD36-related disease, disorder or condition in a subject.

166. Use of the cyclic peptide, pharmaceutically acceptable ester or salt thereof of any one of items 1 to 157, or of the pharmaceutical composition of item 158, for the manufacture of a medicament for treating a CD36-related disease, disorder or condition in a subject.

167. The use of item 165 or 166, wherein said disease, disorder or condition is a TLR2-mediated inflammatory disease, disorder or condition.

168. The use of any one of items 165 to 167, wherein said disease, disorder or condition is atherosclerosis, abnormal angiogenesis, age-related macular degeneration, abnormal lipid metabolism, nonalcoholic fatty liver disease (NAFLD), nonalcoholic steatohepatitis (NASH), abnormal removal of apoptotic cells, ischemia, ischemia-reperfusion injury, ureteral obstruction, fibrinogenesis in chronic kidney diseases, stroke, Alzheimer's disease, diabetes, diabetic nephropathy or obesity.

169. The use of item 168, wherein said disease, disorder or condition is atherosclerosis.

170. The use of item 168, wherein said disease, disorder or condition is age-related macular degeneration.

171. The use of any one of items 165 to 170, wherein the subject is a human subject.

172. The cyclic peptide, pharmaceutical acceptable ester or salt thereof of any one of items 1 to 157, or of the pharmaceutical composition of item 158, for use in the treatment of a CD36-related disease, disorder or condition in a subject.

173. The cyclic peptide, pharmaceutical acceptable ester or salt thereof, or the pharmaceutical composition, for use according to item 172, wherein said disease, disorder or condition is a TLR2-mediated inflammatory disease, disorder or condition.

174. The cyclic peptide, pharmaceutical acceptable ester or salt thereof, or the pharmaceutical composition, for use according to item 172 or 173, wherein said disease, disorder or condition is atherosclerosis, abnormal angiogenesis, age-related macular degeneration, abnormal lipid metabolism, nonalcoholic fatty liver disease (NAFLD), nonalcoholic steatohepatitis (NASH), abnormal removal of apoptotic cells, ischemia, ischemia-reperfusion injury, ureteral obstruction, fibrinogenesis in chronic kidney diseases, stroke, Alzheimer's disease, diabetes, diabetic nephropathy or obesity.

175. The cyclic peptide, pharmaceutical acceptable ester or salt thereof, or the pharmaceutical composition, for use according to item 174, wherein said disease, disorder or condition is atherosclerosis.

176. The cyclic peptide, pharmaceutical acceptable ester or salt thereof, or the pharmaceutical composition, for use according to item 174, wherein said disease, disorder or condition is age-related macular degeneration.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIGS. 4A to 4C: NO production in μM). FIGS. 4D to 4G: Percentage of control (R-FSL-1 only). Data are presented as mean±SEM. Statistical significance was tested using a one-way ANOVA with Bartlett post-test. **, P<0.01 vs. control. 1×10-6 M of the peptides were used for the experiments described in FIGS. 4C and 4G.

DISCLOSURE OF INVENTION

Figure 1:
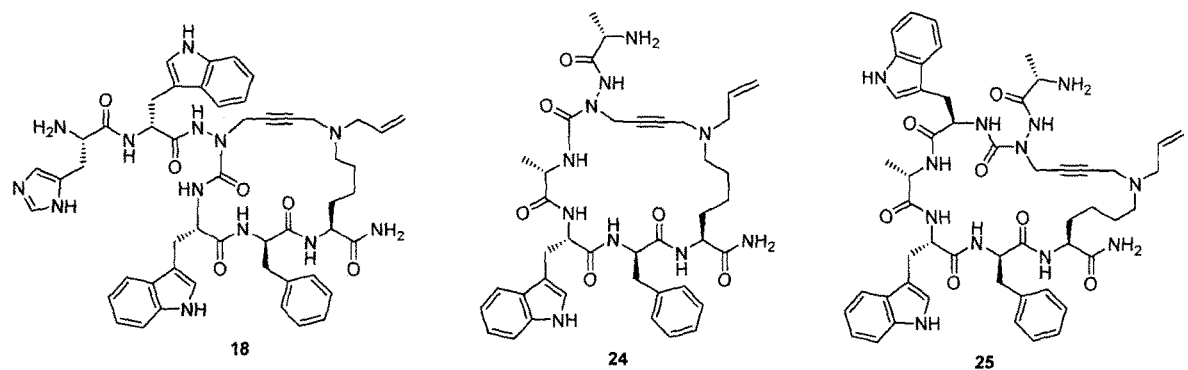
FIG. 1 shows the structure of representative cyclic azapeptides synthesized by 'A3-macrocyclization' after peptide sequence completion. 18=MPE-266; 24=MPE-267; 25=MPE-298.
Figure 2:
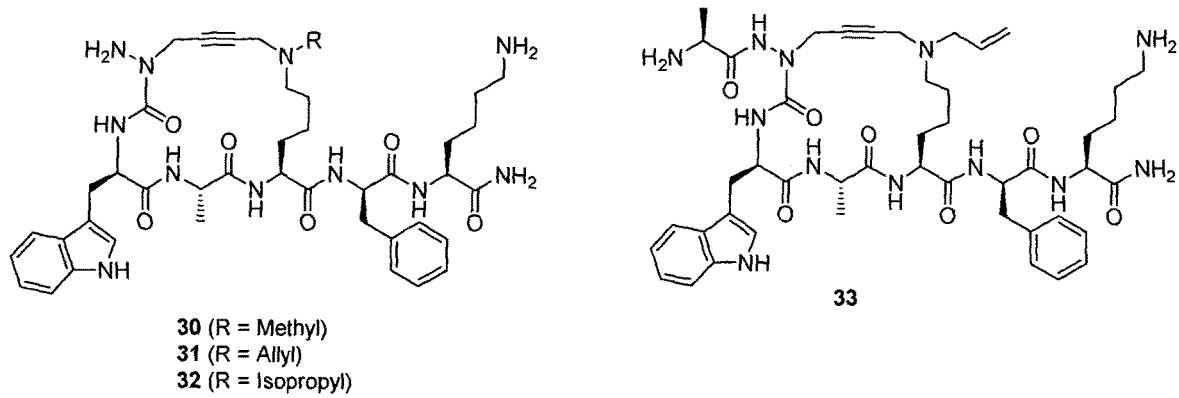
FIG. 2 shows the structure of representative cyclic azapeptides with ε-N-alkylated lysine in the centre of peptide sequence. 30=MPE-290; 31=MPE-291; 32=MPE-293; 33=MPE-300.
Figure 3A:
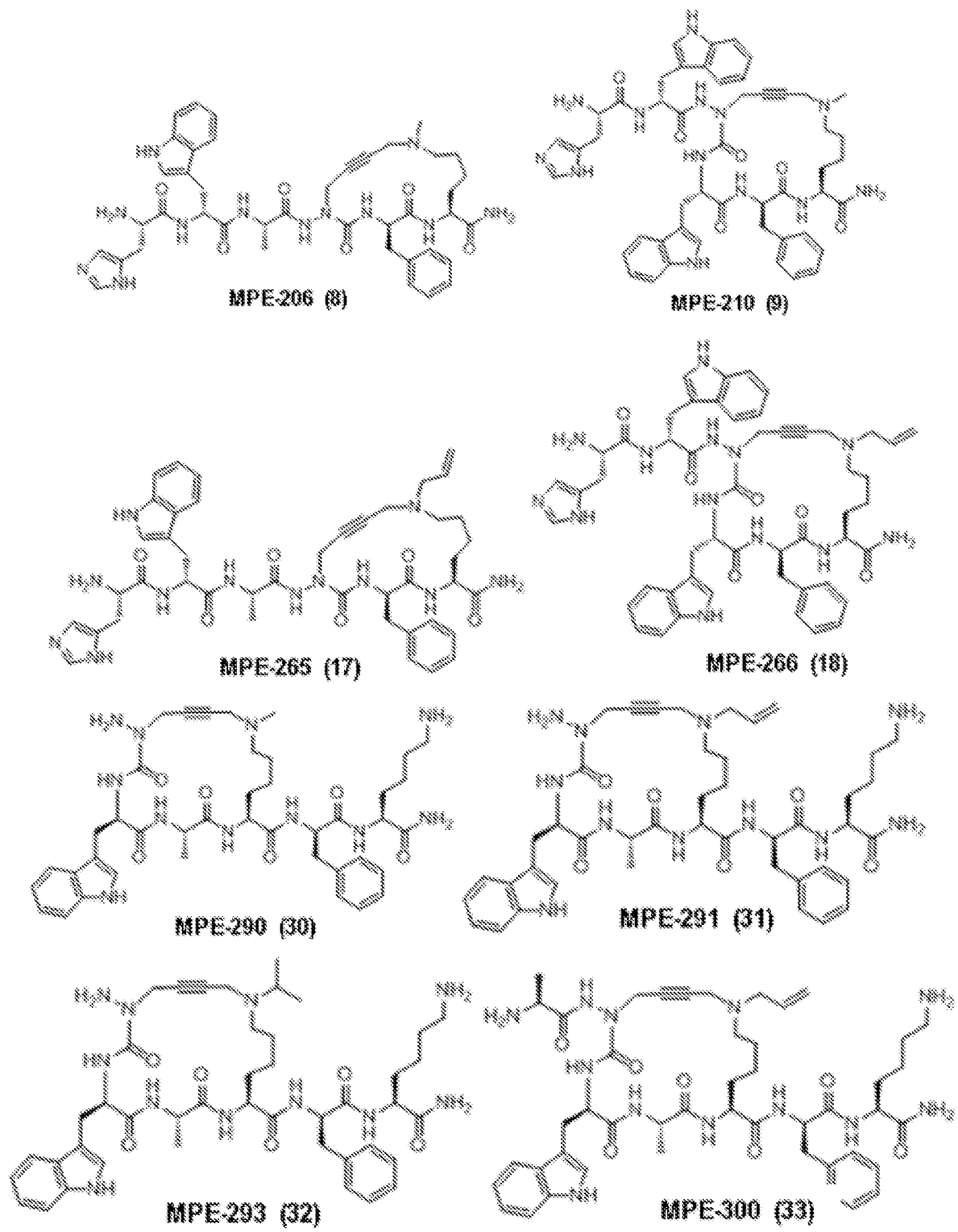
FIGS. 3A to 3E show the structure of cyclic peptides tested for their ability to modulate nitric oxide (NO) production induced by the TLR2 agonist R-FSL-1 in macrophages and/or for their binding to CD36. Compounds MPE-315 and MPE-316 are non-cyclic azapeptides used as controls in certain experiments.
Figure 3B:
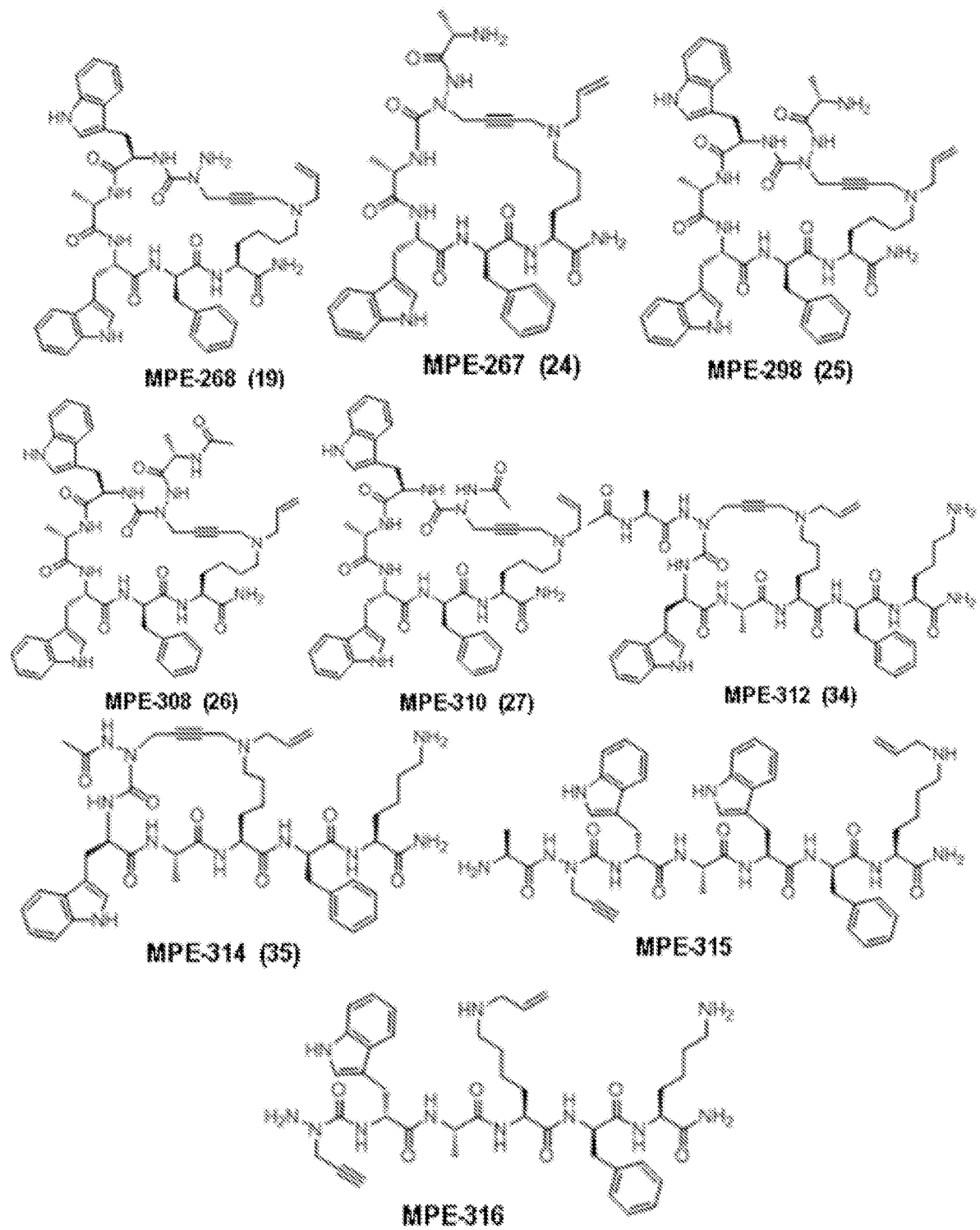
Figure 3C:
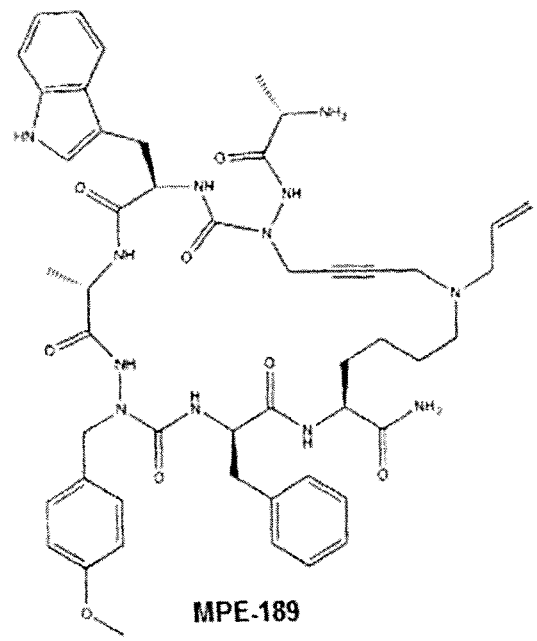
Figure 3C:
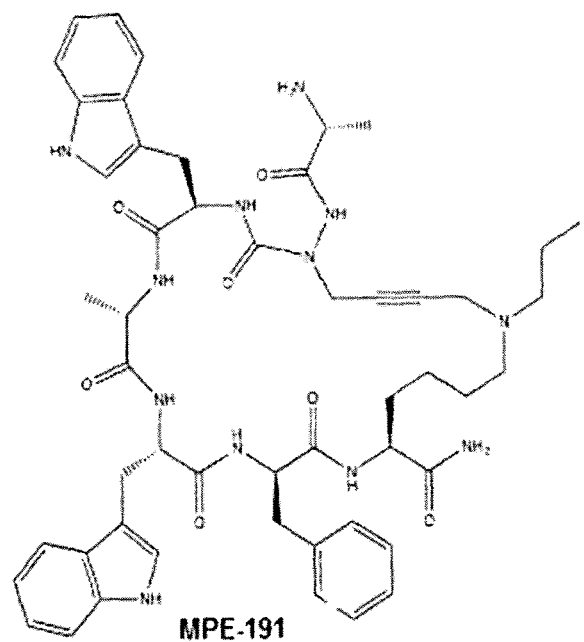
Figure 3C:
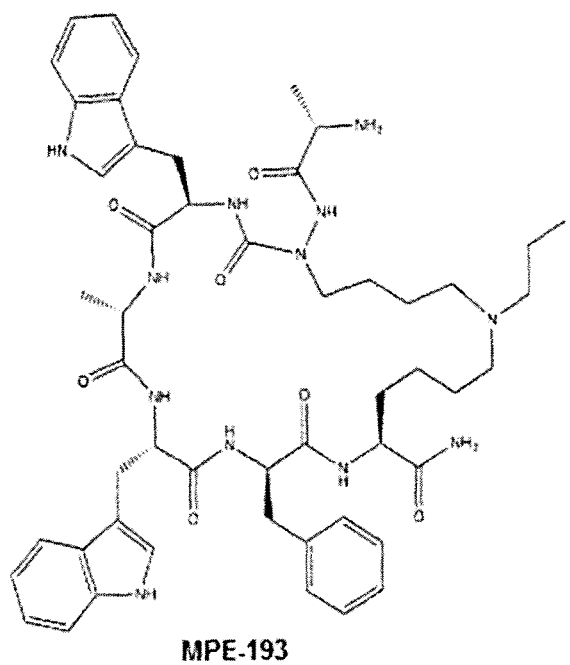
Figure 3C:
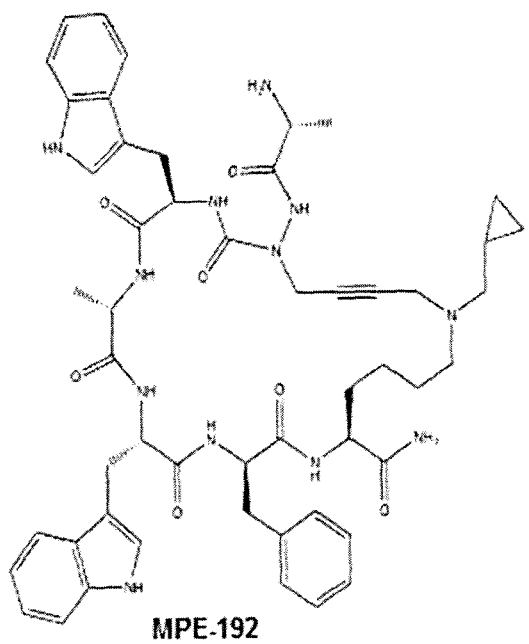
Figure 3D:
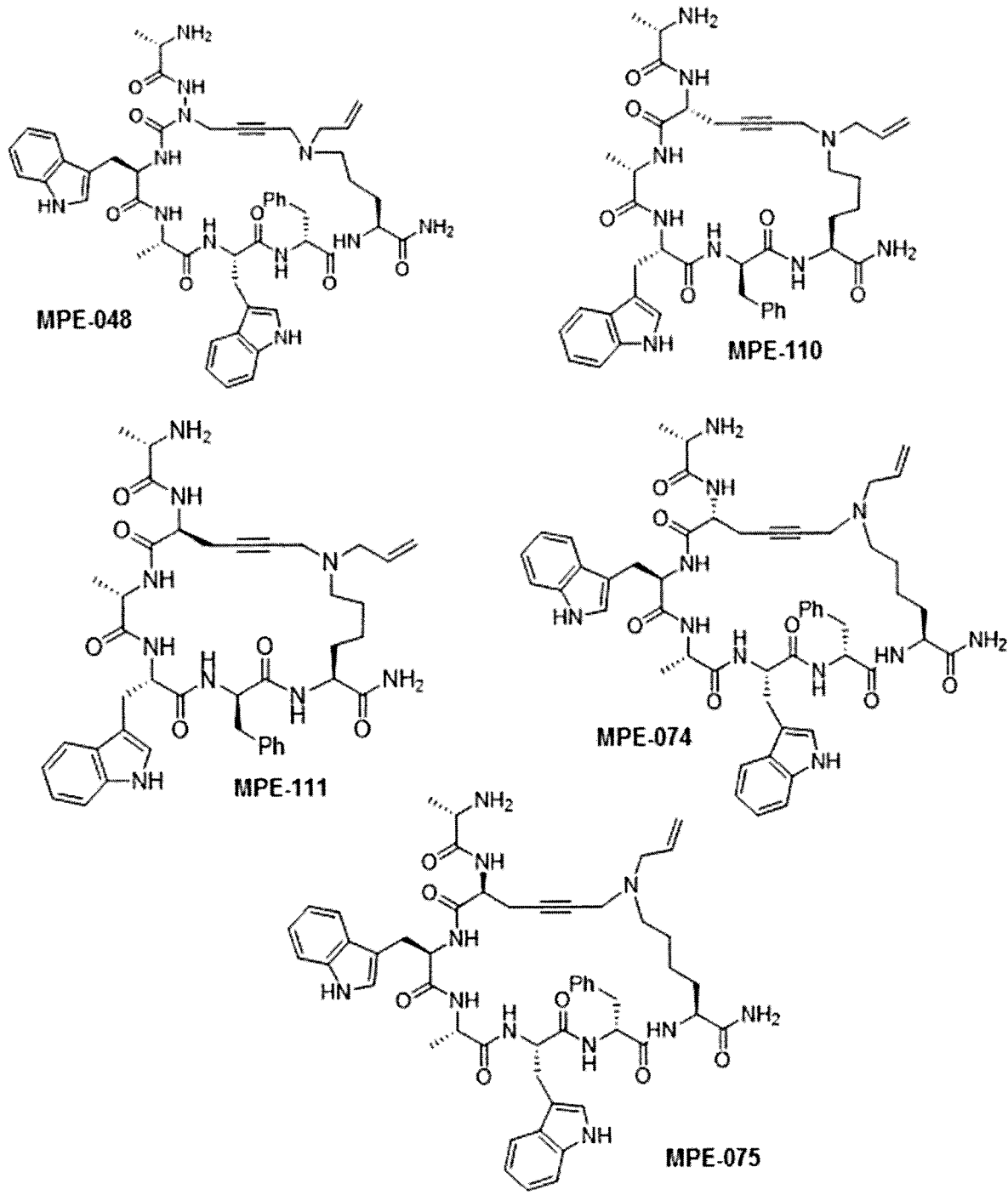
Figure 3E:
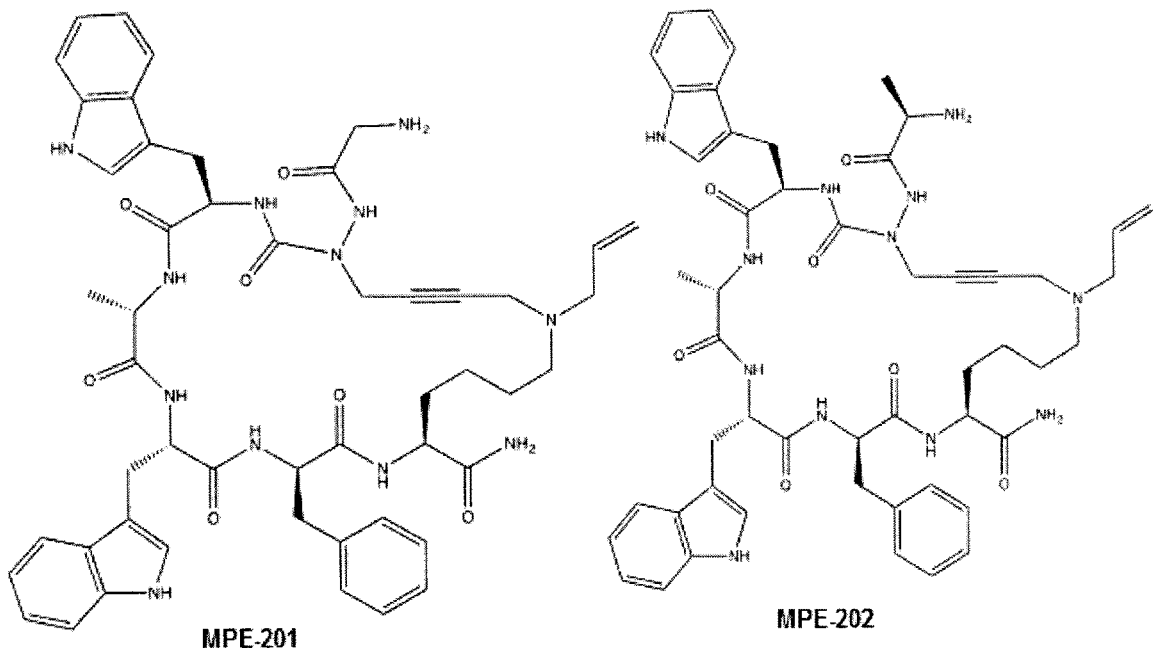
Figure 3E:
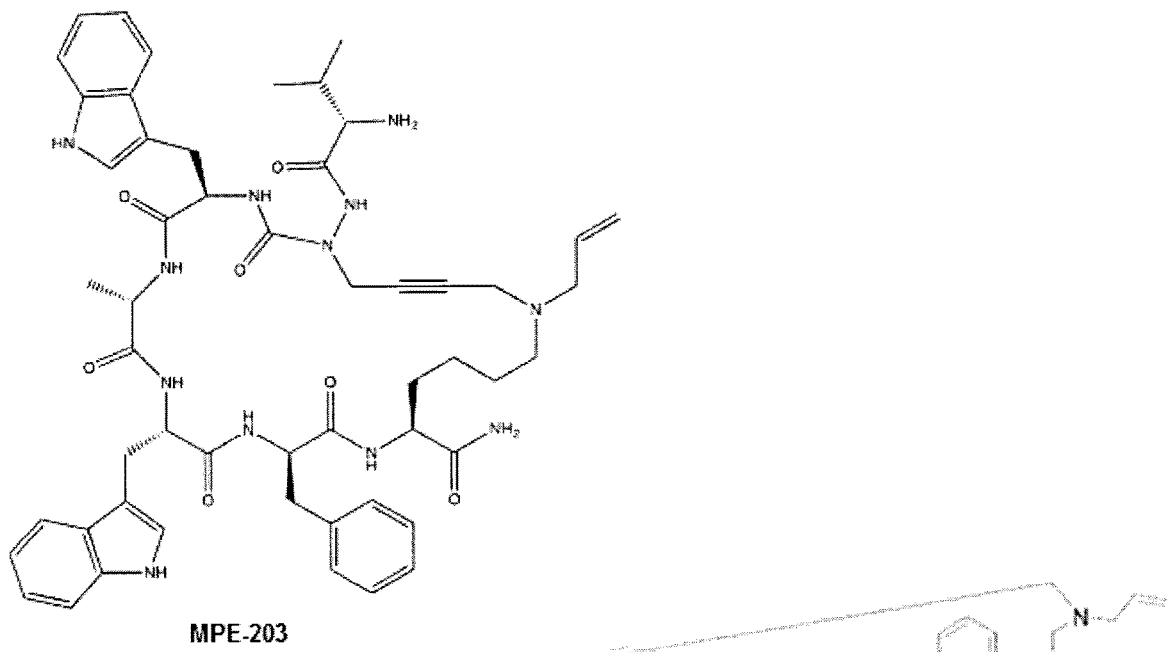
Figure 3E:
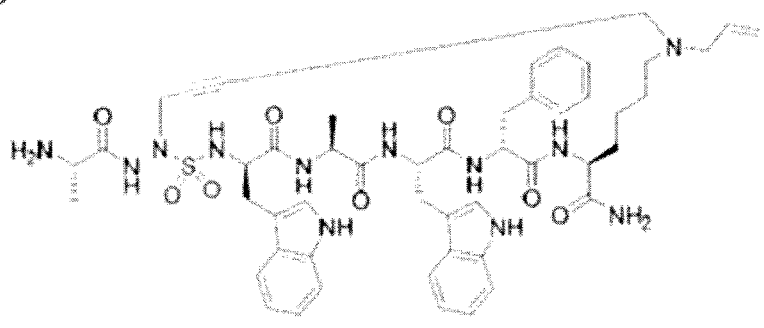

The use of the terms "a" and "an" and "the" and similar referents in the context of describing the invention are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

Similarly, herein a general chemical structure with various substituents and various radicals enumerated for these substituents is intended to serve as a shorthand method of referring individually to each and every molecule obtained by the combination of any of the radicals for any of the substituents. Each individual molecule is incorporated into the specification as if it were individually recited herein. Further, all subsets of molecules within the general chemical structures are also incorporated into the specification as if they were individually recited herein.

All methods described herein can be performed in any suitable order unless otherwise indicated herein or otherwise clearly contradicted by context.

The use of any and all examples, or exemplary language ("e.g.", "such as", etc.) provided herein, is intended merely to better illustrate the invention and does not pose a limitation on the scope of the invention unless otherwise claimed.

Herein, the term "about" has its ordinary meaning. The term "about" is used to indicate that a value includes an inherent variation of error for the device or the method being employed to determine the value, or encompass values close to the recited values, for example within 10% or 5% of the recited values (or range of values).

Unless otherwise defined, all technical and scientific terms used herein have the same meaning as commonly understood by one of ordinary skill in the art to which this invention belongs.

Any and all combinations and subcombinations of the embodiments and features disclosed herein are encompassed by the present invention.

Herein, the terms "alkyl", "alkylene", "alkenyl", "alkenylene", "alkynyl", "alkynylene" and their derivatives (such as alkoxy, alkyleneoxy, etc.) have their ordinary meaning in the art. For more certainty, herein:

| Term | Definition |
| --- | --- |
| alkyl | monovalent saturated aliphatic hydrocarbon radical of general formula —C$_n$H$_{2n+1}$ |
| alkenyl | monovalent aliphatic hydrocarbon radical similar to an alkyl, but comprising at least one double bond |
| alkynyl | monovalent aliphatic hydrocarbon radical similar to an alkyl, but comprising at least one triple bond |
| alkenynyl | monovalent aliphatic hydrocarbon radical similar to an alkyl, but comprising at least one double bond and at least one triple bond |
| alkylene | bivalent saturated aliphatic hydrocarbon radical of general formula —C$_n$H$_{2n}$— (also called alkanediyl) |
| alkenylene | bivalent aliphatic hydrocarbon radical similar to an alkylene, but comprising at least one double bond |
| alkynylene | bivalent aliphatic hydrocarbon radical similar to an alkylene, but comprising at least one triple bond |
| alkenynylene | bivalent aliphatic hydrocarbon radical similar to an alkylene, but comprising at least one double bond and at least one triple bond |
| alkyloxy or alkoxy | monovalent radical of formula —O-alkyl |
| alkyleneoxy | binovalent radical of formula —O-alkylene- |
| alkenyloxy | monovalent radical of formula —O-alkenyl |
| alkenyleneoxy | binovalent radical of formula —O-alkenylene- |
| alkynyloxy | monovalent radical of formula —O-alkynyl |
| alkynyleneoxy | binovalent radical of formula —O-alkynylene |
| haloalkyl | alkyl radical substituted with one or more halogen atom (the halogen atoms being the same or different, preferably being the same), up to and including perhaloalkyls in which the alkyl is completely substituted with halogen atoms |

It is to be noted that, unless otherwise specified, the hydrocarbon chains of these groups can be linear or branched. Further, unless otherwise specified, these groups can contain between 1 and 18 carbon atoms, more specifically between 1 and 12 carbon atoms, between 1 and 6 carbon atoms, between 1 and 3 carbon atoms, or contain 1 or 2 carbon atoms.

Herein, the term "interrupted" as in "alkylene optionally interrupted by a functional group" means that at least one of said functional group is inserted between two adjacent carbon atoms of the radical being interrupted (alkylene in the above example).

Herein, the terms "cycloalkyl", "aryl", "heterocycloalkyl", "heteroaryl" have their ordinary meaning in the art. For more certainty, herein

| Term | Definition |
|---|---|
| cycloalkyl | monovalent saturated aliphatic hydrocarbon radical of general formula $C_nH_{2n-1}$, wherein the carbon atoms are arranged in a ring (also called cycle). |
| heterocycloalkyl | cycloalkyl wherein at least one of the carbon atoms is replaced by a heteroatom, such as nitrogen or oxygen. |
| cycloalkylalkyl | monovalent radical of formula —alkyl, wherein the alkyl is substituted, preferably end-substituted, with cycloalkyl |
| aryl | monovalent aromatic hydrocarbon radical presenting a delocalized conjugated π system, most commonly an arrangement of alternating double and single bonds, between carbon atoms arranged in one or more rings, wherein the rings can be fused (i.e. share two ring atoms), for example: | naphthalene: 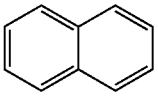

or linked together through a covalent bond, for example:

biphenyl: 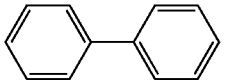

or linked together through a radical that allow continuation of the delocalized conjugated π system between the rings (e.g. —C(=O)—, —NRR—), for example:

benzophenone: 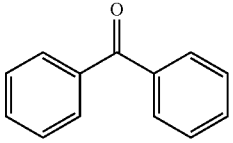

| | |
|---|---|
| aryloxy | monovalent radical of formula —O—aryl |
| arylalkyl | monovalent radical of formula —alkyl, wherein the alkyl is substituted, preferably end-substituted with aryl |
| arylalkylene | bivalent radical of formula —alkylene—, wherein the alkylene is substituted, with aryl |
| heteroaryl | aryl wherein at least one of the carbon atoms is replaced by a heteroatom, such as nitrogen or oxygen, |
| heteroarylalkyl | monovalent radical of formula —alkyl, wherein the alkyl is substituted, preferably end-substituted, with heteroaryl |

It is to be noted that, unless otherwise specified, the ring of the above groups can comprise between 4 and 8, preferably 5 or 6 ring atoms. Further, unless otherwise specified, these groups can contain a total of between 5 and 12 carbon atoms, preferably between 5 and 6 carbon atoms disposed in a single ring, or between 9 to 12 carbon atoms disposed into two rings. A preferred aryl groups is phenyl.

In the studies described herein, the present inventors have described the synthesis and characterization of novel cyclic peptide GHRP-6 analogs, and have shown that such cyclic peptides have the ability to inhibit the overproduction of nitric oxide (NO), a measure of oxidative stress, induced by the TLR2 agonist fibroblast-stimulating lipopeptide (R-FSL-1) in a CD36-expressing macrophage cell line. Representative cyclic peptides were shown to reduce pathological features of AMD and atherosclerosis in animal models.

Cyclic Peptides

In a first aspect, the present invention provides a cyclic peptide of formula (I):

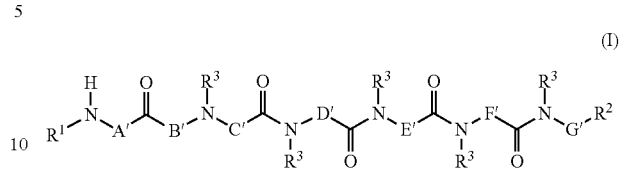

(I)

wherein:
$R^1$ represents a hydrogen atom or an amino-terminal modifying group;
$R^2$ represents —$CO_2H$, —C(=O)—$NH_2$ or a carboxy-terminal modifying group;
$R^3$ represents a hydrogen atom, alkyl, alkenyl, alkynyl, alkenynyl, or aryl;
A' represents —$C(R^{10})(R^{16})$—, —$N(R^{10})$—, or —X—;
B' represents a covalent bond or —$N(R^3)$—X—C(=O)—;
C' represents —$C(R^{11})(R^{16})$—, —$N(R^{11})$—, or —X—;
D' represents —$C(R^{12})(R^{16})$—, —$N(R^{12})$—, or —X—;
E' represents —$C(R^{13})(R^{16})$—, —$N(R^{13})$—, —X—, or —Y—;
F' represents —$C(R^{14})(R^{16})$— or —$N(R^{14})$—; and
G' represents —$C(R^{15})(R^{16})$—, —$N(R^{15})$—, or —Y—;
in which:
$R^{10}$ represents a hydrogen atom, alkyl, aryl, arylalkyl, heteroaryl, or heteroarylalkyl;
$R^{11}$ represents a hydrogen atom, alkyl, aryl, arylalkyl, heteroaryl, or heteroarylalkyl;
$R^{12}$ represents a hydrogen atom, alkyl optionally interrupted by —$N(R^3)$— and/or —O—, aryl, arylalkyl, heteroaryl, or heteroarylalky;
$R^{13}$ represents a hydrogen atom, alkyl, aryl, arylalkyl, heteroaryl, or heteroarylalkyl;
$R^{14}$ represents a hydrogen atom, alkyl, aryl, arylalkyl, heteroaryl, or heteroarylalkyl;
$R^{15}$ represents -alkyl-$N(R^4)_2$, each $R^4$ independently representing a hydrogen atom, alkyl, alkenyl, alkynyl, alkenynyl, aryl, or C(=NH)—$NH_2$; and
$R^{16}$ represents independently a hydrogen atom, alkyl, aryl, arylalkyl, heteroaryl, or heteroarylalkyl;
the aryl, arylalkyl, heteroaryl, and heteroarylalkyl in $R^{10}$, $R^{11}$, $R^{12}$, $R^{13}$, $R^{14}$ and $R^{16}$ being optionally substituted with one or more: hydroxy, halogen atom, alkyl, haloalkyl, alkoxy, cyano (—C≡N), alkylamino, amino ($NH_2$), nitro ($NO_2$), —N(haloalkyl)$_2$, aryl, arylalkyl, arylalkyloxy, or —C(=O)aryl,
with the proviso that the cyclic peptide comprises exactly one —X— and exactly one —Y—, and
with the proviso that no more than two of $R^{11}$, $R^{13}$, and $R^{14}$ are a hydrogen atom, wherein —X— and —Y— together form a bridge of formula (II) or (II'):

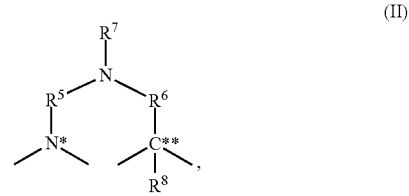

(II)

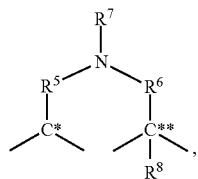
(II')

in which:
* identifies the first atom of —X—,
** identifies the first atom of —Y—,
$R^5$ represents alkylene, alkenylene, alkynylene, or alkenynylene, the alkylene, alkenylene, alkynylene, or alkenynylene being optionally interrupted by —N($R^9$)— and/or —C(=O)—, and the alkylene, alkenylene, alkynylene, or alkenynylene being optionally substituted with one or more alkyl or hydroxyl,
$R^6$ represents alkylene, alkenylene, alkynylene, alkenynylene, or arylalkylene,
$R^7$ represents a hydrogen atom, alkyl, alkenyl, cycloalkylalkyl, or arylalkyl,
$R^8$ represents a hydrogen atom or alkyl, and
$R^9$ represents a hydrogen atom, alkyl, or aryl,
or a pharmaceutically acceptable salt or ester thereof.

$R^2$ and $R^3$

The term "amino-terminal modifying group" refers to a moiety commonly used in the art of peptide chemistry to replace or modify the native $NH_2$ terminal group of the peptide, for example to increase its stability and/or susceptibility to protease digestion. In an embodiment, $R^1$ is a straight chained or branched alkyl group of one to eight carbons, or an acyl group ($R^4$—CO—), wherein $R^4$ is a hydrophobic moiety (e.g., alkyl, such as methyl, ethyl, propyl, butanyl, iso-propyl, or iso-butanyl), or an aroyl group (Ar—CO—), wherein Ar is an aryl group. In an embodiment, the acyl group is a $C_1$-$C_{16}$ or $C_3$-$C_{16}$ acyl group (linear or branched, saturated or unsaturated); in a further embodiment, a saturated $C_1$-$C_6$ acyl group (linear or branched) or an unsaturated $C_3$-$C_6$ acyl group (linear or branched), for example an acetyl group ($CH_3$—CO—, Ac). In an embodiment, $R^1$ represents a hydrogen atom (i.e., the cyclic peptide has a native $NH_2$ terminal group) or an acyl group (linear or branched), such as a $C_1$-$C_6$ acyl group, preferably an acetyl group ($CH_3$—CO—, Ac). In more preferred embodiments, $R^1$ represents a hydrogen atom.

The term "carboxy-terminal modifying group" refers to a moiety commonly used in the art of peptide chemistry to replace or modify the native $CO_2H$ terminal group of the peptide/peptidomimetic, for example to increase its stability and/or susceptibility to protease digestion. In embodiment, the carboxy-terminal modifying group is:
  a hydroxylamine group (NHOH) attached to the carboxyl group (—C(=O)—NHOH),
  an amine attached to the carboxyl group (—C(=O)—$NR^{20}R^{21}$), the amine being a primary, secondary or tertiary amine, and preferably the amine is an aliphatic amine preferably of one to ten carbons, such as methyl amine, iso-butylamine, iso-valerylamine or cyclohexylamine, an aromatic amine or an arylalkyl amine, such as aniline, napthylamine, benzylamine, cinnamylamine, or phenylethylamine, a preferred amine being —$NH_2$,
  a nitrile group (C≡N), or
  a hydroxyalkyl (i.e. an alcohol), preferably $CH_2OH$.

In an embodiment, $R^2$ represents $CO_2H$ (i.e., the cyclic peptide has a native $CO_2H$ terminal group). In another embodiment, $R^2$ is a carboxy-terminal modifying group, preferably —C(=O)—$NR^{20}R^{21}$, more preferably —C(=O)—$NH_2$.

In an embodiment, $R^3$ represents a hydrogen atom.

Bridge of Formula (II) or (II')

In the above cyclic peptide, there is exactly one —X— and exactly one —Y—. In other words, there is only one bridge of formula (II) or (II'); the cyclic peptide thus contains only one cycle, i.e. it is mono-cyclic.

The bridge of formula (II) or (II') is chiral as it comprises one (formula (II)) or two (formula (II')) tetrahedral carbon atoms with four different substituents (atom C** in formula (II) and (II') as well as C* in formula (II')). The above formulas (II) and (II') are meant to cover all isomers of the bridge as well as any mixture thereof, including a racemic mixture. In a preferred embodiment of formula (II), said —X— and said —Y— together form the (S)-enantiomer of the bridge of formula (II). In another embodiment, said —X— and said —Y— together form the (R)-enantiomer of the bridge of formula (II). In yet another embodiment, said —X— and said —Y— together form a mixture of enantiomers of the bridge of formula (II), including a racemic mixture. In a preferred embodiment of formula (II'), said —X— and said —Y— together form the cis-diastereomer of the bridge of formula (II'). In another embodiment, said —X— and said —Y— together form the trans-diastereomer of the bridge of formula (II'). In yet another embodiment, said —X— and said —Y— together form a mixture of diastereomers of the bridge of formula (II').

It will be apparent to the skilled person that the nitrogen atom of the —X— group (N* in formula (II)) replaces the αC atom that would normally be found in a "regular" peptide. As such, this nitrogen atom forms a —N—N— group with the α amino group of the amino acid, thus forming an "aza" amino acid and thus a cyclic azapeptide.

In an embodiment of formula (II) and (II'), $R^5$ represents alkylene or alkenylene or alkynylene, preferably alkylene or alkynylene, more preferably alkynylene. In an embodiment, the alkylene, alkenylene, alkynylene or alkenynylene in $R^5$ is $C_3$-$C_6$, preferably $C_3$-$C_5$, and more preferably Ca. In an embodiment, $R^5$ represents $C_4$ alkynylene or $C_4$ alkynylene, preferably n-but-2-ynylene (i.e. —$CH_2$—C≡C—$CH_2$—) or n-butylene, more preferably n-but-2-ynylene. In an embodiment, the alkylene, alkenylene, alkynylene, or alkenynylene in $R^5$ is interrupted by —N($R^9$)— and/or —C(=O)—. In an embodiment, the alkylene, alkenylene, alkynylene, or alkenynylene in $R^5$ is uninterrupted. In an embodiment, the alkylene, alkenylene, alkynylene, or alkenynylene in $R^5$ is substituted with one or more alkyl or hydroxyl. In an embodiment, the alkylene, alkenylene, alkynylene, or alkenynylene in $R^5$ is unsubstituted.

In an embodiment of formula (II) and (II'), $R^6$ represents $C_3$-$C_6$ alkylene, $C_3$-$C_6$ alkenylene, $C_3$-$C_6$ alkynylene, $C_3$-$C_6$ alkenynylene, or aryl-$C_3$-$C_6$ alkylene, preferably $C_3$-$C_5$ alkylene, $C_3$-$C_5$ alkenylene, $C_3$-$C_5$ alkynylene, $C_3$-$C_5$ alkenynylene, or aryl-$C_3$-$C_5$-alkylene, and more preferably $C_3$-$C_4$ alkylene, $C_3$-$C_4$ alkenylene, $C_3$-$C_6$ alkynylene, $C_3$-$C_6$ alkenynylene, or aryl-$C_3$-$C_4$-alkylene. In preferred embodiments, $R^6$ represents alkylene, such as $C_3$-$C_6$ alkylene or $C_3$-$C_5$ alkylene, preferably $C_3$-$C_4$ alkylene, and more preferably n-propylene (—$CH_2$—$CH_2$—$CH_2$—) or n-butylene (i.e. —$CH_2$—$CH_2$—$CH_2$—$CH_2$—).

In an embodiment of formula (II) and (II'), the arylalkyl in $R^7$ is arylmethyl (i.e. methyl substituted with aryl), preferably benzyl. In an embodiment, the alkyl in $R^7$ is $C_2$-$C_6$ alkyl, preferably $C_2$-$C_4$ alkyl, more preferably $C_3$ alkyl including n-propyl and i-propyl. In an embodiment, the alkenyl in $R^7$ is $C_2$-$C_6$ alkenyl, preferably $C_2$-$C_4$ alkenyl and more preferably $C_3$ alkenyl, most preferably n-prop-2-enyl (—$CH_2$—CH=$CH_2$), which is also called "allyl". In an embodiment, the cycloalkyl in the cycloalkylalkyl in $R^7$ is $C_{3-6}$cycloalkyl, preferably $C_{3-5}$ cycloalkyl, and more preferably $C_3$ cycloalkyl. In an embodiment, the alkyl in the cycloalkylalkyl in $R^7$ is $C_1$-$C_6$ alkyl, preferably $C_1$-$C_3$ alkyl, more preferably methyl. A preferred cycloalkylalkyl is therefore cyclopropylmethyl

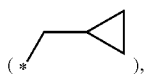

wherein * denotes the point of attachment to the nitrogen atom bearing the $R^7$ substituent). In preferred embodiments, $R^7$ represents alkyl, alkenyl, cycloalkylalkyl, or arylalkyl, preferably alkenyl as defined above.

In an embodiment of formula (II) and (II'), $R^8$ represents alkyl.

In an embodiment of formula (II) and (II'), $R^8$ represents a hydrogen atom.

In an embodiment, —X— and —Y— together form a bridge of formula (II).

In an embodiment, —X— and —Y— together form a bridge of formula (III):

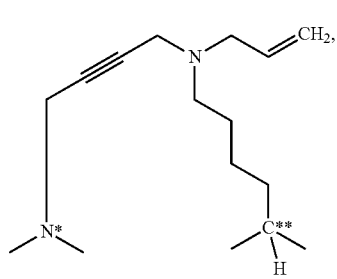

wherein * identifies the first atom of —X— and ** identifies the first atom of —Y—, and which includes both the (R) and (S) enantiomers of the bridge as well as any mixture thereof (including a racemic mixture). Preferably, said —X— and said —Y— together form the (S)-enantiomer of the bridge of formula (III), i.e.:

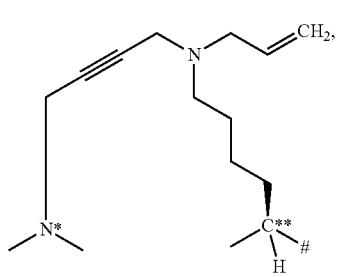

wherein * identifies the first atom of —X—, ** identifies the first atom of —Y—, and a pound sign (#) identifies the bond of the —Y— group that is attached to the neighbouring carbonyl (C=O) group (to distinguish it from the bond attached to the neighbouring nitrogen atom).

In an embodiment, —X— and —Y— together form a bridge of formula (II').

In an embodiment, —X— and —Y— together form a bridge of formula (V):

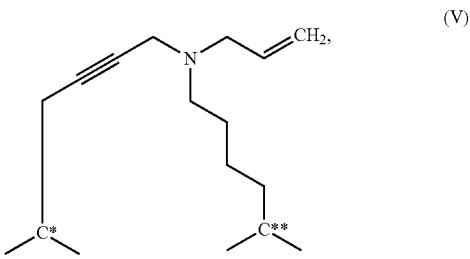

wherein * identifies the first atom of —X— and ** identifies the first atom of —Y—, and which C* and C** are in the D- or L-configuration or any mixture thereof. In embodiment, C* is in the L-configuration. In other embodiments, C** is in the L-configuration. In embodiment, C* is in the L-configuration. In other embodiments, C** is in the L-configuration. In a most preferred embodiment, both C* and C** are in the L-configuration, i.e. said —X— and said —Y— together form the (cis)-diastereomer of the bridge of formula (IV), i.e.:

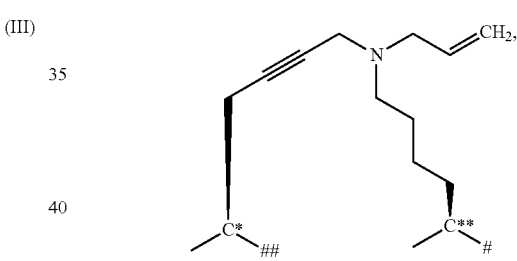

wherein:
identifies the first atom of —X—,
* identifies the first atom of —Y—,
a pound sign (#) identifies the bond of the —Y— group that is attached to the neighbouring carbonyl (C=O) group (to distinguish it from the bond attached to the neighbouring nitrogen atom), and.
two pound signs (##) identifies the bond of the —X— group that is attached to the neighbouring carbonyl (C=O) group (to distinguish it from the bond attached to the neighbouring nitrogen atom).

A' to G'

As noted above, A' can represent —C($R^{10}$)($R^{16}$)—, C' can represent —C($R^{11}$)($R^{16}$)—, D' can represent —C($R^{12}$)($R^{16}$)—, E' can represent —C($R^{13}$)($R^{16}$)—, F' can represent —C($R^{14}$)($R^{16}$)—, and/or G' can represent —C($R^{15}$)($R^{16}$)—. When that is the case, the carbon bearing the $R^{10}$ to $R^{15}$ and $R^{16}$ substituents, together with the —C(=O)— group and the —NH— or —$NR^3$— to which it is attached, form an amino acid residue.

In embodiments, the cyclic peptide is as defined above with the proviso that no more than one (2), and preferably no more than one (1), and preferably none, of $R^{11}$, $R^{13}$, and $R^{14}$ is a hydrogen atom. In embodiments, the cyclic peptide is as defined above with the proviso that no more than one (2), and preferably no more than one (1), and preferably none, of $R^{11}$, $R^{13}$, and $R^{14}$ is a hydrogen atom or alkyl. In embodiments, the cyclic peptide is as defined above with the proviso that no more than one (1), and preferably none, of $R^{11}$, $R^{13}$, and $R^{14}$ is a hydrogen atom or alkyl.

In the above-noted group, the carbon bearing the $R^{10}$ to $R^{15}$ and $R^{16}$ substituents is a stereogenic center and thus may be in the D- or L-configuration, or any mixture thereof. In embodiments, said carbon atom is in the L-configuration. In other embodiments, said carbon atom is in the D configuration. In embodiments, the carbon atom bearing ($R^{10}$) and ($R^{16}$) is in the D- or L-configuration or any mixture thereof, preferably in the L-configuration. In embodiments, the carbon atom bearing ($R^{11}$) and ($R^{16}$) is in the D- or L-configuration or any mixture thereof, preferably in the D-configuration. In embodiments, the carbon atom bearing ($R^{12}$) and ($R^{16}$) is in the D- or L-configuration or any mixture thereof, preferably in the L configuration. In embodiments, the carbon atom bearing ($R^{13}$) and ($R^{16}$) is in the D- or L-configuration or any mixture thereof, preferably in the L-configuration. In embodiments, the carbon atom bearing ($R^{14}$) and ($R^{16}$) is in the D- or L-configuration or any mixture thereof, preferably in the D-configuration. In embodiments, the carbon atom bearing ($R^{15}$) and ($R^{16}$) is in the D- or L-configuration or any mixture thereof, preferably in the L-configuration.

As noted above, the aryl, arylalkyl, heteroaryl, and heteroarylalkyl in $R^{10}$, $R^{11}$, $R^{12}$, $R^{13}$, $R^{14}$ and/or $R^{16}$ are optionally substituted with one or more: hydroxy, halogen atom, alkyl, haloalkyl, alkoxy, cyano (—C≡N), amino ($NH_2$), nitro ($NO_2$), alkylamino (-alkyl-$NH_2$), —N(haloalkyl)$_2$, aryl, arylalkyl, arylalkyloxy, or —C(=O)aryl. Preferred alkyl, haloalkyl, and alkoxy are $C_{1-6}$, preferably $C_{1-4}$, more preferably $C_{1-2}$, preferably $C_1$. Preferred haloalkyl are perhaloalkyl, preferably perfluoroalkyl, more preferably —$CF_3$. Preferred —N(haloalkyl)$_2$ include —N(2-chloroethyl)$_2$. Preferred aryl (as substituent to the aryl, arylalkyl, heteroaryl, or heteroarylalkyl) include phenyl. Preferred arylalkyloxy include benzyloxy. Preferred —C(=O)aryl include benzoyl. Preferred substituents on the alkyl of the arylalkyl and heteroarylalkyl include alkyl, hydroxy, and aryl.

In embodiments, the aryl or heteroaryl of the aryl, arylalkyl, heteroaryl, and heteroarylalkyl include 2 or 3 substituents, which are the same or different, preferably the same, and preferably which are halogen atoms, hydroxy, or alkoxy.

In embodiments, the alkyl in the arylalkyl and/or the heteroarylalkyl in $R^{10}$, $R^{11}$, $R^{12}$, $R^{13}$, $R^{14}$ and/or $R^{16}$ is $C_{1-6}$ alkyl, preferably $C_{1-3}$ alkyl, more preferably $C_{1-2}$ alkyl, and most preferably methyl.

In embodiments, the aryl in the aryl and arylalkyl in $R^{10}$, $R^{11}$, $R^{12}$, $R^{13}$, $R^{14}$ and/or $R^{16}$ is phenyl or naphthyl, preferably phenyl.

The aryl in the aryl and arylalkyl in $R^{10}$, $R^{11}$, $R^{12}$, $R^{13}$, $R^{14}$ and/or $R^{16}$ is either unsubstituted or substituted as noted above, preferably unsubstituted or substituted with one hydroxy group, preferably at position 4 on the phenyl.

In embodiments, the arylalkyl is:
  unsubstituted benzyl (—$CH_2$-phenyl), thus forming the side chain of a phenylalanine residue, preferably a L-phenylalanine residue,
  benzyl substituted with hydroxy, preferably at the para (4) position on the phenyl ring, thus forming the side chain of a tyrosine residue, preferably a L-tyrosine residue, or
  —$CH_2$—$CH_2$-phenyl, thus forming the side chain of a homophenylalanine residue, preferably a L-homophenylalanine residue.

In embodiments, the heteroaryl in the heteroaryl and heteroarylalkyl in $R^{10}$, $R^{11}$, $R^{12}$, $R^{13}$, $R^{14}$ and/or $R^{16}$ is triazolyl, imidazolyl or indolyl, preferably imidazolyl or indolyl, preferably 1H-imidazol-4-yl or 1H-indol-3-yl-.

The heteroaryl in the heteroaryl and heteroarylalkyl in $R^{10}$, $R^{11}$, $R^{12}$, $R^{13}$, $R^{14}$ and/or $R^{16}$ is substituted as noted above or unsubstituted, preferably unsubstituted.

In embodiments, the heteroarylalkyl is:
  1H-indol-3-yl-methyl

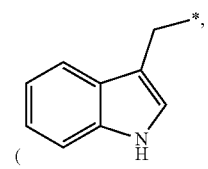

wherein * denotes the point of attachment), thus forming the side chain of a tryptophan residue, preferably a L-tryptophan residue, or
  1H-imidazol-4-yl-methyl

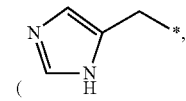

wherein * denotes the point of attachment), thus forming the side chain of a histidine residue, preferably a L-histidine residue.

In embodiments, the alkyl in $R^{16}$ is $C_{1-6}$ alkyl, preferably $C_{1-3}$ alkyl, more preferably $C_{1-2}$ alkyl, and most preferably methyl. In preferred embodiments, $R^{16}$ (all instances) is a hydrogen atom or alkyl, preferably hydrogen.

As noted above, A' represents —C($R^{10}$)($R^{16}$)—, —N($R^{10}$)—, or —X—. In preferred embodiments, A' represents —C($R^{10}$)($R^{16}$)— or —X—. In embodiments, A' represents —C($R^{10}$)($R^{16}$)—. In embodiments, A' represents —N($R^{10}$)—. In embodiments, A' represents —X—.

As noted above, $R^{10}$ represents a hydrogen atom (thus forming a glycine residue), alkyl, aryl, arylalkyl, heteroaryl, or heteroarylalkyl. In preferred embodiments, $R^{10}$ is a hydrogen atom, alkyl, arylalkyl or heteroarylalkyl, more preferably a hydrogen atom, alkyl, or heteroarylalkyl, most preferably alkyl. In preferred embodiments, the alkyl in $R^{16}$ is $C_{1-6}$ alkyl, preferably $C_{1-4}$ alkyl, more preferably $C_{1-2}$ alkyl, yet more preferably methyl, propyl, or butyl, even more preferably methyl (thus forming the side chain of an alanine residue, preferably a L-alanine residue), isopropyl (thus forming a valine residue, preferably a L-valine residue), sec-butyl (thus forming a leucine residue, preferably a L-leucine residue) and isobutyl (thus forming an isoleucine residue, preferably a L-isoleucine residue), and more preferably methyl or isopropyl and most preferably methyl. In preferred embodiments, the heteroaryl in the heteroarylalkyl in $R^{10}$ is imidazolyl, preferably 1H-imidazol-4-yl. In embodiments, the alkyl in the arylalkyl and heteroarylalkyl is $C_1$-6 alkyl, preferably $C_{1-3}$ alkyl, more preferably $C_{1-2}$ alkyl, and most preferably methyl. Thus, in a preferred embodiment, the heteroarylalkyl is 1H-imidazol-4-ylmethyl, thus forming the side chain of a histidine residue, preferably a L-histidine residue.

In preferred embodiments, $R^{10}$ forms a glycine residue, an alanine residue (preferably a L-alanine residue), a valine residue (preferably a L-valine residue), or a histidine residue (preferably a L-histidine residue); more preferably $R^{10}$ forms the side chain of an alanine residue (preferably a L-alanine residue).

In embodiments, B' represents a covalent bond. In embodiments, B' represents —N($R^3$)—X—C(=O)—.

As noted above, C' represents —C($R^{11}$)($R^{16}$)—, —N($R^{11}$)—, or —X—. In preferred embodiments, C' represents —C($R^{11}$)($R^{16}$)— or —X—. In embodiments, C' represents —C($R^{11}$)($R^{16}$)—. In embodiments, C' represents —N($R^{11}$)—. In embodiments, C' represents —X—.

In preferred embodiments, $R^{11}$ represents aryl, arylalkyl, heteroaryl, or heteroarylalkyl, preferably arylalkyl or heteroarylalkyl, and more preferably heteroarylalkyl. More generally, in embodiments, the aryl, arylalkyl, heteroaryl, and heteroarylalkyl in $R^{11}$ is substituted, preferably with hydroxy. In other embodiments, the aryl, arylalkyl, heteroaryl, and heteroarylalkyl group is unsubstituted. In preferred embodiments, the aryl group in the arylalkyl is optionally substituted as noted above, more preferably substituted with one hydroxy group, preferably in position 4. In embodiments, the aryl forming the aryl or the arylalkyl is substituted or unsubstituted phenyl or naphthyl, preferably phenyl unsubstituted or substituted with hydroxy, preferably at position 4. In embodiments, the heteroaryl forming the heteroaryl or heteroarylalkyl is substituted or unsubstituted triazolyl, imidazolyl or indolyl, preferably imidazolyl or indolyl, more preferably 1H-imidazol-4-yl or 1H-indol-3-yl-, more preferably unsubstituted. In embodiments, the alkyl in the arylalkyl and heteroarylalkyl is $C_{1-6}$ alkyl, preferably $C_{1-3}$ alkyl, more preferably $C_{1-2}$ alkyl, and most preferably methyl. Thus, in embodiments, the heteroarylalkyl is 1H-indol-3-yl-methyl, thus forming the side chain of a tryptophan residue, preferably a D-tryptophan residue, or 1H-imidazol-4-yl-methyl, thus forming the side chain of a histidine residue, preferably a D-histidine residue. Preferably, the heteroarylalkyl is 1H-imidazol-4-yl-methyl. Further, in embodiments, the arylalkyl is thus unsubstituted benzyl, thus forming the side chain of a phenylalanine residue, preferably a D-phenylalanine residue, benzyl substituted with hydroxy, preferably at the para position on the phenyl ring, thus forming the side chain of a tyrosine residue, preferably a D-tyrosine residue, or —CH$_2$—CH$_2$-phenyl, thus forming the side chain of a homophenylalanine residue, preferably a D-homophenylalanine residue.

In preferred embodiments, $R^{11}$ forms the side chain of a tryptophan residue, preferably a D-tryptophan residue.

As noted above, D' represents —C($R^{12}$)($R^{16}$)—, —N($R^{12}$)—, or —X—. In preferred embodiments, D' represents —C($R^{12}$)($R^{16}$)— or —X—. In embodiments, D' represents —C($R^{12}$)($R^{16}$)—. In embodiments, D' represents —N($R^{12}$)—. In embodiments, D' represents —X—.

As noted above, $R^{12}$ represents a hydrogen atom, alkyl optionally interrupted by —N($R^3$)— and/or —O—, aryl, arylalkyl, heteroaryl, or heteroarylalkyl, preferably alkyl optionally interrupted by —N($R^3$)— and/or —O—. In preferred embodiments, the alkyl is uninterrupted. In preferred embodiments, the alkyl is $C_{1-6}$ alkyl, preferably $C_{1-4}$ alkyl, more preferably $C_{1-3}$ alkyl, and yet more preferably methyl (thus forming the side chain of an alanine residue, preferably a L-alanine residue).

As noted above, E' represents —C($R^{13}$)($R^{16}$)—, —N($R^{13}$)—, —X—, or —Y—. In embodiments, E' represents —C($R^{13}$)($R^{16}$)—. In embodiments, E' represents —N($R^{13}$)—. In embodiments, E' represents —X—. In embodiments, E' represents —Y—.

In preferred embodiments, $R^{13}$ represents aryl, arylalkyl, heteroaryl, or heteroarylalkyl, preferably heteroarylalkyl (especially when E' represents —C($R^{13}$)—) or arylalkyl (especially when E' represents —N($R^{13}$)—), and more preferably heteroarylalkyl. In embodiments, the aryl, arylalkyl, heteroaryl, and heteroarylalkyl in $R^{13}$ is substituted, preferably with hydroxy or alkoxy, preferably alkoxy, more preferably methoxy, preferably at the para position. In embodiments, the aryl, arylalkyl, heteroaryl, and heteroarylalkyl group in $R^{13}$ is unsubstituted. In embodiments, the aryl forming the aryl or the arylalkyl in $R^{13}$ is substituted or unsubstituted phenyl or naphthyl, preferably phenyl unsubstituted or substituted with hydroxy or alkoxy, preferably alkoxy, more preferably methoxy, preferably at the para position. In embodiments, the heteroaryl forming the heteroaryl or heteroarylalkyl in $R^{13}$ is substituted or unsubstituted substituted or unsubstituted triazolyl, imidazolyl or indolyl, preferably imidazolyl or indolyl, more preferably 1H-imidazol-4-yl or 1H-indol-3-yl-, most preferably unsubstituted. In embodiments, the alkyl in the arylalkyl and heteroarylalkyl is $C_{1-6}$ alkyl, preferably $C_{1-3}$ alkyl, more preferably $C_{1-2}$ alkyl, and most preferably methyl. Thus, in embodiments, the heteroarylalkyl is 1H-indol-3-yl-methyl, thus forming a tryptophan residue, preferably a L-tryptophan residue, or 1H-imidazol-4-yl-methyl, thus forming the side chain of a histidine residue, preferably a L-histidine residue. Preferably, the heteroarylalkyl is 1H-indol-3-yl-methyl. Further, in embodiments, the arylalkyl is thus:
  unsubstituted benzyl, thus forming the side chain of a phenylalanine residue, preferably a L-phenylalanine residue,
  benzyl substituted with hydroxy, preferably at the para position on the phenyl ring, thus forming the side chain of a tyrosine residue, preferably a L-tyrosine residue, or
  benzyl substituted with alkoxy, preferably methoxy, preferably at the para position on the phenyl ring, thus forming the side chain of a O-methyltyrosine residue, preferably a L-O-methyltyrosine residue, or
  —CH$_2$—CH$_2$-phenyl, thus forming a homophenylalanine residue, preferably a L-homophenylalanine residue.

Preferably, the arylalkyl is benzyl substituted with methoxy at the para position.

In preferred embodiments, $R^{13}$ forms the side chain of a tryptophan residue (preferably a L-tryptophan residue), or the side chain of an O-methyltyrosine residue (preferably a L-O-methyltyrosine residue), more preferably $R^{13}$ forms the side chain of a tryptophan residue (preferably a L-tryptophan residue).

As noted above, F' represents —C($R^{14}$)($R^{16}$)— or —N($R^{14}$)—. In embodiments, F' represents —C($R^{14}$)—. In embodiments, F' represents —N($R^{14}$)—.

In preferred embodiments, $R^{14}$ represents aryl, arylalkyl, heteroaryl, or heteroarylalkyl, preferably arylalkyl. In embodiments, the aryl, arylalkyl, heteroaryl, and heteroarylalkyl in $R^{14}$ is substituted, preferably with hydroxy, preferably at the para position on the phenyl ring. In embodiments, the aryl, arylalkyl, heteroaryl, and heteroarylalkyl group in $R^{14}$ is unsubstituted. In embodiments, the aryl forming the aryl or the arylalkyl in $R^{14}$ is substituted or unsubstituted phenyl or naphthyl, preferably phenyl unsubstituted or substituted with hydroxy, preferably at the para position on the phenyl ring. In embodiments, the heteroaryl forming the heteroaryl or heteroarylalkyl in $R^{14}$ is substituted or unsubstituted triazolyl, imidazolyl or indolyl, preferably imidazolyl or indolyl, more preferably 1H-imidazol-4-yl or 1H-indol-3-yl-, more preferably unsubstituted. In embodiments, the alkyl in the arylalkyl and heteroarylalkyl in $R^{14}$ is $C_{1-6}$ alkyl, preferably $C_{1-3}$ alkyl, more preferably $C_{1-2}$ alkyl, and most preferably methyl. Thus, in embodiments, the heteroarylalkyl is 1H-indol-3-yl-methyl, thus forming the side chain of a tryptophan residue, preferably a D-tryptophan residue, or 1H-imidazol-4-yl-methyl, thus forming the side chain of a histidine residue, preferably a D-histidine residue. Further, in embodiments, the arylalkyl is thus:

- unsubstituted benzyl, thus forming the side chain of a phenylalanine residue, preferably a D-phenylalanine residue,
- benzyl substituted with hydroxy, preferably at the para position on the phenyl ring, thus forming the side chain of a tyrosine residue, preferably a D-tyrosine residue, or
- benzyl substituted with alkoxy, preferably methoxy, preferably at the para position, thus forming the side chain of a O-methyltyrosine residue, preferably a D-O-methyltyrosine residue, or
- —$CH_2$—$CH_2$-phenyl, thus forming the side chain of a homophenylalanine residue, preferably a D-homophenylalanine residue.

Preferably, the arylalkyl is unsubstituted benzyl. Hence, in preferred embodiments, In preferred embodiments, $R^{14}$ forms the side chain of a phenylalanine residue (preferably a D-phenylalanine residue).

As noted above, G' represents —$C(R^{15})(R^{16})$—, —$N(R^{15})$—, or —Y—. In preferred embodiments, G' represents —$C(R^{15})(R^{16})$— or —Y—. In embodiments, G' represents —$C(R^{15})$—. In embodiments, G' represents —$N(R^{15})$—. In embodiments, G' represents —Y—.

As noted above, $R^{15}$ represents -alkyl-$N(R^4)_2$, wherein each $R^4$ independently representing a hydrogen atom, alkyl, alkenyl, alkynyl, alkenynyl, aryl, or $C(=NH)$—$NH_2$. In preferred embodiments, the alkyl in -alkyl-$N(R^4)_2$ is $C_{1-6}$ alkyl, preferably $C_{3-5}$ alkyl, more preferably $C_3$ alkyl or $C_4$ alkyl, preferably n-butyl. In preferred embodiments, one or both, preferably both, $R^4$ represents an hydrogen atom. Thus, in preferred embodiments, $R^{15}$ represents aminobutyl (—$CH_2$—$CH_2$—$CH_2$—$CH_2$—$NH_2$), thus forming the side chain of a lysine residue, preferably a L-lysine residue. In another embodiment, $R^{15}$ represents aminopropyl (—$CH_2$—$CH_2$—$CH_2$—$NH_2$), thus forming the side chain of an ornithine residue, preferably a L-ornithine residue Location of —X— and —Y—

As noted above, the cyclic peptide comprises exactly one —X— and exactly one —Y—.

In an embodiment, A' represents —X—. In another embodiment, B' represents —$N(R^3)$—X—$C(=O)$—. In an alternative embodiment, C' represents —X—. In yet another embodiment, D' represents —X—. In yet another embodiment, E' represents —X—. In an embodiment, E' represents —Y—. In another embodiment, G' represents —Y—.

Hence, the X and Y groups in the above formula constitute (for A', C', D', E', and G') or are part of (for B') the following groups:

| Embodiments | Location of -X- | Location of -Y- |
|---|---|---|
| I | A' | E' |
| II | A' | G' |
| III | B' | E' |
| IV | B' | G' |
| V | C' | E' |
| VI | C' | G' |
| VII | D' | E' |
| VIII | D' | G' |
| IX | E' | G' |

In an embodiment, the cyclic peptide is according to any one of the above embodiments I to IX, all of the above embodiments I to IX, or any subset embodiments I to IX. In preferred embodiments, the cyclic peptide is according to embodiment II, IV, IV, VIII, or IX, preferably embodiment IV, IV, VIII, or IX, more preferably embodiment IV or VI, most preferably embodiment IV.

In an embodiment, the cyclic peptide is as defined above, with the added proviso that when E' represents —Y—, A' represents —X— or B' represents —$N(R^3)$—X—$C(=O)$—, thus excluding embodiments V and VII.

In an embodiment, the cyclic peptide is as defined above, with the added proviso that when A' represents —X—, G' does not represents —Y— (i.e. G' represents —$C(R^{15})$— or —$N(R^{15})$—), thus excluding embodiment II.

In a preferred embodiment, A' represents —$C(R^{10})$— or —$N(R^{10})$—. In other words, A' does not represent —X—, thus excluding embodiments I and II.

In a preferred embodiment, G' represents —Y—, thus excluding embodiments I, III, V, and VII. In a most preferred embodiment, B' represents —$N(R^3)$—X—$C(=O)$— and G' represents —Y—, thus excluding embodiment IV.

In embodiment, the cyclic peptide is:

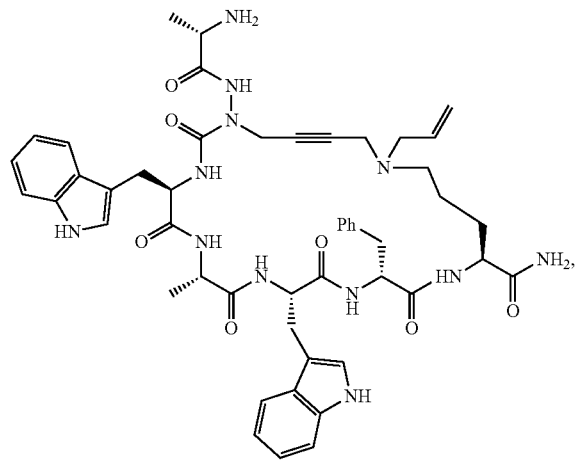

MPE-048

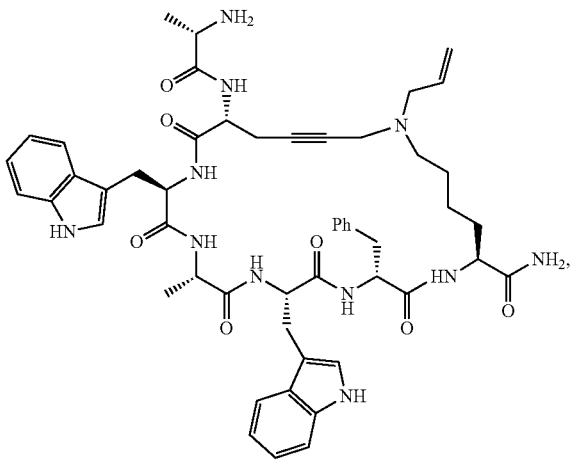

MPE-074

-continued
MPE-075
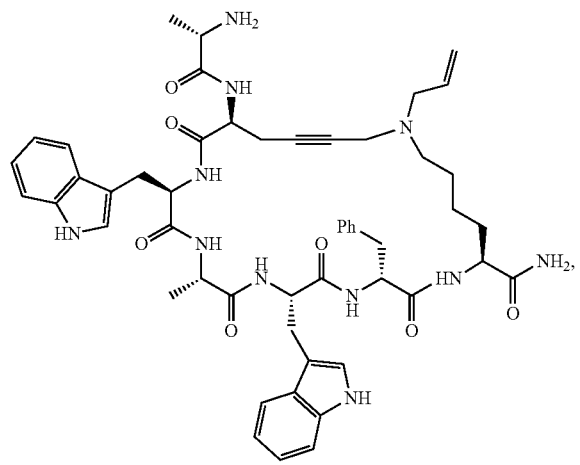
MPE-110
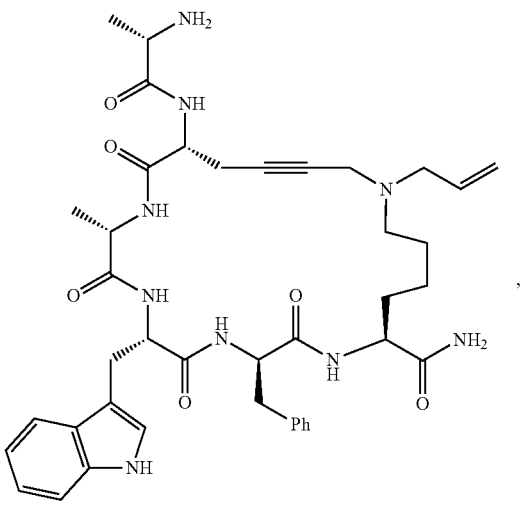
MPE-111
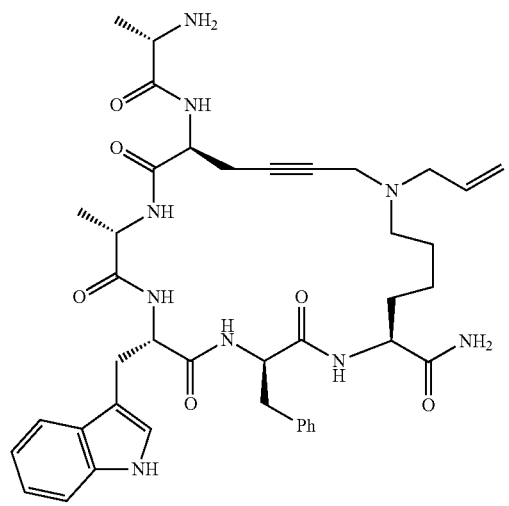
MPE-189
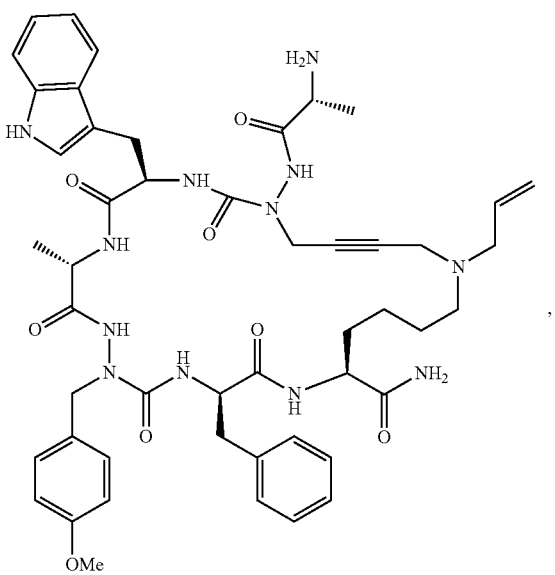
MPE-191
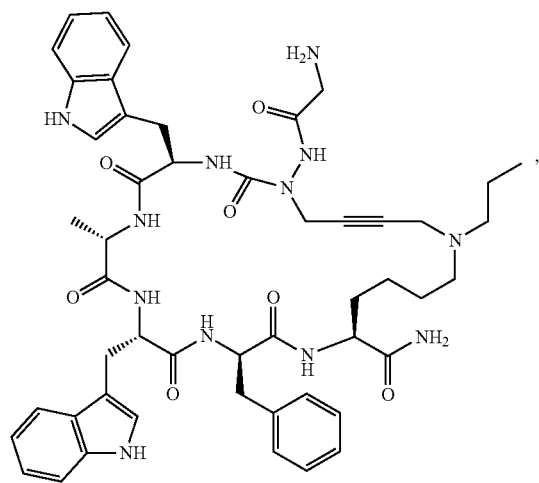
MPE-192
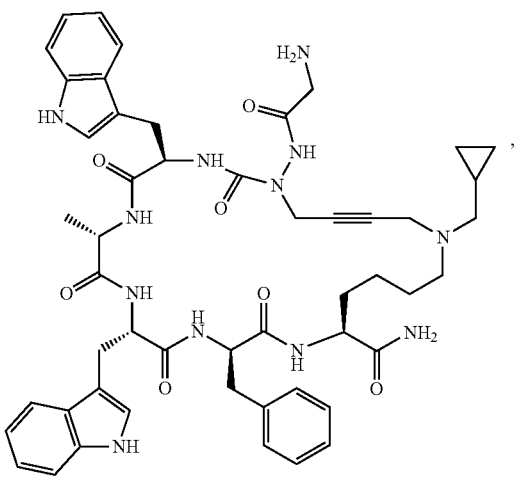

-continued
MPE-193
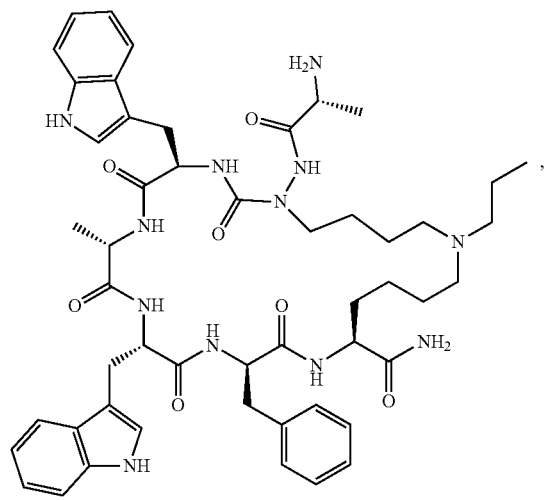
MPE-201
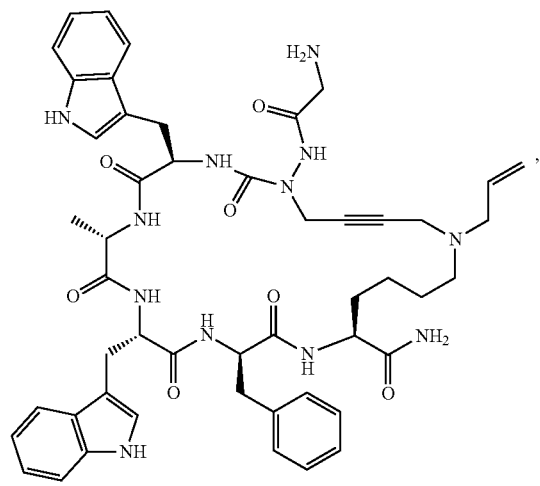
MPE-202
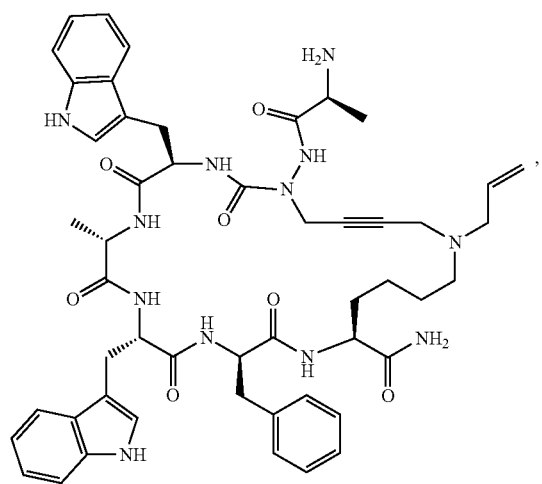
MPE-203
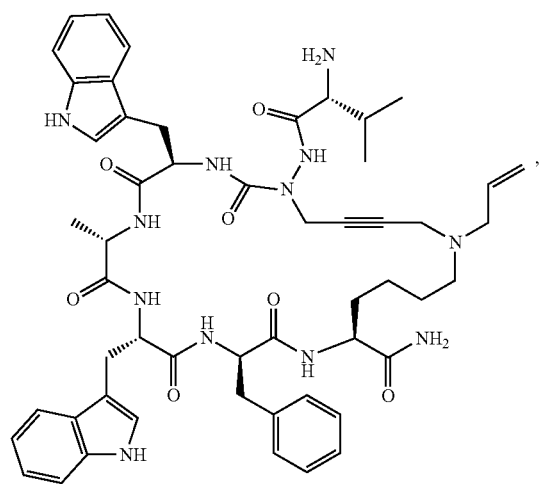
MPE-206 (8)
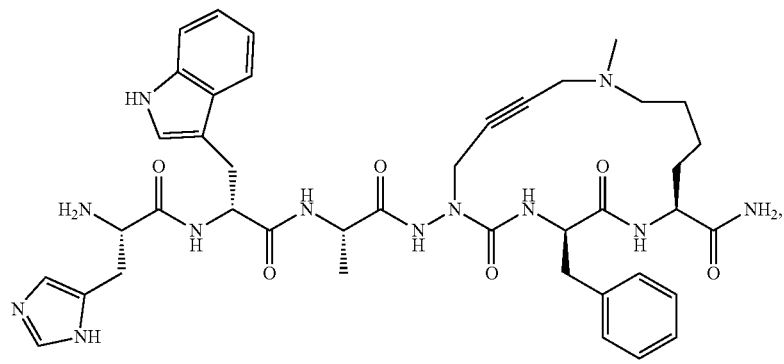

-continued
MPE-210 (9)
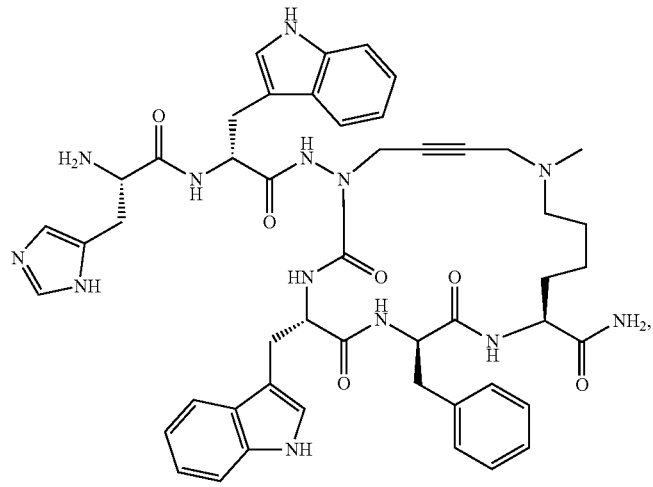
MPE-265 (17)
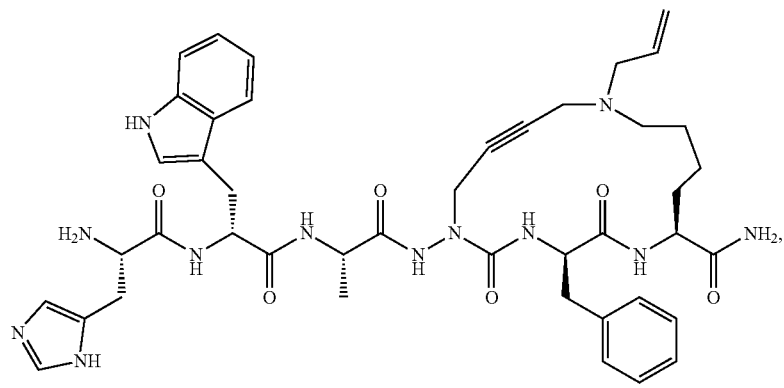
MPE-266
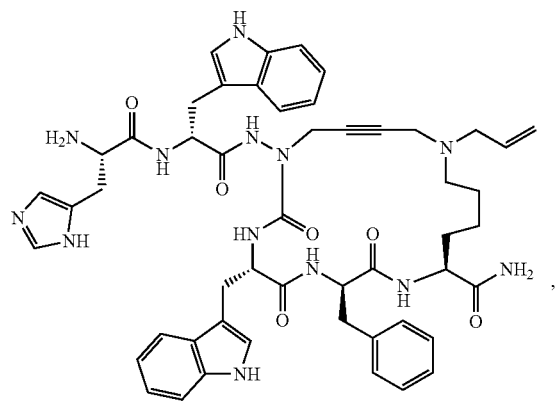
MPE-267
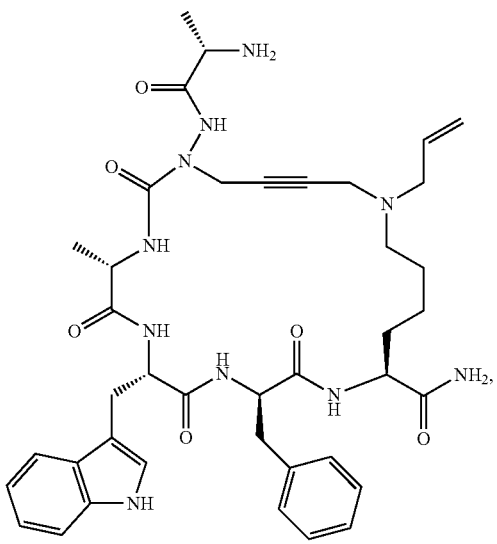

-continued
MPE-290 (30)
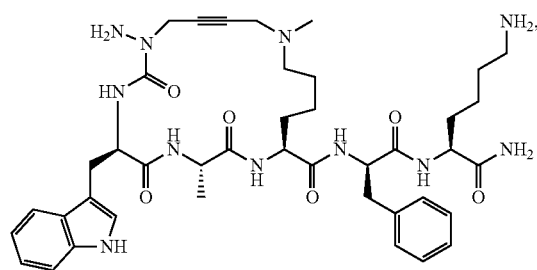
MPE-291 (31)
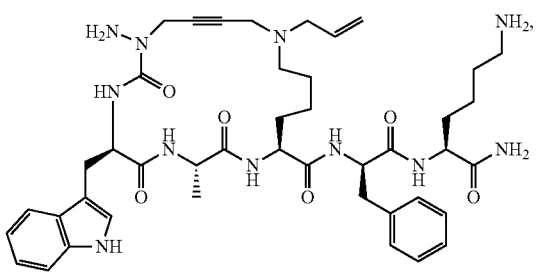
MPE-293 (32)
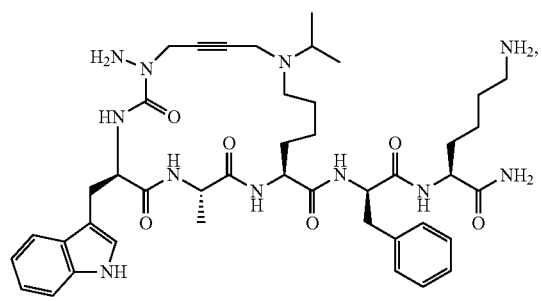
MPE-298
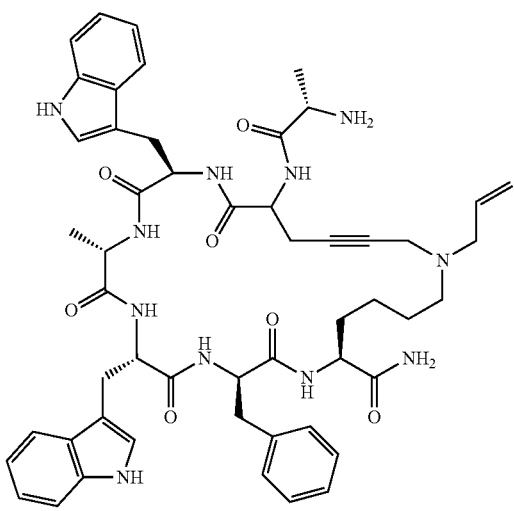
MPE-300
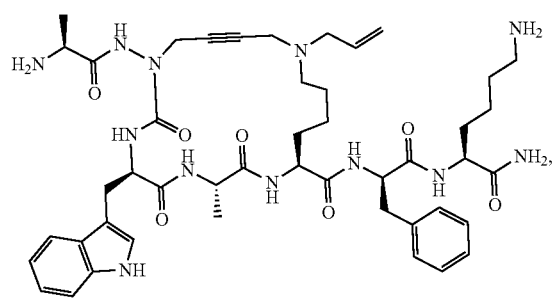
MPE-308
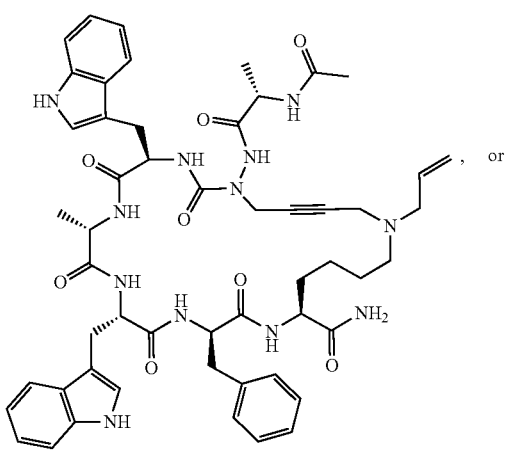
or

MPE-310

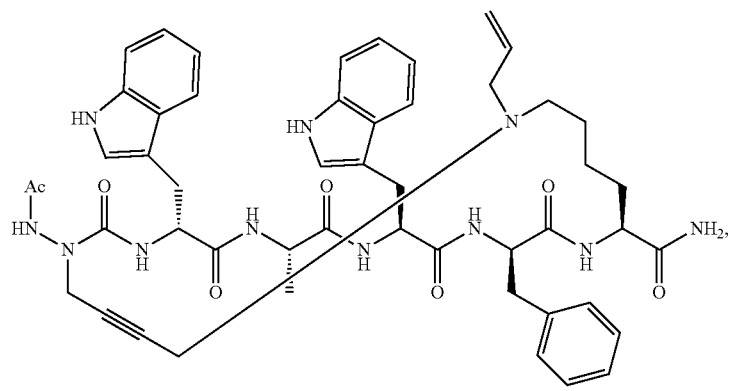

MPE-312 (34)

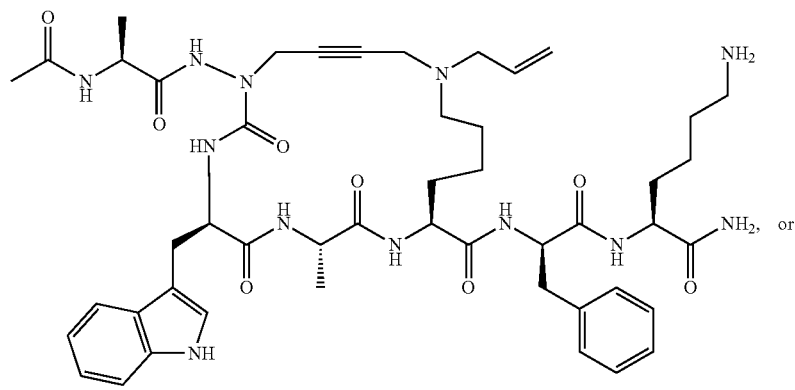

MPE-314 (35)

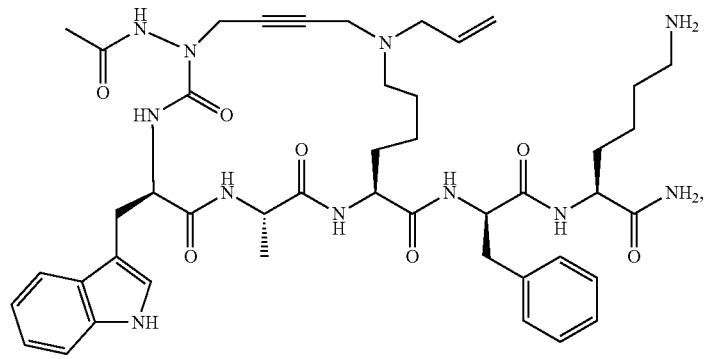

or a pharmaceutically acceptable salt thereof; preferably the cyclic peptide is MPE-075, MPE-111, MPE-189, MPE-191, MPE-192, MPE-266, MPE-267, MPE-298, MPE-300, MPE-308, or MPE-310 or a pharmaceutically acceptable salt thereof; more preferably the cyclic peptide is MPE-267, MPE-298, MPE-075, or MPE-192 or a pharmaceutically acceptable salt thereof. In an embodiment, the cyclic peptide is MPE-267 or a pharmaceutically acceptable salt thereof. In another embodiment, the cyclic peptide is MPE-075 or a pharmaceutically acceptable salt thereof. In another embodiment, the cyclic peptide is MPE-298 or a pharmaceutically acceptable salt thereof. In another embodiment, the cyclic peptide is MPE-192 or a pharmaceutically acceptable salt thereof.

In an embodiment, the cyclic peptide is as defined above, with the added proviso that the cyclic peptide is not:

MPE-268 (19)

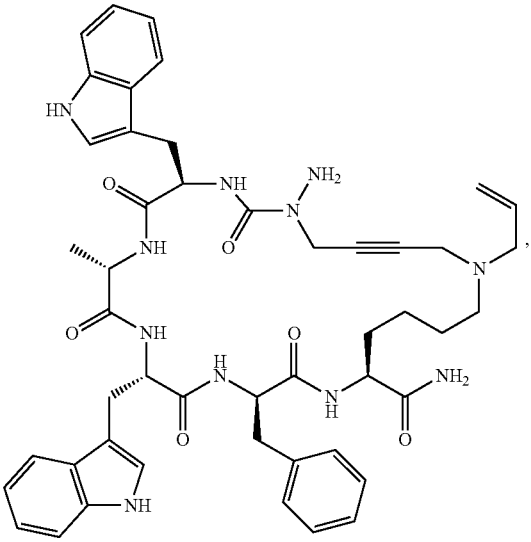

or a pharmaceutically acceptable salt thereof.

In further embodiments, the cyclic peptide is of formula I as defined above except that one or more of the —C(=O)— group or —N(R³)— group in the peptide main chain, i.e. one of the —C(=O)— or —N(R³)— group forming a peptidic bond, is replaced by a similarly reactive group. In preferred embodiments, one or more of the —C(=O)— group in the peptide main chain is replaced by —S(=O)₂—. In preferred embodiments, the —S(=O)₂— group is adjacent to an aza functional group in the cyclic peptide main chain. In another embodiment, the —S(=O)₂— group replaces the C(=O)— between C' and D'.

In further embodiments, the cyclic peptide is of formula I as defined above except that one or more of the —N(R³)— group in the peptide main chain, i.e. one of the —N(R³)— group forming a peptidic bond, is attached to a β-carbon atom rather than to an α carbon atom. The α and β carbon atom being as follows (example shown is leucine):

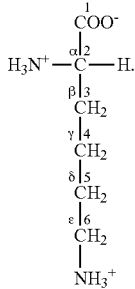

As noted above, in the present invention, there is provided a cyclic peptide of formula (I), as defined above, or a pharmaceutically acceptable salt or ester thereof. In an embodiment, there is provided a cyclic peptide of formula (I) or a pharmaceutically acceptable salt thereof (i.e. in this embodiment, pharmaceutically acceptable esters are excluded). In another embodiment, there is provided a cyclic peptide of formula (I) (i.e., in this embodiment, pharmaceutically acceptable esters and salts are excluded).

The term "salt(s)", as employed herein, denotes acidic salts formed with inorganic and/or organic acids, as well as basic salts formed with inorganic and/or organic bases. Salts for use in pharmaceutical compositions will be pharmaceutically acceptable salts, but other salts may be useful in the production of the compounds described herein.

The term "pharmaceutically acceptable salt" refers to salts of the compounds described herein that are pharmacologically acceptable and substantially non-toxic to the subject to which they are administered. More specifically, these salts retain the biological effectiveness and properties of the compounds and are formed from suitable non-toxic organic or inorganic acids or bases.

For example, these salts include acid addition salts of the compounds described herein which are sufficiently basic to form such salts. Such acid addition salts include acetates, adipates, alginates, lower alkanesulfonates such as a methanesulfonates, trifluoromethanesulfonates or ethanesulfonates, arylsulfonates such as a benzenesulfonates, 2-naphthalenesulfonates, or toluenesulfonates (also known as tosylates), ascorbates, aspartates, benzoates, benzenesulfonates, bisulfates, borates, butyrates, citrates, camphorates, camphorsulfonates, cinnamates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydrogen sulphates, 2-hydroxyethanesulfonates, itaconates, lactates, maleates, mandelates, methanesulfonates, nicotinates, nitrates, oxalates, pamoates, pectinates, perchlorates, persulfates, 3-phenylpropionates, phosphates, picrates, pivalates, propionates, salicylates, succinates, sulfates, sulfonates, tartrates, thiocyanates, undecanoates and the like.

Additionally, acids which are generally considered suitable for the formation of pharmaceutically useful salts from basic pharmaceutical compounds are discussed, for example, by P. Stahl et al., Camille G. (eds.) *Handbook of Pharmaceutical Salts. Properties, Selection and Use.* (2002) Zurich: Wiley-VCH; S. Berge et al., *Journal of Pharmaceutical Sciences* (1977) 66(1) 1-19; P. Gould, *International J. of Pharmaceutics* (1986) 33 201-217; Anderson et al., *The Practice of Medicinal Chemistry* (1996), Academic Press, New York; and in The Orange Book (Food & Drug Administration, Washington, D.C.).

Also, where the compounds described herein are sufficiently acidic, the salts of the invention include base salts formed with an inorganic or organic base. Such salts include alkali metal salts such as sodium, lithium, and potassium salts; alkaline earth metal salts such as calcium and magnesium salts; metal salts such as aluminum salts, iron salts, zinc salts, copper salts, nickel salts and cobalt salts; inorganic amine salts such as ammonium or substituted ammonium salts, such as trimethylammonium salts; and salts with organic bases (for example, organic amines) such as chloroprocaine salts, dibenzylamine salts, dicyclohexylamine salts, diethanolamine salts, ethylamine salts (including diethylamine salts and triethylamine salts), ethylenediamine salts, glucosamine salts, guanidine salts, methylamine salts (including dimethylamine salts and trimethylamine salts), morpholine salts, N,N'-dibenzylethylenediamine salts, N-benzyl-phenethylamine salts, N-methylglucamine salts, phenylglycine alkyl ester salts, piperazine salts, piperidine salts, procaine salts, t-butyl amine salts, tetramethylammonium salts, t-octylamine salts, tris-(2-hydroxyethyl)amine salts, and tris(hydroxymethyl)aminomethane salts.

Such salts can be formed quite readily by those skilled in the art using standard techniques. Indeed, the chemical modification of a pharmaceutical compound (i.e. drug) into a salt is a technique well known to pharmaceutical chemists, (See, e.g., H. Ansel et al., *Pharmaceutical Dosage Forms and Drug Delivery Systems* (6$^{th}$ Ed. 1995) at pp. 196 and 1456-1457). Salts of the compounds described herein may be formed, for example, by reacting the compound with an amount of acid or base, such as an equivalent amount, in a medium such as one in which the salt precipitates or in an aqueous medium followed by lyophilization.

The present invention also encompasses the use of pharmaceutically acceptable prodrug or esters of the cyclic peptides defined herein. The term "ester(s)", as employed herein, refers to cyclic peptides of the invention or salts thereof in which hydroxy groups have been converted to the corresponding esters using, for example, inorganic or organic anhydrides, acids, or acid chlorides. The term "pharmaceutically acceptable esters" refers to esters of the cyclic peptides described herein that are pharmacologically acceptable and substantially non-toxic to the subject to which they are administered. More specifically, these esters retain the biological effectiveness and properties of the cyclic peptides described herein and act as prodrugs which, when administered in vivo, are metabolized or cleaved in such a manner as to produce the parent cyclic peptides.

Examples of esters include among others the following groups (1) carboxylic acid esters; (2) sulfonate esters, such as alkyl- or arylalkyl-sulfonate esters (for example, methanesulfonate ester); (3) phosphonate esters; (4) mono-, di- or triphosphate esters (including phosphoramidic cyclic esters); (5) carbamic acid ester (for example N-methylcarbamic ester); and (6) carbonic acid ester (for exemple methylcabonate), obtained by esterification of the hydroxy groups, the ester grouping comprising for example straight or branched chain alkyl (e.g., ethyl, n-propyl, t-butyl, n-butyl, methyl, propyl, isopropyl, butyl, isobutyl or pentyl), alkoxyalkyl (e.g., methoxymethyl, acetoxymethyl and 2,2-dimethylpropionyloxymethyl), arylalkyl (e.g., benzyl), aryloxyalkyl (e.g., phenoxymethyl), aryl (e.g., phenyl optionally substituted with, for example, halogen, $C_{1-4}$ alkyl, or $C_{1-4}$ alkoxy or amino). Further information concerning the preparation and use of esters for the delivery of pharmaceutical compounds is available in Design of Prodrugs. Bundgaard H ed. (Elsevier, 1985). See also, H. Ansel et al., *Pharmaceutical Dosage Forms and Drug Delivery Systems* (6$^{th}$ Ed. 1995) at pp. 108-109; Krogsgaard-Larsen, et. al., *Textbook of Drug Design and Development* (2$^{nd}$ Ed. 1996) at pp. 152-191; Jarkko Rautio et al., *Nat. Rev. Drug Discov.*, 7, pp. 255-270 (2008); and Pen-Wei Hsieh et al., *Curr. Pharm. Des.*, 15(19), pp. 2236-2250 (2009).

The cyclic peptides described herein may be esterified by a variety of conventional procedures including reacting the appropriate anhydride, carboxylic acid or acid chloride with the alcohol group of a compound described herein. For example, an appropriate anhydride may be reacted with an alcohol in the presence of a base, such as a 1,8-bis[dimethylamino]naphthalene or N,N-dimethylaminopyridine, to facilitate acylation. Also, an appropriate carboxylic acid can be reacted with the alcohol in the presence of a dehydrating agent such as dicyclohexylcarbodiimide, 1-[3-dimethylaminopropyl]-3-ethylcarbodiimide or other water soluble dehydrating agents which are used to drive the reaction by the removal of water, and, optionally, an acylation catalyst. Esterification can also be effected using the appropriate carboxylic acid. Reaction of an acid chloride with the alcohol can also be carried out. When a compound described herein contains a number of free hydroxy groups, those groups not being converted into a prodrug functionality may be protected (for example, using a t-butyl-dimethylsilyl group), and later deprotected. Also, enzymatic methods may be used to selectively phosphorylate or dephosphorylate alcohol functionalities. One skilled in the art would readily know how to successfully carry out these as well as other known methods of esterification of alcohols.

The compounds described herein may exist in unsolvated as well as solvated forms with solvents such as water (hydrates), ethanol (ethanolates), and the like, and it is intended that the invention embrace both solvated and unsolvated forms.

As will be explained in detail below, in embodiments, the above cyclic peptide is a GHRP-6 analog. As such, these compounds can be referred to as "cyclic GHRP-6 analogs" or "cyclic peptide GHRP-6 analogs".

In an embodiment, the cyclic peptide exhibits an $IC_{50}$ of about $1 \times 10^{-5}$ M or less in the competition CD36 binding assay described in the examples below. In another embodiment, the cyclic peptide exhibits an $IC_{50}$ of about $0.5 \times 10^{-6}$ M or less in the competition CD36 binding assay described in the examples below. In another embodiment, the cyclic peptide exhibits an $IC_{50}$ of about $1 \times 10^{-6}$ M or less in the competition CD36 binding assay described in the examples below. In another embodiment, the cyclic peptide exhibits an $IC_{50}$ of about $0.5 \times 10^{-6}$ M or less in the competition CD36 binding assay described in the examples below. In another embodiment, the cyclic peptide exhibits an $IC_{50}$ of $1 \times 10^{-7}$ M or less in the competition CD36 binding assay described in the examples below.

CD36 Modulation

In embodiments, the above cyclic peptides (which are herein also referred to as "the compounds") or pharmaceutically acceptable esters or salts thereof have the ability to modulate (e.g., inhibit) CD36 activity (CD36 modulators). As used herein, the term "modulator" refers to a compound that alters or elicits an activity of CD36. For example, the presence of a modulator may result in an increase or decrease in the magnitude of a certain activity compared to the magnitude of the activity in the absence of the modulator. In certain embodiments, a modulator is an inhibitor or antagonist, which decreases the magnitude of one or more activities. In certain embodiments, an inhibitor completely prevents one or more biological activities. As used herein, the terms "inhibiting," "reducing," "preventing," or "antagonizing," or any variations of these terms as used herein, refer to a measurable decrease of a biological activity. In some embodiments, the decrease is a 10%, 15%, 20%, 30%, 40%, 50%, 60%, 70%, 80%, 90%, or 95% reduction in the biological activity relative to a control.

CD36, also known as FAT, SCARB3, SR-B2, GP88, glycoprotein IV (gpIV) and glycoprotein IIIb (gpIIIb), is an integral membrane protein found on the surface of many cell types in vertebrate animals. CD36 is a member of the class B scavenger receptor family of cell surface proteins. CD36 has been shown to bind many ligands including collagen, thrombospondin, erythrocytes parasitized with *Plasmodium falciparum*, oxidized low density lipoproteins, native lipoproteins, oxidized phospholipids, beta-amyloid and long-chain fatty acids. CD36 was also shown to be involved in Toll-Like Receptor 2 (TLR2) signaling (i.e., to act as a co-receptor for TLR2), and more specifically signaling through TLR2/TLR6 heterodimers. TLR2 is able to recognize a diverse set of pathogen-associated motifs including several components of Gram-positive bacteria such as peptidoglycan, lipoteichoic acid (LTA), lipoarabinomanan, lipoproteins, as well as different LPS from certain Gram-negative bacteria, yeast, spirochete, and fungi. Its promiscuity has been attributed to its unique ability to heterodimerize with TLRs 1 and 6. TLR2 heteromer usage has mainly been investigated using bacterial lipoproteins. Studies using diacylated and triacylated lipoproteins have revealed that TLR2/6 heterodimers are involved in activation by diacylated lipoproteins, whereas triacylated lipoproteins induce activation of the innate immune system independently of TLR6, and mainly through TLR21TLR1 heterodimers. Studies by Hoebe et al. (*Nature* 433, 523-527) and Triantafilou (*The Journal of Biological Chemistry*, 281: 31002-31011) have shed more light into TLR2 heterotypic associations by demonstrating that TLR2/TLR6 heterodimers also require CD36 to sense diacylated lipoproteins, whereas TLR2/TLR1 heterodimers do not. There is also evidence that TLR4 and CD36 play a relevant role in the formation of foam cells induced by oxidized low-density lipoprotein (oxLDL), which is involved in the pathogenesis of atherosclerosis (Chavez-Sanchez, *Hum Immunol.* 2014 April; 75(4):322-9). There is also evidence that CD36-TLR4-TLR6 activation is involved in sterile inflammation induced by atherogenic lipids and β-amyloid, which is associated with atherosclerosis and Alzheimer's disease, respectively (Stewart et al., *Nature Immunology* 11, 155-161 (2010)). CD36 expression/activity has also been associated with fatty liver disease and hepatic steatosis, and more particularly nonalcoholic fatty liver disease (NAFLD) and non-alcoholic steatohepatitis (NASH).

In another aspect, the present invention provides a method for modulating CD36 activity in a cell, said method comprising contacting the cell with an effective amount of the compound, pharmaceutically acceptable ester or salt thereof defined herein. The present invention also provides the use of the compound, pharmaceutically acceptable ester or salt thereof defined herein for modulating CD36 activity in a cell. The present invention also provides the use of the compound or pharmaceutically acceptable ester or salt thereof defined herein for the manufacture of a medicament for modulating CD36 activity in a cell. The present invention also provides the compound or pharmaceutically acceptable ester or salt thereof defined herein for modulating CD36 activity in a cell. In an embodiment, the modulating is inhibiting.

In view of the importance of CD36 in numerous pathways and conditions in animals, the compound or pharmaceutically acceptable ester or salt thereof are useful in the treatment of CD36-related diseases, disorders or conditions. The present invention relates to a method for inhibiting or antagonizing CD36 activity through its interaction with the compound or pharmaceutically acceptable ester or salt thereof.

Examples of diseases and conditions associated with CD36 activity include, but are not limited to atherosclerosis, inflammation (TLR2-, TLR4- and/or TLR6-related inflammation), abnormal angiogenesis, age-related macular degeneration (dry and/or wet forms), abnormal lipid metabolism, nonalcoholic fatty liver disease (NAFLD), nonalcoholic steatohepatitis (NASH), abnormal removal of apoptotic cells, ischemia such as cerebral ischemia and myocardial ischemia, ischemia-reperfusion injury, ureteral obstruction, fibrinogenesis in chronic kidney diseases, stroke, Alzheimer's Disease, diabetes, diabetic nephropathy and obesity.

In another aspect, the present invention provides a method for reducing or inhibiting inflammation, such as TLR2-, TLR4- and/or TLR6-related inflammation (e.g., TLR2/6-related inflammation) in a biological system (cells, subject), said method comprising contacting said biological system with the cyclic peptide or a pharmaceutically acceptable ester or salt thereof described herein. In an embodiment, the cells are immune cells, such as macrophages or monocytes. In another aspect, the present invention provides a method for reducing or inhibiting the production of nitric oxide (NO) and/or pro-inflammatory cytokines/chemokines (e.g., TNFα, IL-1β, CCL2) induced by TLR2 activation/stimulation in a cell (e.g., an immune cell such as a macrophage or monocytes), said method comprising contacting said cell with the cyclic peptide or pharmaceutically acceptable ester or salt thereof described herein. The present invention also relates to the treatment of medical conditions involving the activation of TLR2 (e.g., TLR2/6), and especially immune-mediated and inflammatory diseases. TLR2 has also been implicated to have a role in a wide variety of allergic- and immune-mediated inflammatory diseases such as sepsis, ischemia/reperfusion injury to heart or kidneys, cardiovascular disease, metabolic disease, and atherosclerosis, allergies, asthma, atopy, atopic dermatitis, arthritis (rheumatoid arthritis), systemic lupus erymathosis (SLE), and diabetes (O'Neill et al., 2009, *Pharmacol. Rev.*, vol. 61, p. 177). In another embodiment, the disease is associated with the NLPR3 inflammasome.

In an embodiment, the CD36-related disease, disorder or condition is atherosclerosis, age-related macular degeneration (dry and/or wet forms), fibrinogenesis in chronic kidney diseases or myocardial ischemia/reperfusion injury.

Pharmaceutical Compositions

In an embodiment, the above-mentioned compound or pharmaceutically acceptable ester or salt thereof are comprised in a pharmaceutical composition that further comprises one or more pharmaceutically acceptable carriers, diluents and/or excipients. Such compositions may be prepared in a manner well known in pharmaceutical art. Supplementary active compounds/agents can also be incorporated into the compositions. As used herein "pharmaceutically acceptable carrier", "diluent" or "excipient" includes any and all solvents, buffers, dispersion media, binders, lubricants, diluents, fillers, thickening agents, disintegrants, plasticizers, coatings, barrier layer formulations, lubricants, stabilizing agent, release-delaying agents, coatings, antibacterial, antifungal agents, and the like that are physiologically compatible and that do not interfere with effectiveness of the biological activity of the active ingredients. As those of skill would recognize, a single excipient can fulfill more than two functions at once, e.g., can act as both a binding agent and a thickening agent. As those of skill will also recognize, these terms are not necessarily mutually exclusive. The carrier, diluent and/or excipient can be suitable, for example, for oral, intravenous, parenteral, topical, intradermal, subcutaneous, intramuscular, intracranial, intraorbital, subconjunctival, ophthalmic, intraventricular, intracapsular, intraspinal, intrathecal, epidural, intracisternal, intraperitoneal, intranasal, intrauterine, intramyometrial, sublingual, vaginal, rectal, epidural or pulmonary (e.g., aerosol) administration (see *Remington: The Science and Practice of Pharmacy* by Alfonso R. Gennaro, 2003, 21$^{st}$ edition, Mack Publishing Company).

Useful diluents, e.g., fillers, include, for example and without limitation, dicalcium phosphate, calcium diphosphate, calcium carbonate, calcium sulfate, lactose, cellulose, kaolin, sodium chloride, starches, powdered sugar, colloidal silicon dioxide, titanium oxide, alumina, talc, colloidal silica, microcrystalline cellulose, silicified micro crystalline cellulose and combinations thereof. Fillers that can add bulk to tablets with minimal drug dosage to produce tablets of adequate size and weight include croscarmellose sodium NF/EP (e.g., Ac-Di-Sol®); anhydrous lactose NF/EP (e.g., Pharmatose™ DCL 21); and/or povidone USP/EP.

Binder materials include, for example and without limitation, starches (including corn starch and pregelatinized starch), gelatin, sugars (including sucrose, glucose, dextrose and lactose), polyethylene glycol, povidone, waxes, and natural and synthetic gums, e.g., acacia sodium alginate, polyvinylpyrrolidone (PVP), cellulosic polymers (e.g., hydroxypropyl cellulose, hydroxypropyl methylcellulose (HPMC), methyl cellulose, hydroxyethyl cellulose, carboxymethylcellulose, colloidal silicon dioxide NF/EP (e.g., Cab-O-Sil™ M5P), Silicified Microcrystalline Cellulose (SMCC), e.g., Silicified microcrystalline cellulose NF/EP (e.g., Prosolvm SMCC 90), and silicon dioxide, mixtures thereof, and the like), veegum, and combinations thereof.

Useful lubricants include, for example, canola oil, glyceryl palmitostearate, hydrogenated vegetable oil (type I), magnesium oxide, magnesium stearate, mineral oil, poloxamer, polyethylene glycol, sodium lauryl sulfate, sodium stearate fumarate, stearic acid, talc and, zinc stearate, glyceryl behapate, glyceryl behenate magnesium lauryl sulfate, boric acid, sodium benzoate, sodium acetate, sodium benzoate/sodium acetate (in combination), DL-leucine, calcium stearate, sodium stearyl fumarate, mixtures thereof, and the like.

Bulking agents include, for example: microcrystalline cellulose, for example, AVICEL® (FMC Corp.) or EMCOCEL® (Mendell Inc.), which also has binder properties; dicalcium phosphate, for example, EMCOMPRESS® (Mendell Inc.); calcium sulfate, for example, COMPACTROL® (Mendell Inc.); and starches, for example, Starch 1500; and polyethylene glycols (CARBOWAX®).

Disintegrating or dissolution promoting agents include: starches, clays, celluloses, alginates, gums, crosslinked polymers, colloidal silicon dioxide, osmogens, mixtures thereof, and the like, such as crosslinked sodium carboxymethyl cellulose (AC-DI-SOL®), sodium croscarmelose, sodium starch glycolate (EXPLOTAB®, PRIMO JEL®) crosslinked polyvinylpolypyrrolidone (PLASONE-XL®), sodium chloride, sucrose, lactose and mannitol.

Antiadherents and glidants employable in the core and/or a coating of the solid oral dosage form may include talc, starches (e.g., cornstarch), celluloses, silicon dioxide, sodium lauryl sulfate, colloidal silica dioxide, and metallic stearates, among others.

Examples of silica flow conditioners include colloidal silicon dioxide, magnesium aluminum silicate and guar gum.

Suitable surfactants include pharmaceutically acceptable non-ionic, ionic and anionic surfactants. An example of a surfactant is sodium lauryl sulfate. If desired, the pharmaceutical composition to be administered may also contain minor amounts of nontoxic auxiliary substances such as wetting or emulsifying agents, pH-buffering agents and the like, for example, sodium acetate, sorbitan monolaurate, triethanolamine sodium acetate, triethanolamine oleate, etc. If desired, flavoring, coloring and/or sweetening agents may be added as well.

Examples of stabilizing agents include acacia, albumin, polyvinyl alcohol, alginic acid, bentonite, dicalcium phosphate, carboxymethylcellulose, hydroxypropylcellulose (HPC), colloidal silicon dioxide, cyclodextrins, glyceryl monostearate, hydroxypropyl methylcellulose (HPMC), magnesium trisilicate, magnesium aluminum silicate, propylene glycol, propylene glycol alginate, sodium alginate, carnauba wax, xanthan gum, starch, stearate(s), stearic acid, stearic monoglyceride and stearyl alcohol.

Examples of thickening agent can be for example talc USP/EP, a natural gum, such as guar gum or gum arabic, or a cellulose derivative such as microcrystalline cellulose NF/EP (e.g., Avicel™ PH 102), methylcellulose, ethylcellulose or hydroxyethylcellulose. A useful thickening agent is hydroxypropyl methylcellulose, an adjuvant which is available in various viscosity grades.

Examples of plasticizers include: acetylated monoglycerides; these can be used as food additives; alkyl citrates, used in food packaging, medical products and cosmetics; triethyl citrate (TEC); acetyl triethyl citrate (ATEC), higher boiling point and lower volatility than TEC; tributyl citrate (TBC); acetyl tributyl citrate (ATBC), compatible with PVC and vinyl chloride copolymers; trioctyl citrate (TOC), also used for gums and controlled release medicines; acetyl trioctyl citrate (ATOC), also used for printing ink; trihexyl citrate (THC), compatible with PVC, also used for controlled release medicines; acetyl trihexyl citrate (ATHC), compatible with PVC; butyryl trihexyl citrate (BTHC, trihexyl o-butyryl citrate), compatible with PVC; trimethyl citrate (TMC), compatible with PVC; alkyl sulphonic acid phenyl ester, polyethylene glycol (PEG) or any combination thereof. Optionally, the plasticizer can comprise triethyl citrate NF/EP.

Examples of permeation enhancers include: sulphoxides (such as dimethylsulphoxide, DMSO), azones (e.g. laurocapram), pyrrolidones (for example 2-pyrrolidone, 2P), alcohols and alkanols (ethanol, or decanol), glycols (for example propylene glycol and polyethylene glycol), surfactants and terpenes.

Formulations suitable for oral administration may include (a) liquid solutions, such as an effective amount of active agent(s)/composition(s) suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for compounds/compositions of the invention include ethylenevinyl acetate copolymer particles, osmotic pumps, implantable infusion systems, and liposomes. Formulations for inhalation may contain excipients, (e.g., lactose) or may be aqueous solutions containing, for example, polyoxyethylene-9-lauryl ether, glycocholate and deoxycholate, or may be oily solutions for administration in the form of nasal drops, or as a gel.

Dosage

Compositions within the scope of the present invention should contain the active agent (e.g., the above-mentioned compound or pharmaceutically acceptable ester or salt thereof) in an amount effective to achieve the desired therapeutic effect while minimizing adverse side effects. For the administration of the compound or pharmaceutically acceptable ester or salt thereof, the amount administered should be chosen so as to minimize adverse side effects. The amount of the therapeutic or pharmaceutical composition which is effective in the treatment of a particular disease, disorder or condition will depend on the nature and severity of the disease, the target site of action, the patient's weight, special diets being followed by the patient, concurrent medications being used, the administration route and other factors that will be recognized by those skilled in the art. The dosage will be adapted by the clinician in accordance with conventional factors such as the extent of the disease and different parameters from the patient. Typically, 0.001 to 100 mg/kg/day will be administered to the subject. Further, the effective dose may be 0.5 mg/kg, 1 mg/kg, 5 mg/kg, 10 mg/kg, 15 mg/kg, 20 mg/kg/25 mg/kg, 30 mg/kg, 35 mg/kg, 40 mg/kg, 45 mg/kg, 50 mg/kg, 55 mg/kg, 60 mg/kg, 70 mg/kg, 75 mg/kg, 80 mg/kg, 90 mg/kg or 100 mg/kg, or may range between any two of the foregoing values. Effective doses may be extrapolated from dose response curves derived from in vitro or animal model test systems. For example, in order to obtain an effective mg/kg dose for humans based on data generated from rat studies, the effective mg/kg dosage in rat is divided by six.

MODE(S) FOR CARRYING OUT THE INVENTION

The present invention is illustrated in further details by the following non-limiting examples.

Example 1: Materials and Methods

1. General Experimental Procedures.
   Chemicals:
   Chemicals were used as received from commercial sources without further purification unless stated otherwise. Polystyrene Rink Amide resin (0.50 mmol/g) was purchased from Advanced Chemtech™, and the manufacturer's reported loading of the resin was used in the calculation of the yields of the final products. The syntheses of MPE-308 (26), MPE-310 (27) and MPE-312 (34) were performed on CEM SpheriTide resin (0.85 mmol/g). Reagents including CuI, allyl alcohol, isopropyl alcohol, aq. 37% formaldehyde, benzophenone hydrazone, $Cs_2CO_3$, triphenylphosphine, diisopropyl azodicarboxylate (DIAD), 80% propargyl bromide in toluene, hydroxylamine hydrochloride, pyridine, formic acid (FA), 2-mercaptoethanol and DBU (1,8-diazabicycloundec-7-ene) were purchased from Aldrich®. Fmoc-Lys(Boc)-OH, Fmoc-D-Phe-OH, Fmoc-Trp(Boc)-OH, Fmoc-Ala-OH, Fmoc-D-Trp(Boc)OH, Boc-His(Trt)-OH, Boc-Lys-OH and coupling reagents including diisopropylcarbodiimide (DIC), N,N'-disuccinimidyl carbonate (DSC), hydroxybenzotriazole (HOBt) were purchased from CS Bio™. Fmoc-Lys(o-NBS)—OH and Boc-Lys(o-NBS)—OH were synthesized according to a literature protocol (D. R. Halpin, J. A. Lee, S. J. Wrenn, P. B. Harbury, *Plos Biol.* 2004, 2, 1031-1038). All solvents were obtained from Fisher Scientific. Anhydrous tetrahydrofuran (THF) and methanol were obtained by passage through a solvent filtration system (Glass-Contour, Irvine, CA). Thin-layer chromatography was performed on silica gel 60 F254 plates from Merck™. Analyses by LCMS were performed on either an Agilent™ Technologies 1100 Series instrument with ESI ion-source, single quadropole mass detection and positive mode ionization or a ThermoFinnigan™ LCQ Advantage MS with ESI ion-source, ion-trap mass detection, positive mode ionization and equipped with a Gilson™ LC 322 pump containing auto-sampler and injector. Analyses of crude peptide samples were determined with a Sunfire™ C18 column (pore size: 110 Å, particle size: 3.5 µm; 50×2.1 mm) at a flow rate of 0.4 mL/min using a linear gradient of MeOH or $CH_3CN$ containing 0.1% FA in water. Preparative RP-HPLC was conducted on a Waters™ PrepLC instrument with a reverse-phase Sunfire™ C18 column (pore size: 110 Å, particle size: 5 µm; 150×19 mm) at a flow rate of 10 mL/min and monitored with a UV detector at 214 nm and 254 nm. Linear gradients of 5-40% of MeOH containing 0.1% FA in water containing 0.1% FA were used for peptide purification. Propanol was purchased from JT Baker Inc., Fmoc-chloride was purchased from Chem-Impex International, Inc. Hydrazine hydrate, cyclopropylmethyl alcohol, and 4-methoxybenzaldehyde were purchased from Sigma Aldrich.

Fmoc-Based Peptide Synthesis.

Fmoc-based peptide synthesis was performed under standard conditions (W. D. Lubell, J. W. Blankenship, G. Fridkin, and R. Kaul (2005) "Peptides." Science of Synthesis 21.11, Chemistry of Amides. Thieme, Stuttgart, 713-809) on an automated shaker using polystyrene Rink amide resin (0.50 mmol/g). Couplings of amino acids (3 equiv) were performed in N,N-dimethylformamide (DMF) using DIC (3 equiv) and HOBt (3 equiv). Fmoc deprotections were performed by treating the resin with 20% piperidine in DMF for 30 min. Resin was washed after each coupling and deprotection step sequentially with DMF (3×10 mL), MeOH (3×10 mL), THF (3×10 mL), and DCM (3×10 mL).

Amino Acylation of Semicarbazides.

Coupling onto semicarbazides was performed by using amino acid symmetric anhydrides that were generated in situ (J. Zhang, C. Proulx, A. Tomberg, W. D. Lubell, *Org. Lett.* 2013, 16, 298-301). Amino acid (5 equiv) was treated with DIC (2.5 equiv) for 30 min in DCM (6 mL). After concentration of the reaction mixture using a rotary evaporator, the resulting residue containing the anhydride was dissolved in DMF (6 mL) and transferred to a plastic syringe tube equipped with Teflon™ filter, stopper and stopcock containing swollen resin (~300 mg, 0.15 mmol). The resin mixture was shaken on an automated shaker for 12 h. After filtration, the resin was washed sequentially with DMF (3×10 mL), MeOH (3×10 mL), THF (3×10 mL), and DCM (3×10 mL).

Semicarbazone Deprotection.

Semicarbazone deprotection was performed by treatment with a 1.5 M solution of $NH_2OH \cdot HCl$ in pyridine (6 mL) at 60° C. for 12 h with sonication (D. Sabatino, C. Proulx, S. Klocek, C. B. Bourguet, D. Boeglin, H. Ong, W. D. Lubell, *Org. Lett.* 2009, 11, 3650-3653). The resin was filtered and washed with DMF (3×10 mL), MeOH (3×10 mL), THF (3×10 mL), and DCM (3×10 mL).

Cleavage Test of Resin-Bound Peptide.

An aliquot of peptide bound resin (3-5 mg) was treated with a freshly made solution of $TFA/H_2O/TES$ (95:2.5:2.5, v/v/v, 0.5 mL) for 30 min at room temperature. The cleavage mixture was filtered and the filtrate was concentrated to a reduced volume from which the crude peptide was precipitated with cold ether (1.5 mL). After agitation on a vortex shaker, the mixture was spun in a centrifuge, and the supernatant was decanted leaving a pellet, which was dissolved in methanol (or H₂O, 1 mg/mL) and subjected to LCMS analysis.

Azapeptide Deprotection and Cleavage from Resin.

Rink-amide resin-bound peptide was deprotected and cleaved from the support using a freshly made solution of TFA/H₂O/TES (95:2.5:2.5, v/v/v, 20 mL/g of peptide resin) at rt for 2 h. The resin was filtered and rinsed with 5 mL of TFA. The filtrate and rinses were concentrated until a crude oil persisted, from which a precipitate was obtained by addition of cold ether (10-15 mL). After centrifugation (1200 rpm for 10 min), the supernatant was removed and the crude peptide precipitate was taken up in aqueous acetonitrile (10% v/v) and freeze-dried prior to analysis and purification.

2. Synthesis of Cyclic Aza-GHRP-6 Analogs Employing 'A³-Macrocyclization' on Solid Phase A series of approaches were employed to synthesize the cyclic aza-GHRP-6 analogs. Approach I involved peptide sequence elongation to completion after performing 'A³-macrocyclization' on solid phase, and was employed to synthesize cyclic analogs 8, 9, 17, 18, 19, 30, 31, and 32. Approach II featured 'A³-macrocyclization' as a penultimate step after peptide sequence completion, and was employed to synthesize cyclic analogs 17, 18, 24, 25, 33, 26, 27, 34, and 35.

Synthesis of Cyclic Analogs 8 and 9 Using Approach I:

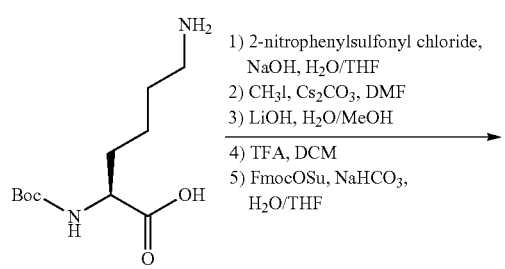

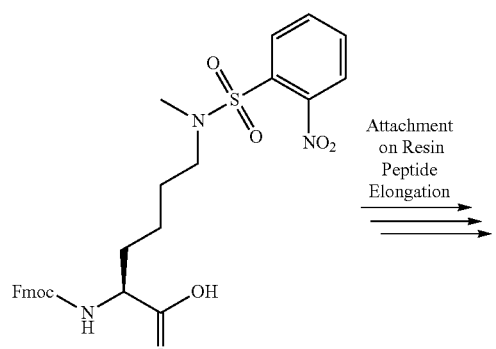

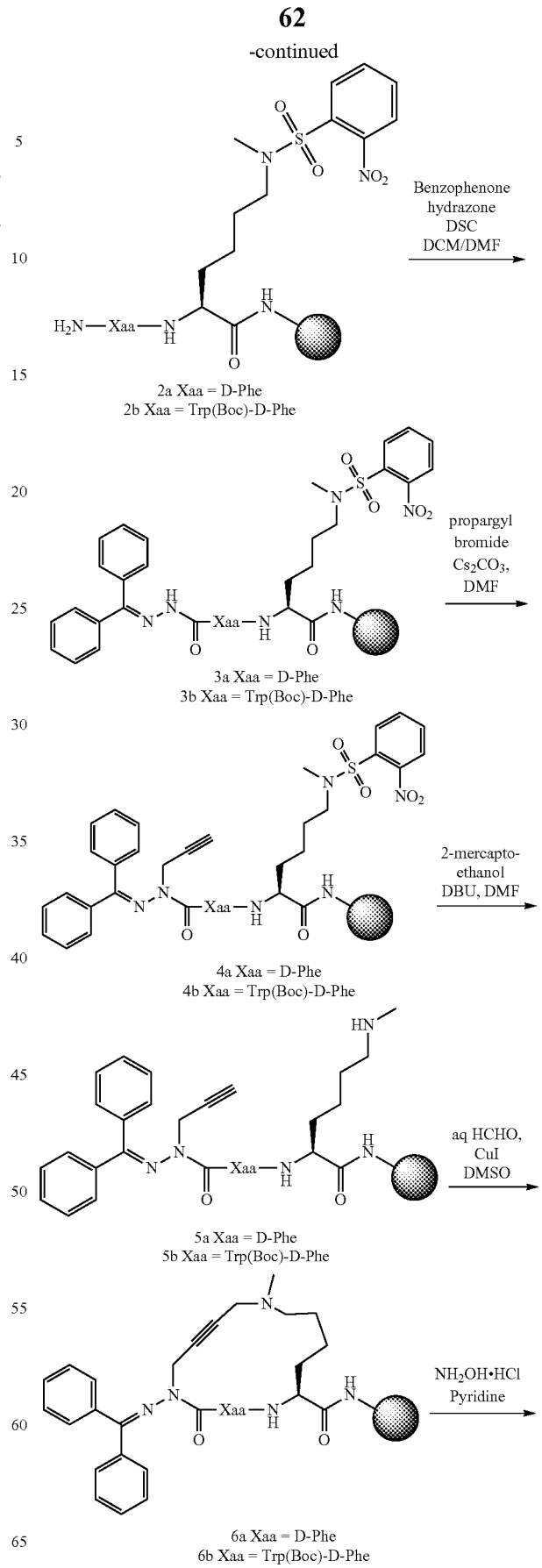

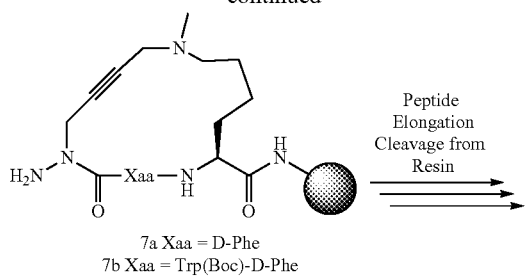

7a Xaa = D-Phe
7b Xaa = Trp(Boc)-D-Phe

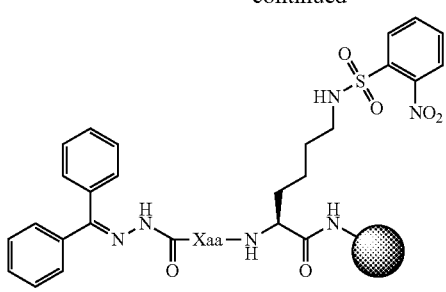

11a Xaa = D-Phe
11b Xaa = Trp(Boc)-D-Phe
11c Xaa = Ala-Trp(Boc)-D-Phe
11d Xaa = D-Trp(Boc)-Ala-Trp-DPhe

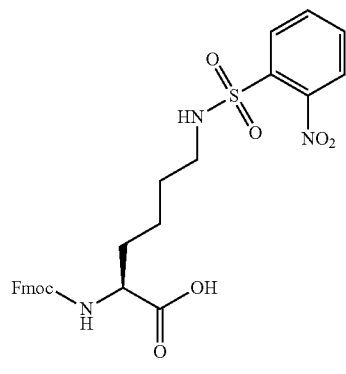

8 Xaa = D-Phe, Yaa = His-D-Trp-Ala
9 Xaa = Trp-D-Phe, Yaa = His-D-Trp

Synthesis of Cyclic Analogs 17, 18 and 19 Using Approach I:

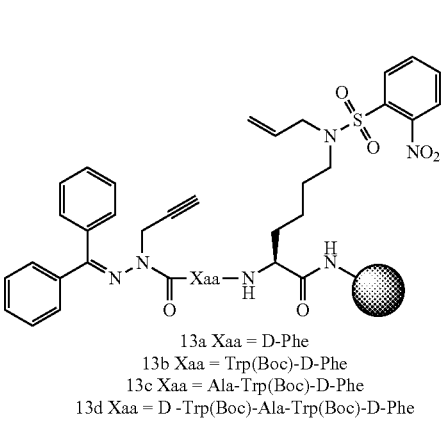

12a Xaa = D-Phe
12b Xaa = Trp(Boc)-D-Phe
12c Xaa = Ala-Trp(Boc)-D-Phe
12d Xaa = D-Trp(Boc)-Ala-Trp(Boc)-D-Phe

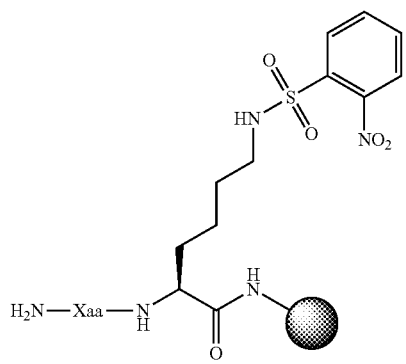

10

13a Xaa = D-Phe
13b Xaa = Trp(Boc)-D-Phe
13c Xaa = Ala-Trp(Boc)-D-Phe
13d Xaa = D-Trp(Boc)-Ala-Trp(Boc)-D-Phe

14a Xaa = D-Phe
14b Xaa = Trp(Boc)-D-Phe
14c Xaa = Ala-Trp(Boc)-D-Phe
14d Xaa = D-Trp(Boc)-Ala-Trp(Boc)-D-Phe

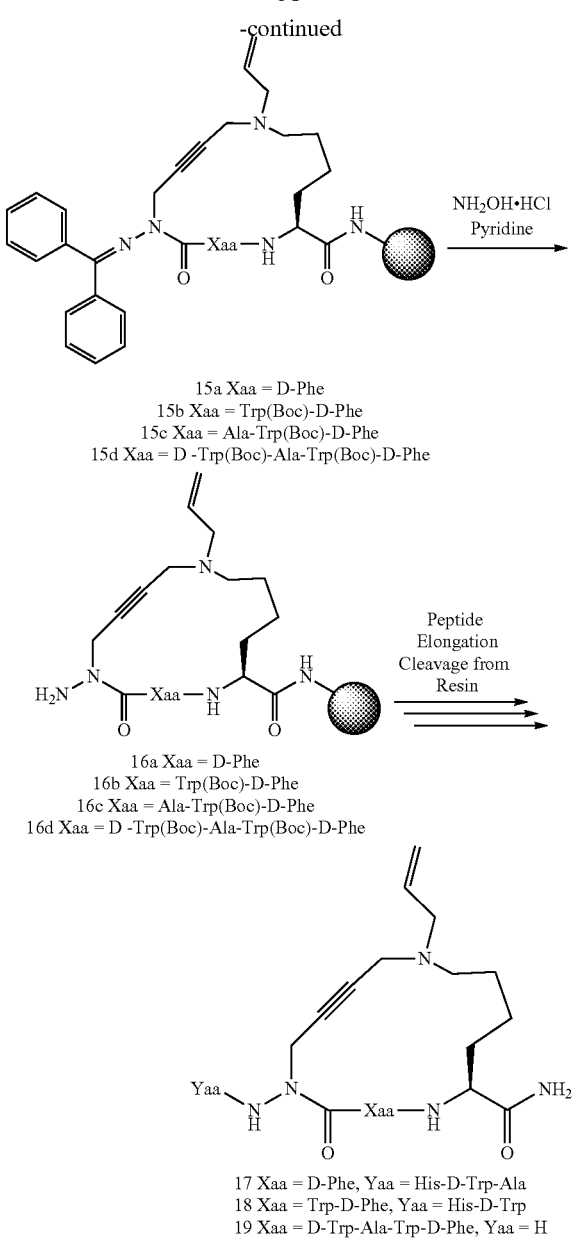

15a Xaa = D-Phe
15b Xaa = Trp(Boc)-D-Phe
15c Xaa = Ala-Trp(Boc)-D-Phe
15d Xaa = D-Trp(Boc)-Ala-Trp(Boc)-D-Phe

16a Xaa = D-Phe
16b Xaa = Trp(Boc)-D-Phe
16c Xaa = Ala-Trp(Boc)-D-Phe
16d Xaa = D-Trp(Boc)-Ala-Trp(Boc)-D-Phe

17 Xaa = D-Phe, Yaa = His-D-Trp-Ala
18 Xaa = Trp-D-Phe, Yaa = His-D-Trp
19 Xaa = D-Trp-Ala-Trp-D-Phe, Yaa = H

Synthesis of Cyclic Azapeptide 17 as a Representative for the Synthesis of Cyclic Azapeptide Using 'A³-Macrocyclization'

Representative Synthesis of Semicarbazone-Protected Aza-Gly on Solid Phase, Synthesis of Semicarbazone 11a.

A solution of N,N'-disuccinimidyl carbonate (DSC, 115 mg, 0.45 mmol) in DMF (3 mL) was treated dropwise with a solution of benzophenone hydrazone (88 mg, 0.45 mmol) in 3 mL of DCM over 15 min, stirred for 1 h at rt, and transferred to a syringe tube equipped with a Teflon™ filter, stopper and stopcock containing swollen D-Phe-Lys(o-NBS) resin (~300 mg, 0.15 mmol). The resin mixture was treated with DIEA (157 µL, 0.90 mmol), shaken on an automated shaker for 12 h and filtered. After filtration, the resin was washed sequentially with DMF (3×10 mL), MeOH (3×10 mL), THF (3×10 mL), and DCM (3×10 mL). Examination by LCMS of a cleaved resin sample showed complete coupling; LCMS (70-95% MeOH containing 0.1% FA in water containing 0.1% FA over 8 min) R.T.=3.40 min; ESI-MS m/z calcd for $C_{35}H_{38}N_7O_7S$ [M+H]⁺ 700.3, found 700.2.

Representative ε-N-Alkylation of o-NBS-Protected Lysine Residue on Solid Phase, Synthesis of Azatripeptide 12a Vacuum dried semicarbazone resin 11a (~300 mg, 0.15 mmol) was suspended in anhydrous THF (3 mL) in a sealed flask under argon. Allyl alcohol (102 µL, 1.5 mmol) in anhydrous THF (1 mL), PPh₃ (197 mg, 0.75 mmol) in anhydrous THF (1 mL) and DIAD (148 µL, 0.75 mmol) in anhydrous THF (1 mL) were sequentially added to the resin mixture. The resin mixture was shaken on an automated shaker for 30 min, and filtered. After filtration, the resin was washed sequentially with DMF (3×10 mL), MeOH (3×10 mL), THF (3×10 mL), and DCM (3×10 mL). Examination by LCMS of a cleaved resin sample showed complete allylation: LCMS (70-95% MeOH containing 0.1% FA in water containing 0.1% FA over 8 min) R.T.=4.97 min; ESI-MS m/z calcd for $C_{38}H_{42}N_7O_7S$ [M+H]⁺ 740.3, found 740.2.

Representative Propargylation of Semicarbazone-Protected Aza-Gly on Solid Phase, Synthesis of Azatripeptide 13a Azatripeptide resin 12a (~300 mg, 0.15 mmol) was swollen in DMF (6 mL) for 30 min in a syringe tube equipped with a Teflon™ filter, stopper and stopcock. The resin mixture was treated with Cs₂CO₃ (293 mg, 0.90 mmol) and propargyl bromide (100 µL, 0.90 mmol, 80% in toluene), shaken on an automated shaker for 24 h, and filtered. After filtration, the resin was washed sequentially with DMF (3×10 mL), MeOH (3×10 mL), THF (3×10 mL), and DCM (3×10 mL). Examination by LCMS of a cleaved resin sample showed complete propargylation: LCMS (70-95% MeOH containing 0.1% FA in water containing 0.1% FA over 8 min) R.T.=5.40 min; ESI-MS m/z calcd for $C_{41}H_{44}N_7O_7S$ [M+H]⁺778.3, found 778.2.

Representative Protocol for the Removal of the o-NBS-Protecting Group on Solid Phase, Synthesis of Azatripeptide 14a Azatripeptide resin 13a (~300 mg, 0.15 mmol) was swollen in DMF (6 mL) for 30 min in a syringe tube equipped with Teflon™ filter, stopper and stopcock, treated with DBU (224 µL, 0.1.5 mmol) and 2-mercaptoethanol (53 µL, 0.75 mmol), shaken on an automated shaker for 30 min, and filtered. After filtration, the resin was washed sequentially with DMF (3×10 mL), MeOH (3×10 mL), THF (3×10 mL), and DCM (3×10 mL). Examination by LCMS of a cleaved resin sample showed complete deprotection: LCMS (50-95% MeOH containing 0.1% FA in water containing 0.1% FA over 8 min) R.T.=1.99 min; ESI-MS m/z calcd for $C_{35}H_{41}N_6O_3$ [M+H]⁺ 593.3, found 593.3.

Representative Protocol for the 'A³-Macrocyclization' on Solid Phase, Synthesis of Cyclic Azatripeptide 15a Azatripeptide resin 14a (~300 mg, 0.15 mmol) was swollen in DMSO (6 mL) for 30 min in a syringe tube equipped with Teflon™ filter, and stopper, treated with CuI (5.7 mg, 0.03 mmol) and aqueous formaldehyde (78 µL, 0.90 mmol, 37% in H₂O), shaken on an automated shaker for 24 h, and filtered. After filtration, the resin was washed sequentially with AcOH/H₂O/DMF (5:15:80, v/v/v, 3×10 mL), THF (3×10 mL), MeOH (3×10 mL), and DCM (3×10 mL). Examination by LCMS of a cleaved resin sample showed complete conversion and a peak with molecular ion consistent with cyclic azatripeptide 15a was observed: LCMS (30-95% MeOH containing 0.1% FA in water containing 0.1% FA over 8 min) R.T.=6.37 min; ESI-MS m/z calcd for $C_{36}H_{41}N_6O_3$ [M+H]⁺ 605.3, found 605.3.

Semicarbazide 16a was obtained by removal of the semicarbazone as described in the general experimental procedures above. Peptide elongation and acylation were then performed using the general procedures described above. After final cleavage from resin, cyclic azapeptide 17 was isolated and purified by prep-HPLC.

Synthesis of Cyclic Analogs 17, 18, 24, 25, 26 and 27 Using Approach II:

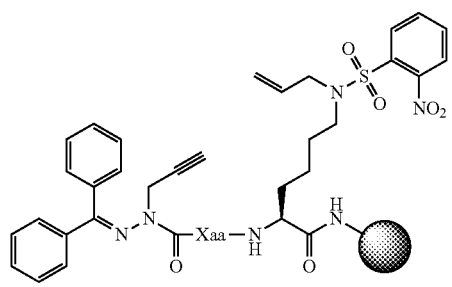

13a Xaa = D-Phe
13b Xaa = Trp(Boc)-D-Phe
13c Xaa = Ala-Trp(Boc)-D-Phe
13d Xaa = D -Trp(Boc)-Ala-Trp(Boc)-D-Phe

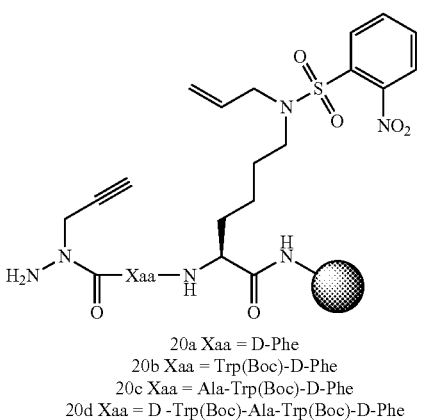

20a Xaa = D-Phe
20b Xaa = Trp(Boc)-D-Phe
20c Xaa = Ala-Trp(Boc)-D-Phe
20d Xaa = D -Trp(Boc)-Ala-Trp(Boc)-D-Phe

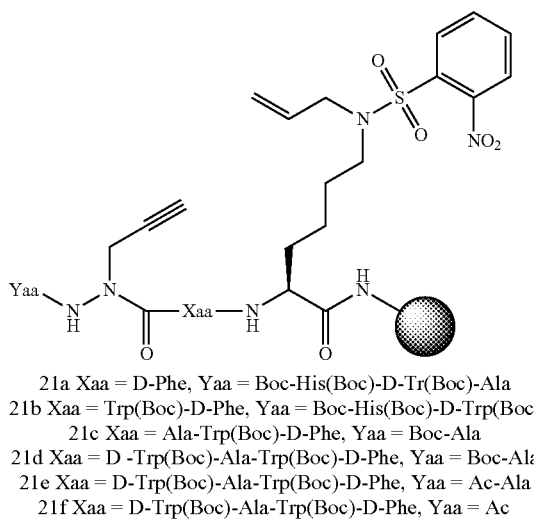

21a Xaa = D-Phe, Yaa = Boc-His(Boc)-D-Tr(Boc)-Ala
21b Xaa = Trp(Boc)-D-Phe, Yaa = Boc-His(Boc)-D-Trp(Boc)
21c Xaa = Ala-Trp(Boc)-D-Phe, Yaa = Boc-Ala
21d Xaa = D -Trp(Boc)-Ala-Trp(Boc)-D-Phe, Yaa = Boc-Ala
21e Xaa = D-Trp(Boc)-Ala-Trp(Boc)-D-Phe, Yaa = Ac-Ala
21f Xaa = D-Trp(Boc)-Ala-Trp(Boc)-D-Phe, Yaa = Ac

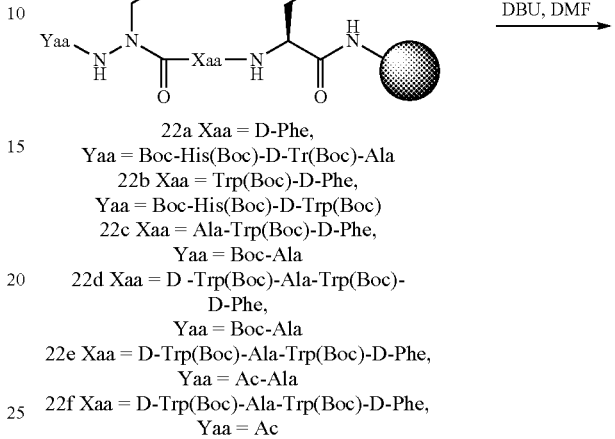

22a Xaa = D-Phe, Yaa = Boc-His(Boc)-D-Tr(Boc)-Ala
22b Xaa = Trp(Boc)-D-Phe, Yaa = Boc-His(Boc)-D-Trp(Boc)
22c Xaa = Ala-Trp(Boc)-D-Phe, Yaa = Boc-Ala
22d Xaa = D -Trp(Boc)-Ala-Trp(Boc)-D-Phe, Yaa = Boc-Ala
22e Xaa = D-Trp(Boc)-Ala-Trp(Boc)-D-Phe, Yaa = Ac-Ala
22f Xaa = D-Trp(Boc)-Ala-Trp(Boc)-D-Phe, Yaa = Ac

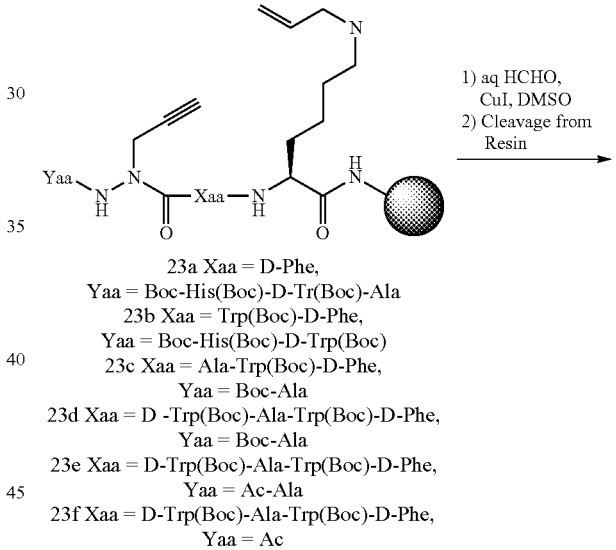

23a Xaa = D-Phe, Yaa = Boc-His(Boc)-D-Tr(Boc)-Ala
23b Xaa = Trp(Boc)-D-Phe, Yaa = Boc-His(Boc)-D-Trp(Boc)
23c Xaa = Ala-Trp(Boc)-D-Phe, Yaa = Boc-Ala
23d Xaa = D -Trp(Boc)-Ala-Trp(Boc)-D-Phe, Yaa = Boc-Ala
23e Xaa = D-Trp(Boc)-Ala-Trp(Boc)-D-Phe, Yaa = Ac-Ala
23f Xaa = D-Trp(Boc)-Ala-Trp(Boc)-D-Phe, Yaa = Ac

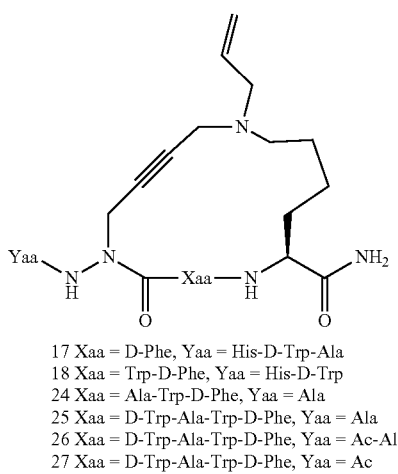

17 Xaa = D-Phe, Yaa = His-D-Trp-Ala
18 Xaa = Trp-D-Phe, Yaa = His-D-Trp
24 Xaa = Ala-Trp-D-Phe, Yaa = Ala
25 Xaa = D-Trp-Ala-Trp-D-Phe, Yaa = Ala
26 Xaa = D-Trp-Ala-Trp-D-Phe, Yaa = Ac-Ala
27 Xaa = D-Trp-Ala-Trp-D-Phe, Yaa = Ac

The syntheses of cyclic analogs 17, 18, 24, 25, 26 and 27 using approach II on solid phase were performed similarly to the protocol described above for the synthesis of cyclic analog 17.

Synthesis of Cyclic Analogs 30, 31, 32, 33, 34 and 35.

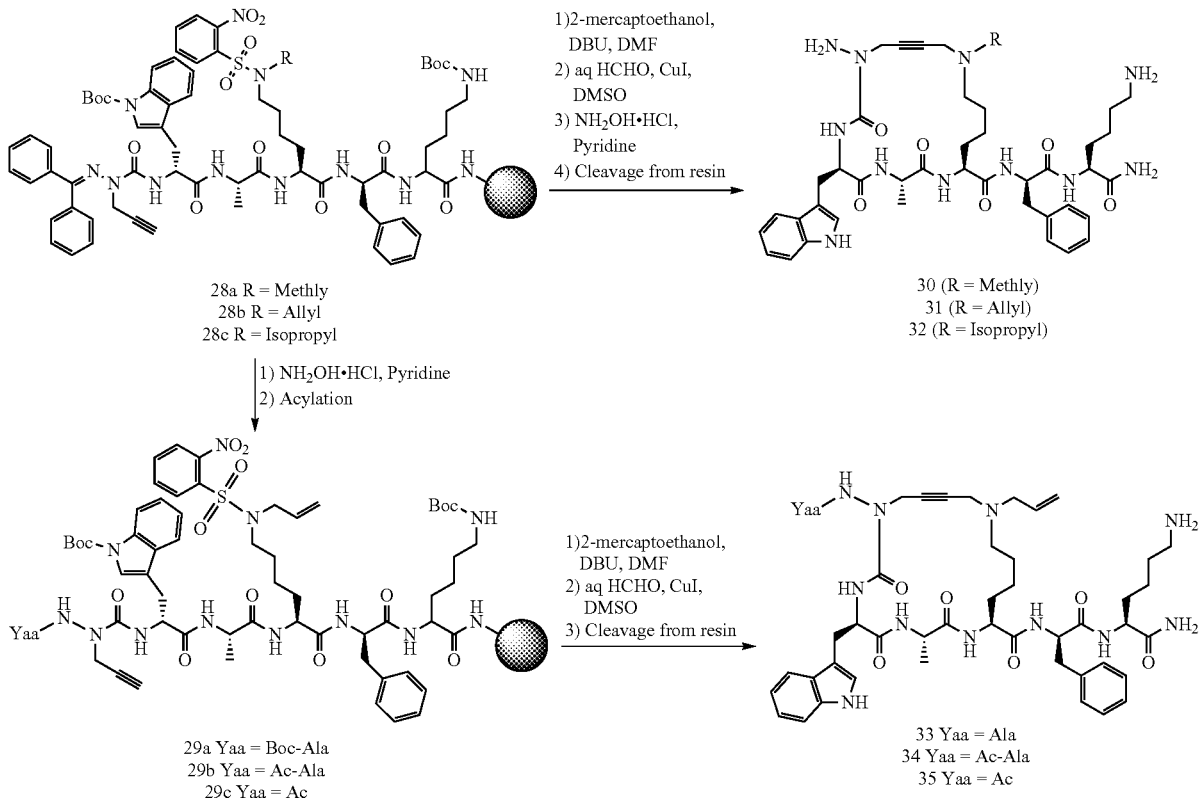

28a R = Methly
28b R = Allyl
28c R = Isopropyl 30 (R = Methly)
31 (R = Allyl)
32 (R = Isopropyl)

29a Yaa = Boc-Ala
29b Yaa = Ac-Ala
29c Yaa = Ac

33 Yaa = Ala
34 Yaa = Ac-Ala
35 Yaa = Ac

The syntheses of cyclic analogs 30, 31 and 32 on solid phase were performed similarly as that described above for the synthesis of cyclic analog 17 using approach I. The syntheses of cyclic analogs 33, 34 and 35 on solid phase were performed similarly as that described above for the synthesis of cyclic analog 17 using approach II.

Analytical LCMS Characterization of Purified Cyclic Azapeptides

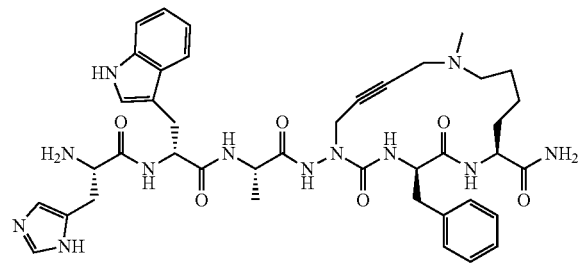

8

LCMS analysis of cyclic azapeptide 8 was performed using a linear gradient of a) 5-60% of MeOH containing 0.1% FA in $H_2O$ containing 0.1% FA over 10 min, then at 5% MeOH for 5 min, R.T=4.49 min; b) 5-60% of MeCN containing 0.1% FA in $H_2O$ containing 0.1% FA over 10 min, then at 5% MeCN for 5 min, R.T=8.39 min; HRMS m/z calcd for $C_{41}H_{53}N_{12}O_6$ $[M+H]^+$ 809.4205, found 809.4201.

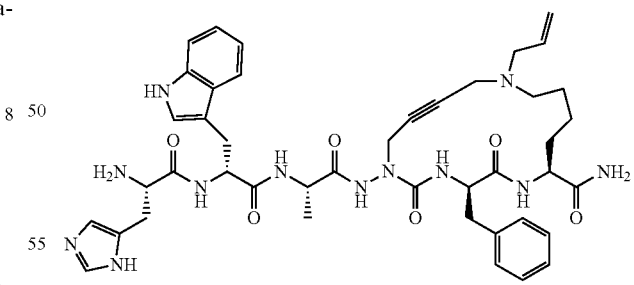

17

LCMS analysis of cyclic azapeptide 17 was performed using a linear gradient of a) 0-95% of MeOH containing 0.1% FA in $H_2O$ containing 0.1% FA over 10 min, then at 100% $H_2O$ for 5 min, R.T=5.98 min b) 0-95% of MeCN containing 0.1% FA in $H_2O$ containing 0.1% FA over 10 min, then at 100% $H_2O$ for 5 min, R.T=5.87 min; HRMS m/z calcd for $C_{43}H_{55}N_{12}O_6$ $[M+H]^+$ 835.4362.4205, found 835.4376.

9

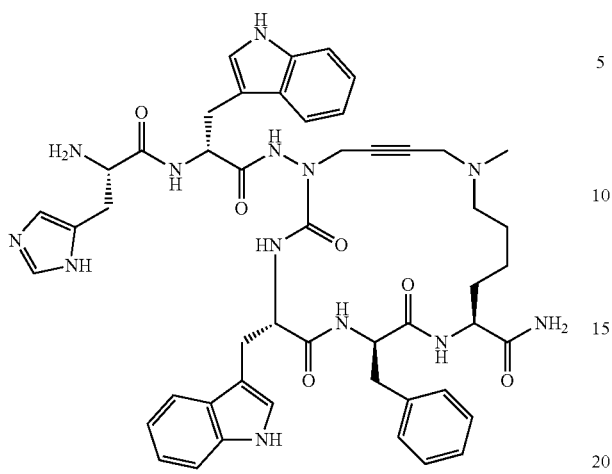

LCMS analysis of cyclic azapeptide 9 (MPE-210) was performed using a linear gradient of a) 5-60% of MeOH containing 0.1% FA in H$_2$O containing 0.1% FA over 10 min, then at 5% MeOH for 5 min, R.T=5.89 min; b) 5-60% of MeCN containing 0.1% FA in H$_2$O containing 0.1% FA over 10 min, then at 5% MeCN for 5 min, R.T=4.40 min; HRMS m/z calcd for C$_{49}$H$_{58}$N$_{13}$O$_6$ [M+H]$^+$ 924.4628, found 924.4627.

19

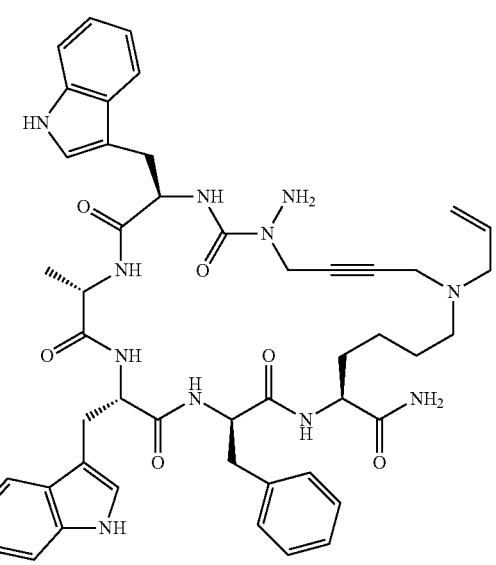

LCMS analysis of cyclic azapeptide 19 was performed using a linear gradient of a) 10-80% of MeOH in H$_2$O containing 0.1% FA over 10 min, then at 10% MeOH for 5 min, R.T=9.57 min; b) 5-60% of MeCN in H$_2$O containing 0.1% FA over 10 min, then at 5% MeCN for 5 min, R.T=7.98 min; HRMS m/z calcd for C$_{48}$H$_{58}$N$_{11}$O$_6$ [M+H]$^+$ 884.4566, found 884.4549.

18

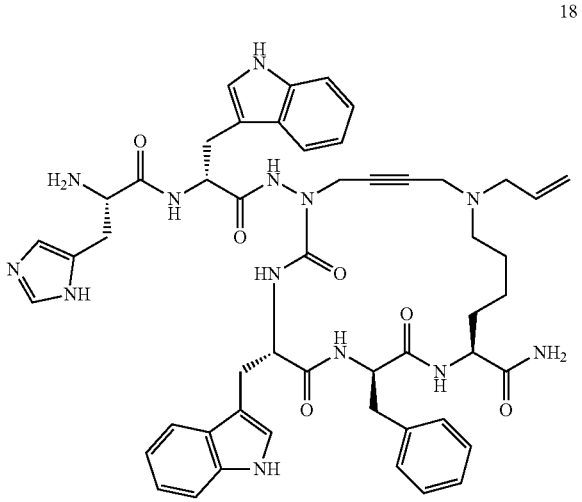 [SMILES: C=CCN1CC#CCN(NC(=O)[C@@H](Cc2c[nH]c3ccccc23)NC(=O)[C@@H](N)Cc2cnc[nH]2)C(=O)N[C@@H](Cc2c[nH]c3ccccc23)C(=O)N[C@H](Cc2ccccc2)C(=O)N[C@H](C(N)=O)CCCC1]

LCMS analysis of cyclic azapeptide 18 was performed using a linear gradient of a) 0-95% of MeOH containing 0.1% FA in H$_2$O containing 0.1% FA over 10 min, then at 100% H$_2$O for 5 min, R.T=6.92 min; b) 0-95% of MeCN containing 0.1% FA in H$_2$O containing 0.1% FA over 10 min, then at 100% H$_2$O for 5 min, R.T=4.67 min; HRMS m/z calcd for C$_{51}$H$_{60}$N$_{13}$O$_6$ [M+H]$^+$ 950.4784, found 950.4787.

24

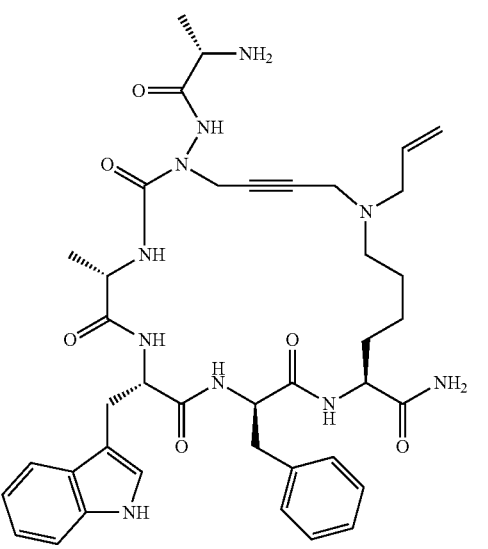

LCMS analysis of cyclic azapeptide 24 was performed using a linear gradient of a) 10-95% of MeOH containing 0.1% FA in H$_2$O containing 0.1% FA over 10 min, then at 10% MeOH for 5 min, R.T=4.99 min; b) 10-95% of MeCN containing 0.1% FA in H$_2$O containing 0.1% FA over 10 min, then at 10% MeCN for 5 min, R.T=5.28 min; HRMS m/z calcd for C$_{40}$H$_{53}$N$_{10}$O$_6$ [M+H]$^+$ 769.4144, found 769.4140.

25

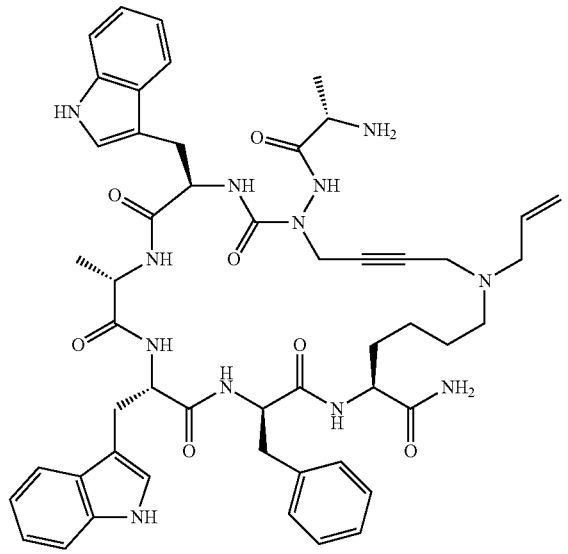

LCMS analysis of cyclic azapeptide 25 was performed using a linear gradient of a) 10-95% of MeOH containing 0.1% FA in H$_2$O containing 0.1% FA over 10 min, then at 10% MeOH for 5 min, R.T=6.29 min; b) 10-95% of MeCN containing 0.1% FA in H$_2$O containing 0.1% FA over 10 min, then at 10% MeCN for 5 min, R.T=6.10 min; HRMS m/z calcd for C$_{51}$H$_{63}$N$_{12}$O, [M+H]$^+$955.4937, found 955.4942.

26

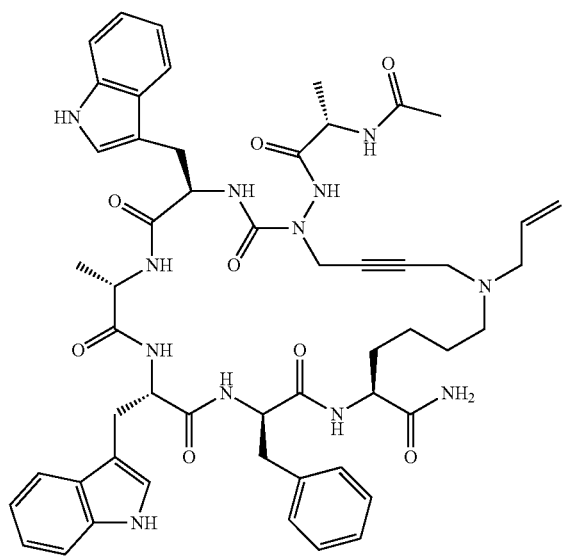

LCMS analysis of cyclic azapeptide 26 was performed using a linear gradient of a) 10-95% of MeOH containing 0.1% FA in H$_2$O containing 0.1% FA over 10 min, then at 10% MeOH for 5 min, R.T=6.46 min; b) 10-95% of MeCN containing 0.1% FA in H$_2$O containing 0.1% FA over 10 min, then at 10% MeCN for 5 min, R.T=5.66 min; HRMS m/z calcd for C$_{53}$H$_{65}$N$_{12}$O$_8$ [M+H]$^+$997.5043, found 997.5031.

27

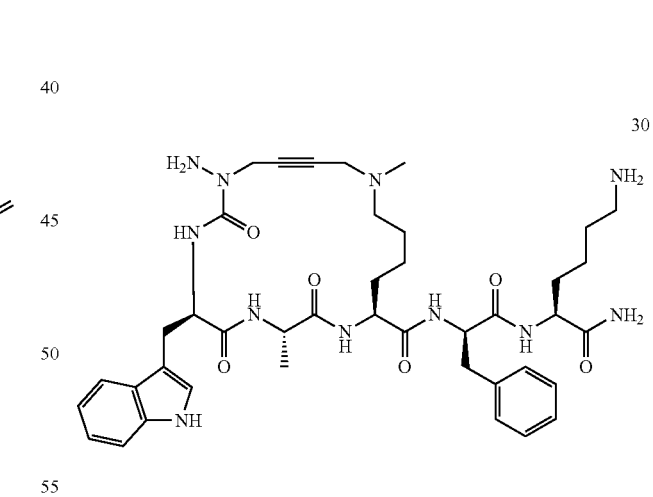

LCMS analysis of cyclic azapeptide 27 was performed using a linear gradient of a) 10-95% of MeOH containing 0.1% FA in H$_2$O containing 0.1% FA over 10 min, then at 10% MeOH for 5 min, R.T=8.33 min; b) 10-95% of MeCN containing 0.1% FA in H$_2$O containing 0.1% FA over 10 min, then at 10% MeCN for 5 min, R.T=5.63 min; HRMS m/z calcd for C$_{50}$H$_{60}$N$_{11}$O$_7$ [M+H]$^+$ 926.4671, found 926.4558.

30

LCMS analysis of cyclic azapeptide 30 was performed using a linear gradient of a) 10-95% of MeOH containing 0.1% FA in H$_2$O containing 0.1% FA over 10 min, then at 10% MeOH for 5 min, R.T=4.92 min; b) 10-95% of MeCN containing 0.1% FA in H$_2$O containing 0.1% FA over 10 min, then at 10% MeCN for 5 min, R.T=5.88 min; HRMS m/z calcd for C$_{41}$H$_{58}$N$_{11}$O$_6$ [M+H]$^+$ 800.4566, found 800.4553.

31

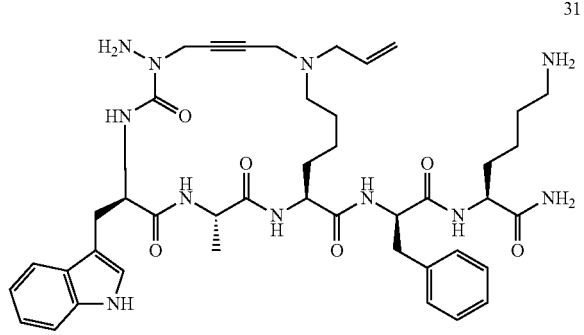 [SMILES: C=CCN1CC#CCN(N)C(=O)N[C@H](Cc2c[nH]c3ccccc23)C(=O)N[C@@H](C)C(=O)N[C@H](C(=O)N[C@H](Cc2ccccc2)C(=O)N[C@@H](CCCCN)C(N)=O)CCCC1]

LCMS analysis of cyclic azapeptide 31 was performed using a linear gradient of a) 10-95% of MeOH containing 0.1% FA in H$_2$O containing 0.1% FA over 10 min, then at 10% MeOH for 5 min, R.T=5.04 min; b) 10-95% of MeCN containing 0.1% FA in H$_2$O containing 0.1% FA over 10 min, then at 10% MeCN for 5 min, R.T=4.71 min; HRMS m/z calcd for C$_{43}$H$_{60}$N$_{11}$O$_6$ [M+H]$^+$ 826.4723, found 826.4718.

32

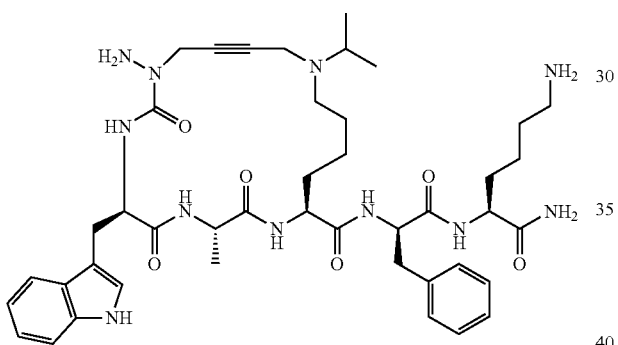

LCMS analysis of cyclic azapeptide 32 was performed using a linear gradient of a) 10-95% of MeOH containing 0.1% FA in H$_2$O containing 0.1% FA over 10 min, then at 10% MeOH for 5 min, R.T=4.97 min; b) 10-95% of MeCN containing 0.1% FA in H$_2$O containing 0.1% FA over 10 min, then at 10% MeCN for 5 min, R.T=4.70 min; HRMS m/z calcd for C$_{43}$H$_{62}$N$_{11}$O$_6$ [M+H]$^+$ 828.4879, found 828.4875.

33

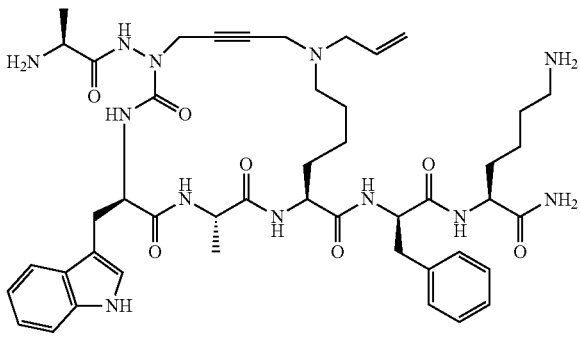

LCMS analysis of cyclic azapeptide 33 was performed using a linear gradient of a) 0-95% of MeOH containing 0.1% FA in H$_2$O containing 0.1% FA over 10 min, then at 100% H$_2$O for 5 min, R.T=4.62 min; b) 0-95% of MeCN containing 0.1% FA in H$_2$O containing 0.1% FA over 10 min, then at 100% H$_2$O for 5 min, R.T=4.47 min; HRMS m/z calcd for C$_{46}$H$_{65}$N$_{12}$O$_7$ [M+H]$^+$897.5094, found 897.5092.

34

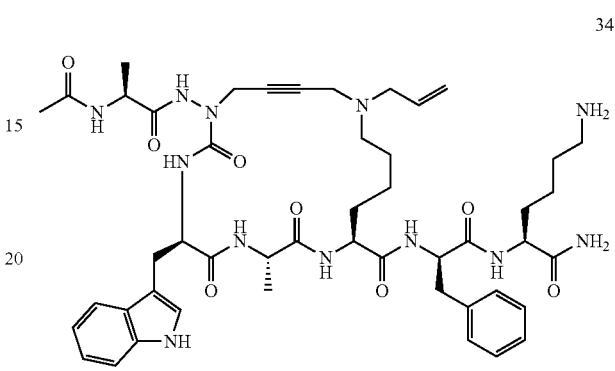

LCMS analysis of cyclic azapeptide 34 was performed using a linear gradient of a) 10-95% of MeOH containing 0.1% FA in H$_2$O containing 0.1% FA over 10 min, then at 10% MeOH for 5 min, R.T=5.50 min; b) 10-95% of MeCN containing 0.1% FA in H$_2$O containing 0.1% FA over 10 min, then at 10% MeCN for 5 min, R.T=3.95 min; HRMS m/z calcd for C$_{45}$H$_{62}$N$_{11}$O$_7$ [M+H]$^+$939.5199, found 939.5186.

35

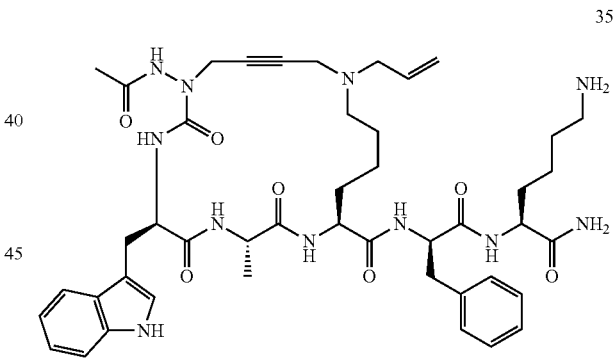

LCMS analysis of cyclic azapeptide 35 was performed using a linear gradient of a) 10-95% of MeOH containing 0.1% FA in H$_2$O containing 0.1% FA over 10 min, then at 10% MeOH for 5 min, R.T=6.07 min; b) 10-95% of MeCN containing 0.1% FA in H$_2$O containing 0.1% FA over 10 min, then at 10% MeCN for 5 min, R.T=4.96 min; HRMS m/z calcd for C$_{48}$H$_{67}$N$_{12}$O$_8$ [M+H]$^+$ 868.4828, found 868.4804.

Effect of Cyclic Peptides on the Release of Nitric Oxide (NO) Induced by the TLR2 Agonist R-FSL-1 in RAW Macrophage Cell Line The murine RAW1 macrophage cell line was obtained from American Type Cell Collection (ATCC #TIB-71), seeded at 1.5×10$^5$ cells/well in Dulbecco's Modified Eagle's medium (DMEM) containing 100 U/mL of penicillin (Pen) and 100 μg/mL of streptomycin (Strep) on a 48-well plate (Costar® #3548), and incubated at 37° C. with 5% CO$_2$.

After 2 h, the cell culture medium of adhered cells was removed and replaced by DMEM-Pen/Strep medium containing 0.2% of bovine serum albumin (BSA), and supplemented with the cyclic peptides at a concentration of $10^{-6}$ or $10^{-7}$ M. MPE-001 (DBG178, His-D-Trp-Ala-AzaTyr-D-Phe-Lys-NH$_2$) and [azaLys$^6$]-GHRP-6 (His-D-Trp-Ala-Trp-D-Phe-azaLys-NH$_2$, negative control) at $10^{-6}$ M were used as positive and negative controls, respectively. After 1 h pre-incubation, the cells were stimulated overnight using the TLR2 ligand fibroblast-stimulating lipopeptide (R-FSL-1) (Invivogen® #L7022) at a concentration of 300 ng/mL. Supernatants were then collected for nitrite production analysis by fluorescence using 2,3-diaminonaphthalene (DAN). Briefly, 25 µL of sample was incubated with 0.5 µg of DAN in a 100 µL final volume of phosphate buffer (50 mM, pH 7.5) at room temperature in the dark. After 15 min, the reaction was stopped with 20 µL of NaOH (2.8N) and the plate was read using a fluorescence plate reader (TECAN® Safire, $\lambda_{exc}$ 365 nm and $\lambda_{em}$ 430 nm).

Binding Experiments.

Rat Heart Membrane Preparation as Source of CD36 for Binding Study.

Hearts from Sprague Dawley rats (300-325 g) from Charles River were cut into small pieces and homogenized with a Polytron® at low speed, 3×15 sec in buffer A (10 mM NaHCO$_3$, 5 mM NaN$_3$, 10 µM Pefabloc®, 0.1 µM Aprotinin, 1 µM Pepstatin A, 1 µM Leupeptin, pH 7.0) at a concentration of 5 ml/9 of tissue. The homogenate was first centrifuged at 8,700×g for 20 min in a Sorvall® centrifuge and the supernatant was collected on ice. The pellet was resuspended and re-homogenized with a Glass-Teflon® Potter by 5 strokes. This homogenate was recentrifuged at 8,700×g for 10 min and the resulting supernatant was combined with the first collected supernatant. The combined supernatant was centrifuged at 35,000×g for 20 min. The pellet fraction obtained was resuspended in Buffer B (20 mM Tris-maleate, 0.6M KCl, pH 6.8) in a volume corresponding to 20 mL/g of fresh tissue using a glass homogenizer with a Teflon pestle. The resulting suspension was centrifuged again at 35,000×g for 60 min. and the pellet fraction obtained was resuspended in Buffer C (10 mM Tris/HCl buffer pH 7.4) and thoroughly homogenized in a glass with a Teflon® pestle (20 ml/g of fresh tissue). This suspension was submitted to another centrifugation at 35,000×g for 60 min. The collected pellet was resuspended in 50 mM Tris/HCl buffer pH 7.4) containing 2 mM EGTA in a final volume corresponding to 1-2 mL/g of fresh tissue. The membrane preparation obtained was frozen at −80° C. Protein concentration was determined using the bicinchoninic acid (BCA) method, employing BSA as standard.

Radioiodination of the Photoactivatable Ligand as Tracer for the Receptor Binding Assay.

The radioiodination of Tyr-Bpa-Ala-Hexarelin was performed as previously described (Ong, H et al. Endocrinology 139: 432-435. 1998). Briefly, 10 nmol of Tyr-Bpa-Ala-Hexarelin was mixed with 100 ng of lactoperoxidase and 1mCi of Na$^{125}$I in a volume of 30 µl of 0.1M sodium acetate buffer pH 5.6. The reaction was started by adding 3 nmol of H$_2$O$_2$ for 5 min at room temperature. This step was repeated twice with a period of 5 min of incubation for each addition. The reaction was stopped by diluting the mixture with 1 mL of 0.1% TFA. The radioiodinated peptide was purified by HPLC on a reverse-phase Vydac® C18 column with a 60-min linear gradient from 20% to 50% of acetonitrile in 0.1% TFA. The eluted radiolabelled tracer was collected, aliquoted (50×10$^6$ cpm/fraction) and stored at −80° C.

Competition Binding Curves.

The receptor binding assays of the photoactivatable ligand were performed as follows: Membranes (50 µg/25 µl) were incubated in the darkness, in 175 µl of 50 mM Tris-HCl pH 7.4 containing 2 mM EGTA (Buffer A) in the presence of a fixed concentration of [$^{125}$I]-Tyr-Bpa-Ala-Hexarelin (250,000 cpm/25 µl) in Buffer B (50 mM Tris-HCl pH 7.4 containing 2 mM EGTA and 0.05% Bacitracin) and in the presence of increasing concentrations from 0.1 to 10 µM of competition ligands: hexarelin (as reference standard), cyclic peptides 26 (MPE-266) 28 (MPE-268), 32 (MPE-267), 33 (MPE-298), 25 (MPE-210), 38 (MPE-308), 35 (MPE-300) 39 (MPE-310), MPE-189, MPE-191, MPE-192, MPE-193, MPE-201, MPE-202, MPE-203, MPE-048, MPE-074, MPE-075, MPE-110, MPE-111 and MPE-400. Binding studies with MPE-298 were done with increasing concentrations from 0.01 to 5 µM of competition ligands. Nonspecific binding was defined as binding not displaced by 50 µM corresponding peptide. All peptide containing solutions were diluted in Buffer B. Buffer A and B were degassed under vacuum, and used in capped tubes in order to minimize lipid peroxidation. Before the incubation period, all tubes were put under a low flow of nitrogen. All material was kept on ice and the binding assay was performed in darkness. After an incubation period of 60 min at 22° C. (vortexing every 15 min), membranes were submitted to irradiation with UV lamps (365 nm) for 15 min at 4° C. After centrifugation at 12,000×g for 15 minutes, the pellets were resuspended in 40 µl of sample buffer (62 mM Tris-HCl, pH 6.8, 2% SDS, 10% glycerol, 15% 2-mercaptoethanol, and 0.05% bromophenol blue), and boiled for 5 min prior to being subjected to electrophoresis. Proteins (50 µg/40 µl) were separated on a 7.5% SDS-PAGE Bio-Rad® Mini-Protean electrophoresis system (150 V for 1 h). The gels resulting from SDS/PAGE were fixed, colored in Coomassie Brilliant Blue R-250, dried, exposed to a storage phosphor intensifying screen (Amersham Biosciences), and analysed using a Typhoon® PhosphorImager (GE Healthcare Life Sciences®). Protein bands were quantified by densitometry and the covalent binding signal of 87 kDa was analyzed by densitometry and ImageQuant™ 5.0 software to set competition curves. The curves were analysed by using software package (Graphpad® prism version 7.0).

Modulation of R-FSL-1 Induced Pro-Inflammatory Cytokine (TNF-α) and Chemokine (CCL2) Release by Cyclic Peptides in RAW Macrophages Model The murine RAW1 macrophage cell line was obtained from American Type Cell Collection (ATCC #TIB-71). RAW cells were seeded at 150,000 cells per well in a 48-well plate (Costar® #3548) and weaned overnight in medium (DMEM supplemented 1% penicillin/streptomycin) at 37° C. with 5% CO2. The next day, the medium was changed to DMEM-1% penicillin/streptomycin supplemented with 0.2% BSA. The cells were first pretreated with 300 µL of azapeptides DBG178 (MPE-133, reference standard), 25 (MPE-210), 26 (MPE-266), 28 (MPE-268), 32 (MPE-267), 33 (MPE-298), 38 (MPE-308), 35 (MPE-300), 39 (MPE-310) and azaLys6-GHRP-6 (as negative control) at 10-7M for 30 min. Then, 100 pt of the TLR2 agonist, R-FSL-1 (300 ng/ml final concentration, R-FSL-1, Invivogen® #L7022) was added for 4 h period of incubation at 37° C. with 5% CO2. At the end of the incubation period, media were collected and stored at −80° C. for TNF-α and CCL-2 assays using ELISA kits (EbioScience® #88-7391 and #88-7324). Results were analyzed by analysis of variance (ANOVA) with post hoc comparisons using Dunnett's test with a statistical software package (Graph Pad Prism® version 7.0). $P<0.05$ was considered statistically significant.

Modulation of IL-1β and TNF-α Secretion in Bone Marrow-Derived Macrophages

Bone marrow-derived macrophages isolation and purification. Bone marrow-derived macrophages (BMDM) were isolated from the tibia and femur of 4-month-old C57Bl/6 mice. Mice were euthanized in a $CO_2$ chamber individually. Tibia and femur were dissected from dead mice after removing the skin and the muscles and stored in cold DMEM before use. The bones are placed in Petri dishes containing sterile PBS and immersed in ice. In a laminar flow of culture, bones are immersed in 70% ethanol for one minute, and then rinsed in sterile PBS. Bones were cut in 2 pieces using sterile forceps and scissors and put in pierced 0.6 mL tubes which were put in 2 mL centrifuge tubes containing 200 µL of DMEM. After 1 min of centrifugation at 6500 RPM, pellets of bone marrow cells were gently resuspended and pooled in a 50 mL tube. Cells were counted and monocytes were purified from the bone marrow cells using the EasySep™ Mouse Monocyte Isolation Kit (StemCell Technologies, #19861) according to the manufacturer instructions. After the purification, monocytes were seeded and induced to macrophages on 100 mm non-adherent petri dishes with DMEM containing 10% FBS and 1% Pen/Strep supplemented with 40 ng/mL of macrophage colony-stimulating factor (M-CSF, Biolegend #576406) for 6 days. The culture medium was changed and renewed after 2 days.

Once induced, adherent BMDM were washed with phosphate buffer saline (PBS), mechanically detached with cell lifter, centrifuged at 400 g for 10 min at 4° C. and plated $5\times10^5$ cells/well in 48-well plates (Costar® #3548) and primed with lipopolysaccharide (LPS 200 ng/mL from *E. Coli*, Sigma-Aldrich, #L4391) for 3 hours. After the priming period the cells were washed and weaned overnight in DMEM containing 1% penicillin/streptomycin. The next day, the medium was changed for DMEM-1% penicillin/streptomycin supplemented with 0.2% BSA. The cells were first pretreated with 300 µL of MPE-298 at concentrations starting from $10^{-6}$ to $10^{-11}$M for 30 min. Then, 100 µL of the TLR2 agonist, R-FSL-1 (300 ng/ml final concentration, R-FSL-1, Invivogen® #L7022) was added for 4 h period of incubation at 37° C. with 5% $CO_2$. 30 min before the end of incubation time, adenosine triphosphate (0.5 mM ATP, Sigma-Aldrich #A2383) was added to induce the release of IL-1β from the cells. At the end of the incubation period, media were collected and stored at −80° C. for IL-1β and TNF-α assay using ELISA kits (EbioScience #88-7013-88 and #88-7391). Statistical significance of data was analyzed by analysis of variance (ANOVA) with post-hoc comparisons using Dunnett's test with statistical software package (Graph Pad Prism version 7.0). P<0.05 was considered statistically significant.

Example 2: Synthesis of Cyclic Aza-GHRP-6 Analogs by $A^3$-Macrocyclization

Tertiary propargylamine bridges were introduced into the peptide by initial incorporation of aza-propargylglycine and ε-N-alkyl-lysine residues into the GHRP-6 peptide sequence, followed by copper-catalyzed macrocyclization using an aldehyde linchpin. The $A^3$-macrocyclization was examined immediately after introduction of the azapropargylglycine residue, as well as after completing the peptide sequence. To seek a diversity-oriented synthesis, two strategies were employed, in which an ε-N-alkyl-lysine residue was introduced respectively at the C-terminal and a central residue of the peptide sequence. With the ε-N-alkyl-lysine residue at the C-terminal, the macrocycle ring-size diversity was varied by azapropargyiglycine position scanning, in which the azapropargylglycyl residue was marched systematically to the N-terminal of the GHRP-6 sequence prior to macrocyclization with formaldehyde. With the ε-N-alkyl-lysine residue centred in the sequence, the influence of various & amino substituents was examined on macrocyclization.

The important step for the effective diversity-oriented synthesis of cyclic azapeptides by $A^3$-macrocyclization was development of solid-phase methods to install the azapropargyiglycine residue and ε-N-alkyl-lysine residue into the peptide sequence prior to the copper-catalyzed macrocyclization using an aldehyde linchpin. The azapropargyiglycine can be inserted by submonomer synthesis of azapeptides on solid phase.[13] The ε-N-alkylated lysine was prepared in solution and then coupled to the resin-bound peptide; however, solid-phase ε-N-alkylation of lysine was also performed by Mitsunobu chemistry on the corresponding ε-N-o-nitrobenzenesulfonyl (o-NBS) amine.[20]

As a proof-of-concept of the $A^3$-macrocyclization, cyclic azatripeptide 8 was pursued by placing ε-N-methyl lysine at the peptide C-terminal and inserting aza-propargyiglycine at the i+2 position. Prior to attachment to Rink amide resin, Fmoc-Lys(methyl, o-NBS)—OH 1 was synthesized from Boc-Lys-OH in solution. After Fmoc group removals and elongation with Fmoc-D-Phe-OH using DIC and HOBt, dipeptide 2a was acylated by the active carbazate prepared from benzophenone hydrazone and N,N'-disuccinimidyl carbonate (DSC) to provide semicarbazone 3a.[14] Propargylation was performed using $Cs_2CO_3$ (300 mol %) and proparyl bromide (600 mol %) to furnish the aza-propargyiglycine 4a in good purity as accessed by LCMS analysis of a cleaved aliquot. After removal of the o-NBS-group with 2-mercaptoethanol and DBU, secondary ε-N-methylamine 5a was ready to test the $A^3$-macrocyclization. Macrocycle 6a was prepared successfully by treating aza-peptide 5a with CuI (20 mol %) and 37% aqueous formaldehyde (600 mol %) in DMSO at rt for 24 h, as verified by LCMS analysis. Elongation of macrocycle 6a to cyclic GHRP-6 analog 8 was accomplished by removal of the semicarbazone with hydroxylamine hydrochloride in pyridine, acylation of the resulting semicarbazide 7a using the symmetric anhydride from treating Fmoc-Ala-OH with DIC, and standard solid-phase peptide synthesis, deprotection and resin cleavage. GHRP-6 macrocycle 8 was isolated in 3.5% overall yield after purification by preparative HPLC. Employing the same strategy, macrocycle 9 was obtained in 2.4% overall yield.

Scheme 1. Synthesis of cylclic by azapeptide 'A3-macrocyclization' using ε-N-methyl-lysine that was previously synthesized in solution.

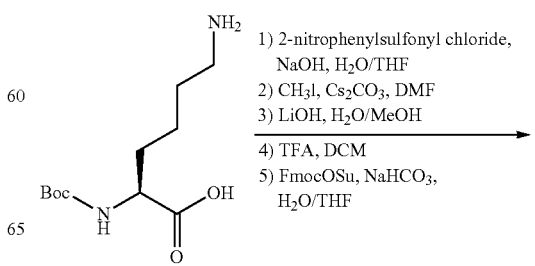

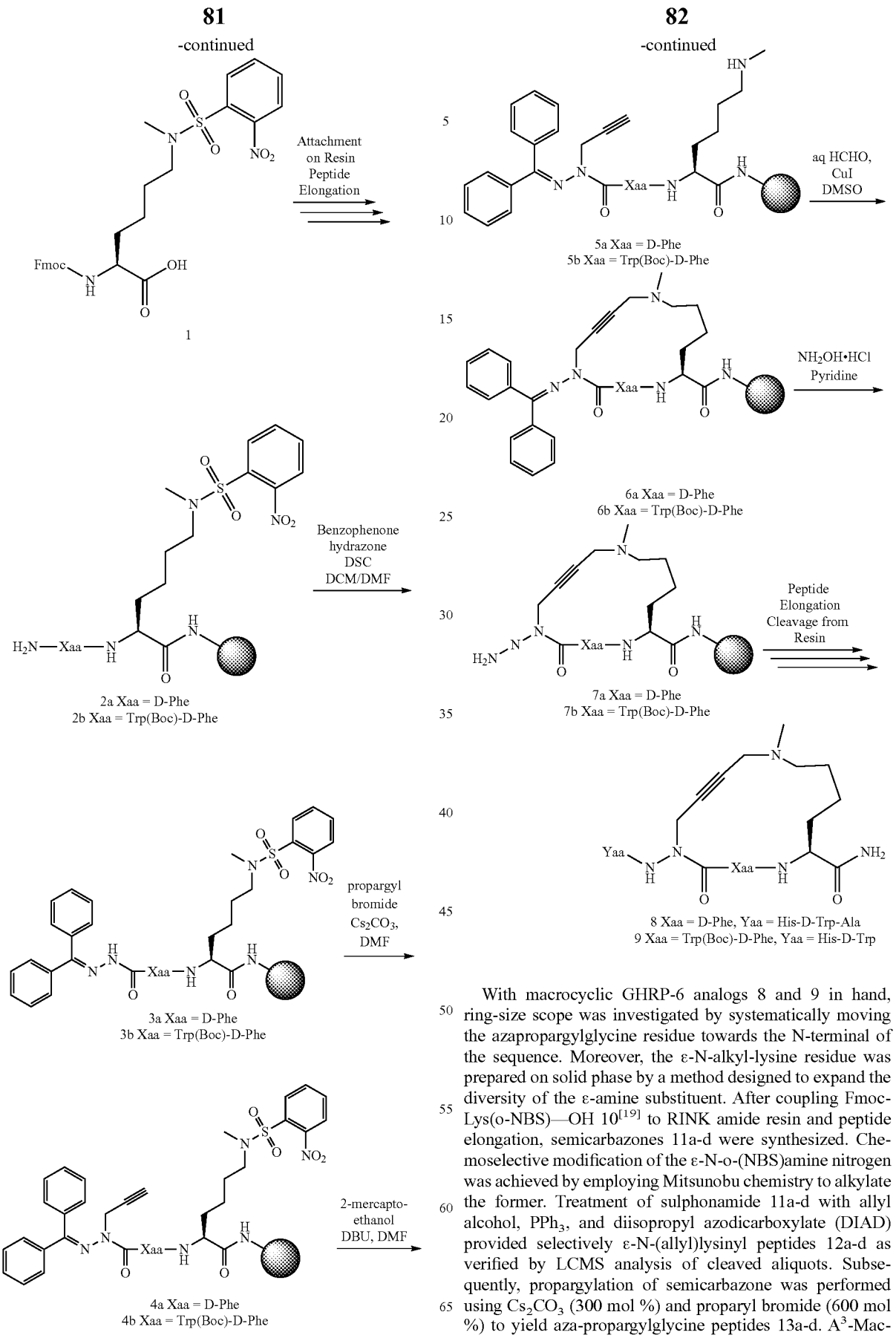

With macrocyclic GHRP-6 analogs 8 and 9 in hand, ring-size scope was investigated by systematically moving the azapropargylglycine residue towards the N-terminal of the sequence. Moreover, the ε-N-alkyl-lysine residue was prepared on solid phase by a method designed to expand the diversity of the ε-amine substituent. After coupling Fmoc-Lys(o-NBS)—OH 10[19] to RINK amide resin and peptide elongation, semicarbazones 11a-d were synthesized. Chemoselective modification of the ε-N-o-(NBS)amine nitrogen was achieved by employing Mitsunobu chemistry to alkylate the former. Treatment of sulphonamide 11a-d with allyl alcohol, PPh$_3$, and diisopropyl azodicarboxylate (DIAD) provided selectively ε-N-(allyl)lysinyl peptides 12a-d as verified by LCMS analysis of cleaved aliquots. Subsequently, propargylation of semicarbazone was performed using Cs$_2$CO$_3$ (300 mol %) and proparyl bromide (600 mol %) to yield aza-propargylglycine peptides 13a-d. A$^3$-Macrocyclization was then performed using the same conditions as discussed above to provide respectively 16-, 19, 21, and 24-membered macrocycles 15a-*d* as verified by LCMS analysis. After cyclization, semicarbazone removal, semicarbazide acylation, peptide elongation and resin cleavage were performed as described above to afford cyclic GHRP-6 analogs 17 and 18 after purification by preparative HPLC (Table 1). Coupling to semicarbazide macrocycles 16c and 16d was however unsuccessful in the syntheses of the corresponding cyclic GHRP-6 analogs. Steric hindrance inhibited apparently, the coupling to the semicarbazide of the larger ring-sizes. Semicarbazide 16d was however cleaved from resin to give cyclic aza-hexapeptide 19 with a N-terminal semicarbazide after purification by preparative HPLC.

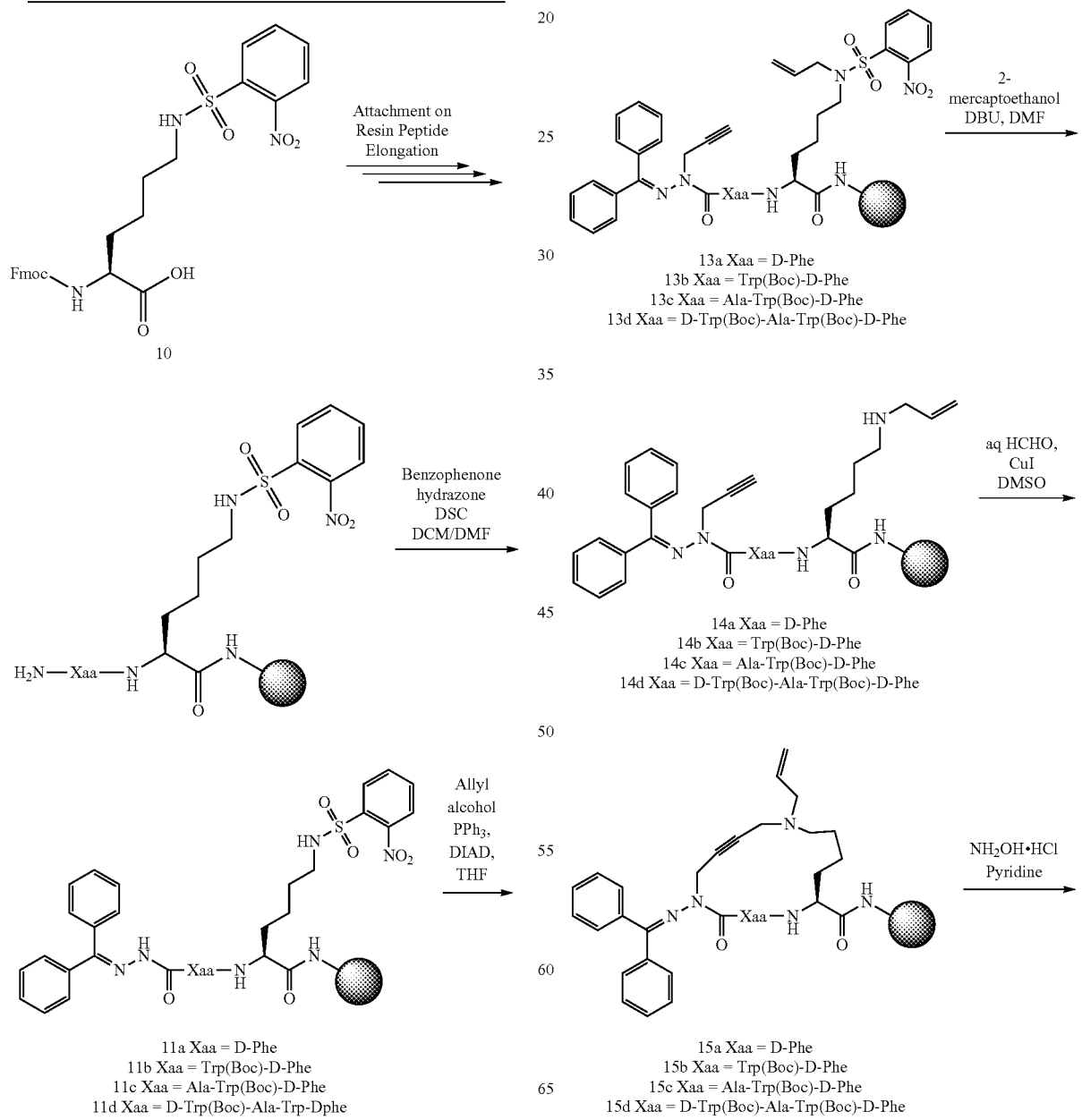

Scheme 2. Synthesis of cyclic azatripeptide by 'A3-macrocyclization' using ε-N-allyl-lysine synthesized on solid phase.

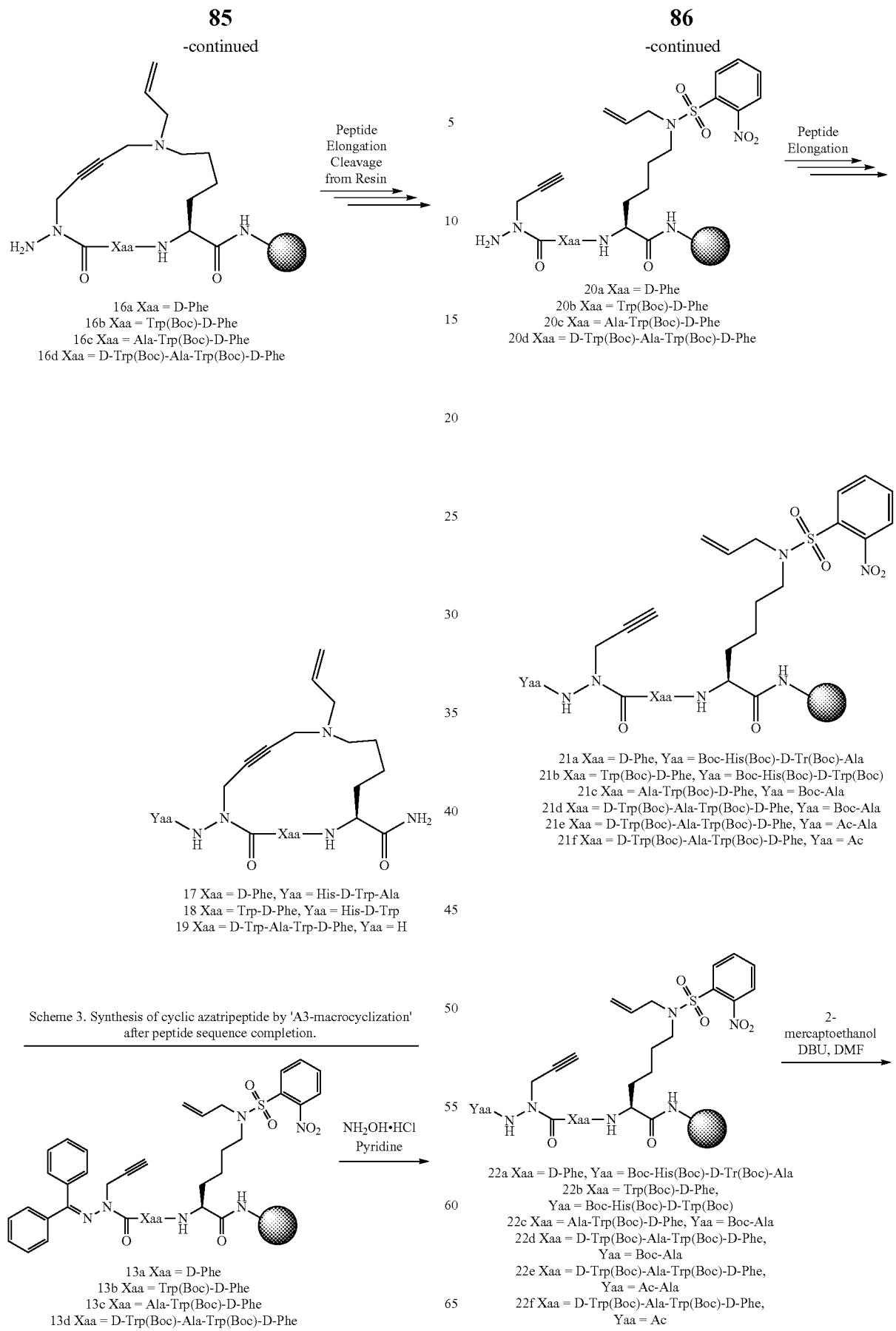

-continued

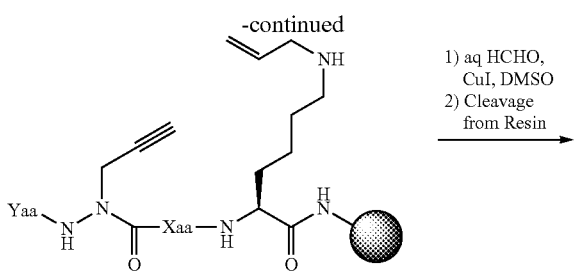

1) aq HCHO, CuI, DMSO
2) Cleavage from Resin

23a Xaa = D-Phe, Yaa = Boc-His(Boc)-D-Tr(Boc)-Ala
23b Xaa = Trp(Boc)-D-Phe,
    Yaa = Boc-His(Boc)-D-Trp(Boc)
23c Xaa = Ala-Trp(Boc)-D-Phe, Yaa = Boc-Ala
23d Xaa = D-Trp(Boc)-Ala-Trp(Boc)-D-Phe,
    Yaa = Boc-Ala
23e Xaa = D-Trp(Boc)-Ala-Trp(Boc)-D-Phe,
    Yaa = Ac-Ala
23f Xaa = D-Trp(Boc)-Ala-Trp(Boc)-D-Phe,
    Yaa = Ac

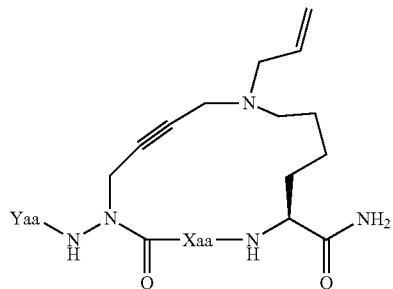

17 Xaa = D-Phe, Yaa = His-D-Trp-Ala
18 Xaa = Trp-D-Phe, Yaa = His-D-Trp
24 Xaa = Ala-Trp-D-Phe, Yaa = Ala
25 Xaa = D-Trp-Ala-Trp-D-Phe, Yaa = Ala
26 Xaa = D-Trp-Ala-Trp-D-Phe, Yaa = Ac-Ala
27 Xaa = D-Trp-Ala-Trp-D-Phe, Yaa = Ac

Failure to elongate semicarbazides 16c and 16d after cyclization promoted investigation of a strategy featuring elongation of the complete linear peptide prior to A3-macrocyclization as the penultimate step before simultaneous deprotection and resin cleavage. Semicarbazone 13a was thus treated with hydroxylamine hydrochloride to liberate the semicarbazide 20a, and the linear peptide was elongated as described for its cyclic counterpart above. Aza-hexapeptide 21a was treated with DBU and 2-mercaptoethanol to selectively remove the o-NBS group. Subsequently, aza-hexapeptide 23a was effectively converted to macrocycle 17 using the standard $A^3$-macrocyclization conditions. Resin cleavage gave cyclic azapeptide 17 in about 2-fold higher yield (1.2%) than the earlier approach, involving peptide elongation after cyclization.

Employing the peptide elongation/$A^3$-macrocyclization approach, linear peptides 22b-d were also successfully converted into macrocyclic aza-GHRP-6 analogs 18, 24 and 25. Cyclic azapeptides 24 and 25 were respectively prepared with N-terminal alanine residues to avoid racemization during coupling to the semicarbazide with histidine, and to add an N-terminal basic amine that may favor biological activity.

The diversity of the ε-amine substituent was explored by the synthesis of cyclic azatetrapeptides 30-32 employing different alcohols as electrophiles in the Mitsunobu reaction: methanol, allyl alcohol and isopropyl alcohol. An ε-N-alkylated lysine was inserted in the peptide sequence to replace the tryptophan residue and an azapropargylglycine was placed at the i+3 position to replace the histidine residue in the GHRP-6 sequence. Cyclic analog 33 was synthesized with an additional alanine in the N-terminal for comparison with analog 31 to study the importance of the N-terminal basic amine.

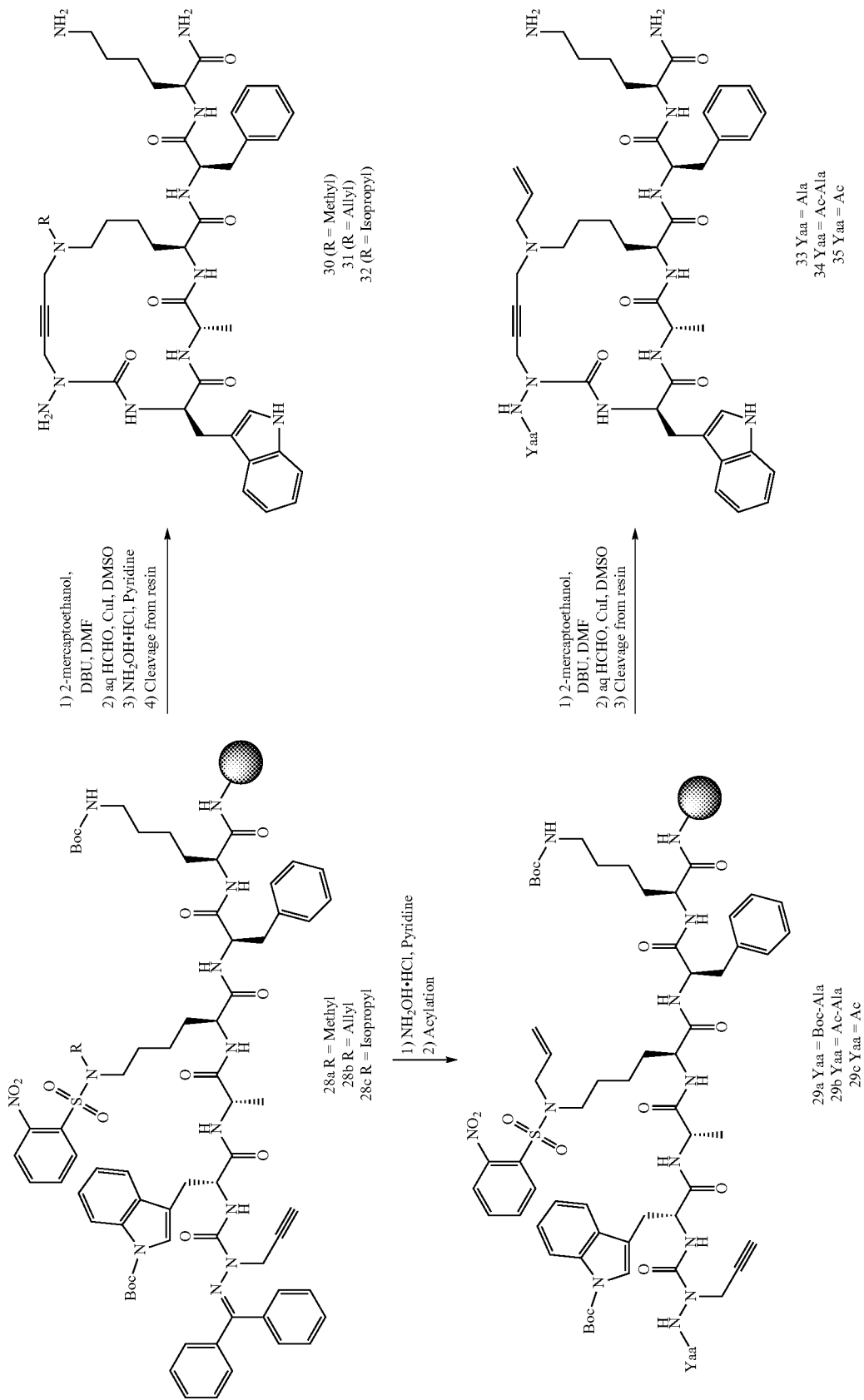
Scheme 4. Synthesis of cyclic azapeptides with ε-N-alkylated lysine in the peptide sequence.

Cyclic azapeptide GHRP-6 analogs were synthesized by the A³-macrocyclization method in yields and purities suitable for biological evaluation (Table 1).

TABLE 1

Yields and purity of the cyclic azapeptide GHRP-6 analogs

| Cyclic Analog | Synthetic Approach | Isolated Yield (%) | Purity[a] | HRMS |
|---|---|---|---|---|
| 8 | I | 3.5 | 99% | 809.4201(809.4206) |
| 9 | I | 2.4 | 99% | 924.4627(924.4628) |
| 17 | I and (II) | 0.5(1.5) | 99% | 835.4376(835.4362) |
| 18 | I and (II) | 0.4(1.1) | 99% | 950.4787(950.4784) |
| 19 | I | 0.5 | 94% | 884.4549(884.4566) |
| 24 | II | 0.9 | 99% | 769.4140(769.4144) |
| 25 | II | 1.1 | 97% | 955.4942(955.4937) |
| 26 | II | 2.0% | 99% | 997.5031(997.5043) |
| 27 | II | 1.6% | 99% | 926.4658(926.4671) |
| 31 | I | 1.5 | 96% | 826.4718(826.4723) |
| 32 | I | 1.2 | 97% | 828.4875(828.4879) |
| 33 | II | 0.9 | 94% | 897.5092(897.5094) |
| 34 | II | 2.5% | 98% | 939.5186(939.5199) |
| 35 | II | 1.4% | 96% | 868.4804(868.4828) |

[a]Determined by LCMS analysis as described above.

Synthesis of Cyclic Analogs MPE-110, MPE-111, MPE-074 and MPE-048
  Solution-Phase Chemistry
  Ornithine Building Block Synthesis

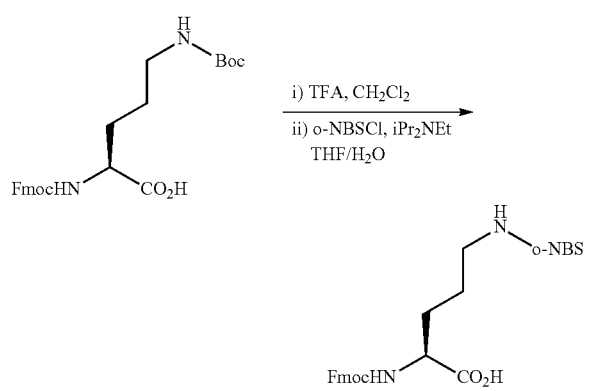

Fmoc-Orn(o-NBS)—OH (RGO1):
  Fmoc-Orn(Boc)-OH (2.02 g, 4.44 mmol) was dissolved in $CH_2Cl_2$ (30 mL) treated with TFA (20 mL) stirred at room temperature for 3 hours, and the volatiles were removed by rotary evaporation. The resulting yellow oil was co-evaporated with toluene to give a residue that was dissolved in THF (40 mL) and water (40 mL) and treated with $iPr_2NEt$ (7.70 mL, 44.2 mmol) and o-NBSCl (1.13 g, 5.08 mmol) in one portion. The reaction was stirred at room temperature for 3 hours, diluted with EtOAc (100 mL) and sequentially washed with aqueous HCl (1 M, 100 mL×3), water (100 mL) and brine (100 mL). The organic layer was dried over $MgSO_4$ and the volatiles were removed by rotary evaporation to give sulfonamide RGO1 (2.4 g, quant.) as a light yellow solid. The amino acid was used without further purification.
  $^1$H NMR (300 MHz, DMSO) δ 8.10 (t, J=5.6 Hz, 1H), 8.03-7.92 (m, 2H), 7.92-7.81 (m, 4H), 7.72 (d, J=7.4 Hz, 2H), 7.61 (d, J=8.0 Hz, 1H), 7.41 (t, J=7.2 Hz, 2H), 7.32 (t, J=7.1 Hz, 2H), 4.34-4.16 (m, 3H), 3.89 (td, J=8.7, 4.6 Hz, 1H), 2.90 (q, J=6.3 Hz, 2H), 1.73 (s, 1H), 1.65-1.43 (m, 3H). $^{13}$C NMR (75 MHz, DMSO) δ 173.7, 156.1, 147.8, 143.8, 140.7, 134.0, 132.7, 132.6, 129.4, 127.7, 127.1, 125.3, 124.4, 120.1, 65.6, 53.5, 46.7, 42.3, 27.9, 26.0. LCMS (10-90% MeOH containing 0.1% formic acid over 10 min) $R_t$=11.04 min. ESI-MS m/z calcd for $C_{26}H_{26}N_3O_8S^+$ [M+H]$^+$ 540.1, found 540.1. Melting point: 108-110° C.

Solid-Phase Chemistry
  Fmoc-based peptide synthesis was performed using standard conditions (W. D. Lubell, J. W. Blankenship, G. Fridkin, and R. Kaul (2005) "Peptides." Science of Synthesis 21.11, Chemistry of Amides. Thieme, Stuttgart, 713-809) on an automated shaker using polystyrene Rink amide resin. The loading was calculated from the UV absorbance for Fmoc-deprotection after the coupling of the first amino acid. Couplings of amino acids (3 equiv.) were performed in DMF using DIC (3 equiv.) and HOBt (3 equiv.) for 3-6 hours. Fmoc-deprotections were performed by treating the resin with 20% piperidine in DMF for 30 min. The resin was washed after each coupling and deprotection step sequentially with DMF (×3), MeOH (×3) THF (×3) and $CH_2Cl_2$ (×3).
  Lysine as AA1

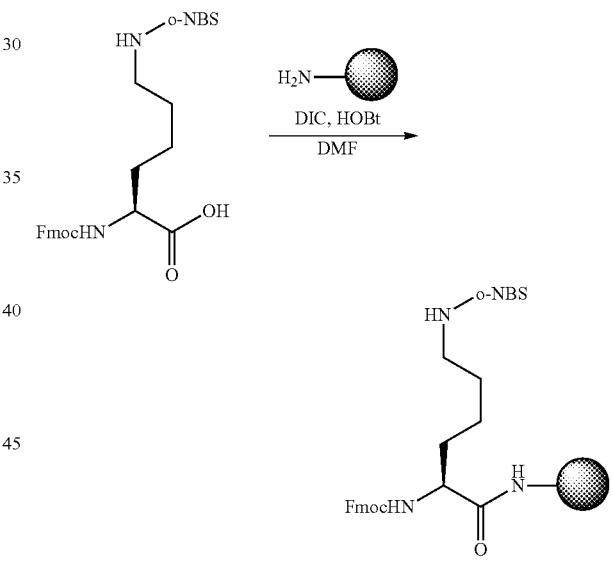

Fmoc-Lys(o-NBS)-Rink Amide Resin RGO7:
  On Rink amide resin (3.00 g) in a syringe fitted with a Teflon™ filter, Fmoc removal was performed by treating the resin with a solution of 20% piperidine in DMF over 30 min. The resin was filtered and washed sequentially with DMF (×3), MeOH (×3) and $CH_2Cl_2$ (×3). Fmoc-Lys(o-NBS)—OH (1.62 g, 2.93 mmol) was dissolved in DMF (20 mL) and treated with DIC (0.7 mL, 4.52 mmol) and HOBt (611 mg, 4.52 mmol), stirred for 3 min. and added to the syringe containing the resin. The mixture was shaken for 14 hours. The resin was then filtered and sequentially washed with DMF (×3), MeOH (×3) and $CH_2Cl_2$ (×3). The resin was dried and the loading was measured at 0.345 mmol/g resin.

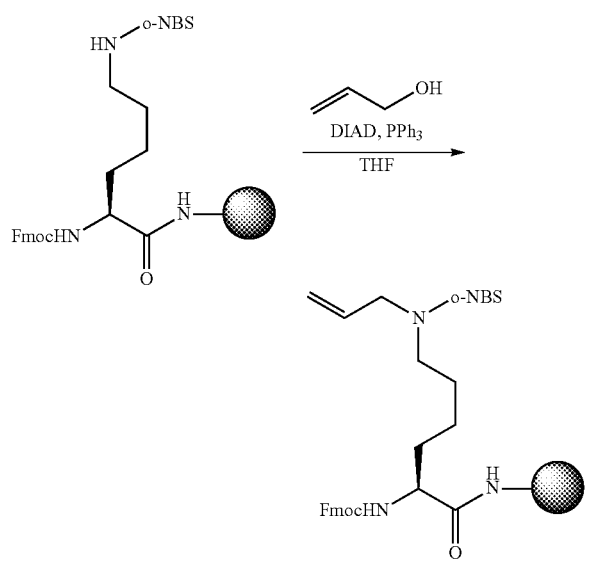

Fmoc-Lys(o-NBS, Allyl)-Rink Amide Resin RGO8:

Vacuum dried Fmoc-Lys(o-NBS)-resin RGO7 (0.441 mmol) was placed in a syringe fitted with a Teflon™ filter, suspended in THF (dry, 5 mL) and treated sequentially with solutions of allyl alcohol (206 µL, 3.03 mmol) in THF (dry, 1 mL), PPh$_3$ (397 mg, 1.51 mmol) in THF (dry, 1 mL), and DIAD (298 µL, 1.51 mmol) in THF (dry, 1 mL). The mixture in the syringe was shaken for 90 min. The resin was filtered and sequentially washed with DMF (×3), MeOH (×3), THF (×3) and CH$_2$Cl$_2$ (×3). Examination by LCMS of a cleaved resin sample (5 mg) showed complete allylation: LCMS (30-95% MeOH containing 0.1% formic acid in water containing 0.1% formic acid over 10 min) R$_t$=8.65 min. ESI-MS m/z calcd for C$_{30}$H$_{33}$N$_4$O$_7$S$^+$ [M+H]$^+$ 593.2, found 593.2.

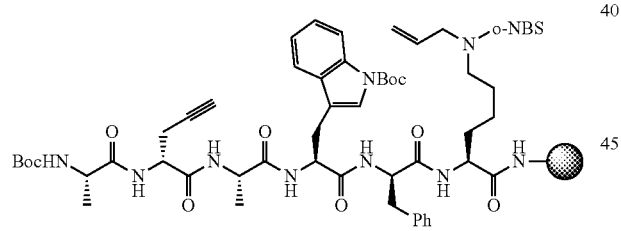

Boc-Ala-D-Pra-Ala-Trp(Boc)-D-Phe-Lys(o-NBS, Allyl)-Rink Amide Resin RGO99:

LCMS (30-95% MeOH containing 0.1% formic acid in water containing 0.1% formic acid over 10 min) R$_t$=5.73 min. ESI-MS m/z calcd for C$_{46}$H$_{57}$N$_{10}$O$_{10}$S$^+$ [M−2Boc+H]$^+$ 941.4, found 941.4.

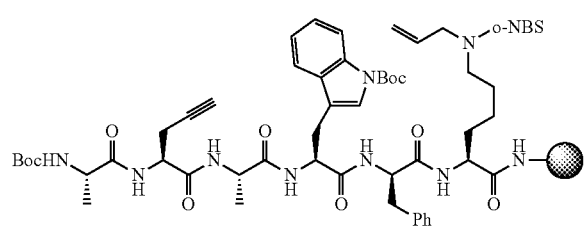

Boc-Ala-L-Pra-Ala-Trp(Boc)-D-Phe-Lys(o-NBS, Allyl)-Rink Amide Resin RGO100:

LCMS (30-95% MeOH containing 0.1% formic acid in water containing 0.1% formic acid over 10 min) R$_t$=5.77 min. ESI-MS m/z calcd for C$_{46}$H$_{57}$N$_{10}$O$_{10}$S$^+$ [M−2Boc+H]$^+$ 941.4, found 941.4.

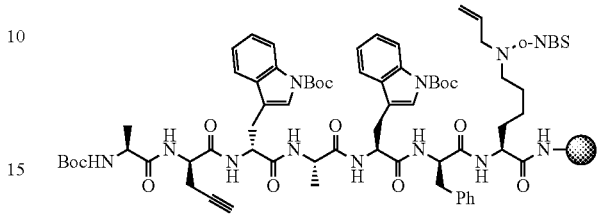

Boc-Ala-D-Pra-D-Trp(Boc)-Ala-Trp-D-Phe-Lys(o-NBS, Allyl)-Rink Amide Resin RGO65:

LCMS (30-95% MeOH containing 0.1% formic acid in water containing 0.1% formic acid over 10 min) R$_t$=6.48 min. ESI-MS m/z calcd for C$_{57}$H$_{67}$N$_{12}$O$_{11}$S$^+$ [M−3Boc+H]$^+$ 1127.5, found 1127.5.

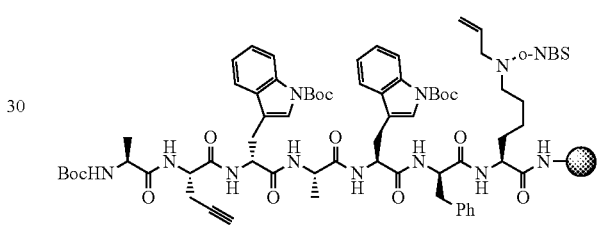

Boc-Ala-L-Pra-D-Trp(Boc)-Ala-Trp-D-Phe-Lys(o-NBS, Allyl)-Rink Amide Resin RGO66:

LCMS (30-95% MeOH containing 0.1% formic acid in water containing 0.1% formic acid over 10 min) R$_t$=6.66 min. ESI-MS m/z calcd for C$_{57}$H$_{67}$N$_{12}$O$_{11}$S$^+$ [M−3Boc+H]$^+$ 1127.5, found 1127.5.

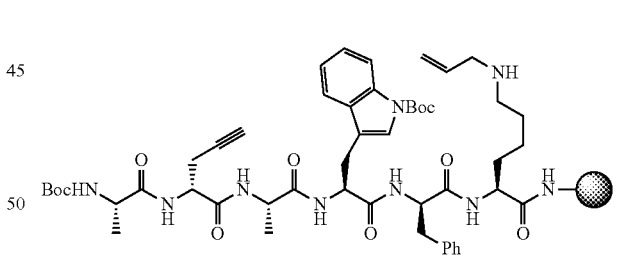

Boc-Ala-D-Pra-Ala-Trp(Boc)-D-Phe-Lys(Allyl)-Rink Amide Resin RGO104:

o-NBS-protected hexapeptide RGO99 (~600 mg, 0.156 mmol) in a syringe fitted with a Teflon™ filter was swollen in DMF (5 mL) and treated with DBU (210 µL, 1.40 mmol) and 2-mercaptoethanol (50 µL, 0.71 mmol). The mixture in the syringe was shaken for 1 h. The resin was filtered and sequentially washed with DMF (×3), MeOH (×3), THF (×3) and CH$_2$Cl$_2$ (×3). Examination by LCMS of a cleaved resin sample (5 mg) showed complete o-NBS-removal: LCMS (30-95% MeOH containing 0.1% formic acid in water containing 0.1% formic acid over 10 min) R$_t$=1.50 min. ESI-MS m/z calcd for C$_{40}$H$_{54}$N$_9$O$_6$$^+$ [M−2Boc+H]$^+$ 756.4, found 756.4.

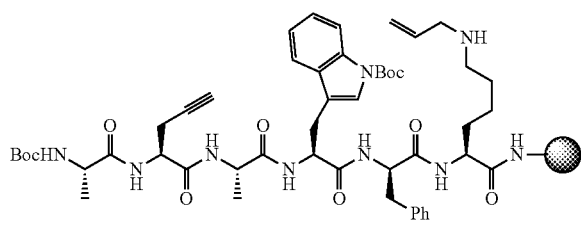 [SMILES: C#CC[C@H](NC(=O)[C@H](C)NC(=O)OC(C)(C)C)C(=O)N[C@@H](C)C(=O)N[C@@H](Cc1cn(C(=O)OC(C)(C)C)c2ccccc12)C(=O)N[C@H](Cc1ccccc1)C(=O)N[C@@H](CCCCNCC=C)C(=O)NC]

Boc-Ala-L-Pra-Ala-Trp(Boc)-D-Phe-Lys(Allyl)-Rink Amide Resin RGO105:

o-NBS-protected hexapeptide RGO100 (~600 mg, 0.14 mmol) in a syringe fitted with a Teflon™ filter was swollen in DMF (5 mL) and treated with DBU (210 µL, 1.40 mmol) and 2-mercaptoethanol (50 µL, 0.71 mmol). The mixture in the syringe was shaken for 1 h. The resin was filtered and sequentially washed with DMF (×3), MeOH (×3), THF (×3) and $CH_2Cl_2$ (×3). Examination by LCMS of a cleaved resin sample (5 mg) showed complete o-NBS-removal: LCMS (30-95% MeOH containing 0.1% formic acid in water containing 0.1% formic acid over 10 min) $R_t$=1.51 min. ESI-MS m/z calcd for $C_{40}H_{54}N_9O_6^+$ [M–2Boc+H]$^+$ 756.4, found 756.4.

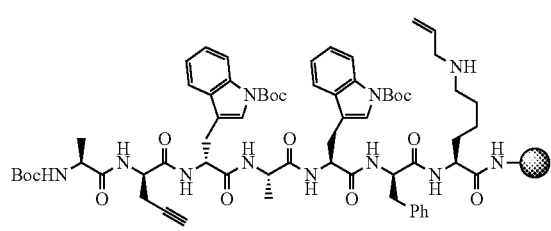 [SMILES: C#CC[C@@H](NC(=O)[C@H](C)NC(=O)OC(C)(C)C)C(=O)N[C@H](Cc1cn(C(=O)OC(C)(C)C)c2ccccc12)C(=O)N[C@@H](C)C(=O)N[C@@H](Cc1cn(C(=O)OC(C)(C)C)c2ccccc12)C(=O)N[C@H](Cc1ccccc1)C(=O)N[C@@H](CCCCNCC=C)C(=O)NC]

Boc-Ala-D-Pra-D-Trp(Boc)-Ala-Trp(Boc)-D-Phe-Lys (allyl)-Rink Amide Resin RGO69:

o-NBS-protected heptapeptide RGO65 (~300 mg, 0.10 mmol) in a syringe fitted with a Teflon™ filter was swollen in DMF (6 mL) and treated with DBU (150 µL, 1.00 mmol) and 2-mercaptoethanol (35 µL, 0.50 mmol). The mixture in the syringe was shaken for 1 h. The resin was filtered and sequentially washed with DMF (×3), MeOH (×3), THF (×3) and $CH_2Cl_2$ (×3). Examination by LCMS of a cleaved resin sample (5 mg) showed complete o-NBS-removal: LCMS (20-80% MeOH containing 0.1% formic acid in water containing 0.1% formic acid over 10 min) $R_t$=4.79 min. ESI-MS m/z calcd for $C_{51}H_{64}N_{11}O_7^+$ [M–3Boc+H]$^+$ 942.5, found 942.5.

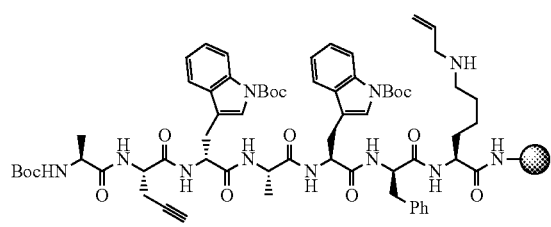 [SMILES: C#CC[C@H](NC(=O)[C@H](C)NC(=O)OC(C)(C)C)C(=O)N[C@H](Cc1cn(C(=O)OC(C)(C)C)c2ccccc12)C(=O)N[C@@H](C)C(=O)N[C@@H](Cc1cn(C(=O)OC(C)(C)C)c2ccccc12)C(=O)N[C@H](Cc1ccccc1)C(=O)N[C@@H](CCCCNCC=C)C(=O)NC]

Boc-Ala-L-Pra-D-Trp(Boc)-Ala-Trp(Boc)-D-Phe-Lys (Allyl)-Rink Amide Resin RGO70:

o-NBS-protected heptapeptide RGO66 (~300 mg, 0.09 mmol) in a syringe fitted with a Teflon™ filter was swollen in DMF (6 mL) and treated with DBU (130 µL, 0.87 mmol) and 2-mercaptoethanol (30 µL, 0.43 mmol). The mixture in the syringe was shaken for 1 h. The resin was filtered and sequentially washed with DMF (×3), MeOH (×3), THF (×3) and $CH_2Cl_2$ (×3). Examination by LCMS of a cleaved resin sample (5 mg) showed complete o-NBS-removal: LCMS (20-80% MeOH containing 0.1% formic acid in water containing 0.1% formic acid over 10 min) $R_t$=5.05 min. ESI-MS m/z calcd for $C_{51}H_{64}N_{11}O_7^+$ [M–3Boc+H]$^+$ 942.5, found 942.5.

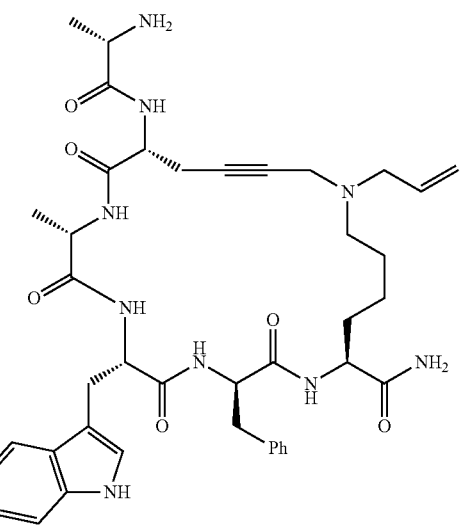

Cyclic Peptide MPE-110:

Hexapeptide resin RGO104 (~600 mg, 0.156 mmol) was swollen in DMSO (6 mL) for 30 min in a syringe tube equipped with Teflon™ filter, and stopper, treated with CuI (5.0 mg, 0.03 mmol) and aqueous formaldehyde (70 µL, 0.94 mmol, 37% in $H_2O$), shaken on an automated shaker for 30 h, and filtered. After filtration, the resin was washed sequentially with AcOH/$H_2O$/DMF (5:15:80, v/v/v, ×3), DMF (×3), THF (×3), MeOH (×3), and DCM (×3). Examination by LCMS of a cleaved resin sample (5 mg) showed complete conversion, and a peak with molecular ion consistent with cyclic hexapeptide MPE-110 was observed: MS m/z calcd for $C_{41}H_{54}N_9O_6^+$ [M+H]$^+$ 768.4, found 768.4.

Resin-bound cyclic peptide MPE-110 was deprotected and cleaved from the support using a freshly made solution of TFA/$H_2O$/TES (95:2.5:2.5, v/v/v, 5 mL) at rt for 2 h. The resin was filtered and rinsed with TFA (5 mL). The filtrate and rinses were concentrated until a crude oil persisted, from which a precipitate was obtained by addition of cold ether (10 mL). After centrifugation (1200 rpm for 10 min), the supernatant was removed and the crude peptide precipitate was taken up in aqueous MeOH (10% v/v) and freeze-dried prior to purification. The resulting light brown fluffy material was purified by preparative HPLC to give cyclic pentapeptide MPE-110 (2.0 mg, 2%) as white fluffy material.

LCMS analysis of cyclic peptide MPE-110 was performed using a linear gradient of a) 10-90% of MeOH containing 0.1% formic acid in $H_2O$ (0.1% formic acid) over 10 min, then at 10% MeOH (0.1% formic acid) for 5 min, $R_t$=4.24 min; b) 10-90% MeCN containing 0.1% formic acid in $H_2O$ containing 0.1% formic acid over 10 min, then at 10% MeCN (0.1% formic acid) for 5 min, $R_t$=1.70 min; HRMS m/z. calcd for $C_{41}H_{54}N_9O_6^+$ [M+H]$^+$ 768.4192, found 768.4176.

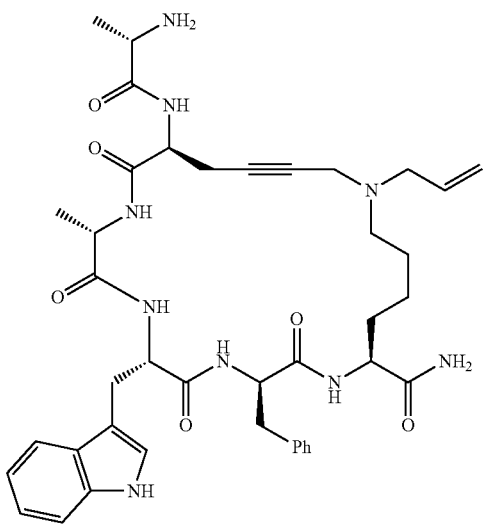 [SMILES: C=CCN1CC#CC[C@H](NC(=O)[C@H](C)N)C(=O)N[C@@H](C)C(=O)N[C@@H](Cc2c[nH]c3ccccc23)C(=O)N[C@H](Cc2ccccc2)C(=O)N[C@H](C(N)=O)CCCC1]

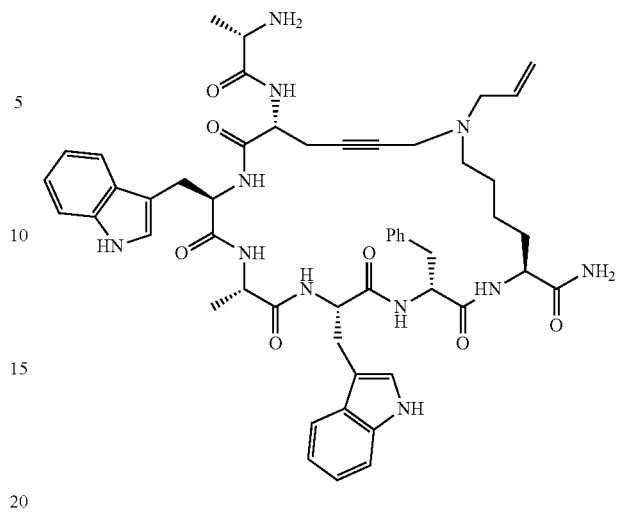

Cyclic Peptide MPE-111:

Hexapeptide resin RGO105 (~600 mg, 0.14 mmol) was swollen in DMSO (6 mL) for 30 min in a syringe tube equipped with Teflon™ filter, and stopper, treated with CuI (5.0 mg, 0.03 mmol) and aqueous formaldehyde (60 µL, 0.84 mmol, 37% in H$_2$O), shaken on an automated shaker for 30 h, and filtered. After filtration, the resin was washed sequentially with AcOH/H$_2$O/DMF (5:15:80, v/v/v, ×3), DMF (×3), THF (×3), MeOH (×3), and DCM (×3). Examination by LCMS of a cleaved resin sample (5 mg) showed complete conversion, and a peak with molecular ion consistent with cyclic hexapeptide MPE-111 was observed: MS m/z. calcd for $C_{41}H_{54}N_9O_6^+$ [M+H]$^+$ 768.4, found 768.4.

Resin-bound cyclic peptide MPE-111 was deprotected and cleaved from the support using a freshly made solution of TFA/H$_2$O/TES (95:2.5:2.5, v/v/v, 5 mL) at rt for 2 h. The resin was filtered and rinsed with TFA (5 mL). The filtrate and rinses were concentrated until a crude oil persisted, from which a precipitate was obtained by addition of cold ether (10 mL). After centrifugation (1200 rpm for 10 min), the supernatant was removed and the crude peptide precipitate was taken up in aqueous MeOH (10% v/v) and freeze-dried prior to purification. The resulting light brown fluffy material was purified by preparative HPLC to give cyclic hexapeptide MPE-111 (2.9 mg, 3%) as white fluffy material.

LCMS analysis of cyclic peptide MPE-111 was performed using a linear gradient of a) 10-90% of MeOH containing 0.1% formic acid in H$_2$O (0.1% formic acid) over 10 min, then at 10% MeOH (0.1% formic acid) for 5 min, $R_t$=4.50 min; b) 10-90% MeCN containing 0.1% formic acid in H$_2$O containing 0.1% formic acid over 10 min, then at 10% MeCN (0.1% formic acid) for 5 min, $R_t$=2.03 min; HRMS m/z. calcd for $C_{41}H_{54}N_9O_6^+$ [M+H]$^+$ 768.4192, found 768.4172.

Cyclic Peptide MPE-074:

Heptapeptide resin RGO69 (~300 mg, 0.10 mmol) was swollen in DMSO (5 mL) for 30 min in a syringe tube equipped with Teflon™ filter, and stopper, treated with CuI (4.0 mg, 0.02 mmol) and aqueous formaldehyde (50 µL, 0.69 mmol, 37% in H$_2$O), shaken on an automated shaker for 29 h, and filtered. After filtration, the resin was washed sequentially with AcOH/H$_2$O/DMF (5:15:80, v/v/v, ×3), DMF (×3), THF (×3), MeOH (×3), and DCM (×3). Examination by LCMS of a cleaved resin sample (5 mg) showed complete conversion, and a peak with molecular ion consistent with cyclic heptapeptide MPE-074 was observed: MS m/z calcd for $C_{52}H_{63}N_{11}NaO_7^+$ [M+Na]$^+$ 976.5, found 976.4.

Resin-bound cyclic peptide MPE-074 was deprotected and cleaved from the support using a freshly made solution of TFA/H$_2$O/TES (95:2.5:2.5, v/v/v, 5 mL) at rt for 2 h. The resin was filtered and rinsed with TFA (5 mL). The filtrate and rinses were concentrated until a crude oil persisted, from which a precipitate was obtained by addition of cold ether (10 mL). After centrifugation (1200 rpm for 10 min), the supernatant was removed and the crude peptide precipitate was taken up in aqueous MeOH (10% v/v) and freeze-dried prior to purification. The resulting light brown fluffy material was purified by preparative HPLC to give cyclic heptapeptide MPE-074 (0.7 mg, 1%) as white fluffy material.

LCMS analysis of cyclic peptide MPE-074 was performed using a linear gradient of a) 10-90% of MeOH containing 0.1% formic acid in H$_2$O (0.1% formic acid) over 10 min, then at 10% MeOH (0.1% formic acid) for 5 min, $R_t$=1.72 min; b) 10-90% MeCN containing 0.1% formic acid in H$_2$O containing 0.1% formic acid over 10 min, then at 10% MeCN (0.1% formic acid) for 5 min, $R_t$=4.24 min; HRMS m/z calcd for $C_{52}H_{63}N_{11}NaO_7^+$ [M+Na]$^+$ 976.4804, found 976.4817.

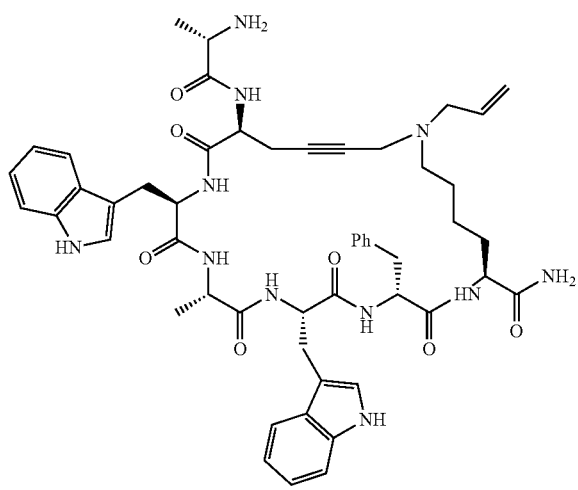 [SMILES: C=CCN1CC#CC[C@H](NC(=O)[C@H](C)N)C(=O)N[C@H](Cc2c[nH]c3ccccc23)C(=O)N[C@@H](C)C(=O)N[C@@H](Cc2c[nH]c3ccccc23)C(=O)N[C@H](Cc2ccccc2)C(=O)N[C@H](C(N)=O)CCCC1]

Cyclic Peptide MPE-075:

Heptapeptide resin RGO69 (~300 mg, 0.09 mmol) was swollen in DMSO (5 mL) for 30 min in a syringe tube equipped with Teflon™ filter, and stopper, treated with CuI (3.0 mg, 0.02 mmol) and aqueous formaldehyde (50 μL, 0.69 mmol, 37% in H₂O), shaken on an automated shaker for 29 h, and filtered. After filtration, the resin was washed sequentially with AcOH/H₂O/DMF (5:15:80, v/v/v, ×3), DMF (×3), THF (×3), MeOH (×3), and DCM (×3). Examination by LCMS of a cleaved resin sample (5 mg) showed complete conversion, and a peak with molecular ion consistent with cyclic heptapeptide MPE-075 was observed: MS m/z calcd for $C_{52}H_{64}N_{11}O_7^+$ [M+H]$^+$ 954.5, found 954.5.

Resin-bound cyclic peptide MPE-075 was deprotected and cleaved from the support using a freshly made solution of TFA/H₂O/TES (95:2.5:2.5, v/v/v, 5 mL) at rt for 2 h. The resin was filtered and rinsed with TFA (5 mL). The filtrate and rinses were concentrated until a crude oil persisted, from which a precipitate was obtained by addition of cold ether (10 mL). After centrifugation (1200 rpm for 10 min), the supernatant was removed and the crude peptide precipitate was taken up in aqueous MeOH (10% v/v) and freeze-dried prior to purification. The resulting light brown fluffy material was purified by preparative HPLC to give cyclic heptapeptide MPE-075 (1.5 mg, 2%) as a white fluffy material.

LCMS analysis of cyclic peptide MPE-075 was performed using a linear gradient of a) 10-90% of MeOH containing 0.1% formic acid in H₂O (0.1% formic acid) over 10 min, then at 10% MeOH (0.1% formic acid) for 5 min, $R_t$=1.89 min; b) 10-90% MeCN containing 0.1% formic acid in H₂O containing 0.1% formic acid over 10 min, then at 10% MeCN (0.1% formic acid) for 5 min, $R_t$=4.47 min; HRMS m/z calcd for $C_{52}H_{64}N_{11}O_7^+$ [M+H]$^+$ 954.4985, found 954.4973.

Ornithine as AA1

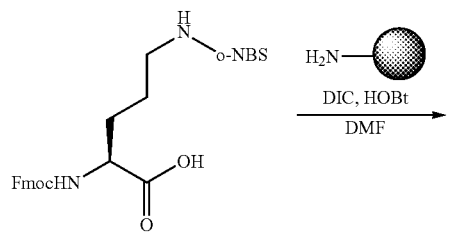

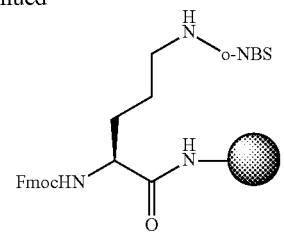

Fmoc-Orn(o-NBS)-Rink Amide Resin RGO3:

Rink amide resin (2.51 g) was placed in a syringe fitted with a Teflon™ filter. The Fmoc group was removed by treating the resin with a solution of 20% piperidine in DMF over 30 min. The resin was filtered and washed sequentially with DMF (×3), MeOH (×3) and CH₂Cl₂ (×3). Fmoc-Orn (o-NBS)—OH (1.33 g, 2.46 mmol) was dissolved in DMF (20 mL) and treated with DIC (0.57 mL, 3.68 mmol) and HOBt (494 mg, 3.66 mmol) and stirred for 3 min, before being transferred to the syringe containing the swollen resin, and the mixture was shaken for 14 hours. The resin was filtered and washed sequentially with DMF (×3), MeOH (×3) and CH₂Cl₂ (×3). The resin was dried and the loading was measured to 0.187 mmol/g resin.

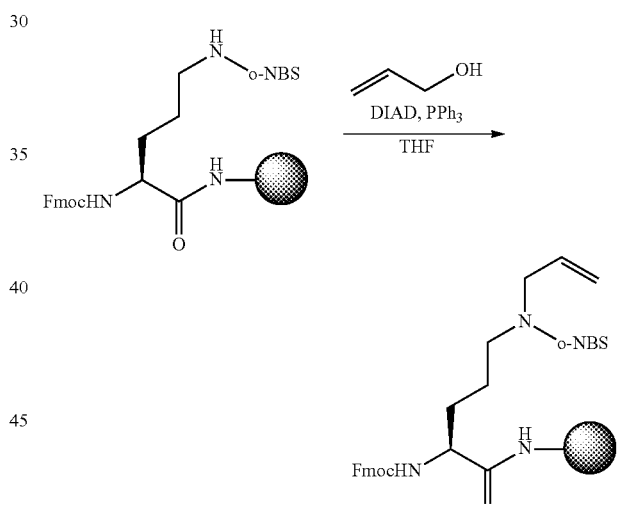

Fmoc-Orn(o-NBS, Allyl)-Rink Amide Resin RGO4:

Vacuum dried Fmoc-Orn(o-NBS)-resin (0.362 mmol) was placed in a syringe fitted with a Teflon™ filter, suspended in THF (dry, 20 mL) and treated sequentially with solutions of allyl alcohol (250 μL, 3.68 mmol) in THF (dry, 1 mL), PPh₃ (482 mg, 1.84 mmol) in THF (dry, 2 mL) and DIAD (360 μL, 1.83 mmol) in THF (dry, 1 mL). The resin mixture in the syringe was shaken for 90 min. The resin was filtered and washed sequentially with DMF (×3), MeOH (×3), THF (×3) and CH₂Cl₂ (×3). Examination by LCMS of a cleaved resin sample (5 mg) showed complete allylation: LCMS (30-95% MeOH containing 0.1% formic acid in water containing 0.1% formic acid over 10 min) $R_t$=8.47 min. ESI-MS m/z calcd for $C_{29}H_{31}N_4O_7S^+$ [M+H]$^+$ 579.2, found 579.2.

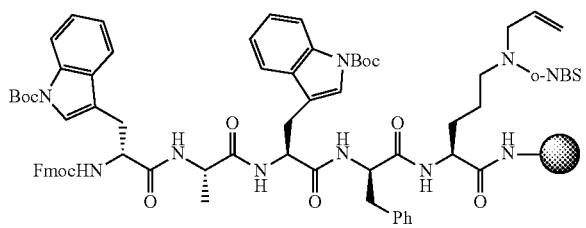

Fmoc-D-Trp(Boc)-Ala-Trp(Boc)-D-Phe-Orn(o-NBS, Allyl)-Rink Amide Resin RGO22:

LCMS (30-95% MeOH containing 0.1% formic acid in water containing 0.1% formic acid over 10 min) $R_t$=6.13 min. ESI-MS m/z calcd for $C_{48}H_{55}N_{10}O_9S^+$ [M-Fmoc-2Boc+H]$^+$ 947.4, found 947.3.

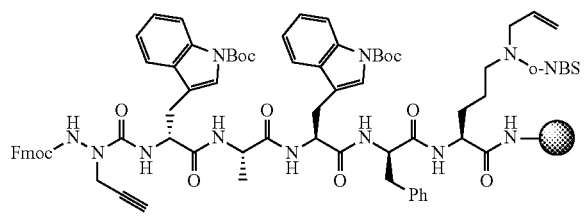

Fmoc-azaPra-D-Trp(Boc)-Ala-Trp(Boc)-D-Phe-Orn(o-NBS, Allyl)-Rink Amide Resin RGO79:

N'-Propargyl-fluorenylmethylcarbazate (248 mg, 0.849 mmol, prepared by alkylation of fluorenylmethylcarbazate with propargylbromide as —N(R$^{10}$)— described below) was dissolved in CH$_2$Cl$_2$ (dry, 40 mL) under argon atmosphere. The solution was cooled to 0° C., treated with a 20% solution of phosgene in toluene (1 mL, 1.87 mmol), warmed to rt, stirred 50 min, and the volatiles were removed by rotary evaporation. The residue was re-dissolved in CH$_2$Cl$_2$ (10 mL) and the volatiles were once again removed by rotary evaporation. The resulting white solid was dissolved in CH$_2$Cl$_2$ (dry, 7 mL) and added to the Fmoc-deprotected pentapeptide RGO22 in a syringe fitted with a Teflon™ filter. The mixture in the syringe was shaken for 28 h. The resin was filtered and washed sequentially with DMF (×3), MeOH (×3), THF (×3) and CH$_2$Cl$_2$ (×3). Examination by LCMS of a cleaved resin sample (5 mg) showed complete coupling: LCMS (30-95% MeOH containing 0.1% formic acid in water containing 0.1% formic acid over 10 min) $R_t$=8.26 min. ESI-MS m/z calcd for $C_{52}H_{59}N_{12}O_{10}S^+$ [M-Fmoc-2Boc+H]$^+$ 1043.4, found 1043.3.

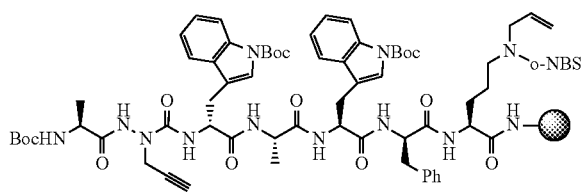

Boc-Ala-azaPra-D-Trp(Boc)-Ala-Trp(Boc)-D-Phe-Orn(o-NBS, Allyl)-Rink Amide RGO29:

Coupling onto the semicarbazide RGO79 was performed by using amino acid symmetric anhydrides that were generated in situ (J. Zhang, C. Proulx, A. Tomberg, W. D. Lubell, *Org. Lett.* 2013, 16, 298-301). The procedure was repeated twice on semicarbazide RGO79. Examination by LCMS of a cleaved resin sample (5 mg) showed complete coupling: LCMS (30-95% MeOH containing 0.1% formic acid in water containing 0.1% formic acid over 10 min) $R_t$=6.39 min. ESI-MS m/z calcd for $C_{55}H_{64}N_{13}O_{11}S^+$ [M-3Boc+H]$^+$ 1114.5, found 1114.4.

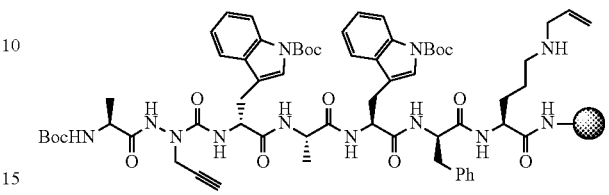

Boc-Ala-azaPra-D-Trp(Boc)-Ala-Trp(Boc)-D-Phe-Orn(Allyl)-Rink Amide RGO30:

o-NBS-protected hetapeptide RGO29 (~1 g, 0.2 mmol) in a syringe fitted with a Teflon™ filter was swollen in DMF (6 mL) and DBU (300 μL, 2.01 mmol) and treated with 2-mercaptoethanol (70 μL, 1.00 mmol). The mixture in the syringe was shaken for 1 h. The resin was filtered and washed sequentially with DMF (×3), MeOH (×3), THF (×3) and CH$_2$Cl$_2$ (×3). Examination by LCMS of a cleaved resin sample (5 mg) showed complete o-NBS-removal: LCMS (30-95% MeOH containing 0.1% formic acid in water containing 0.1% formic acid over 10 min) $R_t$=4.49 min. ESI-MS m/z calcd for $C_{49}H_{61}N_{12}O_7^+$ [M-3Boc+2Na]$^{2+}$ 487.2, found 487.3.

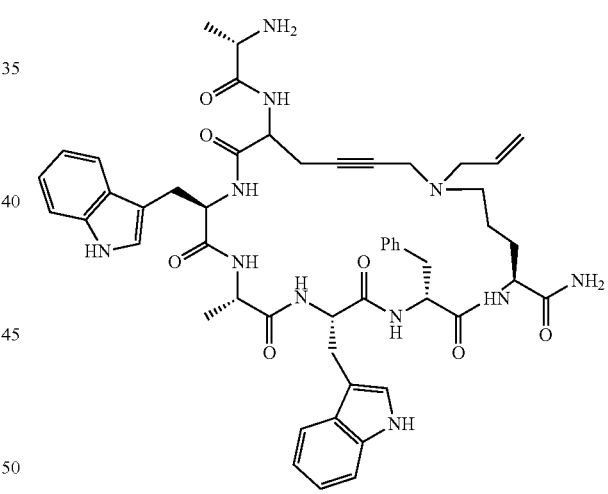

Cyclic Azapeptide MPE-048:

Azaheptapeptide resin RGO30 (~1 g, 0.2 mmol) was swollen in DMSO (8 mL) for 30 min in a syringe tube equipped with Teflon™ filter, and stopper, treated with CuI (7.0 mg, 0.04 mmol) and aqueous formaldehyde (90 μL, 1.2 mmol, 37% in H$_2$O), shaken on an automated shaker for 31 h, and filtered. After filtration, the resin was washed sequentially with AcOH/H$_2$O/DMF (5:15:80, v/v/v, ×3), DMF (×3), THF (×3), MeOH (×3), and DCM (×3). Examination by LCMS of a cleaved resin sample (5 mg) showed complete conversion, and a peak with molecular ion consistent with cyclic azaheptapeptide MPE-048 was observed: MS m/z calcd for $C_{50}H_{61}N_{12}O_7^+$ [M+H]$^+$ 941.5, found 941.4.

Resin-bound cyclic azapeptide MPE-048 was deprotected and cleaved from the support using a freshly made solution of TFA/H$_2$O/TES (95:2.5:2.5, v/v/v, 5 mL) at rt for 2 h. The resin was filtered and rinsed with TFA (5 mL). The filtrate and rinses were concentrated until a crude oil persisted, from which a precipitate was obtained by addition of cold ether (10 mL). After centrifugation (1200 rpm for 10 min), the supernatant was removed and the crude peptide precipitate was taken up in aqueous MeOH (10% v/v) and freeze-dried prior to purification. The resulting light brown fluffy material was purified by preparative HPLC to give cyclic aza-heptapeptide MPE-048 (1.3 mg, 1%) as white fluffy material.

LCMS analysis of cyclic peptide MPE-048 was performed using a linear gradient of a) 10-90% of MeOH containing 0.1% formic acid in H$_2$O (0.1% formic acid) over 10 min, then at 10% MeOH (0.1% formic acid) for 5 min, R$_t$=1.80 min; b10-90% MeCN containing 0.1% formic acid in H$_2$O containing 0.1% formic acid over 10 min, then at 10% MeCN (0.1% formic acid) for 5 min, R$_t$=4.30 min; HRMS m/z calcd for C$_{50}$H$_{60}$N$_{12}$O$_7$Na$^+$ [M+Na]$^+$ 963.4600, found 963.4573.

Synthesis of Cyclic Analogs MPE-189, MPE-201, MPE-202, and MPE-203

Synthesis of Carbazates 2 and 3

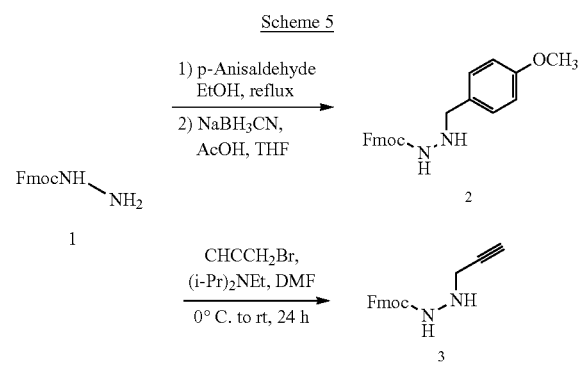

Scheme 5

To a well-stirred solution of fluorenylmethyl carbazate (1, 1 eq., 2.8 g, 11 mmol, prepared according to reference 1) and DIEA (2 eq., 2.85 g, 3.64 mL, 22 mmol) in dry DMF (280 mL) at 0° C., a solution of 3-bromopropyne (0.9 eq., 1.47 g, 1.07 mL, 9.91 mmol, 80 wt. % in toluene) in dry DMF (10 mL) was added drop-wise by cannula over 30 min. The cooling bath was removed. The reaction mixture was allowed to warm to room temperature and stirred for 16 h. The volatiles were evaporated. The residue was partitioned between EtOAc and brine. The aqueous layer was separated and extracted with EtOAc. The combined organic layer was dried over Na$_2$SO$_4$, filtered, and evaporated. The residue was purified by silica gel chromatography eluting with 40% EtOAc in hexane as solvent system to obtain N'-propargyl-fluorenylmethylcarbazate 3 (1.8 g, 62%), as white solid: R$_f$ 0.42 (60% EtOAc); mp 148-149° C.; $^1$H NMR (500 MHz, DMSO-d$_6$) δ 8.82 (s, 1H), 7.89 (d, J=7.5 Hz, 2H), 7.70 (d, J=7.4 Hz, 2H), 7.50-7.43 (m, 2H), 7.37-7.28 (m, 2H), 4.89 (q, J=4.6 Hz, 1H), 4.29 (d, J=6.9 Hz, 2H), 4.22 (t, J=6.1 Hz, 1H), 3.48 (s, 2H), 3.09 (t, J=2.3 Hz, 1H); $^{13}$C NMR (125 MHz, DMSO-d$_6$) δ 156.7, 143.8, 140.7, 127.7 (2C), 127.1 (2C), 125.3 (2C), 120.1 (2C), 81.2, 74.2, 65.6 (2C), 46.6, 39.6 (2C). IR (neat) vmax/cm-1 3304, 3290, 2947, 1699, 1561, 1489, 1448, 1265, 1159, 1021; HRMS m/z calculated for C$_{18}$H$_{17}$N$_2$O$_2$ [M+H]$^+$ 293.1285; found 293.1275.

N'-4-methoxybenzyl-fluorenylmethylcarbazate (2)

N'-4-Methoxybenzyl-fluorenylmethylcarbazate 2 was prepared according to a modification of the reductive amination procedure for carbazate synthesis (Boeglin, D.; Lubell, W. D. "Aza-Amino Acid Scanning of Secondary Structure Suited for Solid-Phase Peptide Synthesis with Fmoc Chemistry and Aza-Amino Acids with Heteroatomic Side-Chains" J. Comb. Chem. 2005, 7(6), 864-878). A suspension of fluorenylmethylcarbazate (1) in EtOH (0.2 M) was treated with 100 mol % of 4-methoxybenzaldehyde, heated at reflux for 2 h, and concentrated in vacuo. The resulting methylidene carbazate was dissolved in THF (0.2 M), treated successively with 110 mol % AcOH and 110 mol % NaBH$_3$CN, stirred for 1 h, and treated with additional NaBH$_3$CN if necessary until completion of the reaction was observed by TLC. The mixture was concentrated in vacuo. The residue was dissolved in EtOAc, washed with aqueous KHSO$_4$ (1 M) and brine, dried over Na$_2$SO$_4$, and concentrated under reduced pressure to yield a white solid that was dissolved in EtOH and heated at reflux for 1 h. The mixture was concentrated under reduced pressure to yield a residue that was purified by flash chromatography to yield carbazate 2 (76%) as white solid: R$_f$ 0.53 (30% EtOAc); $^1$H NMR (300 MHz, CDCl$_3$) δ 7.78 (d, J=7.5 Hz, 2H), 7.58 (d, J=7.6 Hz, 2H), 7.45-7.27 (m, 6H), 6.87 (d, J=7.2, 2H), 6.35 (bs, 1H), 4.48 (bs, 2H), 4.24 (t, J=2.3 Hz, 1H), 3.94 (bs, 2H), 3.81 (s, 3H); $^{13}$C NMR (75 MHz, CDCl$_3$) δ 159.2, 157.2, 143.7, 141.4, 130.3, 129.4, 127.8, 127.1, 125.0, 120.1, 113.9, 66.9, 55.4, 47.2; HRMS m/z calculated for C$_{23}$H$_{22}$N$_2$O$_3$ [M+H]$^+$ 375.1703; found 375.1697.

Synthesis of Cyclic Azapeptides MPE-298, MPE-191 and MPE-192 Employing N-(Fmoc)Aza-Amino Acid Chlorides

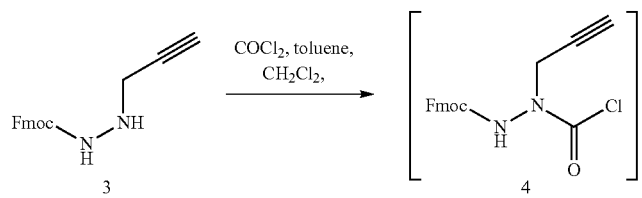

Scheme 6

-continued

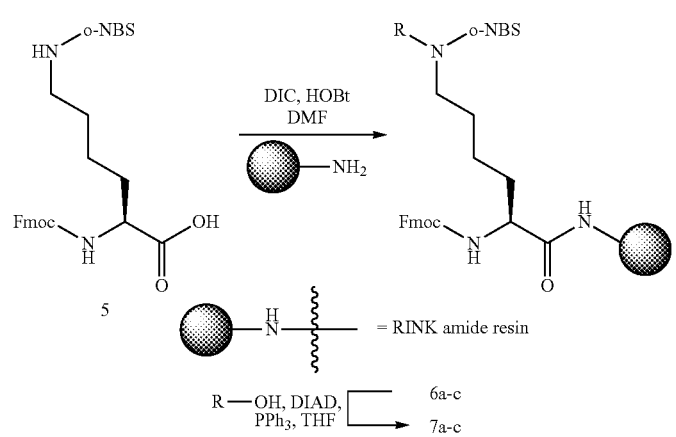

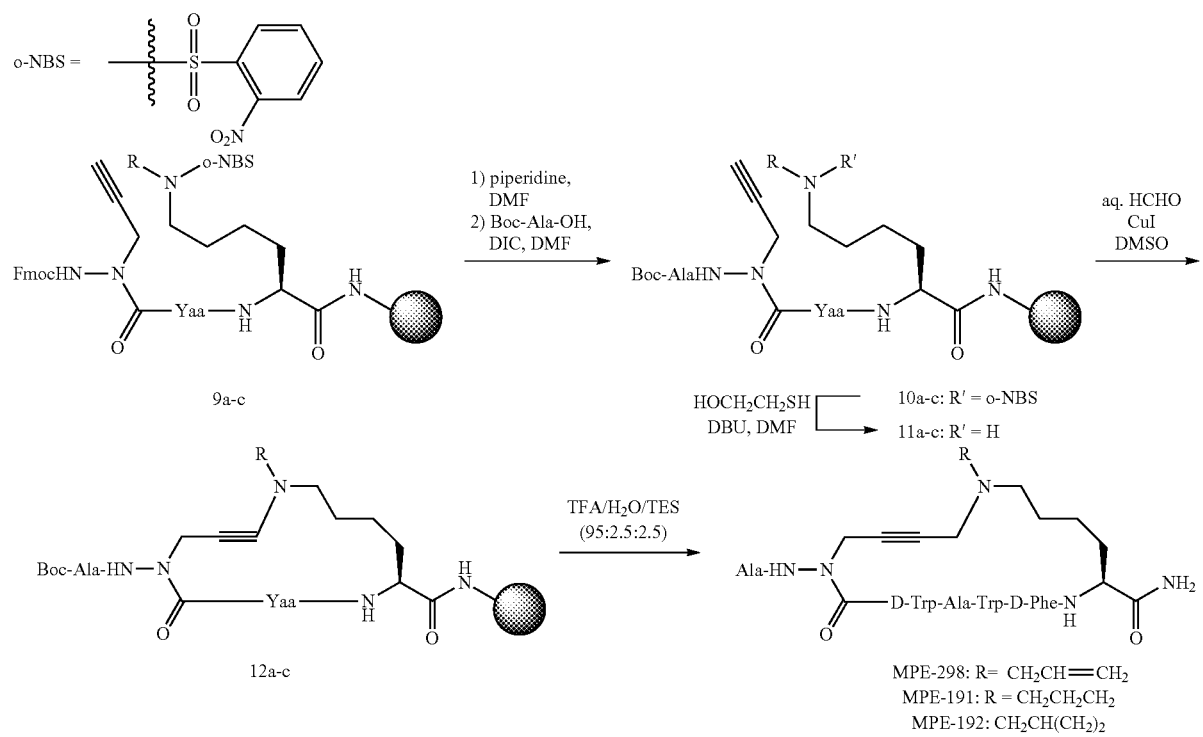

Fmoc-Lys(o-NBS, allyl)-Rink amide resin protocol was described for RGO8 above.

Fmoc-Lys(o-NBS, Allyl)-Rink Amide Resin 7a:

LCMS analysis of a cleaved resin sample of 7a showed complete alkylation; LCMS (10-95% MeOH containing 0.1% FA in water containing 0.1% FA over 10 min); $R_t$=8.67 min; ESI-MS m/z calcd for $C_{30}H_{32}N_4O_7S$ [M+H]$^+$ 593.2, found 593.2.

Fmoc-Lys(o-NBS, Propyl)-Rink Amide Resin 7b:

Examination by LCMS of a cleaved resin sample of 7b showed complete alkylation; LCMS (10-95% MeOH containing 0.1% FA in water containing 0.1% FA over 10 min) $R_t$=8.74 min; ESI-MS m/z calcd for $C_{30}H_{34}N_4O_7S$ [M+H]$^+$ 595.2, found 595.2.

Fmoc-Lys(o-NBS, Cyclopropylmethyl)-Rink Amide Resin 7c:

LCMS analysis of a cleaved resin sample of 7c showed complete alkylation; LCMS (10-95% MeOH containing 0.1% FA in water containing 0.1% FA over 10 min) $R_t$=10.46 min; ESI-MS m/z calcd for $C_{31}H_{34}N_4O_7S$ [M+H]$^+$ 607.2, found 607.2.

Representative Protocol for Coupling of N-(Fmoc)Aza-Amino Acid Chloride to Resin-Bound Peptide.

To a solution of N'-propargyl-fluorenylmethylcarbazate (2, 2.97 mmol) in dry DCM (30 mL) under argon at 0° C., a solution of phosgene in toluene (3.0 mL, 5.93 mmol, 1.93 M) was added drop-wise. After complete consumption of starting material 2 (usually around 15 min as indicated by TLC), the reaction mixture was concentrated in vacuo to yield the corresponding Fmoc-aza-amino acid chloride 4, which was employed without further purification. N-(Fmoc) Aza-amino acid chloride was suspended in dry DCM (10 mL) and added to a syringe tube containing swollen resin 8a, followed by DIEA (5.93 mmol, 1.03 mL). The resin mixture was shaken for 16 h, filtered, and washed sequentially with DMF (3×10 mL), MeOH (3×10 mL), THF (3×10 mL), and DCM (3×10 mL). Examination by LCMS of a cleaved sample of resin 9a (5 mg) showed complete coupling; LCMS (30-95% MeOH containing 0.1% FA in water containing 0.1% FA over 10 min) $R_t$=9.66 min; ESI-MS m/z calcd for $C_{68}H_{70}N_{12}O_{12}S$ [M+H]$^+$ 1279.5, found 1279.5.

Fmoc-aza-Tyr(Me)-D-Phe-Lys(o-NBS, allyl)-Rink amide resin 16 was prepared as described using the representative protocol for N-(Fmoc)aza-amino acid chloride coupling using N'-methoxybenzyl-fluorenylmethylcarbazate 2: LCMS of a cleaved resin sample of 16 showed complete coupling; LCMS (30-95% MeOH containing 0.1% FA in water containing 0.1% FA over 10 min) $R_t$=9.48 min; ESI-MS m/z calcd for $C_{48}H_{51}N_7O_{10}S$ [M+H]$^+$ 918.3, found 918.3.

All other synthetic steps including o-NBS group removal, semicarbazide amino acylation and $A^3$-macrocyclization were performed according to approaches I and II described above to get the final peptide MPE-189.

Synthesis of Cyclic Analog MPE-189 Using Approach III

Scheme 7

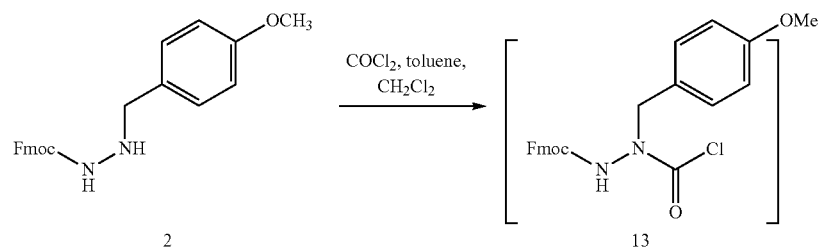

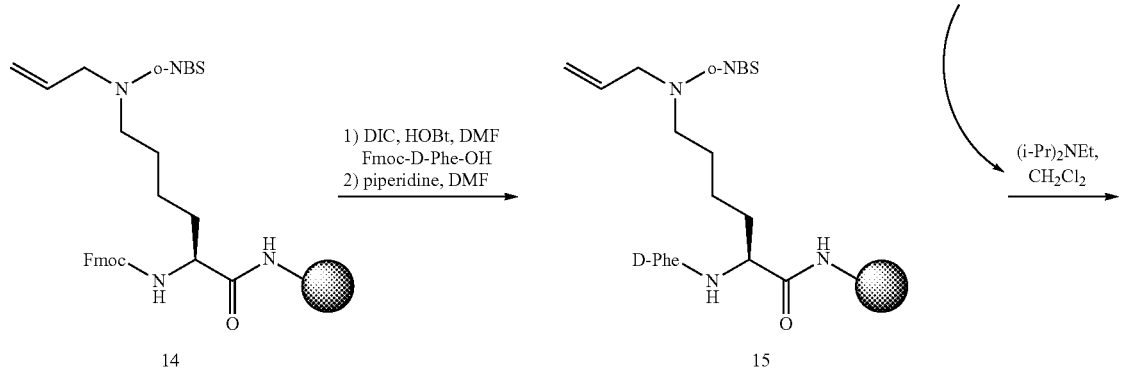

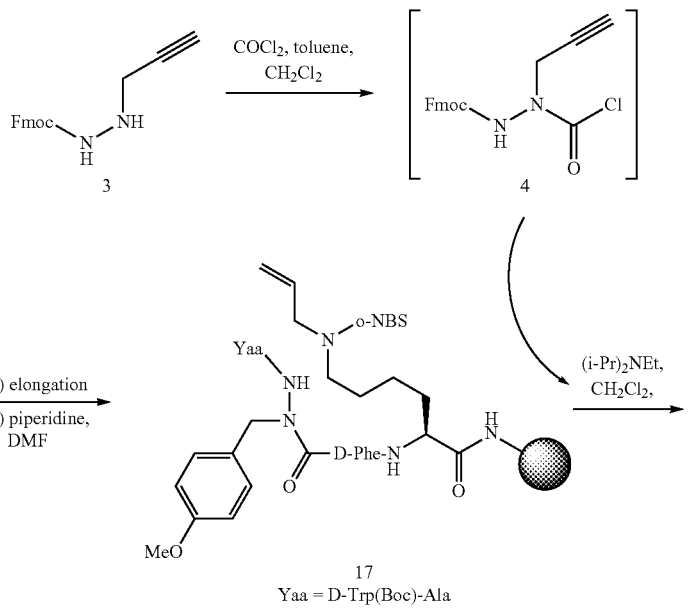

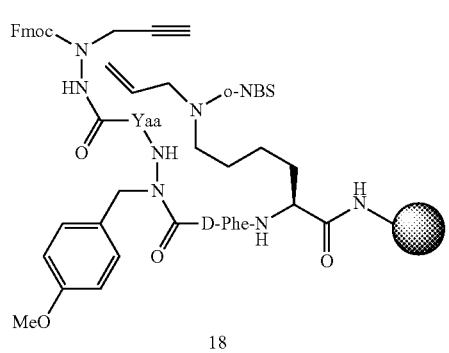

18

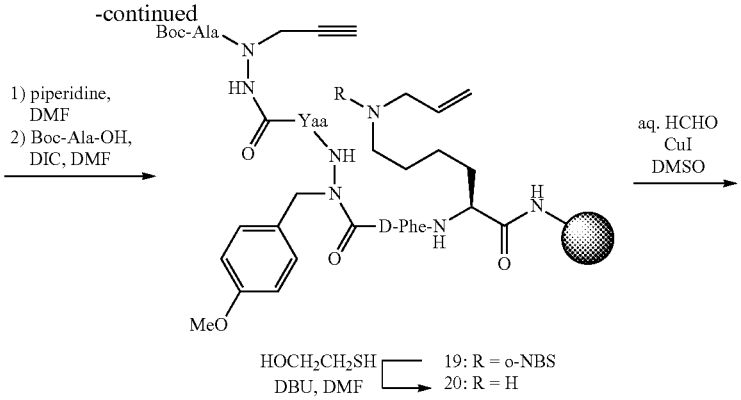

19: R = o-NBS
20: R = H

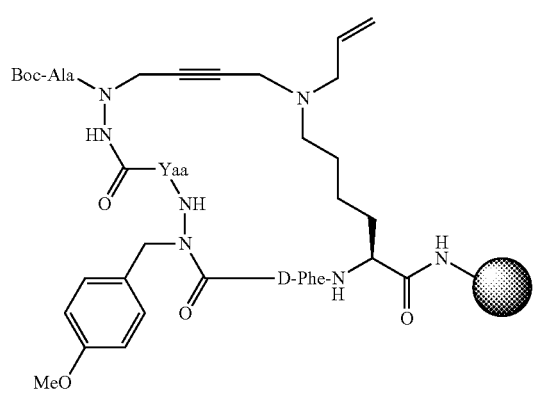

21

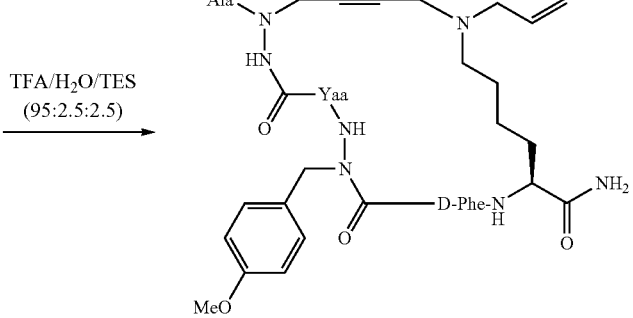

MPE-189

Synthesis of Cyclic Analogs MPE-201, MPE-202, MPE-203

Scheme 8

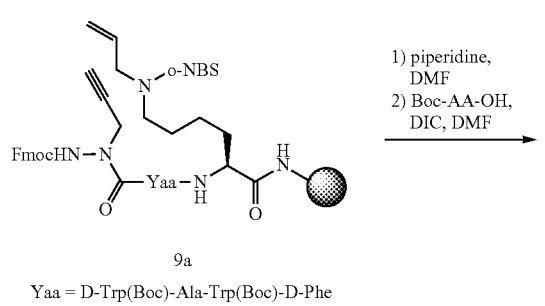

9a
Yaa = D-Trp(Boc)-Ala-Trp(Boc)-D-Phe

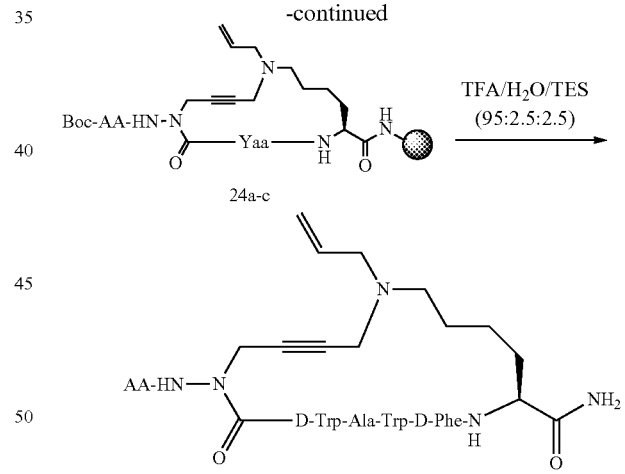

MPE-201: AA = Gly
MPE-202: AA = D-Ala
MPE-203: AA = Val

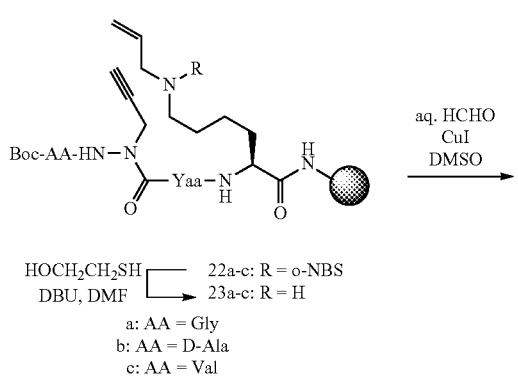

22a-c: R = o-NBS
23a-c: R = H a: AA = Gly
b: AA = D-Ala
c: AA = Val

Boc-Gly-Aza-Pra-D-Trp(Boc)-Ala-Trp(Boc)-D-Phe-Lys(o-NBS, Allyl)-Rink Amide Resin 22a:

LCMS analysis of a cleaved resin sample of 22a showed complete coupling; LCMS (30-95% MeOH containing 0.1% FA in water containing 0.1% FA over 10 min) $R_f$=8.58 min; ESI-MS m/z calcd for $C_{55}H_{63}N_{13}O_{11}S$ [M+H]$^+$ 1114.4, found 1114.4.

Boc-D-Ala-Aza-Pra-D-Trp(Boc)-Ala-Trp(Boc)-D-Phe-Lys(o-NBS, Allyl)-Rink Amide Resin 22b:

LCMS analysis of a cleaved resin sample of 22b showed complete coupling; LCMS (30-95% MeOH containing 0.1%

FA in water containing 0.1% FA over 10 min) $R_t$=8.64 min; ESI-MS m/z calcd for $C_{56}H_{65}N_{13}O_{11}S$ [M+H]$^+$ 1128.4, found 1128.4.

Boc-Val-Aza-Pra-D-Trp(Boc)-Ala-Trp(Boc)-D-Phe-Lys (o-NBS, Allyl)-Rink Amide Resin 22c:

LCMS analysis of a cleaved resin sample of 22c showed incomplete coupling despite repetition; LCMS (30-95% MeOH containing 0.1% FA in water containing 0.1% FA over 10 min) $R_t$=8.73 min; ESI-MS m/z calcd for $C_{58}H_{69}N_{13}O_{11}S$ [M+H]$^+$ 1156.4, found 1156.4.

Saturated Cyclic Azapeptide (MPE-193)

Palladium-on-carbon (10 wt % loading, 1 mg, 0.005 mmol, 100 mol %) was suspended in a solution of peptide MPE-298 (5 mg, 0.005 mmol) in EtOH (0.5 mL), placed under a balloon of hydrogen and stirred for 3 h. After complete disappearance of MPE-298 was observed by LCMS analysis of the reaction mixture, the Pd/C was filtered off, and the volatiles were evaporated to give a residue, which was then purified by reverse phase HPLC (linear gradient of 5-50% of MeOH containing 0.1% FA in water containing 0.1% FA over 30 minutes) to provide MPE-193 (3.7 mg, 74% yield).

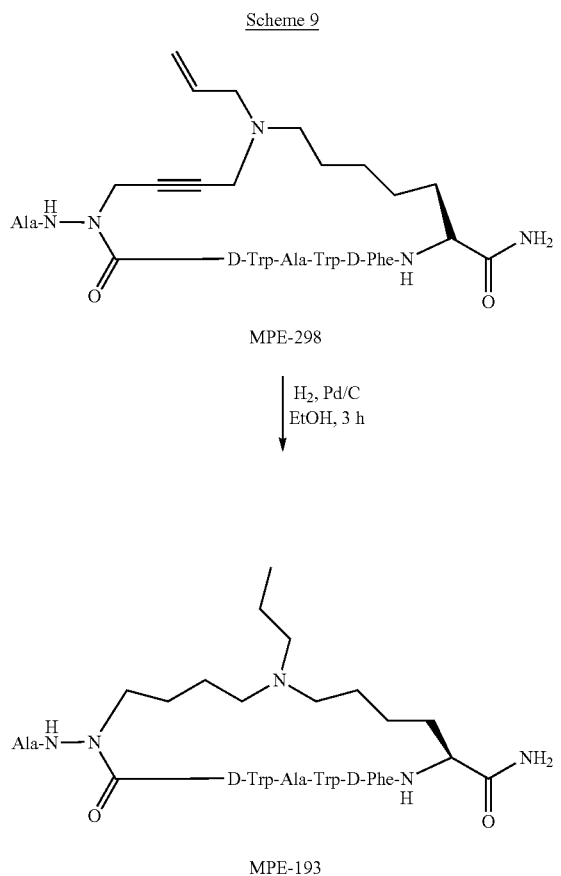

LCMS Analyses of Cyclic Peptides MPE-298, MPE-191, MPE-192, MPE-189, MPE-201, MPE-202, MPE-203 and MPE-193

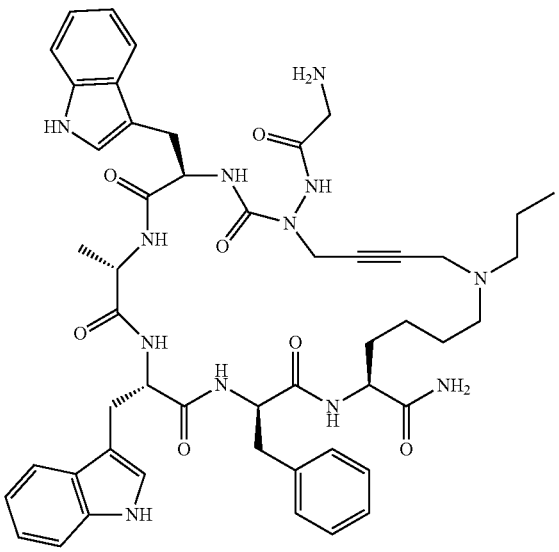

LCMS analysis of cyclic azapeptide MPE-191 was performed using a linear gradient of a) 5-50% of MeOH containing 0.1% FA in H$_2$O containing 0.1% FA over 9 min, then at 5% MeOH for 5 min, R.T=8.01 min; b) 5-50% of MeCN containing 0.1% FA in H$_2$O containing 0.1% FA over 9 min, then at 5% MeCN for 5 min, $R_t$=5.86 min; HRMS m/z calcd for $C_{51}H_{65}N_{12}O_7$ [M+H]$^+$ 957.5094, found 955.5100.

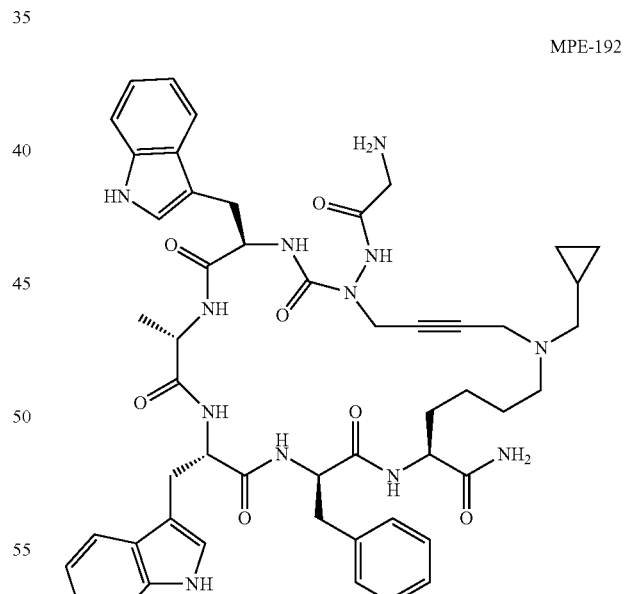

LCMS analysis of cyclic azapeptide MPE-192 was performed using a linear gradient of a) 5-50% of MeOH containing 0.1% FA in H$_2$O containing 0.1% FA over 9 min, then at 5% MeOH for 5 min, R.T=8.12 min; b) 5-50% of MeCN containing 0.1% FA in H$_2$O containing 0.1% FA over 9 min, then at 5% MeCN for 5 min, $R_t$=8.09 min; HRMS m/z calcd for $C_{52}H_{62}N_{12}O_7$ [M+H]$^+$ 969.5094, found 969.5057.

MPE-189

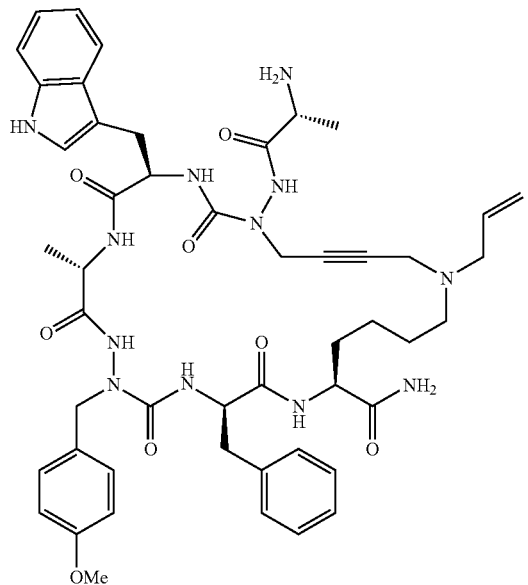

LCMS analysis of cyclic azapeptide MPE-189 was performed using a linear gradient of a) 5-50% of MeOH containing 0.1% FA in H$_2$O containing 0.1% FA over 9 min, then at 5% MeOH for 5 min, R.T=7.83 min; b) 5-50% of MeCN containing 0.1% FA in H$_2$O containing 0.1% FA over 9 min, then at 5% MeCN for 5 min, R$_t$=5.65 min; HRMS m/z calcd for C$_{49}$H$_{62}$N$_{12}$O$_8$ [M+H]$^+$ 947.4886, found 947.4893.

MPE-202

LCMS analysis of cyclic azapeptide MPE-202 was performed using a linear gradient of a) 5-50% of MeOH containing 0.1% FA in H$_2$O containing 0.1% FA over 9 min, then at 5% MeOH for 5 min, R.T=7.93 min; b) 5-50% of MeCN containing 0.1% FA in H$_2$O containing 0.1% FA over 9 min, then at 5% MeCN for 5 min, R$_t$=5.75 min; HRMS m/z calcd for C$_5$H$_{63}$N$_{12}$O$_7$ [M+H]$^+$ 955.4937, found 955.4924.

MPE-201

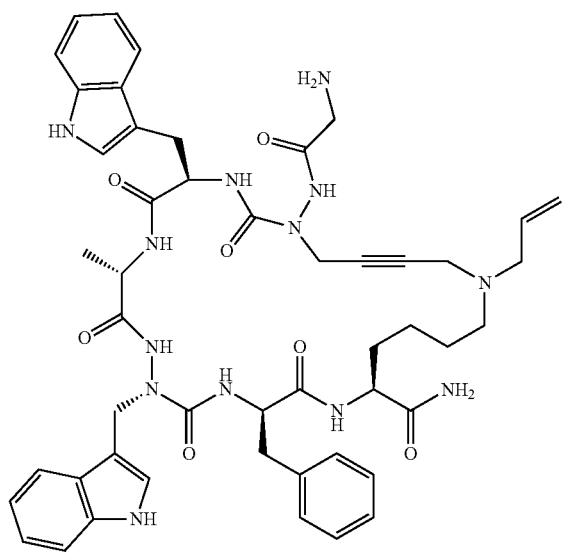

LCMS analysis of cyclic azapeptide MPE-201 was performed using a linear gradient of a) 5-50% of MeOH containing 0.1% FA in H$_2$O containing 0.1% FA over 9 min, then at 5% MeOH for 5 min, R.T=8.01 min; b) 5-50% of MeCN containing 0.1% FA in H$_2$O containing 0.1% FA over 9 min, then at 5% MeCN for 5 min, R$_t$=5.77 min; HRMS m/z calcd for C$_{50}$H$_{61}$N$_{12}$O$_7$ [M+H]$^+$ 941.4781, found 941.4758.

MPE-203

LCMS analysis of cyclic azapeptide MPE-203 was performed using a linear gradient of a) 5-50% of MeOH containing 0.1% FA in H$_2$O containing 0.1% FA over 9 min, then at 5% MeOH for 5 min, R.T=8.45 min; b) 5-50% of MeCN containing 0.1% FA in H$_2$O containing 0.1% FA over 9 min, then at 5% MeCN for 5 min, R$_t$=5.95 min; HRMS m/z calcd for C$_{53}$H$_{66}$N$_{12}$O$_7$ [M+H]$^+$ 983.5250, found 983.5213.

MPE-193

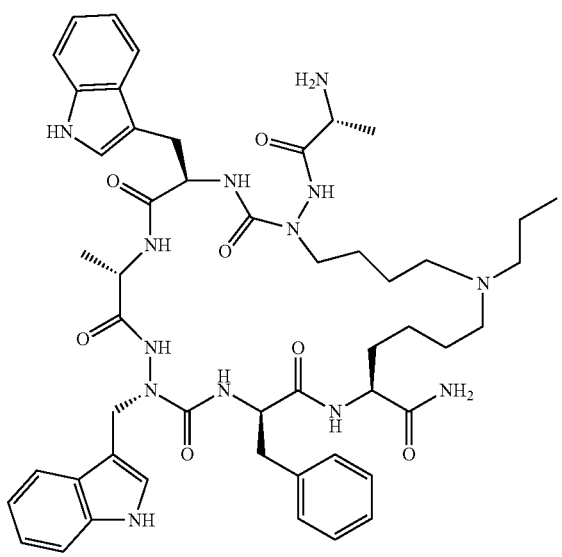

LCMS analysis of cyclic azapeptide MPE-193 was performed using a linear gradient of a) 5-50% of MeOH containing 0.1% FA in H$_2$O containing 0.1% FA over 9 min, then at 5% MeOH for 5 min, R.T=8.09 min; b) 5-50% of MeCN containing 0.1% FA in H$_2$O containing 0.1% FA over 9 min, then at 5% MeCN for 5 min, R$_t$=5.83 min; HRMS m/z calcd for C$_{51}$H$_{69}$N$_{12}$O$_7$ [M+H]$^+$ 961.5407, found 961.5391.

TABLE 2

Yields and purity of the cyclic peptide GHRP-6 analogs MPE-298, MPE-191, MPE-192, MPE-189, MPE-201, MPE-202, MPE-203 and MPE-193

| Cyclic Analog | Isolated Yield (%) | Purity[a] (%) | HRMS (M + H)$^+$ |
|---|---|---|---|
| MPE-298 | 2.2 | 99 | 955.4937 (955.4924) |
| MPE-191 | 1.9 | 99 | 957.5094 (955.5100) |
| MPE-192 | 2.1 | 99 | 969.5094 (969.5057) |
| MPE-189 | 2.8 | 95 | 947.4886 (947.4893) |
| MPE-201 | 3.1 | 99 | 941.4781 (941.4758) |
| MPE-202 | 2.4 | 99 | 955.4937 (955.4924) |
| MPE-203 | 1 | 99 | 983.5250 (983.5213) |
| MPE-193 | 74 | 98 | 961.5407 (961.5391) |

[a]Determined by LCMS analysis as described above.

Synthesis of Cyclic Azasulfurylpeptide MPE-400

Cyclic azasulfurylpeptide MPE-400 was prepared by a route featuring assembly of a protected azasulfuryl tripeptide precursor in solution, coupling to a resin-bound linear peptide sequence, removal of the o-NBS group, A$^3$-macrocyclyzation and resin cleavage (Scheme 10)

Scheme 10 Synthesis of Cyclic Azasulfurylpeptide MPE-400

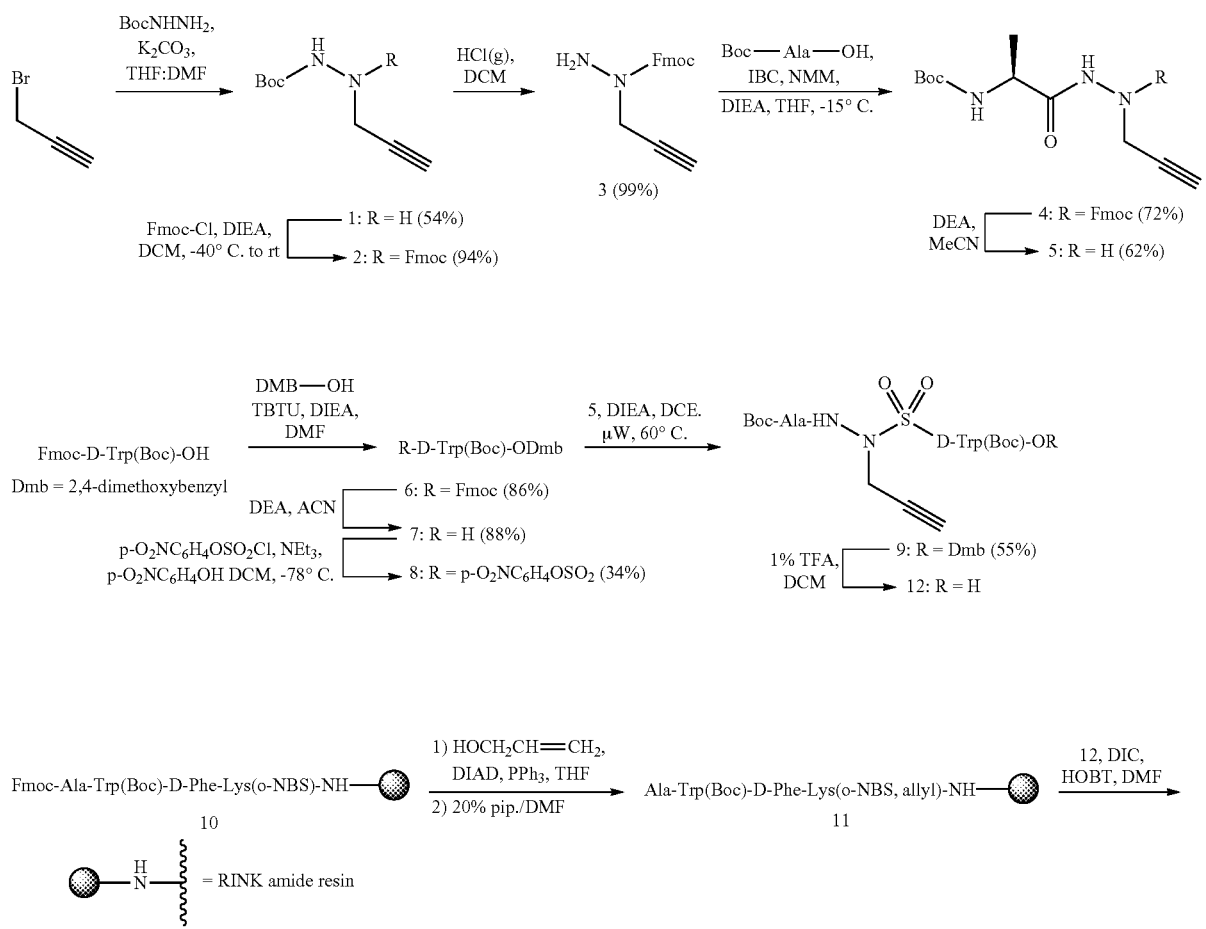

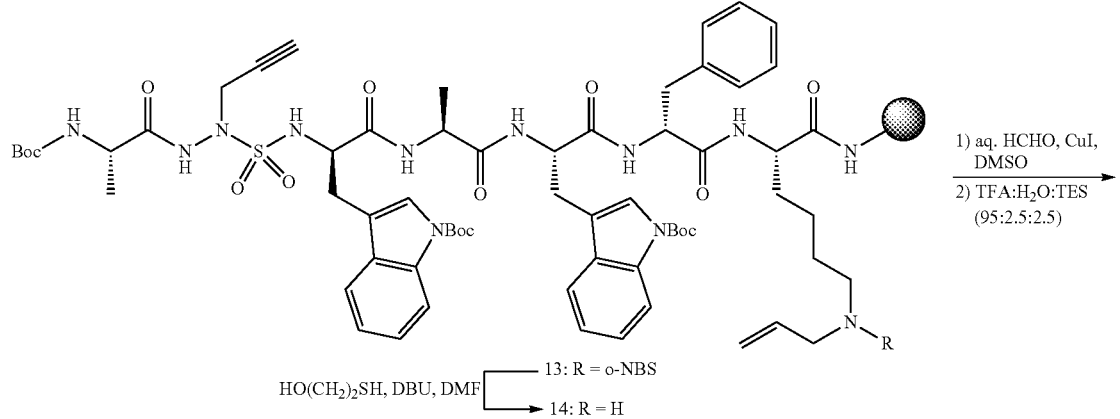

1) aq. HCHO, CuI, DMSO
2) TFA:H₂O:TES (95:2.5:2.5)

HO(CH₂)₂SH, DBU, DMF
13: R = o-NBS
14: R = H

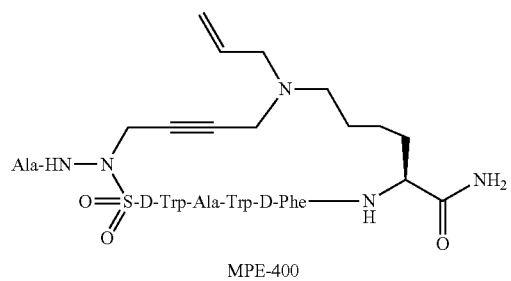

MPE-400

N'-Propargyl-tert-butylcarbazate (1)    N'-Propargyl-N-Fmoc-tert-butylcarbazate (2)

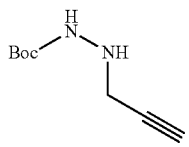

35

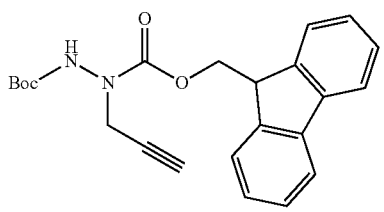 [SMILES: C#CCN(NC(=O)OC(C)(C)C)C(=O)OCC1c2ccccc2-c2ccccc21]

40 tert-Butyl carbazate (1 eq., 2 g, 15.1 mmol) and powdered K₂CO₃ (1.5 eq., 3.14 g, 22.7 mmol) were dissolved in 30 mL of 9:1 THF:DMF, cooled to 0° C., and treated slowly with a solution of propargyl bromide (0.8 eq., 1.3 mL, 12.1 mmol, 80% in toluene) in THF (10 mL). The ice bath was removed. The reaction mixture was allowed to warm to room temperature and stirred overnight. The reaction mixture was washed with H₂O and brine, dried over Na₂SO₄, and concentrated under reduced pressure to a residue that was purified by chromatography on silica gel eluting with a solution of 30-40% EtOAc in hexane. Evaporation of the collected fractions gave carbazate 1 (1.91 g, 6.54 mmol, 54%) as white solid: mp 54-55° C.; $R_f$=0.24 (EtOAc:hexane 1:4). ¹H NMR (500 MHz, CDCl3) δ 6.20 (s, 1H), 4.07 (s, 1H), 3.62 (d, J=2.5 Hz, 2H), 2.24 (t, J=2.5 Hz, 1H), 1.46 (s, 9H); ¹³C NMR (125 MHz, CD3OD) δ 156.5, 81.0, 80.1, 72.5, 41.4, 28.5 (3C); HRMS m/z calculated for $C_8H_{15}N_2O_2$ [M+H]⁺ 171.1128; found 171.1122.

A stirred at −40° C. solution of N'-propargyl-tert-butylcarbazate (1, 1 eq., 0.57 g, 3.35 mmol) and DIEA (1.5 eq., 0.83 mL, 5.02 mmol) in CH₂Cl₂ (40 mL) was slowly treated with a solution of 9-fluorenylmethyl chloroformate (1.1 eq., 0.95 g, 3.68 mmol) in CH₂Cl₂ (10 mL). The cooling bath was removed. The reaction mixture was allowed to warm to room temperature, stirred overnight, washed with H₂O and brine, dried over Na₂SO₄, and concentrated under reduced pressure to a residue, that was purified by chromatography on silica gel eluting with a solution of 10-15% EtOAc in hexane. Evaporation of the collected fractions gave carbazate 2 (1.24 g, 3.15 mmol, 94%) as white solid: mp 93-94° C. $R_f$=0.4 (EtOAc:hexane 1:4). ¹H NMR (500 MHz, CDCl₃) δ 7.77 (d, J=7.6 Hz, 2H), 7.62 (d, J=7.5 Hz, 2H), 7.41 (t, J=7.5 Hz, 2H), 7.34-7.29 (m, 2H), 6.63 (s, 1H), 4.41 (brs, 4H), 4.26 (brs, 1H), 2.30 (s, 1H), 1.50 (s, 9H); ¹³C NMR (125 MHz, CDCl₃) δ 156.7, 154.4, 143.7 (2C), 141.4 (2C), 128.0 (2C), 127.3 (2C), 125.4 (2C), 120.2 (2C), 82.2, 78.1, 72.9, 69.1, 47.1, 39.9, 28.3 (3C); HRMS m/z calculated for $C_{23}H_{25}N_2O_4$ [M+Na]⁺ 415.1628; found 415.1621.

N-Propargyl-fluorenylmethylcarbazate (3)

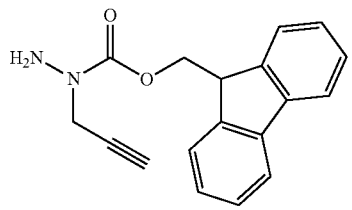 [SMILES: C#CCN(N)C(=O)OCC1c2ccccc2-c2ccccc21]

Dry HCl gas was bubbled into a stirred solution of tert-butylcarbazate 2 (1 eq., 1.1 g, 2.8 mmol). After 2 h, complete consumption of starting material was observed by TLC. The resulting solution was concentrated under reduced pressure to yield pure fluorenylmethylcarbazate 3 (1.09 g, 2.77 mmol, 99%) as white solid which was used without further purification. mp 176° C.; $^1$H NMR (500 MHz, CD$_3$OD) δ 7.82 (d, J=7.6 Hz, 2H), 7.66 (dd, J=7.5, 0.8 Hz, 2H), 7.45-7.39 (m, 2H), 7.36-7.31 (m, 2H), 4.64 (d, J=6.3 Hz, 2H), 4.37-4.31 (m, 3H), 3.03 (t, J=2.5 Hz, 1H); $^{13}$C NMR (125 MHz, CD$_3$OD) δ 155.7, 144.5 (2C), 142.7 (2C), 129.1 (2C), 128.3 (2C), 126.0 (2C), 121.1 (2C), 77.1, 76.2, 70.9, 48.0, 39.7; HRMS m/z calculated for C$_{18}$H$_{17}$N$_2$O$_2$ [M+H]$^+$ 293.1285; found 293.1274.

Fluorenylmethyl N-(Boc)-Alaninyl-aza-proparglylglycinate (4)

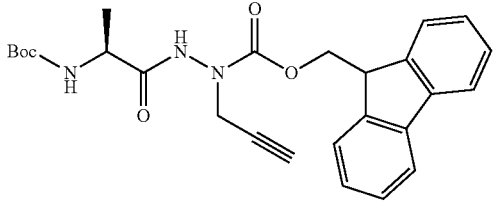 [SMILES: C#CCN(NC(=O)[C@H](C)NC(=O)OC(C)(C)C)C(=O)OCC1c2ccccc2-c2ccccc21]

A solution of N-(Boc)-L-alanine (1.1 eq., 0.513 g, 2.71 mmol) in THF (10 mL) was cooled to −15° C., treated sequentially with isobutyl chloroformate (1.1 eq., 0.353 mL, 2.71 mmol) and N-methylmorpholine (NMM, 2 eq., 0.542 mL, 4.93 mmol), stirred for 15 min, and treated with a solution of carbazate 3 (1 eq., 0.72 g, 2.46 mmol) in THF (15 mL) and DIEA (1 eq., 0.407 mL, 2.46 mmol). After stirring at −15° C. for 1 h, the volatiles were removed under reduced pressure and the residue was purified by chromatography on silica gel eluting with a solution of 30-35% EtOAc in hexane to afford aza-dipeptide 4 (0.82 g, 1.77 mmol, 72%) as white solid: mp 78-79° C.; R$_f$=0.33 (40% EtOAc in hexane); $^1$H NMR (500 MHz, CDCl$_3$) δ 8.39 (brs, 1H), 7.76 (d, J=7.5 Hz, 2H), 7.57 (s, 2H), 7.40 (t, J=7.4 Hz, 2H), 7.34-7.27 (m, 2H), 4.81 (brs, 1H), 4.56-4.42 (m, 2H), 4.37 (s, 2H), 4.23 (brs, 2H), 2.25 (brs, 1H), 1.44 (s, 9H), 1.31 (brs, 3H); $^{13}$C NMR (125 MHz, CDCl$_3$) δ 180.1, 156.0, 143.7, 143.6 (2C), 141.4 (2C), 128.0 (2C), 127.3 (2C), 125.2 (2C), 120.2 (2C), 80.9, 77.7, 73.2, 68.5, 48.5, 47.1, 39.4, 28.5 (3C), 17.4; HRMS m/z calculated for O$_{26}$H$_{30}$N$_3$O$_5$ [M+H]$^+$ 464.2180; found 464.2178.

N-(Boc)Alanine-N'-propargyl-hydrazide (5)

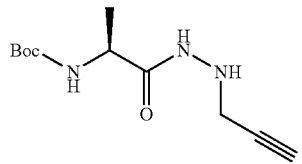

A solution of aza-dipeptide 4 (1 eq., 0.82 g, 1.77 mmol) in MeCN (15 mL), was treated with diethylamine (DEA, 27.4 eq., 3.55 g, 5 mL, 48.5 mmol), and stirred at rt for 1.5 h. The volatiles were evaporated to give a residue that was purified by flash chromatography on silica gel eluting with a gradient of 60-80% EtOAc in hexanes containing 2% triethylamine to afford hydrazide 5 (0.265 g, 1.1 mmol, 62%) as white solid: mp 75-76° C.; R$_f$ 0.21 (40% EtOAc in hexanes containing 2% triethylamine); $^1$H NMR (500 MHz, CDCl$_3$) δ 7.96 (s, 1H), 4.99 (brs, 1H), 4.71 (s, 1H), 4.16 (s, 1H), 3.61 (s, 2H), 2.23 (t, J=2.5 Hz, 1H), 1.44 (s, 9H), 1.37 (d, J=7.1 Hz, 3H); $^{13}$C NMR (125 MHz, CDCl3) δ 172.4, 155.6, 80.6, 79.7, 72.7, 48.9, 41.2, 28.5 (3C), 18.2; HRMS m/z calculated for C$_{11}$H$_{20}$N$_3$O$_3$ [M+H]$^+$ 242.1499; found 242.1494.

N-(Fmoc)-N''-(Boc)-D-Tryptophan 2,4-dimethoxy-benzyl ester (6)

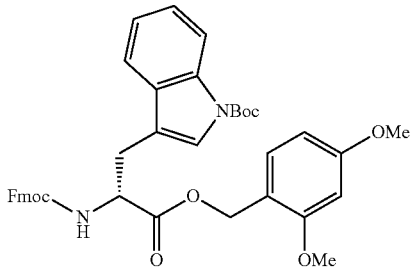

N-(Fmoc)-N$^{in}$-(Boc)-D-Tryptophan (1 eq., 4.5 g, 8.55 mmol), TBTU (1 eq., 2.74 g, 8.55 mmol) and di-isopropylethylamine (DIEA, 2 eq., 2.82 mL, 17.1 mmol) were dissolved in DMF (20 mL), stirred at rt for 30 min under argon atmosphere, treated with an injection of a solution of 2,4-dimethoxybenzyl alcohol (1.1 eq., 1.58 g, 9.4 mmol, prepared according to Feng, L.; Lv, K.; Liu, M.; Wang, S.; Zhao, J.; You, X.; Li, S.; Cao, J.; Guo, H. *Eur. J. Med. Chem.* 2012, 55, 125-136) in DMF (5 mL), and stirred at rt for 4 h. The reaction mixture was diluted with EtOAc and washed with water (2×100 mL) and brine (2×100 mL). The organic phases were combined, dried over Na$_2$SO$_4$, filtered and evaporated to a residue that was purified by flash chromatography on silica gel eluting with 20% EtOAc in hexane to afford ester 6 (4.97 g, 7.35 mmol, 86%) as white solid: mp 67-68° C.; Rf 0.29 (20% EtOAc in hexane); $^1$H NMR (500 MHz, CDCl$_3$) δ 8.11 (brs, 1H), 7.76 (d, J=7.6 Hz, 2H), 7.58-7.48 (m, 3H), 7.44 (s, 1H), 7.42-7.36 (m, 2H), 7.33-7.26 (m, 3H), 7.21 (t, J=7.3 Hz, 1H), 7.11 (d, J=8.0 Hz, 1H), 6.46-6.39 (m, 2H), 5.44 (d, J=8.0 Hz, 1H), 5.12 (s, 2H), 4.78 (dd, J=13.6, 5.4 Hz, 1H), 4.40-4.28 (m, 2H), 4.19 (t, J=7.3 Hz, 1H), 3.80 (s, 3H), 3.79 (s, 3H), 3.33-3.20 (m, 2H), 1.65 (s, 9H); $^{13}$C NMR (125 MHz, CDCl$_3$) δ 171.7, 161.7, 159.2, 155.8, 149.7, 144.0, 143.9, 141.4 (2C), 131.7 (2C), 127.8 (2C), 127.2 (2C), 125.3 (2C), 124.6 (2C), 124.5, 124.4, 122.8, 120.1, 119.0, 115.8, 115.4, 115.1, 104.2, 98.7, 83.8, 67.3, 63.4, 55.5 (2C), 54.4, 47.3, 28.3 (3C), 28.0; HRMS m/z calculated for $C_{40}H_{41}N_2O_8$ [M+H]$^+$ 677.2857; found 677.2859.

$N^{in}$-(Boc)-D-Tryptophan 2,4-dimethoxybenzyl ester (7)

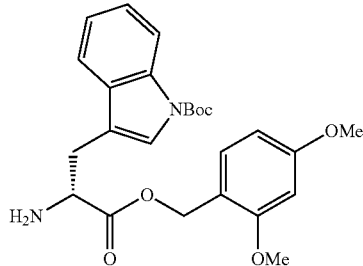 [SMILES: COc1ccc(COC(=O)[C@H](N)Cc2cn(C(=O)OC(C)(C)C)c3ccccc23)c(OC)c1]

Ester 6 (1 eq., 4.2 g, 6.21 mmol) was dissolved in MeCN (62 mL), treated with diethylamine (18.3 mL, 334 mmol), stirred at rt for 2 h, and the solution was evaporated to a residue that was purified by flash chromatography on silica gel eluting with 40% EtOAc in hexane containing 2% triethylamine to afford amine 7 (2.48 mg, 5.46 mmol, 88%) as an oil. $^1$H NMR (500 MHz, CDCl$_3$) δ 8.12 (s, 1H), 7.55 (d, J=7.6 Hz, 1H), 7.47 (s, 1H), 7.33-7.28 (m, 1H), 7.25-7.20 (m, 1H), 7.14 (d, J=8.1 Hz, 1H), 6.47-6.43 (m, 2.3 Hz, 2H), 5.12 (s, 2H), 3.84 (dd, J=7.7, 5.0 Hz, 1H), 3.81 (s, 3H), 3.81 (s, 3H), 3.23-3.15 (m, 1H), 3.01-2.94 (m, 1H), 1.66 (s, 9H); $^{13}$C NMR (125 MHz, CDCl$_3$) δ 175.3, 161.5, 159.2, 149.7, 135.6, 131.6, 130.6, 124.5, 124.3, 122.6, 119.1, 116.4, 116.2, 115.4, 104.1, 98.7, 83.6, 62.6, 55.53, 55.50, 54.7, 30.5, 28.3 (3C); HRMS m/z calculated for $C_{25}H_{31}N_2O_6$ [M+H]$^+$ 455.2177; found 455.2172.

4-Nitrophenyl sulfamidate of —$N^{in}$-(Boc)-D-Tryptophan 2,4-dimethoxybenzyl ester (8)

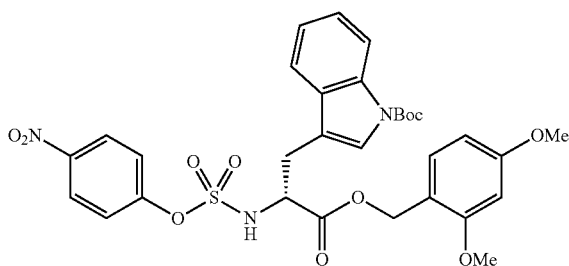 [SMILES: COc1ccc(COC(=O)[C@@H](Cc2cn(C(=O)OC(C)(C)C)c3ccccc23)NS(=O)(=O)Oc2ccc([N+](=O)[O-])cc2)c(OC)c1]

A solution of 4-nitrophenyl chlorosulfate (2 eq., 2.3 g, 9.68 mmol, prepared according to Fettes, K. J.; Howard, N.; Hickman, D. T.; Adah, S.; Player, M. R.; Torrence, P. F.; Micklefield, J. *J. Chem. Soc., Perkin Trans.* 1 2002, 485-495) in dry DCM (25 mL) at −78° C. was treated drop-wise with a solution of amine 7 (1 eq., 2.2 g, 4.84 mmol), 4-nitrophenol (3 eq., 2.02 g, 14.5 mmol) and triethylamine (TEA, 6 eq., 4.04 mL, 29 mmol) in dry DCM (100 mL), and stirred for 1.5 h. The cooling bath was removed and the reaction mixture was allowed to warm rt with stirring for 1 h. The reaction mixture was evaporated to a residue that was purified by flash chromatography eluting with 40% Et$_2$O in petroleum ether to afford fractions contaminated with 4-nitrophenol. The collected fractions were evaporated, dissolved in DCM (25 mL), washed with sat. NaHCO$_3$ (aq, 3×25 mL), dried over MgSO$_4$, filtered and evaporated to afford sulfamidate 8 (1.08 g, 1.65 mmol, 34%) as white solid: mp 48-50° C.; Rf 0.30 (40% Et$_2$O in petroleum ether); $^1$H NMR (500 MHz, CDCl$_3$) δ 8.11-8.10 (m, 1H), 8.10-8.09 (m, 1H), 7.50 (d, J=7.7 Hz, 1H), 7.45 (s, 1H), 7.35-7.30 (m, 1H), 7.26-7.18 (m, 3H), 7.10 (d, J=8.0 Hz, 1H), 6.92-6.88 (m, 1H), 6.46-6.41 (m, 2H), 5.63 (d, J=8.5 Hz, 1H), 5.17-5.08 (m, 2H), 4.59-4.53 (m, 1H), 3.82 (s, 3H), 3.79 (s, 3H), 3.32-3.22 (m, 2H), 1.67 (s, 9H); $^{13}$C NMR (125 MHz, CDCl$_3$) δ 170.6, 162.0, 161.5, 159.4, 154.4, 149.6, 146.0, 132.2, 130.2, 126.4, 125.5, 124.91, 124.86, 122.9, 122.3, 118.9, 115.8, 115.5, 115.2, 113.7, 104.3, 98.7, 84.3, 64.2, 57.2, 55.59, 55.55, 28.8, 28.3 (3C). HRMS m/z calculated for $C_{31}H_{33}N_3O_{11}S$ [M+Na]$^+$ 678.1728; found 678.1720.

N-(Boc)-Alaninyl-aza-propargylsulfurylglycinyl-$N^{in}$-(Boc)-D-tryptophan 2,4-dimethoxybenzyl ester (9)

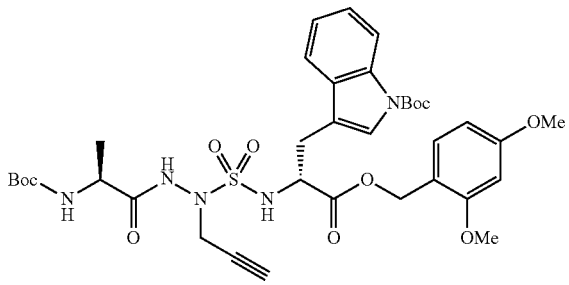 [SMILES: C#CCN(NC(=O)[C@H](C)NC(=O)OC(C)(C)C)S(=O)(=O)N[C@H](Cc1cn(C(=O)OC(C)(C)C)c2ccccc12)C(=O)OCc1ccc(OC)cc1OC]

Hydrazide 5 (1.2 eq., 0.2 g, 0.829 mmol) was added to a microwave vessel containing a solution of sulfamidate 8 (1 eq., 0.453 g, 0.691 mmol) in dichloroethane (4.5 mL). The mixture was treated with TEA (2 eq., 0.14 g, 0.192 mL, 1.38 mmol), at which point the solution turned yellow. The vessel was sealed and heated to 60° C. using microwave irradiation for 3 h. The volatiles were evaporated. The residue was purified by flash chromatography on silica gel eluting with a solution of 40-50% EtOAc in hexane. The collected fractions were evaporated to a residue, which was dissolved in DCM (25 mL), washed with sat. NaHCO$_3$ (3×25 mL), dried over MgSO$_4$, filtered and evaporated to afford azasulfuryl tripeptide 9 (0.29 g, 0.383 mmol, 55%) as white solid: Rf 0.25 (40% EtOAc in hexane); mp 79° C.; $^1$H NMR (500 MHz, CDCl$_3$) δ 8.30 (s, 1H), 8.08 (brs, 1H), 7.58 (d, J=7.7 Hz, 1H), 7.45 (s, 1H), 7.29 (t, J=7.3 Hz, 1H), 7.22 (t, J=7.2 Hz, 1H), 7.12 (d, J=7.8 Hz, 1H), 6.46-6.41 (m, 2H), 5.47 (d, J=7.0 Hz, 1H), 5.08 (d, J=2.7 Hz, 2H), 4.95 (brs, 1H), 4.65-4.58 (m, 1H), 4.32-4.24 (m, 1H), 4.23-4.16 (m, 1H), 4.16-4.08 (m, 1H), 3.82 (s, 3H), 3.80 (s, 3H), 3.27 (t, J=4.5 Hz, 2H), 2.32 (t, J=2.4 Hz, 1H), 1.66 (s, 9H), 1.42 (s, 9H), 1.33 (d, J=7.1 Hz, 3H); $^{13}$C NMR (125 MHz, CDCl$_3$) δ 171.8, 171.6, 161.7, 159.2, 149.7, 131.9, 130.7 126.3, 124.8, 124.6, 122.8, 119.4, 115.8, 115.5, 115.3, 114.4, 104.3, 98.7, 83.8, 81.0, 76.4, 75.0, 63.9, 56.4, 55.5 (2C), 49.2, 42.0, 28.49, 28.42 (3C), 28.35 (3C), 17.3; HRMS m/z calculated for $C_{36}H_{48}N_5O_{11}S$ [M+H]$^+$ 758.3066; found 758.3061.

123

Ala-Trp-D-Phe-Lys(o-NBS, allyl)-NH-Rink resin (11)

124

N-(Boc)-Ala-azasulfurylpropargylglycinyl-D-Trp(Boc)-Ala-Trp-D-Phe-Lys(o-NBS, allyl)-NH-Rink resin (13)

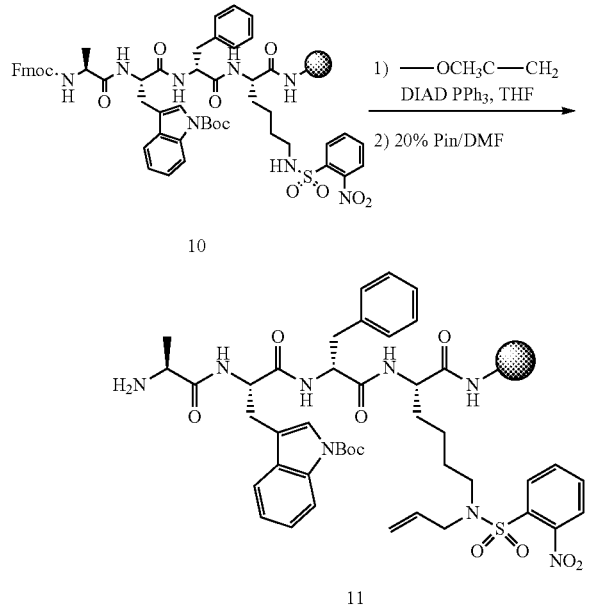

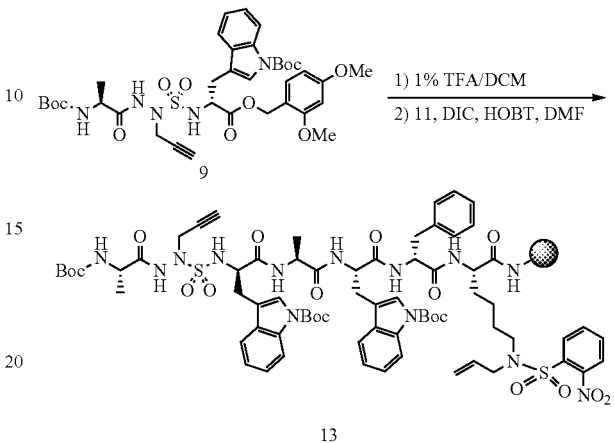

Vacuum dried resin 10 (1 eq., 4.26 g, 1.5 mmol) in a syringe fitted with a Teflon™ filter was suspended in anhydrous THF (42.6 mL), placed under argon, and treated sequentially with solutions of allyl alcohol (10 eq., 1.02 mL, 15 mmol) in anhydrous THF (14.2 mL), PPh$_3$ (5 eq., 1.97 g, 7.5 mmol) in anhydrous THF (14.2 mL), and DIAD (5 eq., 1.49 mL, 7.5 mmol) in anhydrous THF (14.2 mL). The resin mixture was shaken on an automated shaker for 30 min, and filtered, and washed successively using 15 sec agitations with DMF (3 times), MeOH (3 times) and DCM (3 times), sequentially. The resin was vacuum dried. A 0.5 g resin sample was treated with 20% piperidine in DMF (10 mL) to afford resin 11. Examination by LCMS of a cleaved resin sample (2-3 mg) showed complete allylation: LCMS [10-90% MeOH containing 0.1% formic acid (FA) in water (0.1% FA) over 9 min, then at 10% MeOH (0.1% FA) in water (0.1% FA) for 5 min] $R_f$=7.937 min. ESI-MS m/z calculated for $C_{38}H_{47}N_8O_8S$ [M-Boc+H]+775.32; found 775. 3.

2,4-Dimethoxybenzyl ester 9 (180 mg, 0.238 mmol) was treated with 1% of TFA in DCM (5 mL) for 1 h at rt. The volatiles were evaporated and the residue was treated with Et$_2$O (5 mL) to provide a precipitate that was filtered. The filtrate was evaporated to afford N-(Boc)alaninyl-azasulfurylpropargylglycinyl-D-N$^{in}$(Boc)tryptophan (12). In a syringe fitted with a Teflon™ filter, resin 11 (1 eq., 460 mg, 0.173 mmol) was swollen in DMF (5 mL). Meanwhile, a solution of tripeptide 12 (1.2 eq., 126 mg, 0.208 mmol), and HOBt (1.2 eq., 28.1 mg, 0.208 mmol) in DMF (5 mL) was stirred for 5 min, treated with DIC (1.2 eq., 32.4 µL, 0.208 mmol) stirred for 5 min and then added to the resin. The resin mixture was shaken for 18 h at room temperature. The resin was filtered, washed and filtered successively using 15 sec agitations with DMF (3 times), MeOH (3 times) and DCM (3 times), sequentially, to afford resin 13. Examination by LCMS of a cleaved resin sample (2-3 mg) showed coupling product: LCMS [50-90% MeOH containing 0.1% FA in water (0.1% FA) over 8.5 min, then at 50% MeOH (0.1% FA) in water (0.1% FA) for 5.5 min] $R_f$=6.251 min. ESI-MS m/z calculated for $C_{55}H_{66}N_{13}O_{12}S$ [M−3Boc+H]+ 1164.43; found 1164.3.

N-(Boc)-Ala-azasulfurylpropargylglycinyl-D-Trp(Boc)-Ala-Trp-D-Phe-Lys(allyl)-NH-Rink resin 14

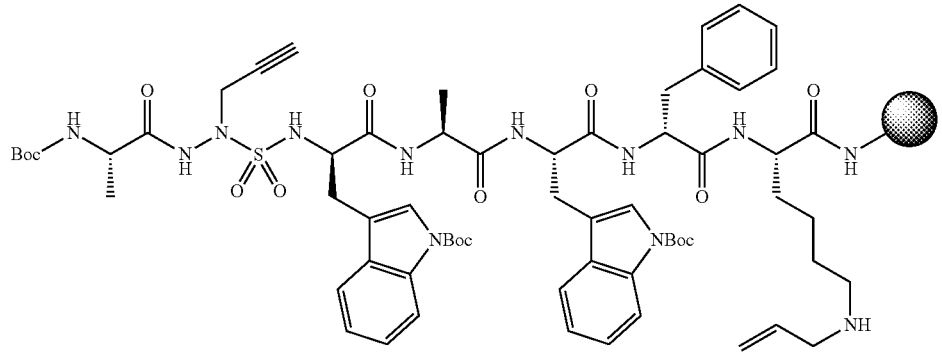 [SMILES: C#CCN(NC(=O)[C@H](C)NC(=O)OC(C)(C)C)S(=O)(=O)N[C@H](Cc1cn(C(=O)OC(C)(C)C)c2ccccc12)C(=O)N[C@@H](C)C(=O)N[C@@H](Cc1cn(C(=O)OC(C)(C)C)c2ccccc12)C(=O)N[C@H](Cc1ccccc1)C(=O)N[C@@H](CCCCNCC=C)C(=O)NC]

Azatripeptide resin 13 (1 eq., 300 mg, 0.0925 mmol) was swollen in DMF (6 mL) for 30 min in a syringe tube equipped with Teflon™ filter, stopper and stopcock, treated with DBU (10 eq., 138 µL, 0.925 mmol) and 2-mercaptoethanol (5 eq., 32.5 µL, 0.462 mmol), shaken on an automated shaker for 30 min, and filtered. After filtration, the resin was washed and filtered successively using 15 sec agitations with DMF (3 times), MeOH (3 times) and DCM (3 times), sequentially, to afford resin 14. Examination by LCMS of a cleaved resin sample (2-3 mg) showed complete removal of the o-NBS group: LCMS [10-90% MeOH (0.1% FA) in water (0.1% FA) over 10 min, then at 10% MeOH (0.1% FA) in water (0.1% FA) for 5 min] $R_t$=7.464 min. ESI-MS m/z calculated for $C_{49}H_{63}N_{13}O_8S$ [M−3Boc+H]$^+$ 979.45; found 979.4.

Cyclic Azasulfurylpeptide MPE-400:

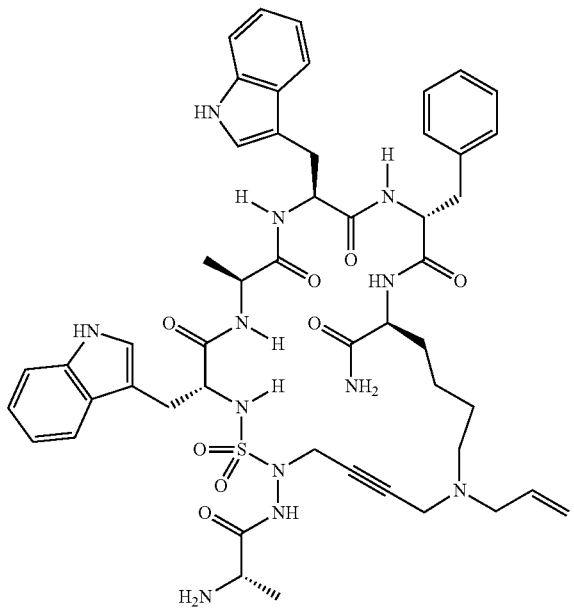 [SMILES: C=CCN1CC#CCN(NC(=O)[C@H](C)N)S(=O)(=O)N[C@H](Cc2c[nH]c3ccccc23)C(=O)N[C@@H](C)C(=O)N[C@@H](Cc2c[nH]c3ccccc23)C(=O)N[C@H](Cc2ccccc2)C(=O)N[C@H](C(N)=O)CCCC1]

Azasulfurylpeptide resin 14 (1 eq., 282 mg, 0.0925 mmol) was swollen in DMSO (6 mL) for 30 min in a syringe tube equipped with Teflon™ filter and stopper, treated with CuI (0.2 eq., 3.52 mg, 0.0185 mmol) and aqueous formaldehyde (6 eq., 41.6 µL, 0.555 mmol), shaken on an automated shaker for 24 h, and filtered. After filtration, the resin was washed sequentially with AcOH/H$_2$O/DMF (5:15:80, v/v/v, 3×10 mL), THF (3×10 mL), MeOH (3×10 mL), and DCM (3×10 mL). Examination by LCMS of a cleaved resin sample (2-3 mg) showed complete conversion and a peak was observed having molecular ion consistent with cyclic azasulfuryltripeptide MPE-400: LCMS [10-90% MeOH (0.1% FA) in water (0.1% FA) over 10 min, then at 10% MeOH (0.1% FA) in water (0.1% FA) for 5 min] Rt=7.75; ESI-MS m/z calcd for $C_{50}H_{63}N_{12}O_8S$ [M+H]$^+$ 991.45; found 991.4.

Resin-bound cyclic peptide was deprotected and cleaved from the support using a freshly made solution of TFA:H$_2$O: TES (95:2.5:2.5, v/v/v, 6 mL) for 3 h in a cold room at 4° C. The resin was filtered and rinsed with TFA (6 mL). The filtrate and rinses were concentrated until a crude oil persisted, from which a precipitate was obtained by addition of cold ether (10-15 mL). After centrifugation (1200 rpm for 10 min), the ethereal solvent was decanted and the crude peptide precipitate was recovered, dissolved in aqueous acetonitrile (10% v/v) and freeze-dried. The resulting light brown fluffy material was purified by preparative HPLC to give cyclic peptide MPE-400 (1.0 mg, 1%) as white fluffy material: LCMS analysis of purified cyclic azasulfurylpeptide MPE-400 was performed on a Sunfire™ column using a linear gradient: [5%-50% MeOH (0.1% FA) in water (0.1% FA) over 9 min, then at 5% MeOH (0.1% FA) in water (0.1% FA) for 5.0 min]>99% purity, Rt 8.115 min; [5%-50% MeCN (0.1% FA) over 9 min, then at 5% MeCN (0.1% FA) for 5.0 min]>99% purity, Rt 5.987 min; HRMS m/z calculated for [M+H]$^+$ $C_{50}H_{63}N_{12}O_8S$ 991.4607; found 991.4657.

Figure 4A:
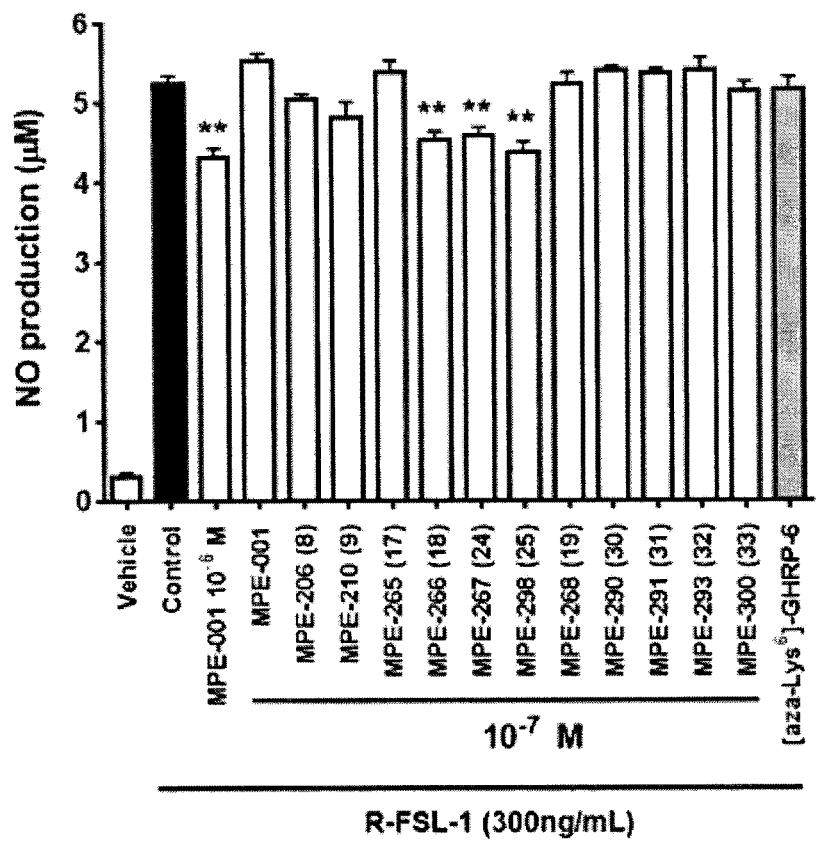
FIGS. 4A to 4G show the effect of cyclic peptides on nitric oxide (NO) production induced by the TLR2 agonist R-FSL-1 in the RAW macrophage cell line.
Figure 4B:
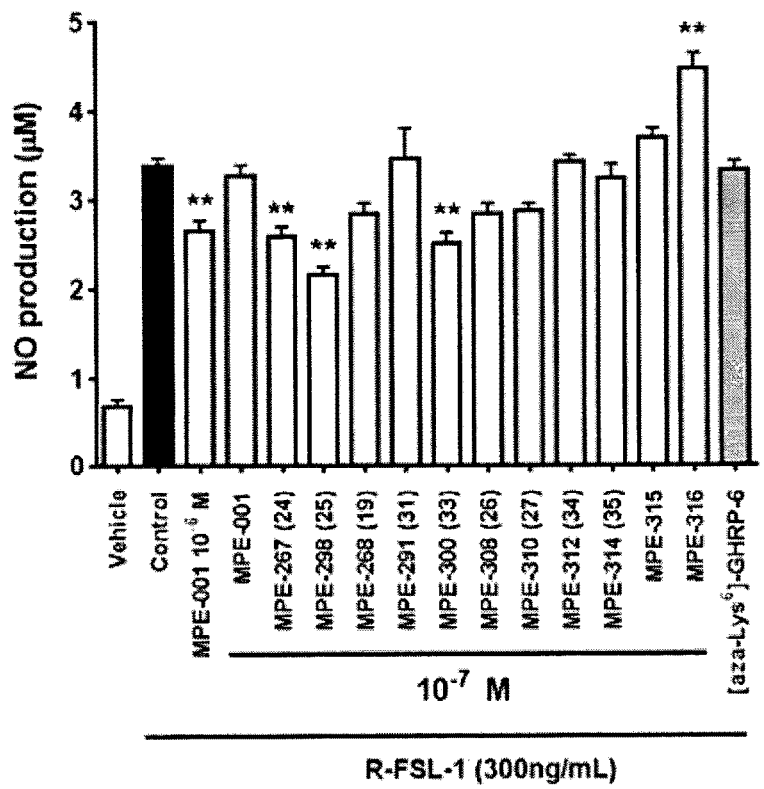
Figure 4C:
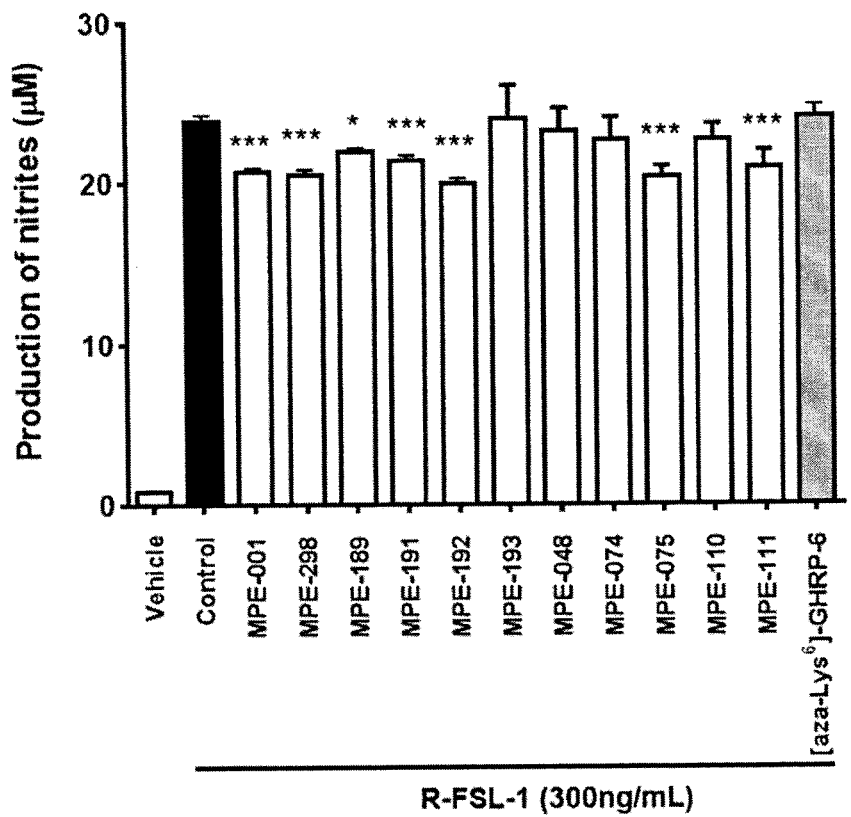
Figure 4D:
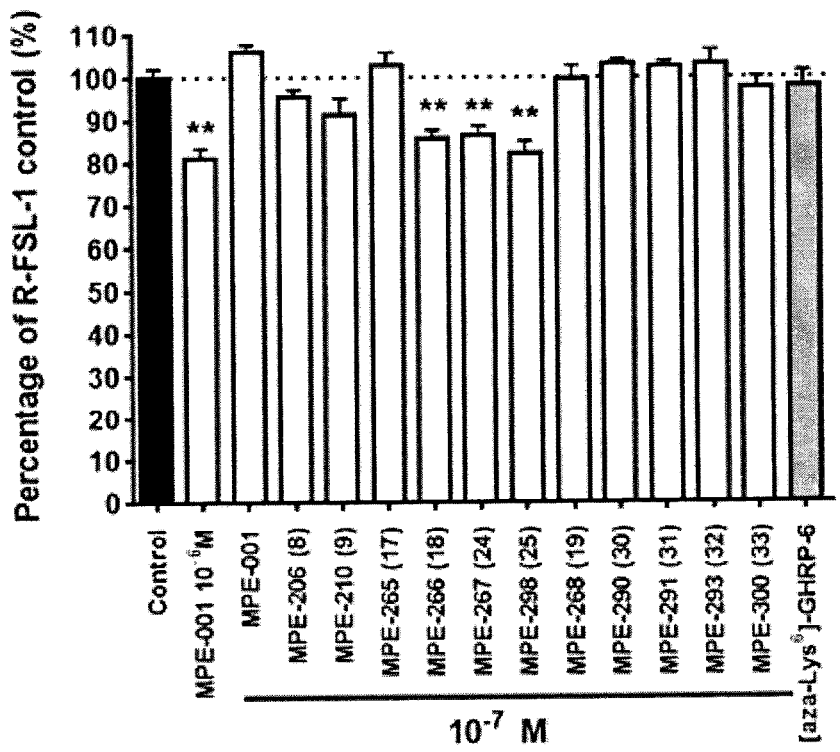
Figure 4E:
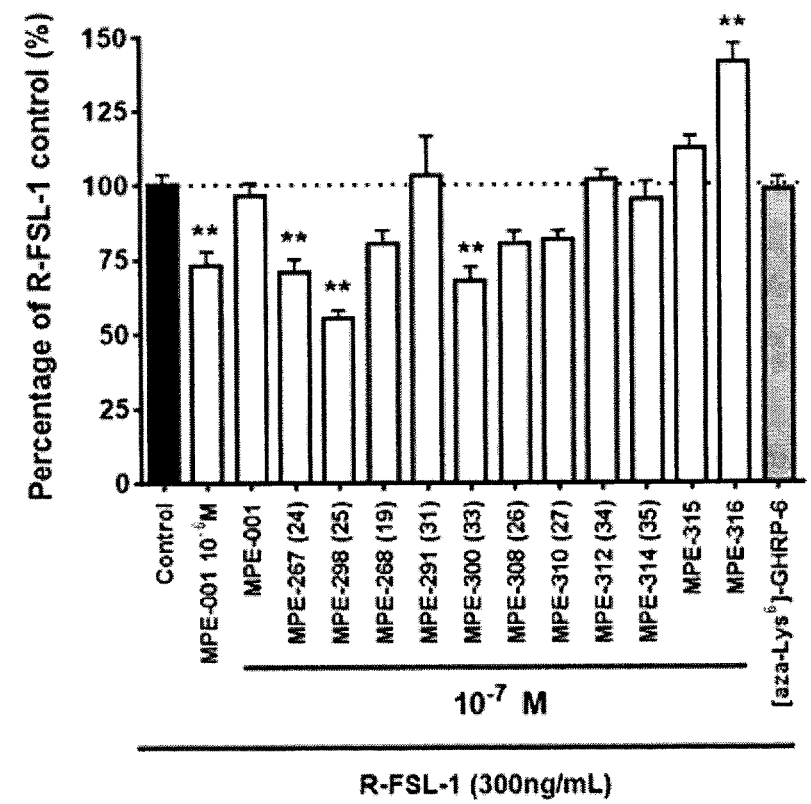
Figure 4F:
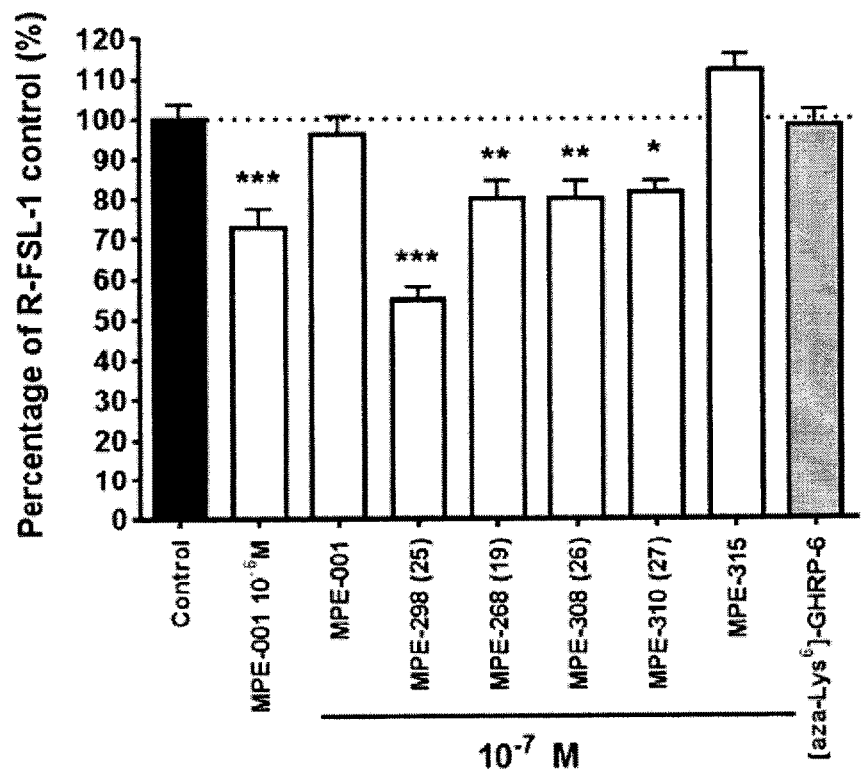
Figure 4G:
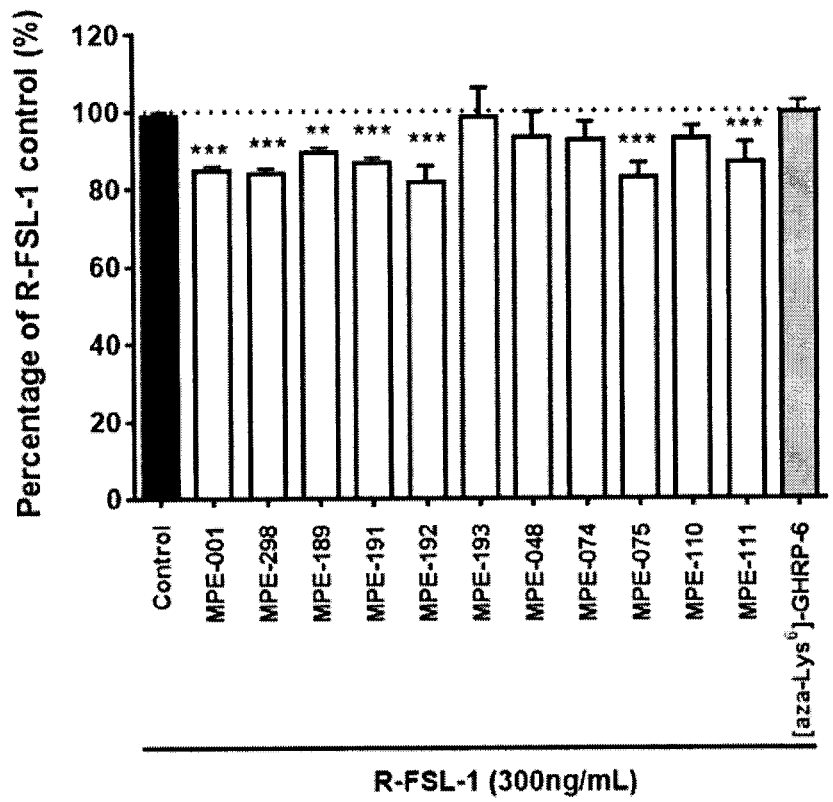
Figure 5A:
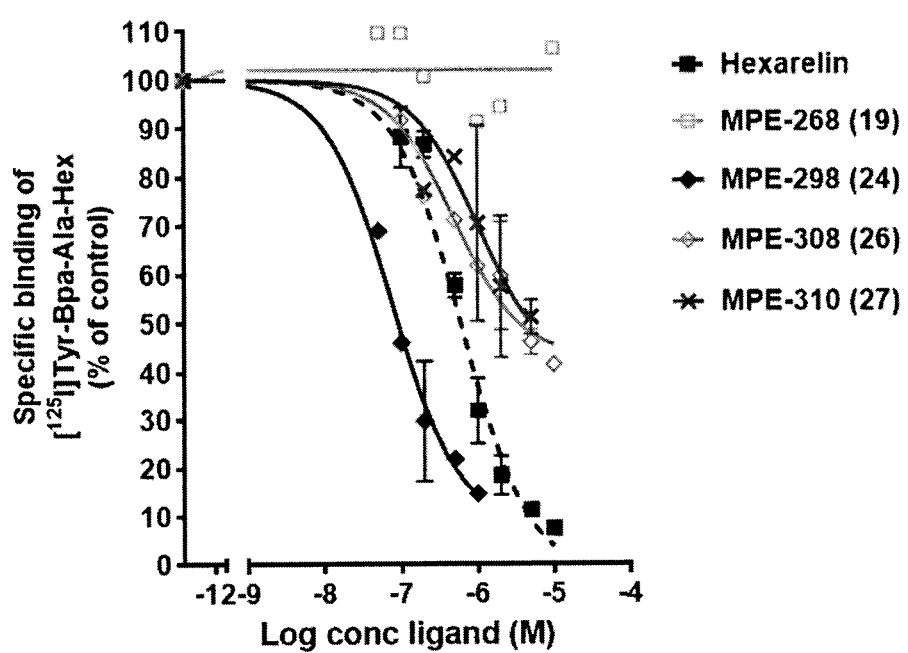
FIGS. 5A to 5E show competition curves for cyclic peptides for the binding of photoactivable [$^{125}$I]-Tyr-Bpa-Ala-Hexarelin to CD36 in rat cardiac membranes.
Figure 5B:
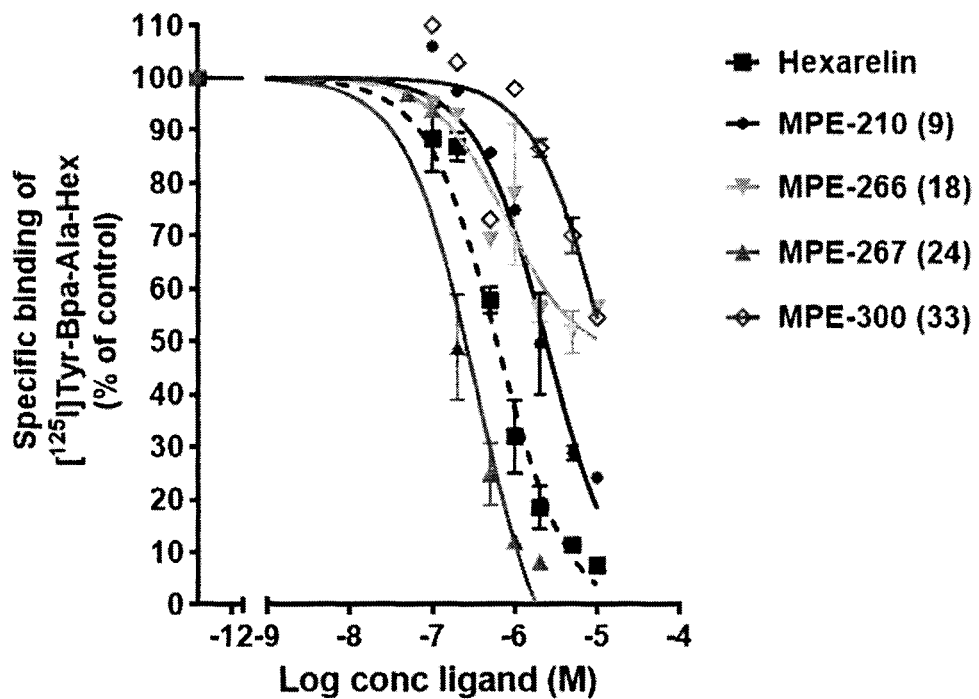
Figure 5C:
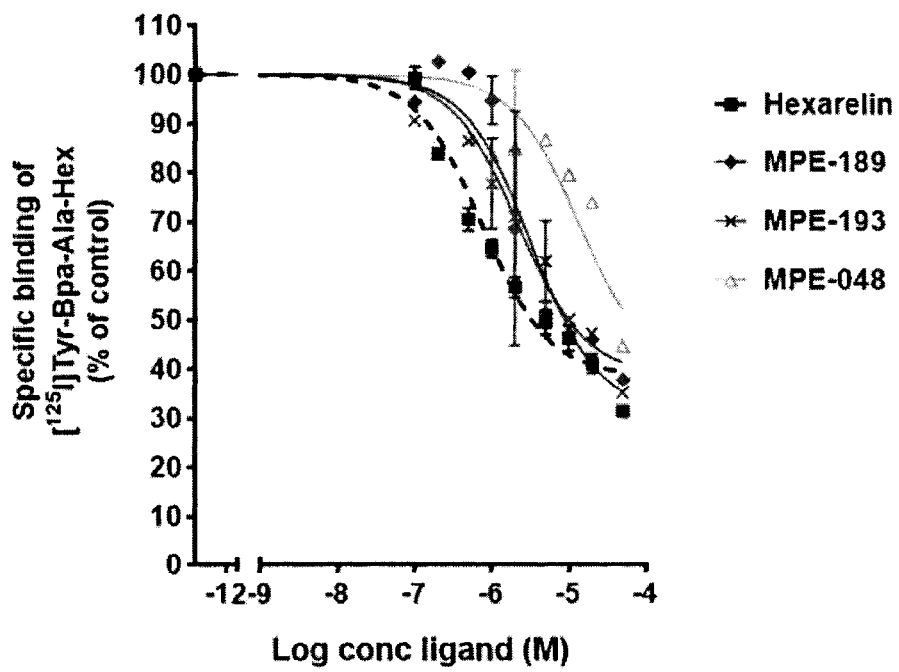
Figure 5D:
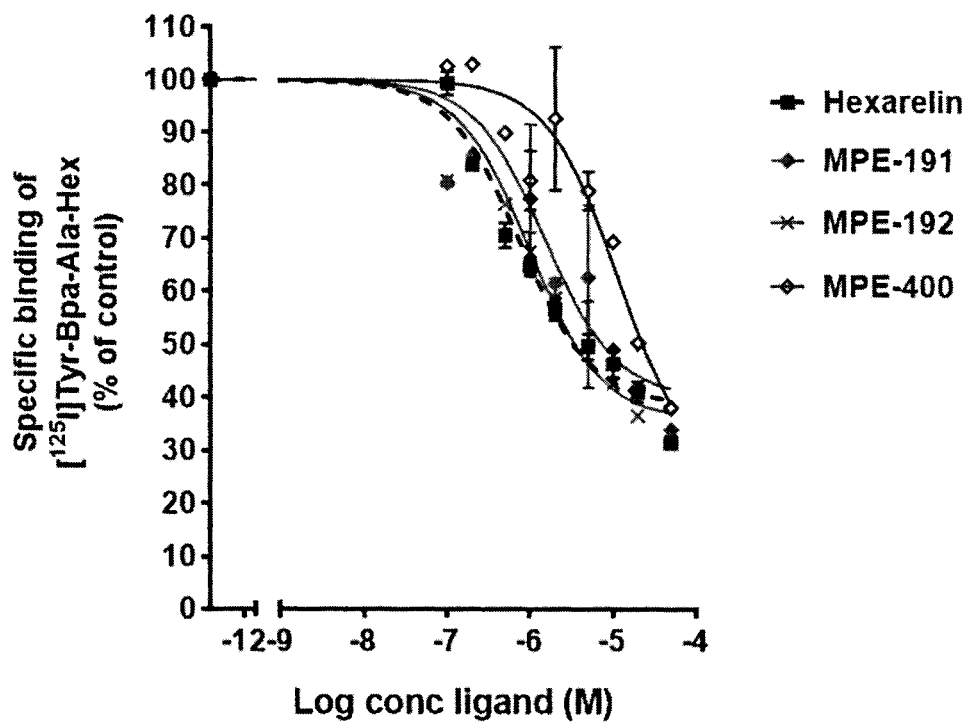
Figure 5E:
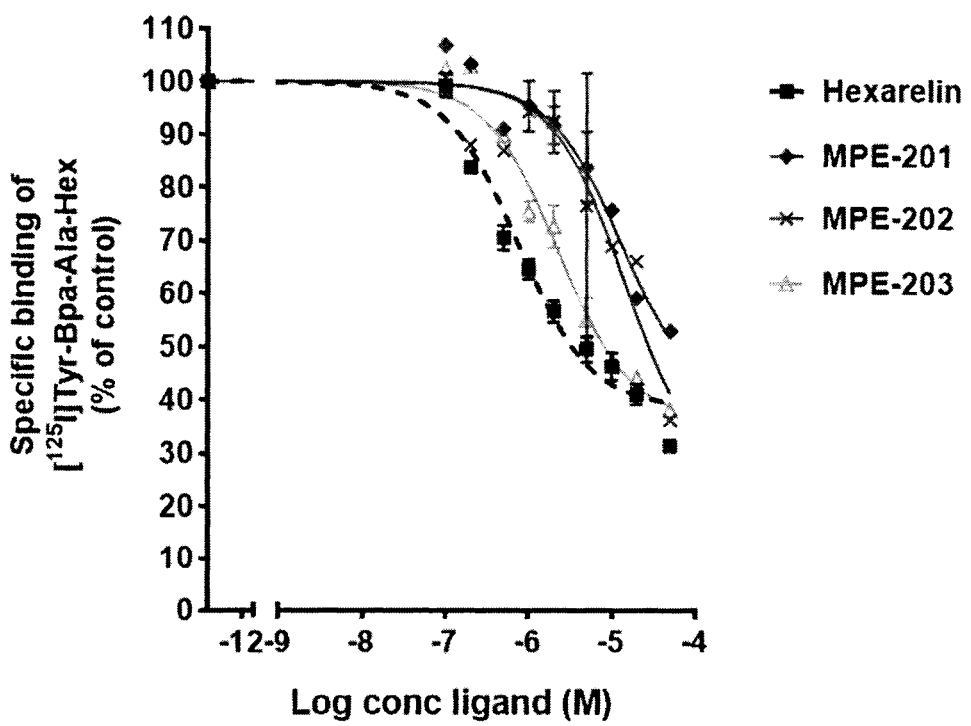
Figure 5F:
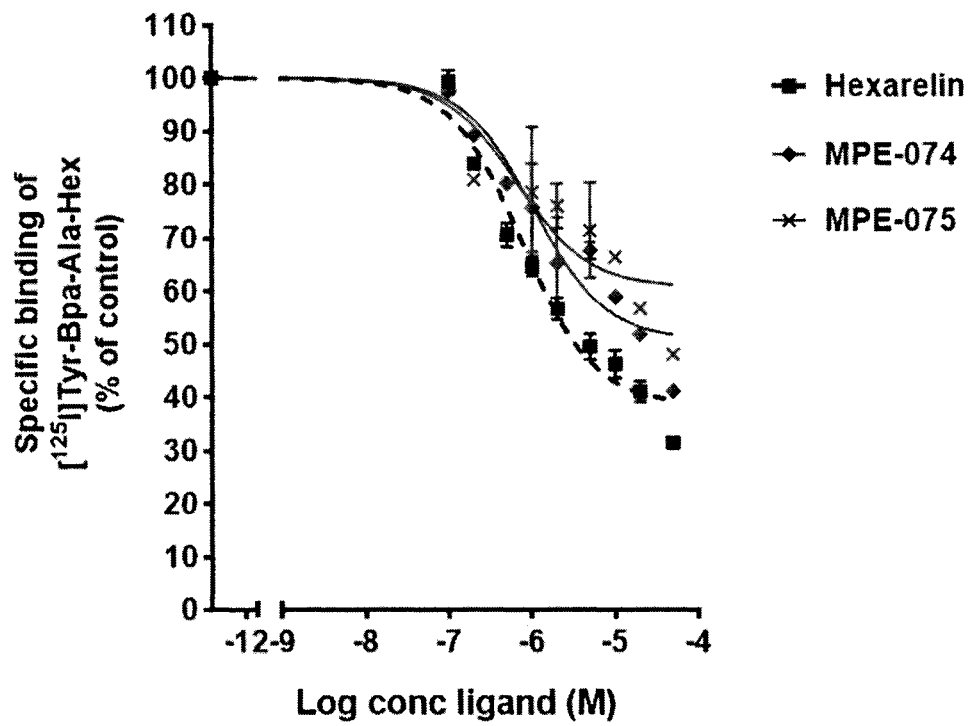
Figure 5G:
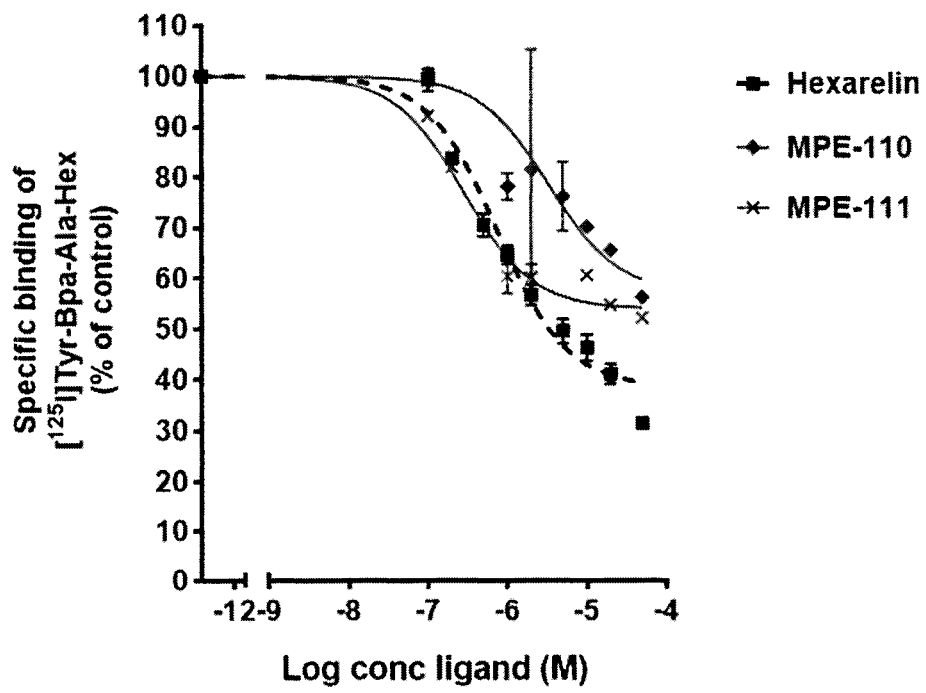

Example 3: Effect of Cyclic Peptides on R-FSL-1-Mediated Nitric Oxide Production The capacity of cyclic peptide GHRP-6 analogs to modulate the overproduction of nitric oxide (NO), a measure of oxidative stress, induced by the TLR2 agonist fibroblast-stimulating lipopeptide (R-FSL-1) was examined by measuring nitrite production in a RAW macrophage cell line. As presented in FIGS. 4A to 4F, treatment with cyclic peptides 18 (MPE-266), 24 (MPE-267), 25 (MPE-298), 33 (MPE-300), MPE-189, MPE-191, MPE-192, MPE-075, and MPE-111 led to a significant suppression of R-FSL-1-mediated NO production at the concentration tested. A noticeable reduction of NO production was also observed using cyclic peptides 19 (MPE-268), 26 (acetylated, MPE-308) and 27 (MPE-310) (about 80% of control), albeit without reaching significance according to the statistical test and threshold used (P<0.01 vs. control, one-way ANOVA with Bartlett post-test). Further analyses on selected cyclic peptides (MPE-298, MPE-268, MPE-308, MPE-310 and MPE-315) revealed that treatment with cyclic peptides MPE-268, MPE-298, MPE-308 and MPE-310 led to a significant suppression of R-FSL-1-mediated NO production at a concentration of 10$^{-7}$ M, which was more important than that obtained with positive control MPE-001 at the same concentration (FIG. 4F). No significant effect on R-FSL-1-mediated NO production was measured in cells treated with non-cyclic azapeptide MPE-315, consistent with the results depicted in FIGS. 4B and 4E.

Example 4: Affinity of Cyclic Peptides for CD36

The binding affinity to CD36 of representative cyclic peptides, including those that featured significant or noticeable inhibition of R-FSL-1-induced NO production in RAW cells, was assessed based on their ability to compete with the radiolabeled [$^{125}$I]-Tyr-Bpa-Ala-Hexarelin for CD36 on purified membranes from heart rat. The results presented in FIGS. 5A-G and Table 2 show that the cyclic azapeptides 25 (MPE-298) and 24 (MPE-267) featured the highest binding affinity towards CD36 compared to hexarelin, with IC$_{50}$ of 0.07 and 0.24 µM, respectively. Cyclic azapeptide 26 (MPE-308), resulting from the N-terminal acylation of MPE-298, featured a shift of the affinity binding towards CD36, with an IC$_{50}$ of 0.67 µM. Cyclic azapeptides 18 (MPE-266) and 27 (MPE-310) also exhibited an affinity similar to that of hexarelin (0.5-0.89 µM). Cyclic azapeptides 9 (MPE-210) and 33 (MPE-300) were able to bind to CD36 albeit with lower affinity (IC$_{50}$ of 2.06 and 10 µM, respectively). Several other cyclic peptides tested (MPE-189, MPE-191, MPE-192, MPE-193, MPE-048, MPE-074, MPE-075, MPE-110, MPE-111, MPE-201, MPE-202, MPE-203 and MPE-400) exhibited detectable binding to CD36 with IC$_{50}$ ranging from 0.24 µM (for MPE-111) to 14.3 µM (for MPE-202) (FIGS. 5C-5G). The affinity of the cyclic peptides tested was typically higher or comparable to that of positive control MPE-001, which exhibits an $IC_{50}$ of about 2 µM.

TABLE 2

Binding affinity of cyclic peptides for CD36

| Compound | $IC_{50}$ (µM) |
| --- | --- |
| Hexarelin | 0.50 |
| 9 (MPE-210) | 2.06 |
| 18 (MPE-266) | 0.68 |
| 24 (MPE-267) | 0.24 |
| 19 (MPE-268) | ND |
| 25 (MPE-298) | 0.07 |
| 33 (MPE-300) | 10.6 |
| 26 (MPE-308) | 0.67 |
| 27 (MPE-310) | 0.89 |
| MPE-189 | 3.26 |
| MPE-191 | 1.49 |
| MPE-192 | 0.98 |
| MPE-193 | 2.21 |
| MPE-048 | 13.7 |
| MPE-074 | 1.04 |
| MPE-075 | 0.66 |
| MPE-110 | 3.32 |
| MPE-111 | 0.24 |
| MPE-201 | 12.9 |
| MPE-202 | 14.3 |
| MPE-203 | 2.26 |
| MPE-400 | 11.6 |

Figure 6A:
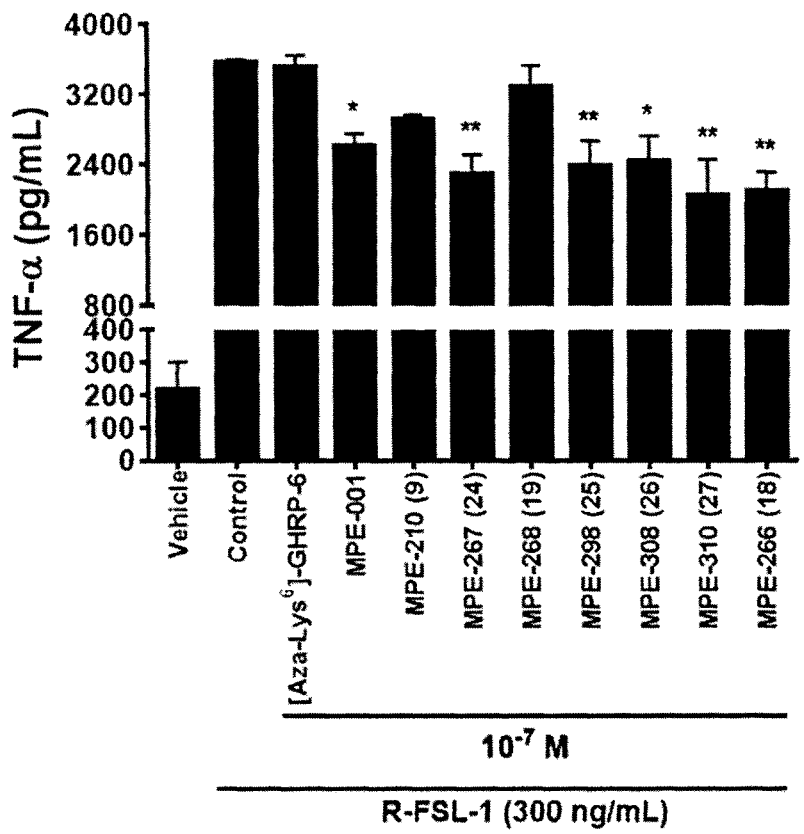
FIGS. 6A and 6B show the modulatory effect of cyclic azapeptides on TLR2-mediated pro-inflammatory cytokine (TNF-α, FIG. 6A) and chemokine (CCL-2, FIG. 6B) secretion from murine RAW macrophages. * P<0.05;  P<0.01; * P<0.001 vs. R-FSL-1 control; +P<0.05 vs. positive control MPE-001 (DBG178).
Figure 6B:
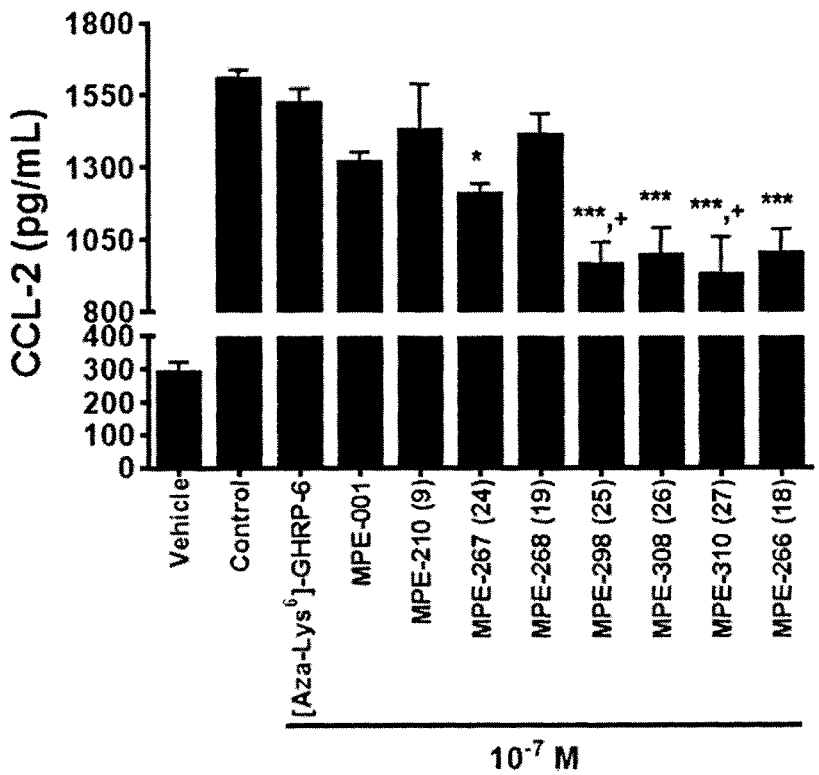

Representative cyclic peptides that featured significant or noticeable inhibition of NO production were tested respectively for ability to modulate R-FSL-1-induced pro-inflammatory cytokine (TNF-α) and chemokine (CCL-2) release; the results are depicted at FIGS. 6A and 6B, respectively. Cyclic azapeptides 18 (MPE-266), 24 (MPE-267), 25 (MPE-298), 26 (MPE-308) and 27 (MPE-310) exhibited significant inhibitory effect on R-FSL-1-induced TNF-α and CCL-2 release at the concentration tested ($10^{-7}$ M). The inhibitory effect of cyclic azapeptides 25 (MPE-298) and 27 (MPE-310) on R-FSL-1 induced CCL-2 release was significantly higher than that of reference standard azapeptide DBG178 (MPE-001). Cyclic azapeptide 19 (MPE-268), which displayed no significant binding affinity towards CD36 in the assay described above, and compound 9 (MPE-210), had no significant effect on R-FSL-1-induced TNF-α and CCL-2 release at the concentration tested ($10^{-7}$ M).

Figure 7A:
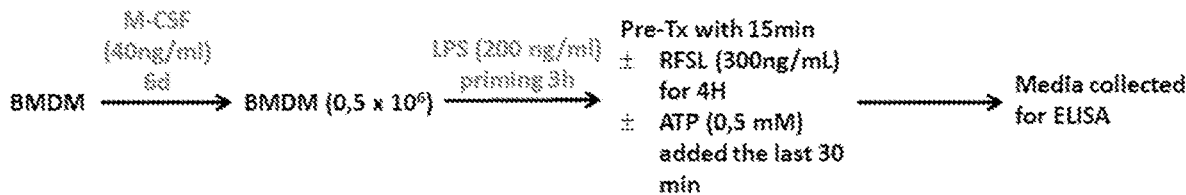
FIG. 7A shows a scheme of the experimental protocol design for assessing the effect of cyclic peptide MPE-298 on IL-1β and TNF-α secretion by bone marrow derived macrophages (BMDM) primed with TLR ligands.
Figure 7B:
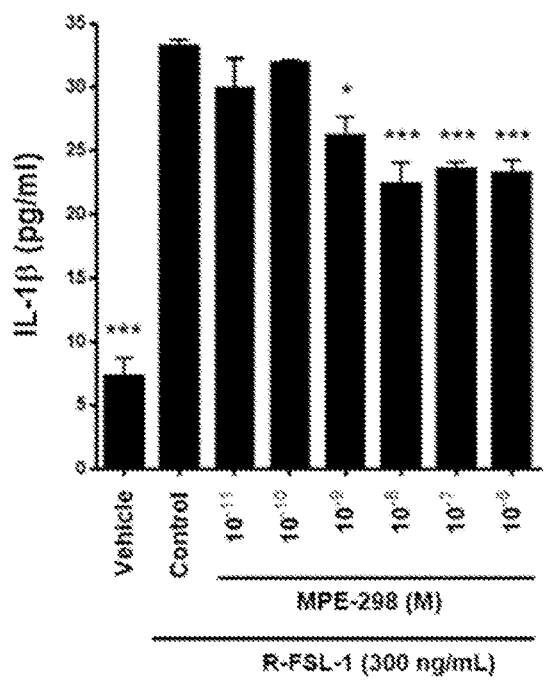
FIGS. 7B and 7C are graphs showing the secretion of IL-1β (FIG. 7B) and TNF-α (FIG. 7C) by murine BMDM primed with TLR ligands in the presence of increasing amounts of cyclic peptide MPE-298. *, P<0.05; , P<0.01 and *, P<0.001 vs. R-FSL-1 control.
Figure 7C:
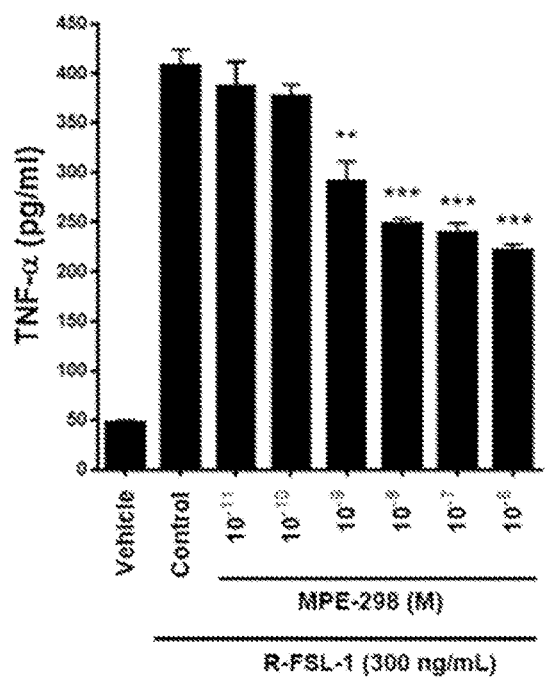

Cyclic peptide 298 was also able to inhibit the secretion of pro-inflammatory cytokines IL-1β and TNF-α induced by R-FSL-1 in bone marrow-derived macrophages (FIGS. 7B-7C), thus providing evidence that the cyclic peptide interferes with NLRP3 inflammasome activity.

Example 5: Effect of Cyclic Peptide MPE-298 in a Model of Atherosclerosis

Methods.

Figure 8A:
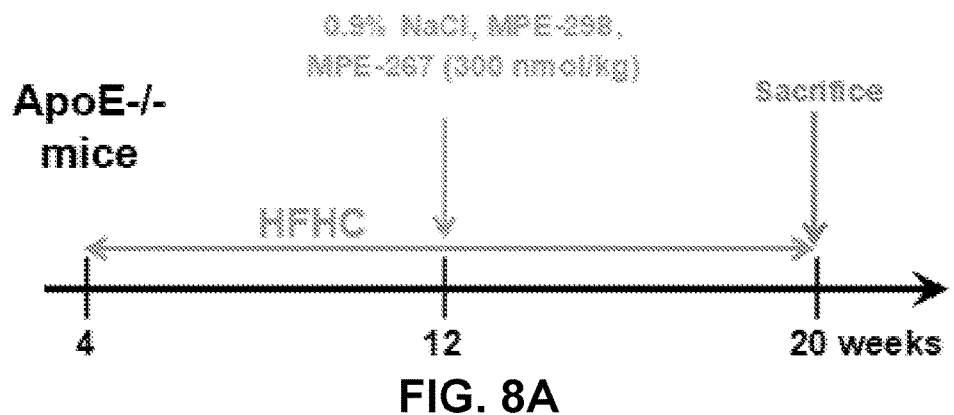
FIG. 8A shows a scheme of the experimental protocol design for assessing the effect of cyclic peptides in a murine atherosclerosis model. Cyclic peptides or 0.9% NaCl were administered daily by subcutaneous injections to ApoE−/− mice fed a high fat high cholesterol diet from 4 weeks of age.

Experiments were performed in male apoE−/− mice fed an atherogenic diet (D12108, cholate-free AIN-76A semi-purified diet, Research Diets Inc., New Brunswick, NJ) from 4 weeks of age. MPE-298 (300 nmol/kg), MPE-267 (300 nmol/kg) or vehicle (0.9% NaCl), were administered by daily by subcutaneous (s.c.) injections for 8 weeks, from 12 weeks of age, as shown schematically in FIG. 8A.

Results and Discussion.

Figure 8B:
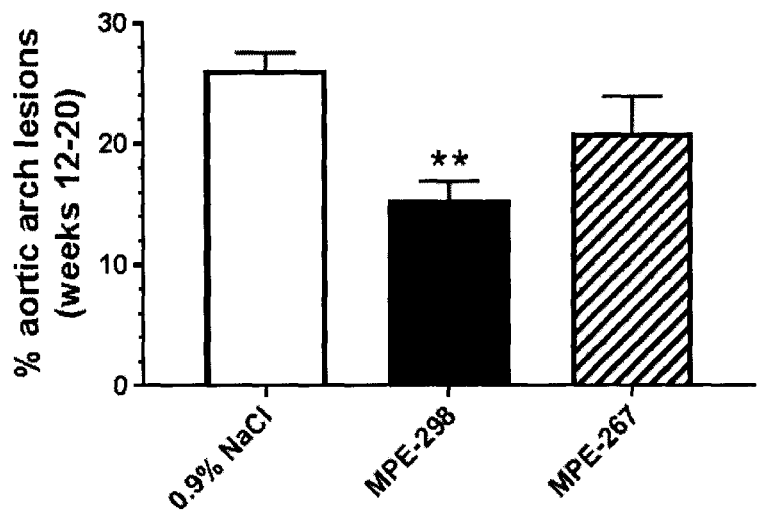
FIG. 8B is a graph showing the quantitative assessment of aortic arch lesions expressed as % aortic arch area in vehicle- (0.9% NaCl), MPE-298- and MPE-267-treated ApoE−/− mice. ** P<0.01 versus 0.9% NaCl. n=11 for vehicle and MPE-298, and n=10 for MPE-267.

The results depicted in FIG. 8B show that chronic treatment of the animals with cyclic peptides MPE-267 and MPE-298 reduced aortic lesions by 28% and 42% (p<0.01), respectively, relative to 0.9% NaCl (vehicle), providing evidence that the cyclic peptides exhibit anti-atherosclerotic activity.

Example 6: Effect of Cyclic Peptide MPE-298 in a Model of Dry Age-Related Macular Degeneration (AMD)

Experimental Model.

Figure 9A:
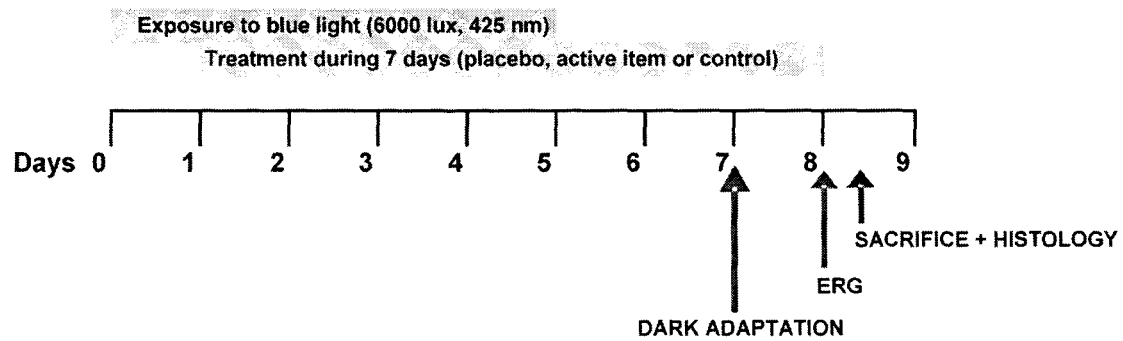
FIG. 9A shows a scheme of the experimental protocol design for assessing the effect of cyclic peptide MPE-298 in a murine dry AMD model.

The acute model of light-induced retinal degeneration uses short exposure to blue light to induce photoreceptor cell death leading to loss of vision (Grimm and Remé, *Methods Mol Biol.* 2013; 935: 87-97). Mice were exposed mice to intense blue light (wavelength=425 nm; exposure intensity=6000 lux) for five (5) successive days. The treatment was started one day after start of blue-light exposure (D1), for seven (7) successive days of daily subcutaneous (s.c) administration at 289 nmol/kg of test item solutions (MPE-001 and MPE-298). On Day 7, mice were dark adapted for electroretinography (ERG) analysis. On Day 8, a set of electrodes were disposed on the mice, which were exposed to light flash for ERG recording. Then, mice were sacrificed and eyes collected to histology and immunofluorescence studies (FIG. 9A).

Electroretinography (ERG) Analysis.

ERGs were recorded from wildtype and age matched knockout mice on Espion® ERG Diagnosys machine and a ColorDome® Ganzfeld stimulator (Diagnosys LLC, Lowell, MA). Mice were dark adapted overnight and anesthesized intraperitoneally with a mixture of Ketamine (100 mg/kg) and Xylazine solution (20 m/kg). Pupils were dilated using atropine and phenylephrine. A drop of methylcellulose was placed on the corneal surface to prevent corneal dehydration. Mouse body temperature was maintained at 37° C. using heated water pad.

Flash ERG were measured using corneal DTL Plus electrodes (Diagnosys® LLC). The electrodes were placed on the surface of cornea. Needle electrode on the forehead served as a reference electrode, and a needle electrode near the base of the tail served as ground. Scotopic responses were simultaneously recorded from both eyes of the dark-adapted animals at the following increasing light intensities: 0.5, 1.0, 3.0 and 10.0 cd-s/m². Ten waveforms responses were averaged in each step. All procedures were performed in dark room under dim red-light illumination. The amplitude and latency of major ERG components were measured with the Espion® software (Diagnosys® LLC). ERG results were presented at the light intensity of 3.0 cd-s/m². The ERG a-wave amplitudes were measured from the baseline to the primary negative peak and the b-wave was measured from the trough of the a-wave to the maximum of the fourth positive peak.

Retinal Tissues Preparations and Immunofluorescence.

For cryosections, mouse eyes were fixed in 4% paraformaldehyde and cryoprotected using 30% sucrose. They were embedded in optimal cutting temperature (OCT) compound (Leica®), frozen in liquid nitrogen, and stored at −80° C. Cryostat frozen sections (10 µm thick; Leica® CM 3050S) were made and mounted on gelatin-coated slides for immunofluorescence analysis. For flatmounts, mouse eyes were fixed in 4% paraformaldehyde for 15 minutes at room temperature, and sectioned at the limbus; the anterior segments were discarded. The posterior eye cups consisting of RPE/choroid/Sclera complex were collected and prepared for immunofluorescence analysis.

Retinal sections and RPE/choroid flatmounts were treated with PBS solution containing 0.1% Triton®×100 and 10%

FBS or 5% BSA (saturation buffer) for 45 min. Specimens were incubated overnight at 4° C. with primary antibodies diluted in saturation buffer. We performed immunofluorescence using monoclonal rat anti-F4/80 (ab6640, Abcam®) and polyclonal rabbit anti-IL-1p (ab9722, Abcam) The corresponding secondary antibodies: AlexaFluor® 488-conjugated (Invitrogen Life Technology®) and AlexaFluor® 647-conjugated (New England Biolabs®), were used to reveal the primary antibodies, and sections were counterstained with DAPI (Sigma-Aldrich®). The tissue preparation was washed three times with 5 min washing cycles in saturation buffer and flatmounts prepared for fluorescence microscopy (IX81 Olympus®, Richmond Hill, Canada). All immunostainings were repeated at least three times, and staining that omitted the primary antibody served as negative control.

Quantification of Activated Microglia/Macrophages in Sub-Retinal Space.

At least 3 retina flatmounts were used to count subretinal immune cells. F4/80-stained cells were counted on RPE flatmounts from control and illuminated mice injected with saline, MPE-001 or MPE-298. The cell number was expressed as the mean number of F4/80-positive cells per $mm^2$.

Quantification of Photoreceptor Layer Thickness.

At least 3 retinal cryosections per eye and per condition were used to measure the thickness of photoreceptors layers. Twelve measures per retinal section were performed in the superior and inferior poles around the optical nerve. Analysis of layer thickness was performed using the Image J software (http://imagej.nih.gov/). The area under the curves was integrated using the statistical analysis program (Prism® software version 5.01; Graphpad® Software, San Diego, CA).

Statistical Analysis.

All experiments were repeated at least 3 times. Statistical analysis was performed using GraphPad® Prism software. Data with 3 conditions were analyzed using the one-way ANOVA with Newman Keuls post-test. Data with more than 3 conditions were analyzed using the one-way ANOVA with Dunnett's post-test. Numerical results were expressed as mean±SEM. Statistical significance was set on the basis of P value. n.s. $P>0.05$; * $P<0.05$,  $P<0.01$, * $P<0.001$.

Figure 9B:
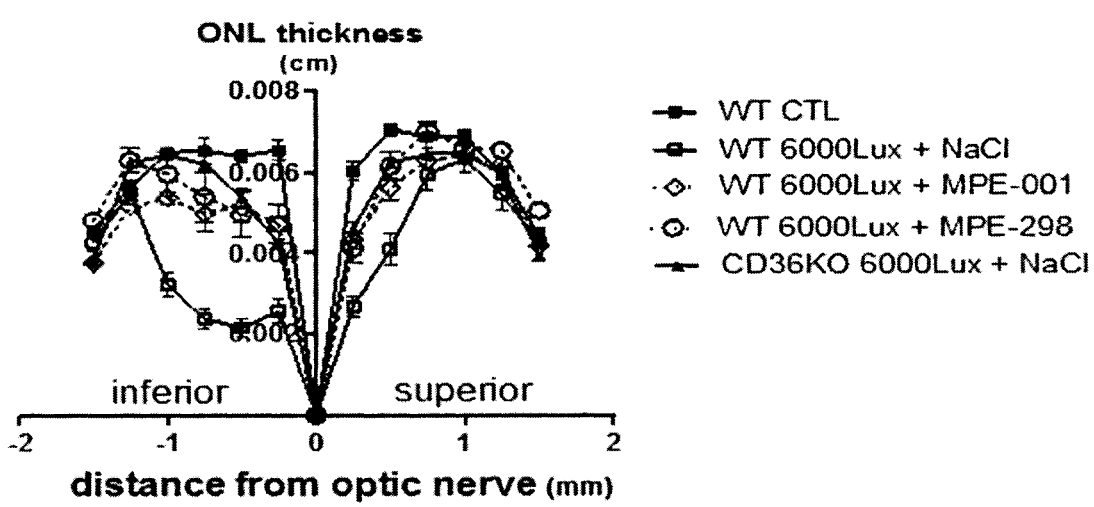
FIG. 9B is a spider graph presenting outer nuclear layer (ONL) thickness from both side of the optic nerve from wild-type (WT) or CD36$^{-/-}$ (KO) mice. WT CTL=WT mice not exposed to blue light, no treatment; WT 6000Lux+NaCl=WT mice exposed to blue light and treated with saline solution; WT 6000Lux+MPE-001=WT mice exposed to blue light and treated with MPE-001 peptide; WT 6000Lux+MPE-298=WT mice exposed to blue light and treated with MPE-298 cyclic peptide; CD36KO 6000Lux+NaCl=CD36$^{-/-}$ mice exposed to blue light and treated with saline solution.
Figure 9C:
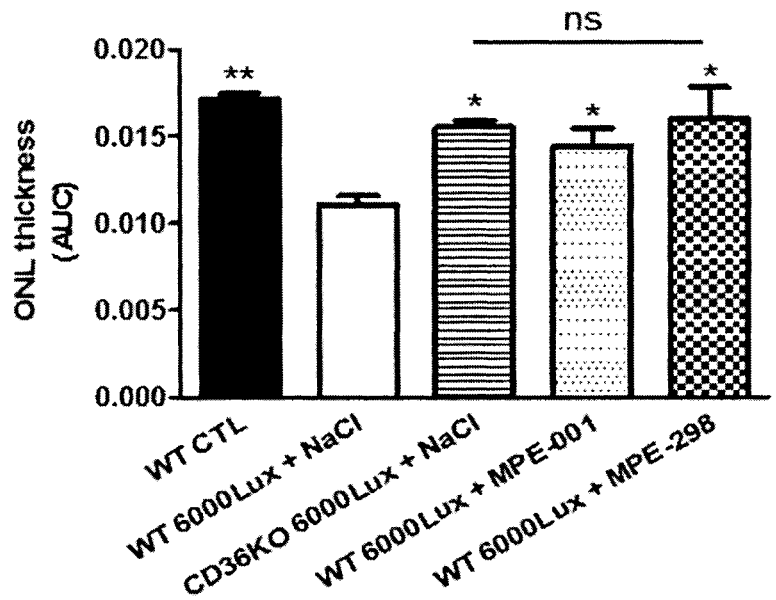
FIG. 9C is a graph showing the area under the curves (AUC) from ONL thickness measurements in the different groups of mice. ** P<0.01, * P<0.05 vs WT 6000Lux+NaCl.
Figure 10A:
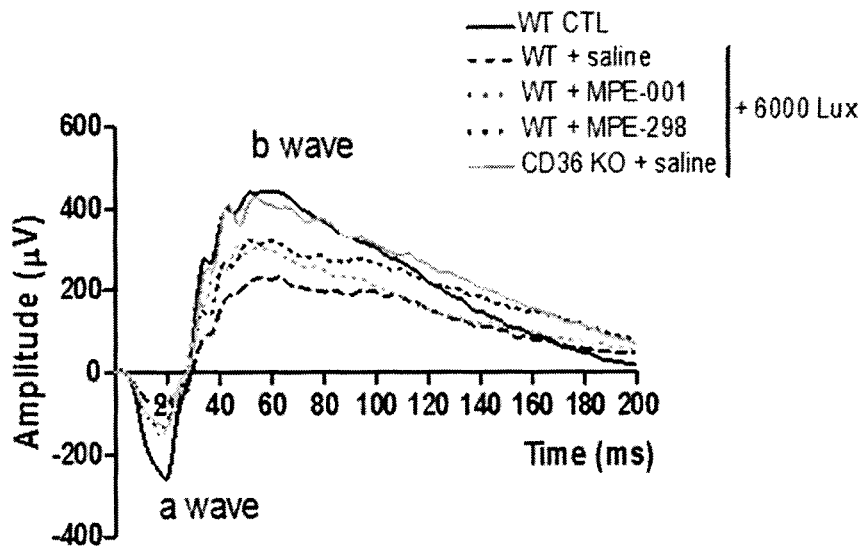
FIG. 10A shows representative ERG responses in the different groups of mice.
Figure 10B:
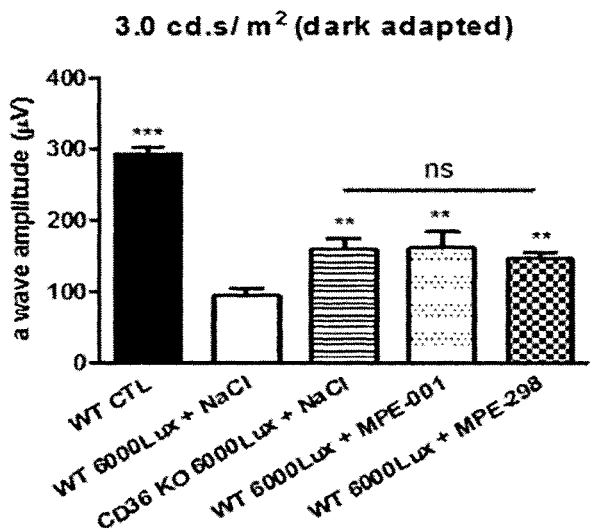
FIGS. 10B and 10C are graphs depicting the quantification of the a wave (FIG. 10B) and b wave (FIG. 10B) amplitude in the different groups of mice measured at the light intensity of 3.0 cd-s/m$^2$ (dark adapted). * P<0.001,  P<0.01 vs WT 6000Lux+NaCl.
Figure 10C:
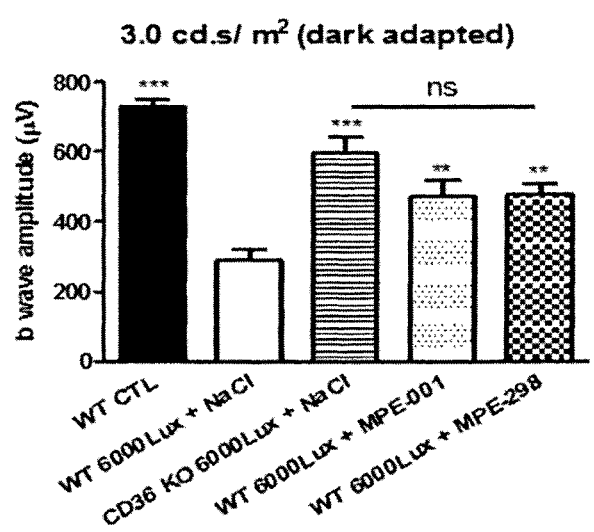
Figure 11A:
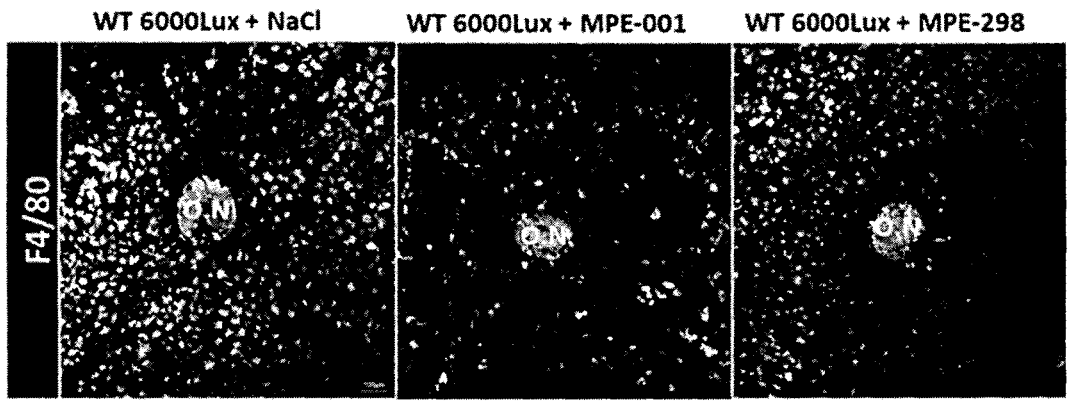
FIG. 11A is a confocal microscopy image of RPE flatmounts from mice exposed to blue-light irradiation treated with saline, MPE-001 or MPE-298, and stained with an anti-F4/80 antibody (white). O.N.=optic nerve.
Figure 11B:
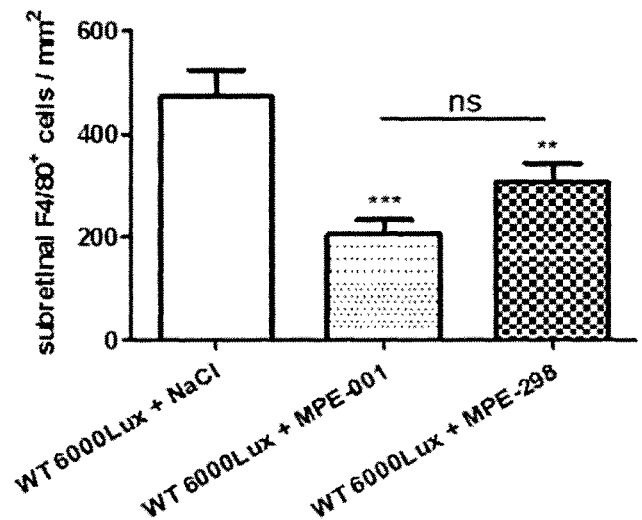
FIGS. 11B and 11C are graphs showing the quantification of total F4/80-positive cells (FIG. 11B) and IL-1β-expressing F4/80-positive cells (FIG. 11C) in RPE flatmounts from mice exposed to blue-light irradiation treated with saline, MPE-001 or MPE-298. * P<0.001,  P<0.01 vs WT 6000Lux+NaCl.
Figure 11C:
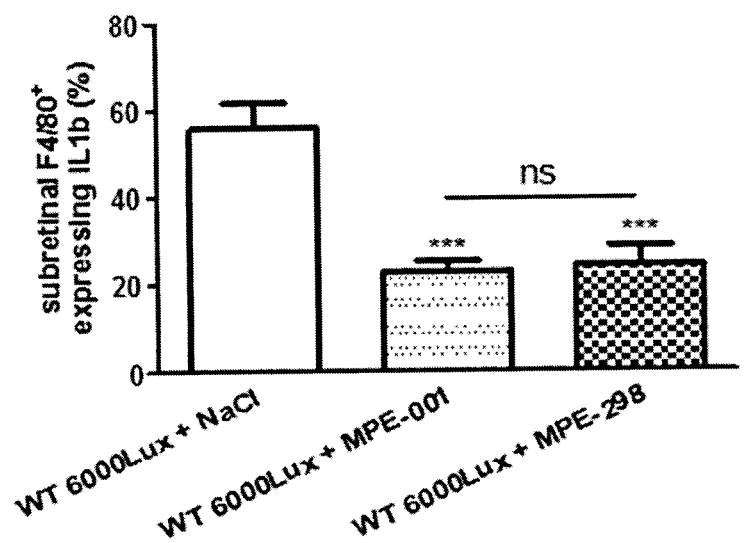

Results. Exposure to intense blue light induces retinal damages comparable to the damages associated with age-related macular degeneration (AMD). In view of the involvement of CD36 in AMD, a representative cyclic GHRP-6 analog (MPE-298) was examined for potential to prevent or reduce the damages induced by intense blue light exposure. The results presented in FIGS. 9B and 9C show that treatment with cyclic azapeptide MPE-298 preserved ONL thickness in the mice exposed to intense blue light, and thus induced a protection against photoreceptor degeneration in this model. ONL thickness in MPE-298-treated mice was comparable to that measured in CD36KO mice. To determine whether such protection against photoreceptor degeneration was associated with improved retinal function, ERG analyses were performed on the different groups of mice. As shown in FIGS. 10A-10C, MPE-298 treatment was associated with a significant improvement of retinal function relative to control treatment with saline solution, as evidenced by an increased in a wave and b wave amplitudes. MPE-298 treatment was shown to reduce subretinal inflammation induced by blue light exposure, as demonstrated by a reduction in immune cell infiltration, and notably IL-1β-expressing (pro-inflammatory) immune cells, in the retina (FIGS. 11A-C).

The results thus provide evidence that the cyclic GHRP-6 analogs described herein may be useful for the treatment of inflammatory disorders of the retina, such as AMD.

Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", "an" and "the" include corresponding plural references unless the context clearly dictates otherwise.

REFERENCES (1) Akira, S.; Uematsu, S.; Takeuchi, O. Pathogen recognition and innate immunity. Cell 2006, 124, 783.
(2) Kawai, T.; Akira, S. The role of pattern-recognition receptors in innate immunity: update on Toll-like receptors. Nat. Immunol. 2010, 11, 373.
(3) Piccinini, A.; Midwood, K. DAMPening inflammation by modulating TLR signalling. Mediators of inflammation 2010, 2010, 1.
(4) Brown, K. L; Cosseau, C; Gardy, J. L; Hancock, R. E. Complexities of targeting innate immunity to treat infection. Trends Immunol. 2007, 28, 260.
(5) Connolly, D. J.; O'Neill, L. A. New developments in Toll-like receptor targeted therapeutics. Curr. Opin. Pharmacol. 2012, 12, 510.
(6) Keogh, B.; Parker, A. E. Toll-like receptors as targets for immune disorders. Trends Pharmacol. Sci. 2011, 32, 435.
(7) Dunne, A.; Marshall, N. A.; Mills, K. H. TLR based therapeutics. Curr. Opin. Pharmacol. 2011, 11, 404.
(8) Schneider, A. R.; Sari, Y. Therapeutic Perspectives of Drugs Targeting Toll-Like Receptors Based on Immune Physiopathology Theory of Alzheimer's Disease. CNS Neurol. Disord. Drug Targets 2014, 13, 909.
(9) Arslan, F.; Smeets, M. B.; O'Neill, L. A.; Keogh, B.; McGuirk, P.; Timmers, L.; Tersteeg, C; Hoefer, I. E.; Doevendans, P. A.; Pasterkamp, G. Myocardial ischemia/reperfusion injury is mediated by leukocytic Toll-like receptor-2 and reduced by systemic administration of a novel anti-Toll-like receptor-2 antibody. Circulation 2010, 121, 80.
(10) Opsona Therapeutics (May 19, 2014). Placebo-Controlled Study to Evaluate the Safety and Efficacy of OPN-305 in Preventing Delayed Renal Graft Function. Retrieved from http://www.clinicaltrials.gov/ct2/show/NCT01794663?term=opsona&rank=1
(11) Triantafilou, M.; Gamper, F. G.; Lepper, P. M.; Mouratis, M. A.; Schumann, C; Harokopakis, E.; Schifferle, R. E.; Hajishengallis, G.; Triantafilou, K. Lipopolysaccharides from atherosclerosis-associated bacteria antagonize TLR4, induce formation of TLR2/1/CD36 complexes in lipid rafts and trigger TLR2-induced inflammatory responses in human vascular endothelial cells. Cell. Microbiol. 2007, 9, 2030.
(12) Picard, E.; Houssier, M.; Bujold, K.; Sapieha, P.; Lubell, W.; Dorfman, A.; Racine, J.; Hardy, P.; Febbraio, M.; Lachapelle, P. CD36 plays an important role in the clearance of oxLDL and associated age-dependent subretinal deposits. Aging (Albany NY) 2010, 2, 981.
(13) Sheedfar et al., Aging (Albany NY). 2014 April; 6(4):281-95.
(14) Wilson et al., Endocrinology. 2016 February; 157(2): 570-85.

What is claimed is:
1. A cyclic peptide that binds to CD36, wherein the cyclic peptide has one of the following structures:
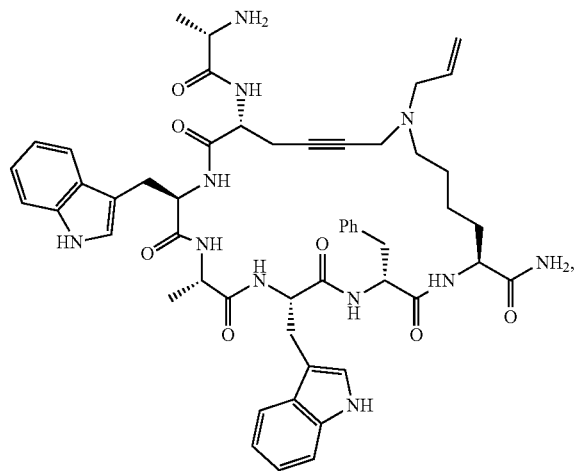
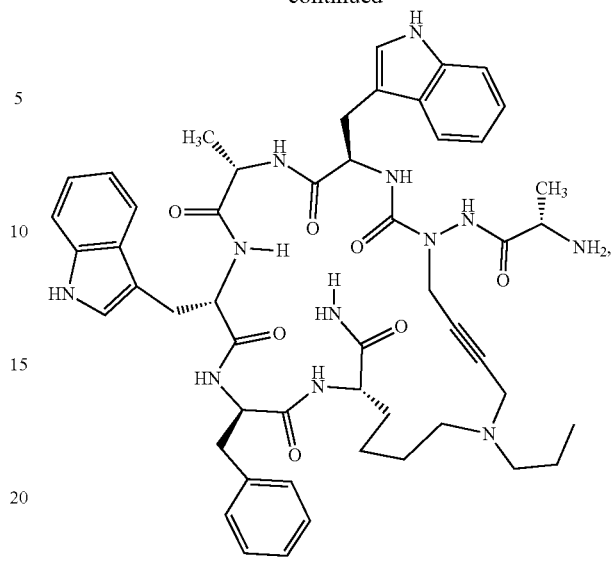
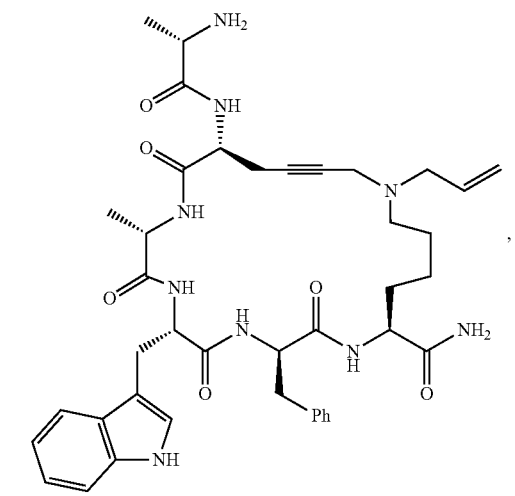
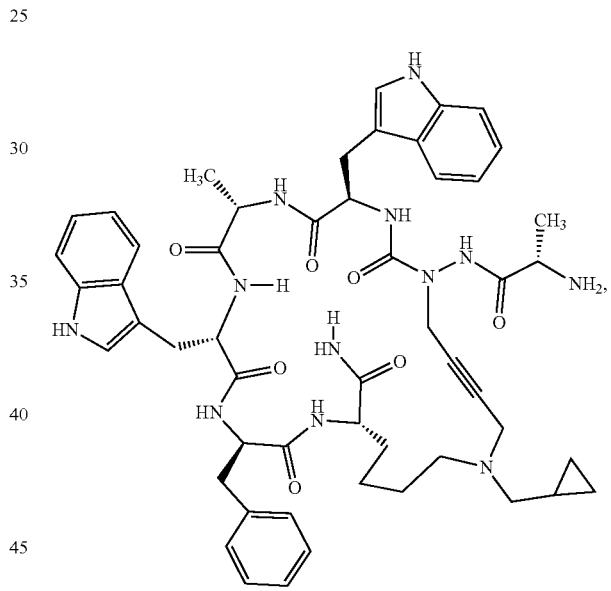
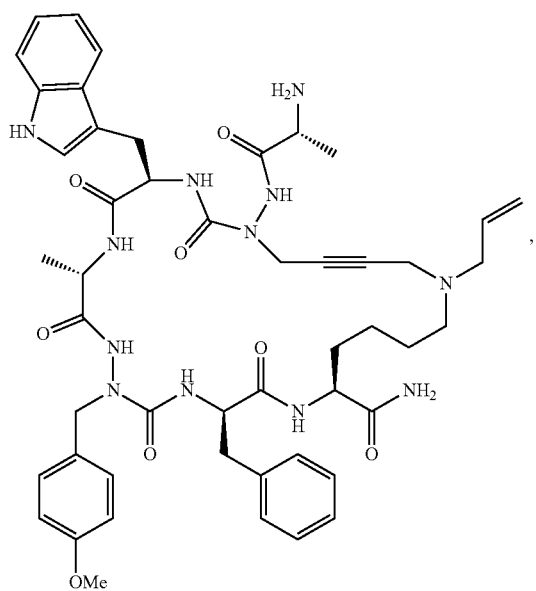
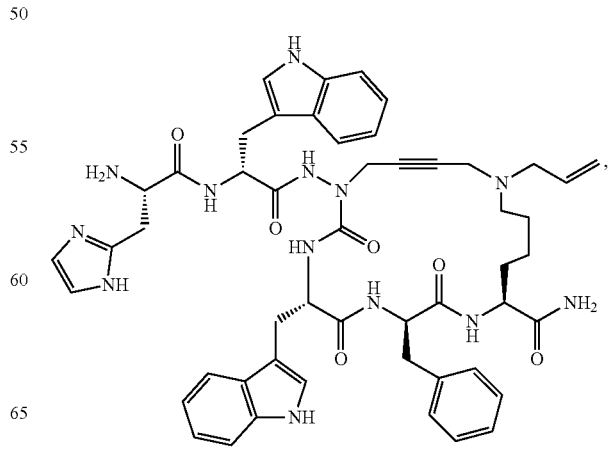

133
-continued
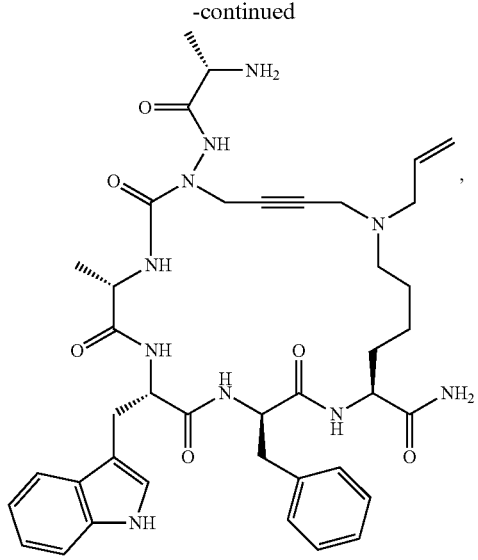
,
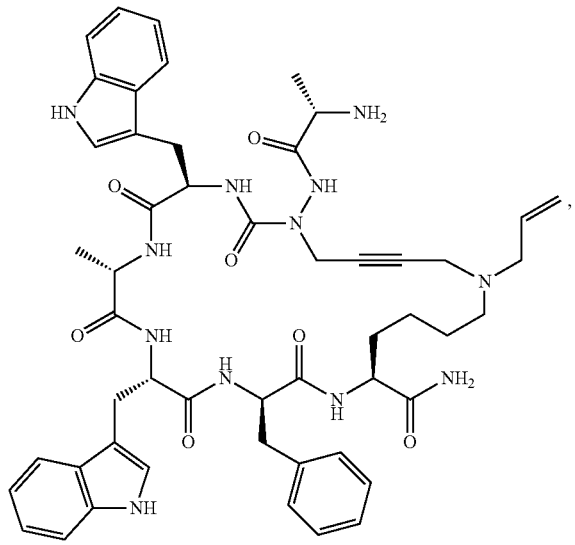
,
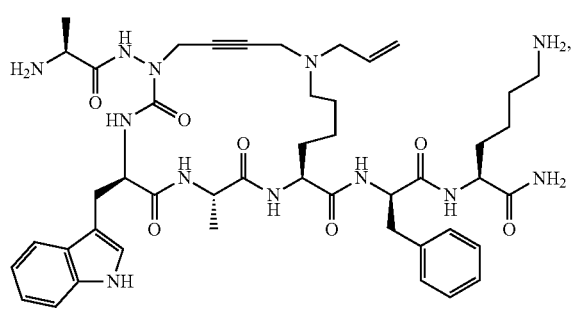
,
134
-continued
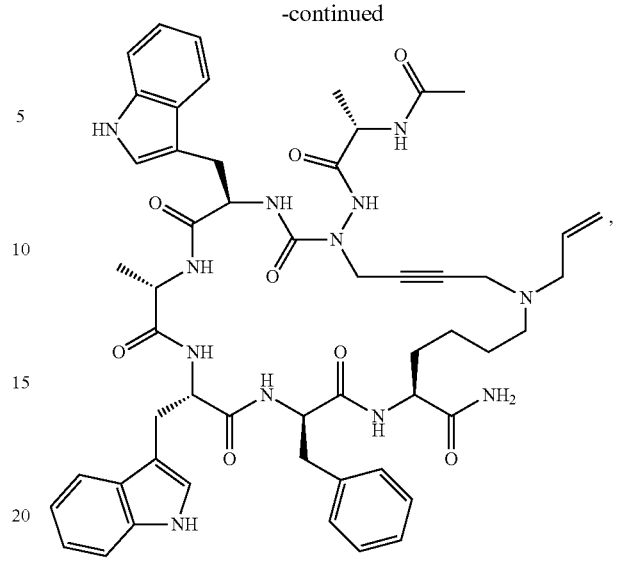
or a pharmaceutically acceptable salt thereof.
2. The cyclic peptide or pharmaceutically acceptable salt thereof of claim 1, being:
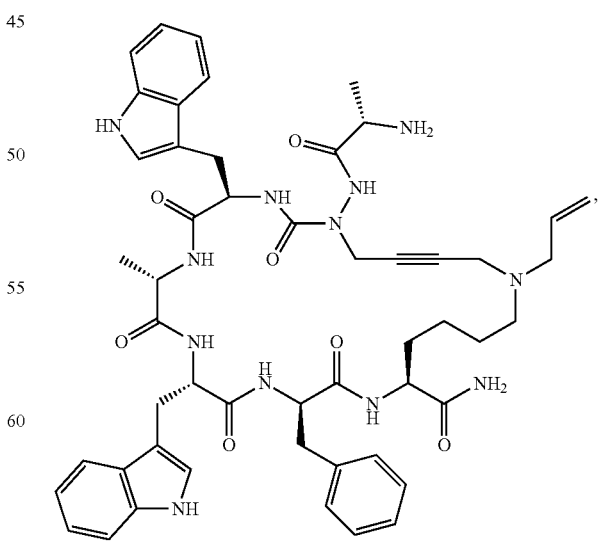
or a pharmaceutically acceptable salt thereof.

3. The cyclic peptide or pharmaceutically acceptable salt thereof of claim 1, being:

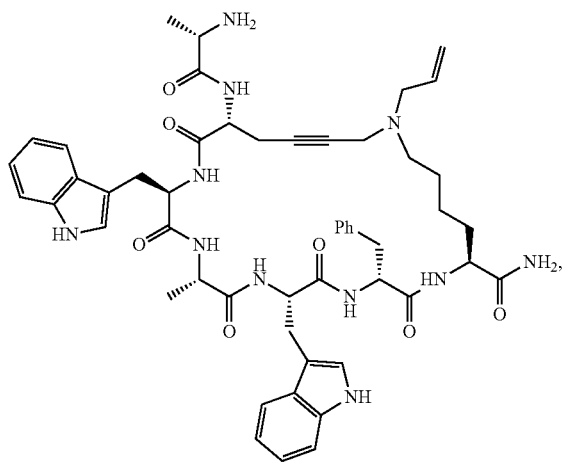 [SMILES: C=CCN1CC#CC[C@@H](NC(=O)[C@H](C)N)C(=O)N[C@H](Cc2c[nH]c3ccccc23)C(=O)N[C@@H](C)C(=O)N[C@@H](Cc2c[nH]c3ccccc23)C(=O)N[C@H](Cc2ccccc2)C(=O)N[C@H](C(N)=O)CCCC1]

or a pharmaceutically acceptable salt thereof.

4. The cyclic peptide or pharmaceutically acceptable salt thereof of claim 1, being:

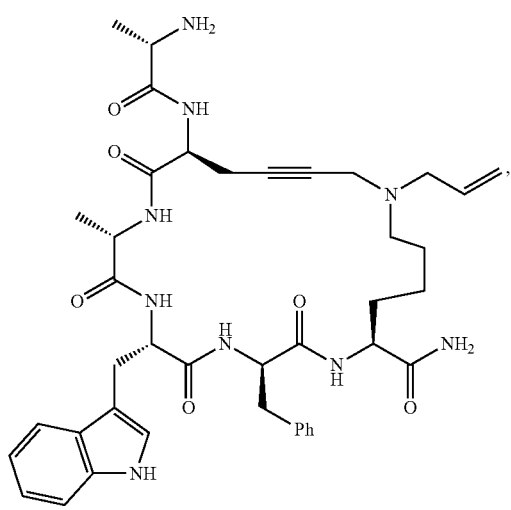 [SMILES: C=CCN1CC#CC[C@H](NC(=O)[C@H](C)N)C(=O)N[C@@H](C)C(=O)N[C@@H](Cc2c[nH]c3ccccc23)C(=O)N[C@H](Cc2ccccc2)C(=O)N[C@H](C(N)=O)CCCC1]

or a pharmaceutically acceptable salt thereof.

5. The cyclic peptide or pharmaceutically acceptable salt thereof of claim 1, being:

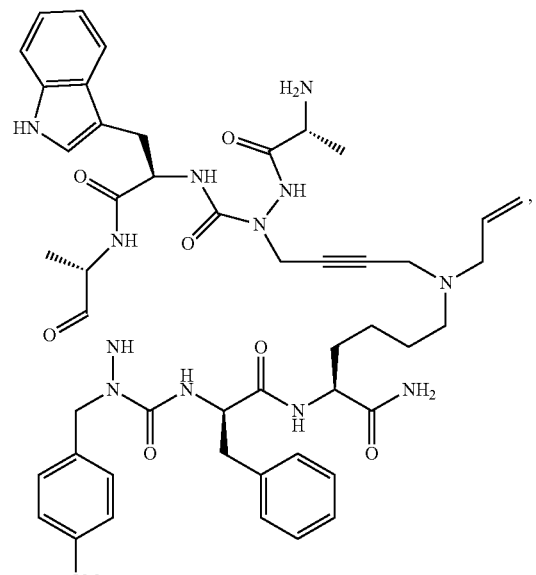

or a pharmaceutically acceptable salt thereof.

6. The cyclic peptide or pharmaceutically acceptable salt thereof of claim 1, being:

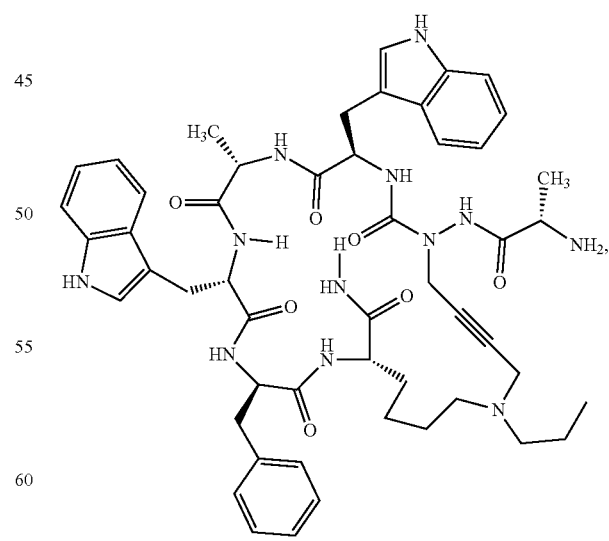

or a pharmaceutically acceptable salt thereof.

7. The cyclic peptide or pharmaceutically acceptable salt thereof of claim 1, being:

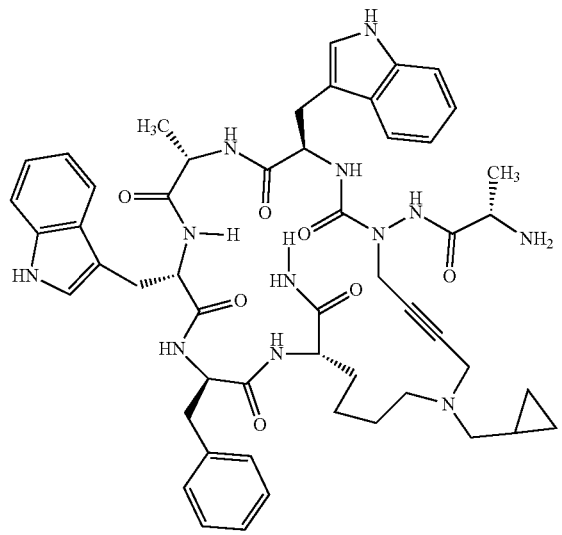 [SMILES: CCCN1CC#CCN(NC(=O)[C@H](C)N)C(=O)N[C@H](Cc2c[nH]c3ccccc23)C(=O)N[C@@H](C)C(=O)N[C@@H](Cc2c[nH]c3ccccc23)C(=O)N[C@H](Cc2ccccc2)C(=O)N[C@H](C(N)=O)CCCC1]

or a pharmaceutically acceptable salt thereof.

8. The cyclic peptide or pharmaceutically acceptable salt thereof of claim 1, being:

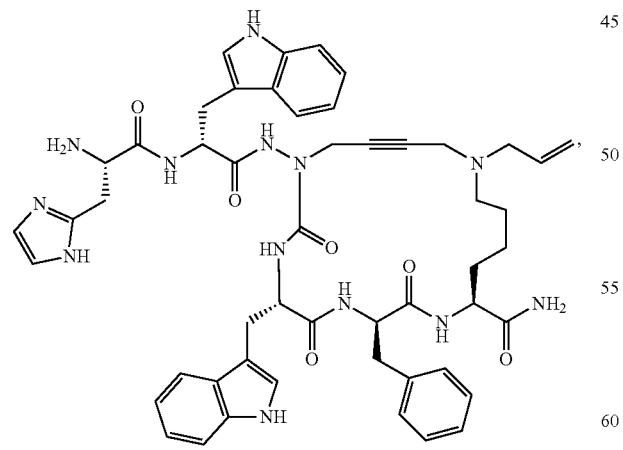

or a pharmaceutically acceptable salt thereof.

9. The cyclic peptide or pharmaceutically acceptable salt thereof of claim 1, being:

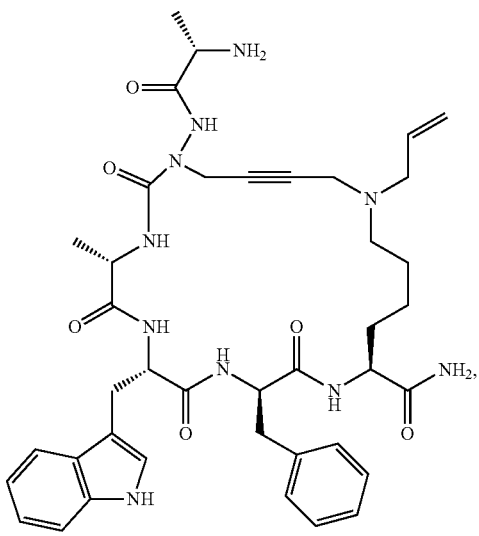 [SMILES: C=CCN1CC#CCN(NC(=O)[C@H](C)N)C(=O)N[C@@H](C)C(=O)N[C@@H](Cc2c[nH]c3ccccc23)C(=O)N[C@H](Cc2ccccc2)C(=O)N[C@H](C(N)=O)CCCC1]

or a pharmaceutically acceptable salt thereof.

10. The cyclic peptide or pharmaceutically acceptable salt thereof of claim 1, being:

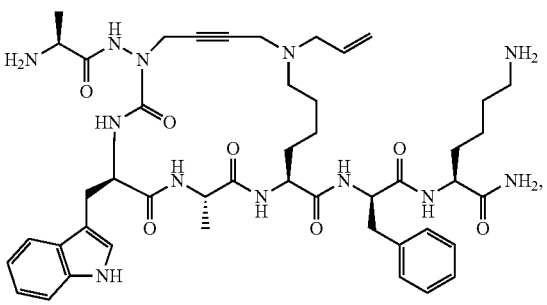 [SMILES: C=CCN1CC#CCN(NC(=O)[C@H](C)N)C(=O)N[C@H](Cc2c[nH]c3ccccc23)C(=O)N[C@@H](C)C(=O)N[C@H](C(=O)N[C@H](Cc2ccccc2)C(=O)N[C@@H](CCCCN)C(N)=O)CCCC1]

or a pharmaceutically acceptable salt thereof.

11. The cyclic peptide or pharmaceutically acceptable salt thereof of claim 1, being:

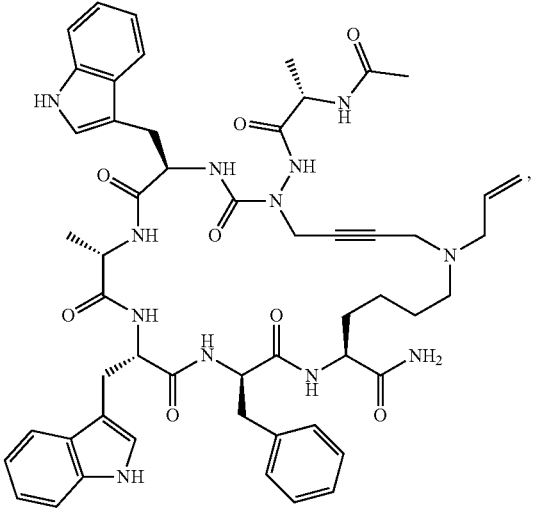 [SMILES: C=CCN1CC#CCN(NC(=O)[C@H](C)NC(C)=O)C(=O)N[C@H](Cc2c[nH]c3ccccc23)C(=O)N[C@@H](C)C(=O)N[C@@H](Cc2c[nH]c3ccccc23)C(=O)N[C@H](Cc2ccccc2)C(=O)N[C@H](C(N)=O)CCCC1]

or a pharmaceutically acceptable salt thereof.

12. The cyclic peptide or pharmaceutically acceptable salt thereof of claim 1, being:

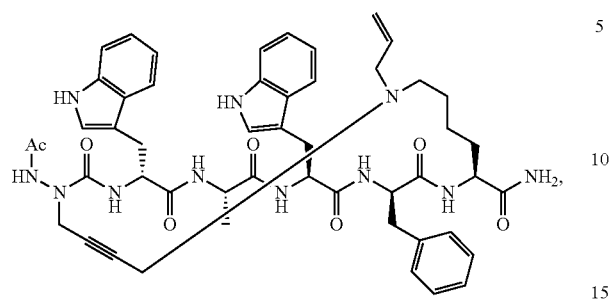

or a pharmaceutically acceptable salt thereof.

13. A method of treating a CD36-related disease, disorder or condition, the method comprising administering to a subject in need thereof an effective amount of the cyclic peptide or pharmaceutically acceptable salt thereof of claim 1, wherein the CD36-related disease, disorder or condition is atherosclerosis or age-related macular degeneration.

14. The method of claim 13, wherein said CD36-related disease, disorder or condition is age-related macular degeneration.

15. A method of treating a CD36-related disease, disorder or condition, the method comprising administering to a subject in need thereof an effective amount of the cyclic peptide or pharmaceutically acceptable salt thereof of claim 2, wherein the CD36-related disease, disorder or condition is atherosclerosis or age-related macular degeneration.

* * * * *